US010679730B2

(12) United States Patent
Rosner et al.

(10) Patent No.: US 10,679,730 B2
(45) Date of Patent: Jun. 9, 2020

(54) PROGNOSTIC AND PREDICTIVE BREAST CANCER SIGNATURE

(71) Applicant: The University of Chicago, Chicago, IL (US)

(72) Inventors: Marsha Rosner, Chicago, IL (US); Miao Sun, Chicago, IL (US); Unjin Lee, Chicago, IL (US)

(73) Assignee: The University of Chicago, Chicago, IL (US)

( * ) Notice: Subject to any disclaimer, the term of this patent is extended or adjusted under 35 U.S.C. 154(b) by 1046 days.

(21) Appl. No.: 14/952,265

(22) Filed: Nov. 25, 2015

(65) Prior Publication Data

US 2016/0078167 A1    Mar. 17, 2016

Related U.S. Application Data

(63) Continuation-in-part of application No. PCT/US2014/039807, filed on May 28, 2014.

(60) Provisional application No. 61/828,103, filed on May 28, 2013, provisional application No. 62/090,809, filed on Dec. 11, 2014.

(51) Int. Cl.
| | |
|---|---|
| *G16B 25/00* | (2019.01) |
| *C12Q 1/6886* | (2018.01) |
| *G01N 33/574* | (2006.01) |
| *A61K 31/706* | (2006.01) |
| *A61K 45/06* | (2006.01) |
| *A61K 31/405* | (2006.01) |
| *A61K 31/52* | (2006.01) |
| *A61K 31/7068* | (2006.01) |
| *A61K 31/506* | (2006.01) |
| *A61K 31/167* | (2006.01) |

(52) U.S. Cl.
CPC ............ *G16B 25/00* (2019.02); *A61K 31/167* (2013.01); *A61K 31/405* (2013.01); *A61K 31/506* (2013.01); *A61K 31/52* (2013.01); *A61K 31/706* (2013.01); *A61K 31/7068* (2013.01); *A61K 45/06* (2013.01); *C12Q 1/6886* (2013.01); *G01N 33/57415* (2013.01); *C12Q 2600/118* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

| 2009/0192100 A1 | 7/2009 | Vater et al. ............... 514/44 R |
| 2010/0048499 A1 | 2/2010 | Desai et al. ............... 514/34 |
| 2012/0114670 A1 | 5/2012 | Land et al. ............... 424/174.1 |

OTHER PUBLICATIONS

Lee et al. A Prognostic Gene Signature for Metastasis-Free Survival of Triple Negative Breast Cancer Patients. PLOS one Dec. 11, 2013, vol. 8, Issue 12, e82125, pp. 1-13 (Year: 2013).*
Minn et al. Genes that mediate breast cancer metastasis to lung. Nature 2005, vol. 436, No. 28, pp. 518-524 (Year: 2005).*
Katz et al. Epigenetic reprogramming in breast cancer: From new targets to new therapies. Annals of Medicine 2014, vol. 46, No. 6, pp. 397-408 (Year: 2014).*
Bertucci et al. Basal Breast Cancer: A Complex and Deadly Molecular Subtype. Current Molecular Medicine 2012, vol. 12, No. 1; pp. 96-110 (Year: 2012).*
Acosta et al., "DNA methylation changes in murine breast adenocarcinomas allow the identification of candidate genes for human breast carcinogenesis", *Mamm Genome*, 22(3-4):249-59, 2011.
Enerly E, et al. (2011) "miRNA-mRNA integrated analysis reveals roles for miRNAs in primary breast tumors." *PLoS One*, 6(2):e16915.
Faber J, et al. (2009) "HOXA9 is required for survival in human MLL-rearranged acute leukemias.", *Blood*, 113(11):2375-2385.
Gilbert et al., "HOXA9 regulates BRCA1 expression to modulate human breast tumor phenotype", *J Clin Invest*, 120(5): 1535-50, 2010.
Hagemann et al., "Azacytidine and Decitabine Induce Gene-Specific and Non-Random DNA Demethylation in Human Cancer Cell Lines", *PLoS One*, 6(3): e17388, 2011.
Han et al., (2008) "SATB1 reprogrammes gene expression to promote breast tumour growth and metastasis.", *Nature*, 452(7184):187-193.
Hsu Ch, et al. (2012) "TET1 suppresses cancer invasion by activating the tissue inhibitors of metalloproteinases." *Cell Rep* 2(3):568-579.
International Search Report and Written Opinion issued in PCT/US14/39807, dated Jun. 12, 2015.
Kang Y, et al. (2003) "A multigenic program mediating breast cancer metastasis to bone.", *Cancer Cell*, 3(6):537-549.
Liang et al., (2012) "Transcriptional network analysis identifies BACH1 as a master regulator of breast cancer bone metastasis.", *J Biol Chem*, 287: 33533-33544.
Minn et al., (2012) "Identification of novel metastasis suppressor signaling pathways for breast cancer.", *Cell Cycle*, 11: 2452-2457.
Mira et al., (2009) "The GAB2 signaling scaffold promotes anchorage independence and drives a transcriptional response associated with metastatic progression of breast cancer.", *Oncogene*, 28: 4444-4455.

(Continued)

*Primary Examiner* — Olivia M. Wise
(74) *Attorney, Agent, or Firm* — Norton Rose Fulbright US LLP

(57) ABSTRACT

Embodiments of the invention are directed to methods of determining the prognosis of a breast cancer patient by evaluating a specified set of genes. Specifically, methods may comprise calculating a prognosis score based on a particular algorithm. Also disclosed are compositions, kits and methods for treating cancer in a subject in need thereof are disclosed involving one or more upstream activators and/or downstream effectors of TET1.

11 Claims, 44 Drawing Sheets
Specification includes a Sequence Listing.

(56) References Cited

OTHER PUBLICATIONS

Ono et al. (2002) "LCX, leukemia-associated protein with a CXXC domain, is fused to MLL in acute myeloid leukemia with trilineage dysplasia having t(10;11)(q22;q23)." *Cancer Res* 62(14):4075-4080.

Pan et al., (2011) "Activation of the glucocorticoid receptor is associated with poor prognosis in estrogen receptor-negative breast cancer.", *Cancer Res*, 71: 6360-6370.

Shah N, Sukumar S (2010) "The Hox genes and their roles in oncogenesis." *Nat Rev Cancer* 10(5):361-371.

Sun et al., "HMGA2/TET1/HOXA9 signalling pathway regulates breast cancer growth and metastasis", *Proc Natl Acad Sci USA*, 110(24): 9920-5, 2013.

Wend et al., "WNT10B/b-catenin signalling induces HMGA2 and proliferation in metastatic triple-negative breast cancer.", *EMBO Mol Med*, 5(2): 264-79, 2013.

Winter et al., (2011) "Chromatin immunoprecipitation to analyze DNA binding sites of HMGA2." *PLoS One* 6(4):e18837.

Yun et al., (2011) "Signalling pathway for RKIP and Let-7 regulates and predicts metastatic breast cancer", *EMBO J* 30: 4500-4514.

\* cited by examiner

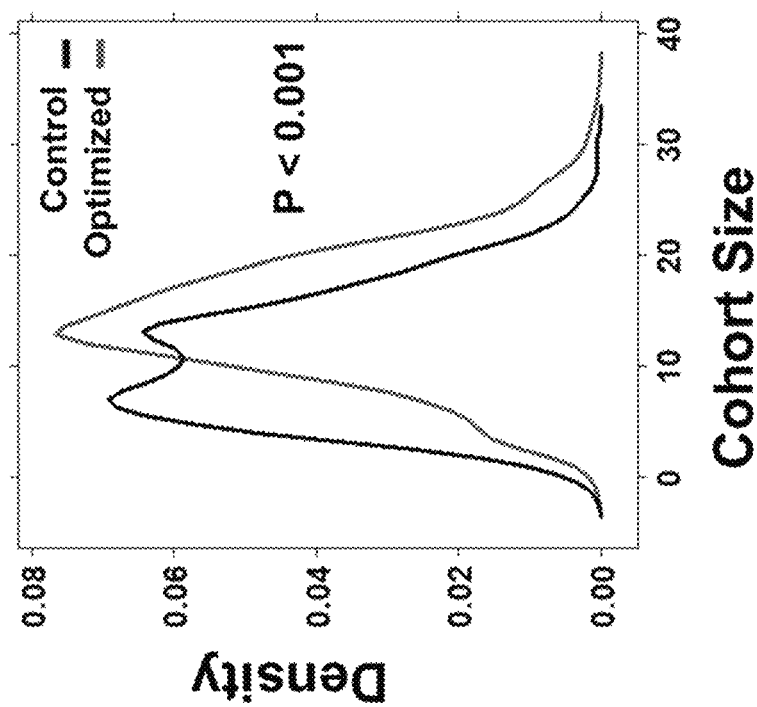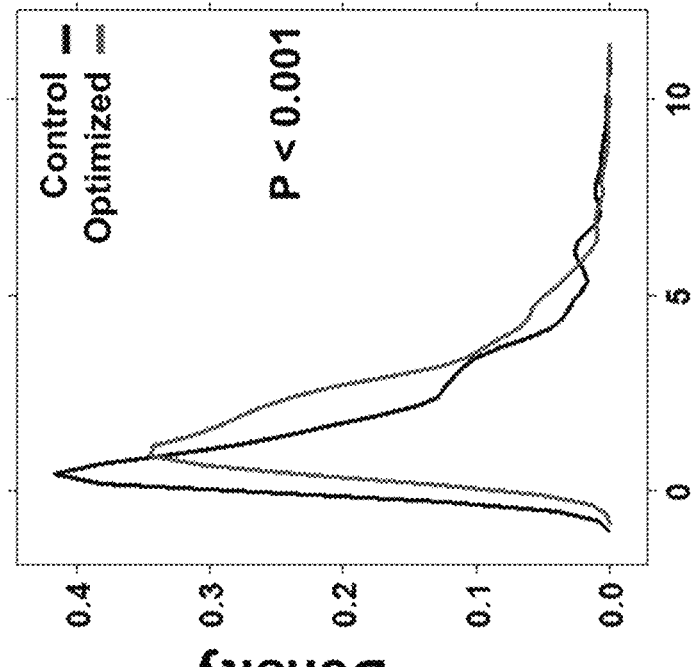
FIG. 1A-B

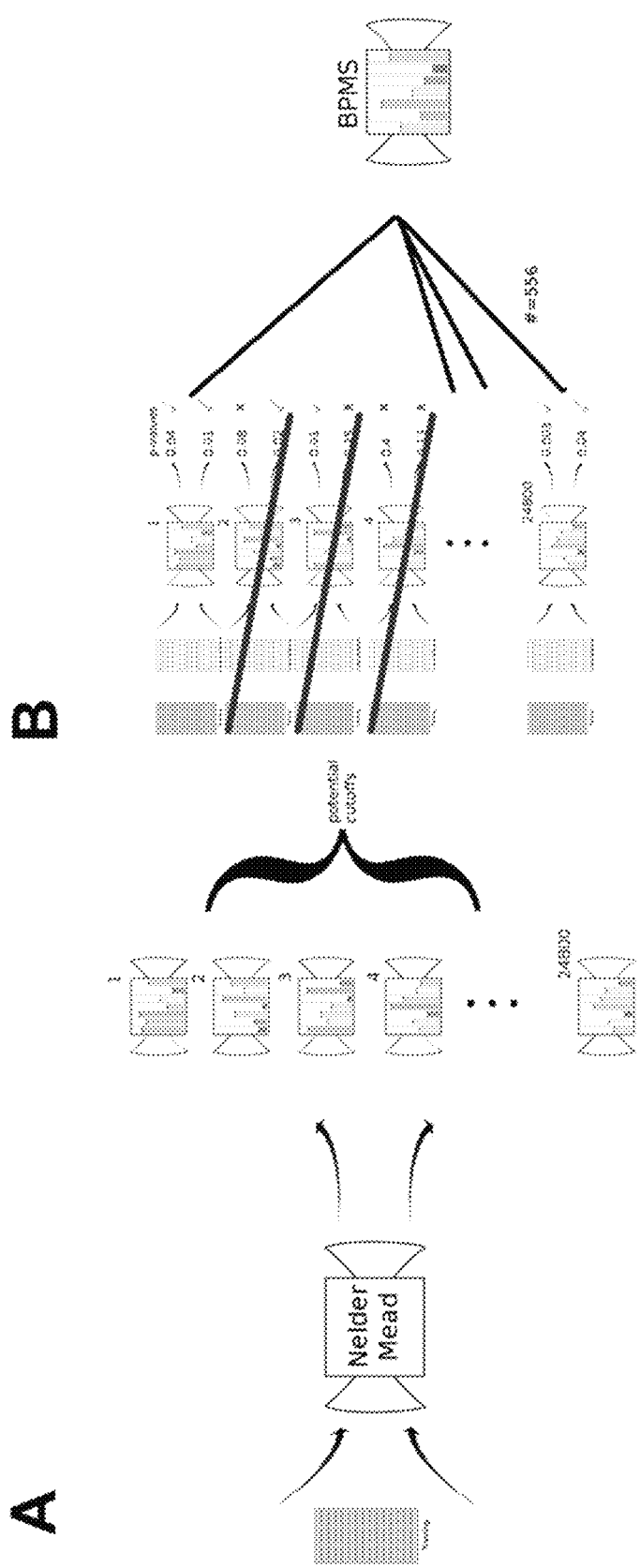
FIG. 2A-B

```
# The Rdata workspace envirnment is too large to upload to the AACR submission process
# Thus we have hosted that file on our server: http://rosner.bsd.uchicago.edu/wiki/Wiki.jsp?
page=AACR_Submission_RData
# It is available for download under the "Attach (1)" tab and is processed with the code presented here
in R.

#This function operates the entire machinery to generate the BPMS and analyze the BPMS
#First step is to load the required data
#Second step is to generate the BPMS signature
#Third step is to perform the random signature test
#Fourth step is to generate plots for the BPMS
setGeneric("main", signature="new.results",
        function(new.results=F, iterBPMS=25000, nSig=1500, iterPerSig=2500) standardGeneric("main"))

setMethod("main", c("new.results" = "logical"),
        function(new.results, iterBPMS, nSig, iterPerSig){ trainingSet <- brca871.train
                cvSet <- brca871.test
                testSet <- brca443.zdata
                testSet2 <- brca341.zdata
                totTrainingSet <- brca871.zdata
                metagenes.train <- metagenes.varfilt.871.train
                metagenes.cv <- metagenes.varfilt.871.test
                metagenes.test <- metagenes.varfilt.443
                metagenes.test2 <- genMetaGenes(brca341.zdata, geneset.varfilt)
                metagenes.totTrain <- metagenes.varfilt
                pdata.totTrain <- brca871.pdata
                pdata.test <- brca443.pdata
                pdata.test2 <- brca341.pdata
                index.tnbc.test <- brca443.tnbc if(new.results){
                        #Generate BPMS signature
                        cutoffs <- genBPMSSig(rbind(brca871.train, metagenes.varfilt.871.train),
                                rbind(brca871.test, metagenes.varfilt.871.test), brca871.pdata,
geneset.bpms, iterBPMS)

optim.new <- T
                        pipeline.control.cmbd <- NULL
                        index.iszero <- NULL
                        index.notzero <- NULL

#Random signature test
                        bpms.rand.pval <- genPValRandomGenes(rbind(trainingSet, metagenes.train),
                                rbind(cvSet, metagenes.cv), testSet, pdata.totTrain, pdata.test, nSig,
iterPerSig,
                                cutoffs, geneset.varfilt)
                }
                else{
                        cutoffs <- newcutoffs.v2 optim.new <- F
                        pipeline.control.cmbd <- pipeline.control.cmbd
                        index.iszero <- index.iszero
                        index.notzero <- index.notzero bpms.rand.pval <- hypotest.bpms.443
                } print("BPMS is ")
                print(cutoffs)
                print("Venn hypothesis testing gives ")
                print(bpms.rand.pval)
```

FIG. 16A

```
                par(ask=T)
                for(i in 1:22){
                        genBPMSplot(i, trainingSet, cvSet, testSet, totTrainingSet, metagenes.train,
metagenes.cv,
                                metagenes.test, metagenes.totTrain, pdata.totTrain, pdata.test,
                                cutoffs, index.tnbc.test, T, T, optim.new, pipeline.control.cmbd,
index.iszero,                           index.notzero)
                }
})

#This function generates KM plots with standard formatting for publishing
setGeneric("plotKM", signature = "pdata",
        function(pdata, sig, main, xlab, ylab, cols, MFS, met, pval, legend.bool=T, pval.bool=T)
standardGeneric("plotKM"))

setMethod("plotKM", c("pdata" = "data.frame"),
        function(pdata, sig, main, xlab, ylab, cols, MFS, met, pval, legend.bool, pval.bool){
                require(survival)

sfit <- survfit(Surv(MFS, met) ~ sig, data=pdata, conf.type="none")

plot(sfit, col=cols, lwd=4, cex.lab=1.5, cex.axis=2.0, font=2, family='sans', xaxt="n",
yaxt="n")

customlabels <- seq(0, 25, by=5)
        axis(1, at=customlabels, labels=customlabels, cex.axis=2.0, font=2)

customlabels.y <- seq(0, 1, by=0.25)
        axis(2, at=customlabels.y, labels=customlabels.y, cex.axis=2.0, font=2)

#title(main=main, col.main="black", cex.main=3.0)
                legend("topright", legend=c(main), bty="n", cex=2.5)

if(pval < 0.001) {
                  legend("bottomright", legend=c("P < 0.001"), bty="n", cex=2)
                }
                else
                {
                  legend("bottomright", legend=c(paste("P = ", pval, sep="")), bty="n", cex=2)
                }
                #plot(sfit, main=main, xlab=xlab, ylab=ylab, col=cols, lwd=3, cex.lab=1.5, cex.axis=1.25)
                #if(legend.bool) legend("topright", col=cols, lty=1, lwd=3, legend=levels(sig))
                #if(pval.bool) legend("bottomleft", legend=c(paste("P = ", pval, sep="")), bty="n", cex=2)
                #if(pval.bool) legend("bottomright", legend=c(paste("p-value = ", pval, sep="")),
bty="n", cex=1.25)
        })

#This function generates KM plots with standard formatting for publishing
setGeneric("plotKMS", signature = "pdata",
        function(pdata, sig, main, xlab, ylab, cols, MFS, met, pval, legend.bool=T, pval.bool=T)
standardGeneric("plotKMS"))

setMethod("plotKMS", c("pdata" = "data.frame"),
        function(pdata, sig, main, xlab, ylab, cols, MFS, met, pval, legend.bool, pval.bool){
                require(survival)

sfit <- survfit(Surv(MFS, met) ~ sig, data=pdata)
                sdif <- survdiff(Surv(MFS, met) ~ sig, data=pdata)

pdata.5 <- pdata
```

FIG. 16B

```
                pdata.5$met[pdata$MFS >= 5] <- 0
                pdata.5$MFS[pdata$MFS >= 5] <- 5 sdif.5 <- survdiff(Surv(pdata.5$MFS, pdata.5$met) ~ sig, data=pdata.5)
                #pval.5 <- 1 - pchisq(sdif.5$chisq, 1)

pval.5 <- summary(coxph(Surv(pdata.5$MFS, pdata.5$met ) ~ sig, pdata.5))$sctest[3]

pval.5 <- signif(pval.5, digits=1)

#plot(sfit, main=main, xlab=xlab, ylab=ylab, col=cols, lwd=3, cex.lab=1.5, cex.axis=1.25)
                #abline(v = 5,lty = 3)

#legend(5.5, 0.11, legend=c(paste("p-value = ", signif(pval.5, digits=3), sep="")),
bty="n", cex=1.25)
                plot(sfit, col=cols, lwd=4, cex.lab=1.5, cex.axis=2, font=2, family='sans', xaxt="n",
yaxt="n")
                abline(v = 5,lty = 3);

customlabels <- seq(0, 25, by=5)
        axis(1, at=customlabels, labels=customlabels, cex.axis=2, font=2)

customlabels.y <- seq(0, 1, by=0.25)
        axis(2, at=customlabels.y, labels=customlabels.y, cex.axis=2.0, font=2)

#title(main=main, col.main="black", cex.main=3.0)
                legend("topright", legend=c(main), bty="n", cex=2.5)

if(pval.5 < 0.001) {
                  legend("bottomright", legend=c("P < 0.001"), bty="n", cex=2)
                }
                else
                {
                  legend("bottomright", legend=c(paste("P = ", pval.5, sep="")), bty="n", cex=2)
                } if(legend.bool) legend("topright", col=cols, lty=1, lwd=3, legend=levels(sig))
                #if(pval.bool) legend("bottomright", legend=c(paste("p-value = ", pval, sep="")),
bty="n", cex=1.25)
        })

#This function uses a case switch to display plots in a uniform formatting
#See notes below as to required data in the workspace
setGeneric("genBPMSplot", signature = "index",
        function(index, trainingSet, cvSet, testSet, totTrainingSet, metagenes.train, metagenes.cv,
metagenes.test, metagenes.totTrain, pdata.totTrain, pdata.test, cutoffs, index.tnbc.test, legend.bool=T,
pval.bool=T, optim.new=F, pipeline.control.cmbd=NULL, index.iszero=NULL, index.notzero=NULL)
standardGeneric("genBPMSplot"))

setMethod("genBPMSplot", c("index" = "numeric"),
        function(index, trainingSet, cvSet, testSet, totTrainingSet, metagenes.train, metagenes.cv,
metagenes.test, metagenes.totTrain, pdata.totTrain, pdata.test, cutoffs, index.tnbc.test, legend.bool,
pval.bool, optim.new, pipeline.control.cmbd, index.iszero, index.notzero){
                require(survival)

xlab <- "Years"
                ylab <- "Metastasis Free Survival"

switch(index,
                        #1: BPMS in 295
                        {
```

FIG. 16C

```
                                        pdata <- brca295.pdata
                                        sig <- ensembleAdjustable.v2.wrapper(rbind(brca295.zdata, genMetaGenes
(brca295.zdata, geneset.varfilt)), names(newcutoffs.v2), newcutoffs.v2)
                                        sig <- as.factor(sig)
                                        pval <- summary(coxph(Surv(MFS, met ) ~ sig, pdata))$sctest[3]
                                        pval <- signif(pval, digits=1)
                                        main <- "BPMS in BrCa295"
                                        cols <- c("red", "black")
                                        plotKM(pdata, sig, main, xlab, ylab, cols, MFS, met, pval, legend.bool,
pval.bool)
                                        plotKMS(pdata, sig, main, xlab, ylab, cols, MFS, met, pval, legend.bool,
pval.bool)
                                },

#2: BPMS in 341
                        {
                                        pdata <- brca341.pdata
                                        sig <- ensembleAdjustable.v2.wrapper(rbind(brca341.zdata, genMetaGenes
(brca341.zdata, geneset.varfilt)), names(newcutoffs.v2), newcutoffs.v2)
                                        sig <- as.factor(sig)
                                        pval <- summary(coxph(Surv(MFS, met ) ~ sig, pdata))$sctest[3]
                                        pval <- signif(pval, digits=1)
                                        main <- "BrCa341"
                                        cols <- c("red", "black")
                                        plotKM(pdata, sig, main, xlab, ylab, cols, MFS, met, pval, legend.bool,
pval.bool)
                                        plotKMS(pdata, sig, main, xlab, ylab, cols, MFS, met, pval, legend.bool,
pval.bool)
                                },

#3: BPMS in 443
                        {
                                        pdata <- pdata.test
                                        sig <- ensembleAdjustable.v2.wrapper(rbind(testSet, metagenes.test), names
(cutoffs), cutoffs)
                                        sig <- as.factor(sig)
                                        pval <- summary(coxph(Surv(MFS, met ) ~ sig, pdata))$sctest[3]
                                        pval <- signif(pval, digits=1)
                                        main <- "BrCa443"
                                        cols <- c("red", "black")
                                        plotKM(pdata, sig, main, xlab, ylab, cols, MFS, met, pval, legend.bool,
pval.bool)
                                        plotKMS(pdata, sig, main, xlab, ylab, cols, MFS, met, pval, legend.bool,
pval.bool)
                                },

#4: BPMS in 871
                        {
                                        pdata <- pdata.totTrain
                                        sig <- ensembleAdjustable.v2.wrapper(rbind(totTrainingSet,
metagenes.totTrain), names(cutoffs), cutoffs)
                                        sig <- as.factor(sig)
                                        pval <- summary(coxph(Surv(MFS, met ) ~ sig, pdata))$sctest[3]
                                        pval <- signif(pval, digits=1)
                                        main <- "BrCa871";
                                        cols <- c("red", "black")
                                        plotKM(pdata, sig, main, xlab, ylab, cols, MFS, met, pval, legend.bool,
pval.bool)
                                        plotKMS(pdata, sig, main, xlab, ylab, cols, MFS, met, pval, legend.bool,
pval.bool)
                                },

#5: BPMS in Mamma Poor/443
                        {
                                        pdata <- pdata.test
```

FIG. 16D

```
                         mammapoor <- which(pdata.test[,"mamma"] == "poor")
                         pdata <- pdata.test[mammapoor,]
                         sig <- ensembleAdjustable.v2.wrapper(rbind(testSet, metagenes.test)
[,mammapoor], names(cutoffs), cutoffs)
                         sig <- as.factor(sig)
                         pval <- summary(coxph(Surv(MFS, met) ~ sig, pdata))$sctest[3]
                         pval <- signif(pval, digits=1)
                         main <- "Mamma/Poor"
                         cols <- c("red", "black")
                         plotKM(pdata, sig, main, xlab, ylab, cols, MFS, met, pval, legend.bool,
pval.bool)
                 },

#6: BPMS in Mamma Good/443
                 {
                         pdata <- pdata.test
                         mammagood <- which(pdata.test[,"mamma"] == "good")
                         pdata <- pdata.test[mammagood,]
                         sig <- ensembleAdjustable.v2.wrapper(rbind(testSet, metagenes.test)
[,mammagood], names(cutoffs), cutoffs)
                         sig <- as.factor(sig)
                         pval <- summary(coxph(Surv(MFS, met) ~ sig, pdata))$sctest[3]
                         pval <- signif(pval, digits=1)
                         main <- "Mamma/Good"
                         cols <- c("red", "black")
                         plotKM(pdata, sig, main, xlab, ylab, cols, MFS, met, pval, legend.bool,
pval.bool)
                 },

#7: BPMS in RS High/443
                 {
                         pdata <- pdata.test
                         rshigh <- which(pdata.test[,"RSclass"] == "high")
                         pdata <- pdata.test[rshigh,]
                         sig <- ensembleAdjustable.v2.wrapper(rbind(testSet, metagenes.test)
[,rshigh], names(cutoffs), cutoffs)
                         sig <- as.factor(sig)
                         pval <- summary(coxph(Surv(MFS, met) ~ sig, pdata))$sctest[3]
                         pval <- signif(pval, digits=1)
                         main <- "RS/High"
                         cols <- c("red", "black")
                         plotKM(pdata, sig, main, xlab, ylab, cols, MFS, met, pval, legend.bool,
pval.bool)
                 },

#8: BPMS in RS Int/443
                 {
                         pdata <- pdata.test
                         rsint <- which(pdata.test[,"RSclass"] == "int")
                         pdata <- pdata.test[rsint,]
                         sig <- ensembleAdjustable.v2.wrapper(rbind(testSet, metagenes.test)
[,rsint], names(cutoffs), cutoffs)
                         sig <- as.factor(sig)
                         pval <- summary(coxph(Surv(MFS, met) ~ sig, pdata))$sctest[3]
                         pval <- signif(pval, digits=1)
                         main <- "RS/Int"
                         cols <- c("red", "black")
                         plotKM(pdata, sig, main, xlab, ylab, cols, MFS, met, pval, legend.bool,
pval.bool)
                 },

#9: BPMS in RS Low/443
                 {
                         pdata <- pdata.test
                         rslow <- which(pdata.test[,"RSclass"] == "low")
                         pdata <- pdata.test[rslow,]
                         sig <- ensembleAdjustable.v2.wrapper(rbind(testSet, metagenes.test)
```

FIG. 16E

```
[,rslow], names(cutoffs), cutoffs)
                        sig <- as.factor(sig)
                        pval <- summary(coxph(Surv(MFS, met) ~ sig, pdata))$sctest[3]
                        pval <- signif(pval, digits=1)
                        main <- "RS/Low"
                        cols <- c("red", "black")
                        plotKM(pdata, sig, main, xlab, ylab, cols, MFS, met, pval, legend.bool,
pval.bool)
                },

#8: BPMS in PAM50 Basal/443
                {
                        pdata <- pdata.test
                        pam50basal <- which(pdata.test[,"pam50"] == "Basal")
                        pdata <- pdata.test[pam50basal,]
                        sig <- ensembleAdjustable.v2.wrapper(rbind(testSet, metagenes.test)
[,pam50basal], names(cutoffs), cutoffs)
                        sig <- as.factor(sig)
                        pval <- summary(coxph(Surv(MFS, met) ~ sig, pdata))$sctest[3]
                        pval <- signif(pval, digits=1)
                        main <- "Basal"
                        cols <- c("red", "black")
                        plotKM(pdata, sig, main, xlab, ylab, cols, MFS, met, pval, legend.bool,
pval.bool)
                },

#9: BPMS in PAM50 LumA/443 - no BPMS in luma
                {
                        pdata <- pdata.test
                        pam50luma <- which(pdata.test[,"pam50"] == "LuminalA")
                        pdata <- pdata.test[pam50luma,]
                        sig <- ensembleAdjustable.v2.wrapper(rbind(testSet, metagenes.test)
[,pam50luma], names(cutoffs), cutoffs)
                        sig <- as.factor(sig)
                        #pval <- summary(coxph(Surv(MFS, met) ~ sig, pdata))$sctest[3]
                        pval <- 0.00
                        pval <- signif(pval, digits=1)
                        main <- "Lum-A"
                        cols <- c("black")
                        plotKM(pdata, sig, main, xlab, ylab, cols, MFS, met, pval, legend.bool,
pval.bool)
                },

#10: BPMS in PAM50 LumB/443
                {
                        pdata <- pdata.test
                        pam50lumb <- which(pdata.test[,"pam50"] == "LuminalB")
                        pdata <- pdata.test[pam50lumb,]
                        sig <- ensembleAdjustable.v2.wrapper(rbind(testSet, metagenes.test)
[,pam50lumb], names(cutoffs), cutoffs)
                        sig <- as.factor(sig)
                        pval <- summary(coxph(Surv(MFS, met) ~ sig, pdata))$sctest[3]
                        pval <- signif(pval, digits=1)
                        main <- "Lum-B"
                        cols <- c("red", "black")
                        plotKM(pdata, sig, main, xlab, ylab, cols, MFS, met, pval, legend.bool,
pval.bool)
                },

#11: BPMS in PAM50 Her2/443
                {
                        pdata <- pdata.test
                        pam50her2 <- which(pdata.test[,"pam50"] == "HER2")
                        pdata <- pdata.test[pam50her2,]
                        sig <- ensembleAdjustable.v2.wrapper(rbind(testSet, metagenes.test)
[,pam50her2], names(cutoffs), cutoffs)
                        sig <- as.factor(sig)
```

FIG. 16F

```
                            pval <- summary(coxph(Surv(MFS, met) ~ sig, pdata))$sctest[3]
                            pval <- signif(pval, digits=1)
                            main <- "HER2"
                            cols <- c("red", "black")
                            plotKM(pdata, sig, main, xlab, ylab, cols, MFS, met, pval, legend.bool,
pval.bool)
                       },

#12: BPMS in PAM50 Normal/443
                       {
                            pdata <- pdata.test
                            pam50normal <- which(pdata.test[,"pam50"] == "Normal")
                            pdata <- pdata.test[pam50normal,]
                            sig <- ensembleAdjustable.v2.wrapper(rbind(testSet, metagenes.test)
[,pam50normal], names(cutoffs), cutoffs)
                            sig <- as.factor(sig)
                            pval <- summary(coxph(Surv(MFS, met) ~ sig, pdata))$sctest[3]
                            pval <- signif(pval, digits=1)
                            main <- "Normal"
                            cols <- c("red", "black")
                            plotKM(pdata, sig, main, xlab, ylab, cols, MFS, met, pval, legend.bool,
pval.bool)
                       },

#13: BPMS in Prolif ER-/HER2-/443
                       {
                            pdata <- pdata.test
                            ern.her2n <- which(pdata.test[,"subtype3"] == "ern.her2n")
                            pdata <- pdata.test[ern.her2n,]
                            sig <- ensembleAdjustable.v2.wrapper(rbind(testSet, metagenes.test)
[,ern.her2n], names(cutoffs), cutoffs)
                            sig <- as.factor(sig)
                            pval <- summary(coxph(Surv(MFS, met) ~ sig, pdata))$sctest[3]
                            pval <- signif(pval, digits=1)
                            main <- "ER-/HER2-"
                            cols <- c("red", "black")
                            plotKM(pdata, sig, main, xlab, ylab, cols, MFS, met, pval, legend.bool,
pval.bool)
                       },

#14: BPMS in Prolif ER+/HER2-/443
                       {
                            pdata <- pdata.test
                            erp.her2n <- which(pdata.test[,"subtype3"] == "erp.her2n")
                            pdata <- pdata.test[erp.her2n,]
                            sig <- ensembleAdjustable.v2.wrapper(rbind(testSet, metagenes.test)
[,erp.her2n], names(cutoffs), cutoffs)
                            sig <- as.factor(sig)
                            pval <- summary(coxph(Surv(MFS, met) ~ sig, pdata))$sctest[3]
                            pval <- signif(pval, digits=1)
                            main <- "ER+/HER2-"
                            cols <- c("red", "black")
                            plotKM(pdata, sig, main, xlab, ylab, cols, MFS, met, pval, legend.bool,
pval.bool)
                       },

#15: BPMS in Prolif HER2/443
                       {
                            pdata <- pdata.test
                            her2 <- which(pdata.test[,"subtype3"] == "her2")
                            pdata <- pdata.test[her2,]
                            sig <- ensembleAdjustable.v2.wrapper(rbind(testSet, metagenes.test)
[,her2], names(cutoffs), cutoffs)
                            sig <- as.factor(sig)
                            pval <- summary(coxph(Surv(MFS, met) ~ sig, pdata))$sctest[3]
                            pval <- signif(pval, digits=1)
                            main <- "HER2"
```

FIG. 16G

```
                              cols <- c("red", "black")
                              plotKM(pdata, sig, main, xlab, ylab, cols, MFS, met, pval, legend.bool,
pval.bool)
                    },

#16: BPMS in TNBC/443
                    {
                              pdata <- pdata.test
                              pdata <- pdata.test[index.tnbc.test,]
                              sig <- ensembleAdjustable.v2.wrapper(rbind(testSet, metagenes.test)
[,index.tnbc.test], names(cutoffs), cutoffs)
                              sig <- as.factor(sig)
                              pval <- summary(coxph(Surv(MFS, met) ~ sig, pdata))$sctest[3]
                              pval <- signif(pval, digits=1)
                              main <- "TNBC"
                              cols <- c("red", "black")
                              plotKM(pdata, sig, main, xlab, ylab, cols, MFS, met, pval, legend.bool,
pval.bool)
                    },

#17: BPMS in Chemo
                    {
                              brca.all.ann <- rbind(brca341.ann,brca443.ann,brca871.ann)

brca341.pdata <- as.matrix(brca341.pdata)
                              brca443.pdata <- cbind(brca443.pdata$MFS, brca443.pdata$met)
                              brca871.pdata <- cbind(brca871.pdata$MFS, brca871.pdata$met)

brca.all.pdata <- rbind(brca341.pdata,brca443.pdata,brca871.pdata)

genes.common  <- intersect(rownames(brca341.zdata),rownames
(brca871.zdata))
                              brca341.zdata.common <- subset(brca341.zdata, rownames(brca341.zdata) %in
% genes.common)
                              brca443.zdata.common <- subset(brca443.zdata, rownames(brca443.zdata) %in
% genes.common)
                              brca871.zdata.common <- subset(brca871.zdata, rownames(brca871.zdata) %in
% genes.common)

brca.all.zdata <- cbind
(brca341.zdata.common,brca443.zdata.common,brca871.zdata.common)

brca.all.ann.untreated <- subset(brca.all.ann, brca.all.ann[,8] == 1)
                              brca.all.pdata.untreated <- subset(brca.all.pdata, brca.all.ann[,8] == 1)
                              brca.all.zdata.untreated <- t(subset(t(brca.all.zdata), brca.all.ann[,8]
== 1))

brca.all.ann.chemo <- subset(brca.all.ann, brca.all.ann[,8] == 2)
                              brca.all.pdata.chemo <- subset(brca.all.pdata, brca.all.ann[,8] == 2)
                              brca.all.zdata.chemo <- t(subset(t(brca.all.zdata), brca.all.ann[,8] ==
2))

brca.all.ann.adj <- rbind(brca.all.ann.untreated, brca.all.ann.chemo)
                              brca.all.pdata.adj <- rbind(brca.all.pdata.untreated,
brca.all.pdata.chemo)
                              brca.all.zdata.adj <- cbind(brca.all.zdata.untreated,brca.all.zdata.chemo)

brca.all.ann.adj.bpms <- subset(brca.all.ann.adj, brca.all.ann.adj[,4] ==
1)
                              brca.all.pdata.adj.bpms <- subset(brca.all.pdata.adj, brca.all.ann.adj[,4]
== 1)
                              brca.all.zdata.adj.bpms <- t(subset(t(brca.all.zdata.adj),
brca.all.ann.adj[,4] == 1))

sfit.adj.bpms <-survfit(Surv(brca.all.pdata.adj.bpms[,1],
brca.all.pdata.adj.bpms[,2])~brca.all.ann.adj.bpms[,8], data=data.frame(brca.all.zdata.adj.bpms))
```

FIG. 16H

```
                        sdif.adj.bpms <- survdiff(Surv(brca.all.pdata.adj.bpms[,1],
brca.all.pdata.adj.bpms[,2])~brca.all.ann.adj.bpms[,8], data=data.frame(brca.all.zdata.adj.bpms))
                        pval <- 1 - pchisq(sdif.adj.bpms$chisq, 1)

sig <- c("Treated BPMS ", "Untreated BPMS ")
                        pval <- signif(pval, digits=1)
                        main <- "    Adjuvant \nChemotherapy "
                        cols <- c("blue", "red")
                        lines <- c(4,1)

plot(sfit.adj.bpms, col=cols, lwd=4, lty=lines, cex.lab=1.5,
cex.axis=2.0, font=2, family='sans', xaxt="n", yaxt="n")

customlabels <- seq(0, 25, by=5)
                        axis(1, at=customlabels, labels=customlabels, cex.axis=2.0, font=2)

customlabels.y <- seq(0, 1, by=0.25)
                        axis(2, at=customlabels.y, labels=customlabels.y, cex.axis=2.0, font=2)

#title(main=main, col.main="black", cex.main=3.0)
                        #legend("topright", legend=c(main), bty="n", cex=1.5)

if(pval < 0.001) {
                        legend("right", legend=c("P < 0.001"), bty="n", cex=2)
                        }
                        else
                        {
                        legend("right", legend=c(paste("P = ", pval, sep="")), bty="n", cex=2)
                        }
                        par(font=2)
                        legend("bottomleft", col=cols, lty=lines, cex=1.5, lwd=3, legend=sig)
                        legend("topright", legend=c(main), bty="n", cex=2, xjust=0.5)

};
                #18: Optimization curve
                #should change to do internally, calling optimControl.wrapper?
                #need pipeline.control.cmbd, index.notzero, index.iszero
                {
                        if(optim.new == T){
                                trainSet <- rbind(trainingSet, metagenes.train)
                                cvSet <- rbind(cvSet, metagenes.cv)
                                pData <- pdata.totTrain
                                geneset <- names(cutoffs)
                                pipeline.control.cmbd <- analysisPipelineRPMS.control(trainSet,
cvSet, pData, geneset, 2500,
T)
                                index.notzero <- optimControl.indexiszero(pipeline.control.cmbd,
                                index.iszero <- optimControl.indexiszero(pipeline.control.cmbd)
                        } require(lattice)

optim.not <- data.frame('cohort' = pipeline.control.cmbd
[index.notzero,"RPMSSizeTest"])
                        optim.zero <- data.frame('cohort' = pipeline.control.cmbd
[index.iszero,"RPMSSizeTest"])

optim.not$veg <- 'Control'
                        optim.zero$veg <- 'Optimized' pvalNums <- rbind(optim.zero, optim.not)

cols <- c("red", "black")
```

FIG. 16I

```
                              main <- "Cohort Size Optimization"
                              xlab <- "Cohort Size"

densityplot(pvalNums$cohort, groups=pvalNums$veg, cex = 3, col=cols,
                                        par.settings = list(superpose.line = list(col=c("black", "red"),
lwd=3)),
                                        auto.key = list(corner = c(0.95, 0.95)), xlab=xlab, plot.points =
FALSE, lwd=3, scales=list(x=list(cex=2,font=2), y=list(cex=2,font=2))))

optim.zero <- data.frame('score' = -log10(pipeline.control.cmbd
[index.iszero,"pvalueTest"]))
                              optim.not <- data.frame('score' = -log10(pipeline.control.cmbd
[index.notzero,"pvalueTest"]))

optim.zero$values <- 'Control'
                              optim.not$values <- 'Optimized' pvalNums <- rbind(optim.zero, optim.not)

cols <- c("black", "red")
                              main <- "P-value Optimization"
                              xlab <- "-log10(p-value)"

densityplot(pvalNums$score, groups=pvalNums$values, cex = 3, col=cols,
                                        par.settings = list(superpose.line = list(col=c("black", "red"),
lwd=3)),
                                        auto.key = list(corner = c(0.95, 0.95)), xlab=xlab, plot.points =
FALSE, lwd=3, scales=list(x=list(cex=2,font=2), y=list(cex=2,font=2))))
                              },
                              #19: qqplot let7/871
                              {
                                        main <- "Meta-LET7"
                                        qqnorm(metagenes.totTrain[1,], cex.axis=2.0, font=2)
                                        qqline(metagenes.totTrain[1,], lwd=3, col=c("red"))
                                        legend("topleft", legend=c(main), bty="n", cex=2.5)
                              },

#20: qqplot bach1/871
                              {
                                        main <- "Meta-BACH1"
                                        qqnorm(metagenes.totTrain[2,], cex.axis=2.0, font=2)
                                        qqline(metagenes.totTrain[2,], lwd=3, col=c("red"))
                                        legend("topleft", legend=c(main), bty="n", cex=2.5)
                              }
                              )
                    })

#This function uses the output of analysisPipelineRPMS.control
#and identifies those parameters that were not optimized by
#the optimizer. These parameters are un-optimized solutions - therefore
#randomly distributed solutions
setGeneric("optimControl.indexiszero", signature="pipeline.control.cmbd",
        function(pipeline.control.cmbd, bool.notzero = F) standardGeneric("optimControl.indexiszero"))

setMethod("optimControl.indexiszero", c("pipeline.control.cmbd" = "data.frame"),
        function(pipeline.control.cmbd, bool.notzero){
                    changeMat <- matrix(nrow=2500, ncol=7)
                    changeMat[,1] <- pipeline.control.cmbd[,"RKIP.before"] - pipeline.control.cmbd
[,"RKIP.after"]
                    changeMat[,2] <- pipeline.control.cmbd[,"MMP1.before"] - pipeline.control.cmbd
[,"MMP1.after"]
                    changeMat[,3] <- pipeline.control.cmbd[,"SPP1.before"] - pipeline.control.cmbd
[,"SPP1.after"]
```

FIG. 16J

```
                changeMat[,4] <- pipeline.control.cmbd[,"HMGA2.before"] - pipeline.control.cmbd
[,"HMGA2.after"]
                changeMat[,5] <- pipeline.control.cmbd[,"CXCR4.before"] - pipeline.control.cmbd
[,"CXCR4.after"]
                changeMat[,6] <- pipeline.control.cmbd[,"MetaLET7.before"] - pipeline.control.cmbd
[,"MetaLET7.after"]
                changeMat[,7] <- pipeline.control.cmbd[,"MetaBACH1.before"] - pipeline.control.cmbd
[,"MetaBACH1.after"]

changeVector <- apply(changeMat, 1, sum)

if(!bool.notzero) return(which(changeVector == 0))
                else return(which(!changeVector == 0))

})

#This function executes the pipeline for the control case
#returns a data.frame with initial parameters and optimized parameters
setGeneric("analysisPipelineRPMS.control", signature = "trainSet",
        function(trainSet, testSet, pData, geneset, iter) standardGeneric("analysisPipelineRPMS.control"))

setMethod("analysisPipelineRPMS.control", c("trainSet" = "matrix"),
        function(trainSet, testSet, pData, geneset, iter){ results <- data.frame(RKIP.before=vector(), MMP1.before=vector(), SPP1.before=vector(),
HMGA2.before=vector(),
                        CXCR4.before=vector(), MetaLET7.before=vector(), MetaBACH1.before=vector(),
                        RKIP.after=vector(), MMP1.after=vector(), SPP1.after=vector(), HMGA2.after=vector
(),
                        CXCR4.after=vector(), MetaLET7.after=vector(), MetaBACH1.after=vector(),
RPMSSizeTrain=vector(),
                        pvalueTrain=vector(), RPMSSizeTest=vector(), pvalueTest=vector())
                #colnames(results)[1:7] <- geneset here, we take out metagene dependence as well as the verbose actions
                pData.train <- pData[rownames(pData) %in% colnames(trainSet),]
                pData.test <- pData[rownames(pData) %in% colnames(testSet),]

fcn.rpms.train <- function(x) ensembleCostFcn.v2(trainSet, pData.train, geneset, x)

for(i in 1:iter){
                        initparms <- rnorm(7, sd=0.7)
                        #if we have more than 0 init parms larger that 0.5 in magnitude, rescale by 100
                        if(sum(abs(initparms) > 0.7) > 0) initparms[abs(initparms) > 0.7] <- initparms
[abs(initparms) > 0.7] / 100 beforePoint <- initparms
                        names(beforePoint) <- geneset fit <- optim(initparms, fcn.rpms.train)
                        parms <- fit$par afterPoint <- as.numeric(parms)
                        names(afterPoint) <- geneset rpms.group.train <- ensembleAdjustable.v2(trainSet, geneset, parms)
                        size.train <- sum(rpms.group.train)
                        pval.train <- summary(coxph(Surv(MFS, met)~rpms.group.train, pData.train))$sctest
["pvalue"]

#test these parms
                        rpms.group.test <- ensembleAdjustable.v2(testSet, geneset, parms)
                        size.test <- sum(rpms.group.test)
                        pval.test <- summary(coxph(Surv(MFS, met)~rpms.group.test, pData.test))$sctest
["pvalue"]
```

FIG. 16K

```
                              this.result <- c(beforePoint, afterPoint, size.train, pval.train, size.test,
pval.test)

results[i,] <- this.result
                } return(results)
        })

#This function generates the p-value for random gene signatures,
#generating 1500 random gene signatures with 2500 pipeline iterations each
setGeneric("genPValRandomGenes", signature = "trainSet",
        function(trainSet, cvSet, testSet, pDataTrain, pDataTest, nSig, iterPerSig, BPMS.cuts, geneset)
standardGeneric("genPValRandomGenes"))

setMethod("genPValRandomGenes", c("trainSet" = "matrix"),
        function(trainSet, cvSet, testSet, pDataTrain, pDataTest, nSig, iterPerSig, BPMS.cuts, geneset){
                optimSolutions <- analysisPipeline.sampleGenes.parallel(trainSet, cvSet, pDataTrain,
                        7, iterPerSig, nSig)

optimCuts <- lapply(optimSolutions, getCVCuts)

optimPVals <- lapply(optimCuts, function(x) analyzeCutoff(testSet, pDataTest, x))

testSetMetaGene <- genMetaGenes(testSet, geneset)
                bpms.testSet <- ensembleAdjustable.v2.wrapper(rbind(testSet, testSetMetaGene), names
(BPMS.cuts), BPMS.cuts)
                bpms.pval <- summary(coxph(Surv(MFS, met) ~ bpms.testSet, pDataTest))$sctest[3]

total.pval <- sum(optimPVals < bpms.pval)/length(optimPVals)

return(total.pval)
        })

#This function generates BPMS cutoffs
#input should include meta-genes for train and cvsets, also geneset is names of cutoffs
setGeneric("genBPMSSig", signature="trainSet",
        function(trainSet, cvSet, pData, geneset, iter) standardGeneric("genBPMSSig"))

setMethod("genBPMSSig", c("trainSet" = "matrix"),
        function(trainSet, cvSet, pData, geneset, iter){
                cutoffs <- analysisPipelineRPMS.v2(trainSet, cvSet, pData, geneset, iter)
                BPMS.cutoffs <- getCVCuts(cutoffs)

return(BPMS.cutoffs)
        })

#This function generates a set of cutoffs using the cross validation stage
#The input is output from the analysisPipelineRPMS.sampleGenes.parallel
#the output is the mean cutoff values from solutions producing significance in
#both training and cross validation
setGeneric("getCVCuts", signature="cutoffResults",
        function(cutoffResults, sizeIntersect = F) standardGeneric("getCVCuts"))

setMethod("getCVCuts", c("cutoffResults" = "data.frame"),
        function(cutoffResults, sizeIntersect){ trainPValues <- cutoffResults[,9]
                testPValues <- cutoffResults[,11]

sigTrain <- which(trainPValues < 0.05)
                sigTest <- which(testPValues < 0.05)
```

FIG. 16L

```
                sigCV <- intersect(sigTrain, sigTest)
                size <- length(sigCV)

meanCutoff <- colMeans(cutoffResults[sigCV, 1:7])

if(sizeIntersect) return(size)
                return(meanCutoff)
        })

#This function takes a set of cutoff values and returns a set of pvalues for
#that set of cutoffs in the inputted dataset(testing set) and the inputted pdata
setGeneric("analyzeCutoff", signature="dataSet",
        function(dataSet, pData, cutoff) standardGeneric("analyzeCutoff"))

setMethod("analyzeCutoff", c("dataSet" = "matrix"),
        function(dataSet, pData, cutoff){ if(is.na(cutoff[1])) pvalue <- 1
                else{
                        geneset <- names(cutoff)

in.rpms <- ensembleAdjustable.v2(dataSet, geneset, cutoff)
                        pvalue <- summary(coxph(Surv(MFS, met) ~ in.rpms, pData))$sctest["pvalue"]
                } return(pvalue)

})

#This function generates a gene signature for sets of random genes
#using analysisPipelineRPMS.v2, as well as sample to select random gene sets
#this is a multicore function, you may switch saveOne to TRUE to at least save one core
#pipelineIter is number of potential cutoffs to generate for each signature
#sampleIter is the number of signatures to generate
setGeneric("analysisPipeline.sampleGenes.parallel", signature="trainSet",
        function(trainSet, testSet, pData, nGenes, pipelineIter, sampleIter, saveOne = F, setNumberCores
= 0) standardGeneric("analysisPipeline.sampleGenes.parallel"))

setMethod("analysisPipeline.sampleGenes.parallel", c("trainSet" = "matrix"),
        function(trainSet, testSet, pData, nGenes, pipelineIter, sampleIter, saveOne, setNumberCores){
                require(parallel)
                require(survival)

nCores <- detectCores()
                if(saveOne) nCores <- nCores - 1
                if(setNumberCores > 0) nCores <- setNumberCores iterPerCore <- round(pipelineIter/nCores)
                results.parallel <- list()

for(i in 1:sampleIter){
                        geneset <- rownames(trainSet)[sample(1:nrow(trainSet), nGenes)]
                        print(paste("Iteration ", i, sep=""))
                        print(geneset)
                        processes <- list()

for(j in 1:nCores){
                                processes[[j]] <- mcparallel(analysisPipelineRPMS.v2(trainSet, testSet,
pData, geneset, iterPerCore))
                        } resultPerGene <- mccollect(processes)
```

FIG. 16M

```
                        resultPerGeneCollapsed <- do.call("rbind", resultPerGene)
                        results.parallel[[i]] <- resultPerGeneCollapsed
                }
                return(results.parallel)
        })

#This function takes in a gene set and returns a data.frame with the first few
#columns showing an individual solution as well as its characteristic values
#for training and validation sets
setGeneric("analysisPipelineRPMS.v2", signature = "trainSet",
        function(trainSet, testSet, pData, geneset, iter) standardGeneric("analysisPipelineRPMS.v2"))

setMethod("analysisPipelineRPMS.v2", c("trainSet" = "matrix"),
        function(trainSet, testSet, pData, geneset, iter){
                results <- data.frame(RKIP=vector(), MMP1=vector(), SPP1=vector(), HMGA2=vector(),
                        CXCR4=vector(), MetaLET7=vector(), MetaBACH1=vector(), RPMSSizeTrain=vector(),
                        pvalueTrain=vector(), RPMSSizeTest=vector(), pvalueTest=vector())
                colnames(results)[1:7] <- geneset here, we take out metagene dependence as well as the verbose actions
                #we also adjust for non-RPMS geneset and deal with the annoying survdiff error by
replacing with coxph pData.train <- pData[rownames(pData) %in% colnames(trainSet),]
                pData.test <- pData[rownames(pData) %in% colnames(testSet),]

fcn.rpms.train <- function(x) ensembleCostFcn.v2(trainSet, pData.train, geneset, x)

for(i in 1:iter){
                        initparms <- rnorm(7, sd=0.7)
                        #if we have more than 0 init parms larger that 0.5 in magnitude, rescale by 100
                        if(sum(abs(initparms) > 0.7) > 0) initparms[abs(initparms) > 0.7] <- initparms[abs
(initparms) > 0.7] / 100
                        fit <- optim(initparms, fcn.rpms.train)
                        parms <- fit$par
                        rpms.group.train <- ensembleAdjustable.v2(trainSet, geneset, parms)
                        size.train <- sum(rpms.group.train)

pval.train <- summary(coxph(Surv(MFS, met)~rpms.group.train, pData.train))$sctest
["pvalue"]

#test these parms
                        rpms.group.test <- ensembleAdjustable.v2(testSet, geneset, parms)
                        size.test <- sum(rpms.group.test)

pval.test <- summary(coxph(Surv(MFS, met)~rpms.group.test, pData.test))$sctest
["pvalue"]

this.result <- c(parms, size.train, pval.train, size.test, pval.test)
                        results[i,] <- this.result
                }
                return(results)
        })

#Cost function to be minimized
setGeneric("ensembleCostFcn.v2", signature = "dataSet",
        function(dataSet, pdata, geneset, cutoffs) standardGeneric("ensembleCostFcn.v2"))

setMethod("ensembleCostFcn.v2", c("dataSet" = "matrix"),
        function(dataSet, pdata, geneset, cutoffs){
```

FIG. 16N

```
            require(survival)
            #adjusted for non-RPMS geneset as well as catching the annoying survdiff error is.rpms <- ensembleAdjustable.v2(dataSet, geneset, cutoffs)

rpms.percent is non-rpms percent (to minimize)
            rpms.percent <- 1 - sum(is.rpms)/ncol(dataSet)

pval <- summary(coxph(Surv(MFS, met)~ is.rpms, pdata))$sctest["pvalue"]

#adjust pvals to help search - alternatively we could scale the p-values to a
            #function expanding the dynamic range, but I'd rather not
            if(pval >= 0.05) pval <- 2*pval
            if(pval >= 0.05 && pval < 0.05) pval <- 0.05
            if(pval >= 0.01 && pval < 0.05) pval <- 0.05
            if(pval >= 0.005 && pval < 0.01) pval <- 0.01
            if(pval < 0.005) pval <- 0.005 we estimate rpms.percent to be on [.9, 1] while desired pvals on (0, .05]
            #so we scale rpms.percent to be 0.1*(rpms.percent-0.9)
            #we then make adjustments to punish low percents
            rpms.percent.weight <- 0.5*(rpms.percent-0.9)
            costfcn <- pval + rpms.percent.weight return(costfcn)
    })

#This function is a wrapper for the signature generator
#to change values of c(TRUE, FALSE) to c("BPMS", "Not BPMS")
setGeneric("ensembleAdjustable.v2.wrapper", signature = "dataSet",
        function(dataSet, geneset, cutoffs) standardGeneric("ensembleAdjustable.v2.wrapper"))

setMethod("ensembleAdjustable.v2.wrapper", c("dataSet" = "matrix"),
        function(dataSet, geneset, cutoffs){
            sig <- ensembleAdjustable.v2(dataSet, geneset, cutoffs)

sig.levels <- rep(0, length(sig))
            sig.levels[sig] <- "BPMS"
            sig.levels[!sig] <- "Not BPMS"

return(sig.levels)
    })

#This function generates a list with length = #samples
#each position in the list represents an individual sample
#and the value in that list indicates whether or not a sample is a
#BPMS sample
setGeneric("ensembleAdjustable.v2", signature = "dataSet",
        function(dataSet, geneset, cutoffs) standardGeneric("ensembleAdjustable.v2"))

setMethod("ensembleAdjustable.v2", c("dataSet" = "matrix"),
        function(dataSet, geneset, cutoffs){ require(survival)

rpms.val - 7 x (# samples) data frame w/ rpms vals
            #scores - (7 + 1) x (# samples) data frame of scores and sum scores
            #is.rpms - list of (# samples), boolean
            rpms.val <- matrix(NA, nrow = 7, ncol = ncol(dataSet))
            rownames(rpms.val) <- geneset
            colnames(rpms.val) <- colnames(dataSet)
            rpms.val[1,] <- -dataSet[geneset[[1]],]
            rpms.val[2,] <- dataSet[geneset[[2]],]
            rpms.val[3,] <- dataSet[geneset[[3]],]
```

FIG. 16O

```
            rpms.val[4,] <- dataSet[geneset[[4]],]
            rpms.val[5,] <- dataSet[geneset[[5]],]
            rpms.val[6,] <- dataSet[geneset[[6]],]
            rpms.val[7,] <- dataSet[geneset[[7]],]

#Score samples based on reltn to median
            scores <- matrix(0, nrow = 8, ncol = ncol(dataSet))
            rownames(scores) <- c(geneset, "All")
            colnames(scores) <- colnames(dataSet)
            for (i in 1:7){
                    scores[i, ] <- ifelse(rpms.val[i,] > cutoffs[i], 1, 0)
            } scores[8,] <- colSums(scores)

Bin RPMS
            is.rpms <- scores[8,] == 7 return(is.rpms)
    })

#This function returns metagenes meta-let7 and meta-bach1 using genesets
setGeneric("genMetaGenes", signature = "dataSet",
        function(dataSet, geneSets) standardGeneric("genMetaGenes"))

setMethod("genMetaGenes", c("dataSet" = "matrix"),
        function(dataSet, geneSets){ require(GSA)
            require(Biobase)

#geneSets[[1]] is let7, [[2]] is bach1
            #GSA.obj.$genename - temp GSA objects for metagene metagene <- matrix(NA, nrow = 2, ncol = ncol(dataSet))
            rownames(metagene) <- c("MetaLET7", "MetaBACH1")
            colnames(metagene) <- colnames(dataSet)

#get metagene vals
            colSums2 <- function(x, w) {
                    w.perc <- w/sum(w)
                    dat <- apply(x, 2, function(x) sum(x*w.perc))
                    return(dat)
            }

GSA.func.obj <- GSA.func(dataSet, dataSet["PESM1",], rownames(dataSet),
genesets=geneSets, resp.type="Quantitative", minsize=10, maxsize=2000, restand.basis="data")

len <- length(GSA.func.obj$gene.ind)
            xs <- t(scale(t(dataSet), center = GSA.func.obj$mean, scale = GSA.func.obj$sd))
            val <- matrix(NA, nrow = len, ncol = ncol(dataSet))

for (i in 1:len) {
                    if (!is.null(GSA.func.obj$gene.ind[[i]])) {
                            gene.set <- match(geneSets[[i]], rownames(dataSet))
                            gene.set <- gene.set[!is.na(gene.set)]
                            geneind <- gene.set[GSA.func.obj$gene.ind[[i]]]
                            val[i, ] <- colSums2(xs[geneind, , drop = F], w=GSA.func.obj$gene.scores
[geneind])
                    }
            } metagene[1,] <- val[1,]
            metagene[2,] <- val[2,]

return(metagene)
```

This function returns data frame containing nSig independently generated cutoffs using
#iterPERsignature many iterations per each signature
setGeneric("convergeBPMS", signature = "trainSet",
       function(trainSet, cvSet, pData, geneset, iterPERsignature, nSig) standardGeneric("convergeBPMS"))

setMethod("convergeBPMS", c("trainSet" = "matrix"),
       function(trainSet, cvSet, pData, geneset, iterPERsignature, nSig){
              results <- data.frame(PEBP1=vector(), MMP1=vector(), SPP1=vector(), HMGA2=vector(),
CXCR4=vector(),
                     MetaLET7=vector(), MetaBACH1=vector())

colnames(results) <- geneset for(i in 1:nSig){
                     results[i,] <- genBPMSSig(trainSet, cvSet, pData, geneset, iterPERsignature)
              } return(results)
       })

#This function is a wrapper to enable multicore functionality for convergeBPMS
setGeneric("convergeBPMS.parallel", signature="trainSet",
   function(trainSet, cvSet, pData, geneset, iterPERsignature, nSig) standardGeneric
("convergeBPMS.parallel"))

setMethod("convergeBPMS.parallel", c("trainSet" = "matrix"),
   function(trainSet, cvSet, pData, geneset, iterPERsignature, nSig){
       require(parallel)

nCores <- detectCores()
              iterPerCore <- round(nSig/nCores)

for(j in 1:nCores){
                     processes[[j]] <- mcparallel(convergeBPMS(trainSet, cvSet, pData, geneset,
iterPERsignature, iterPerCore))
              } result <- mccollect(processes)
              resultCollapsed <- do.call("rbind", result)

return(resultCollapsed)

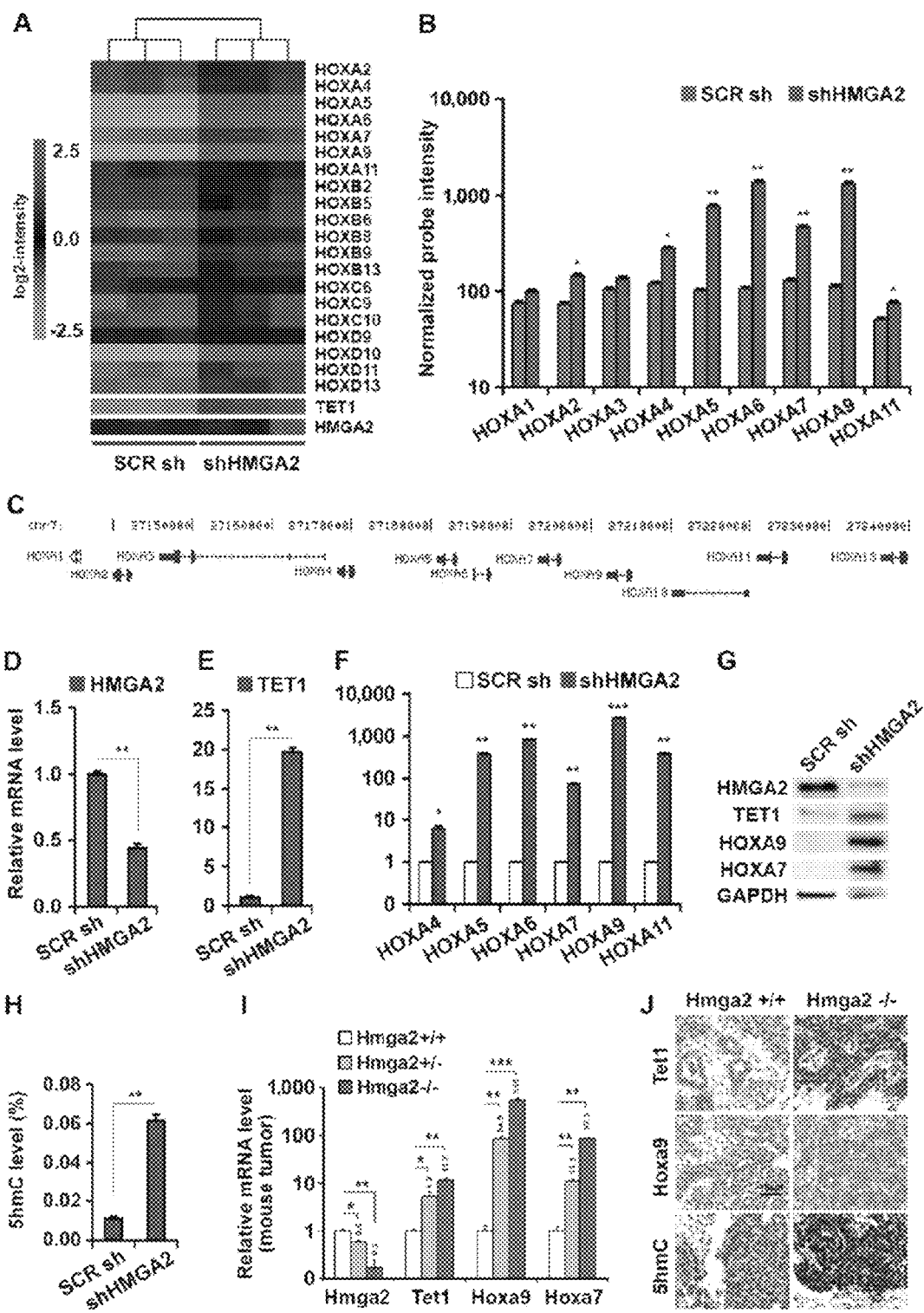
FIG. 17A-J

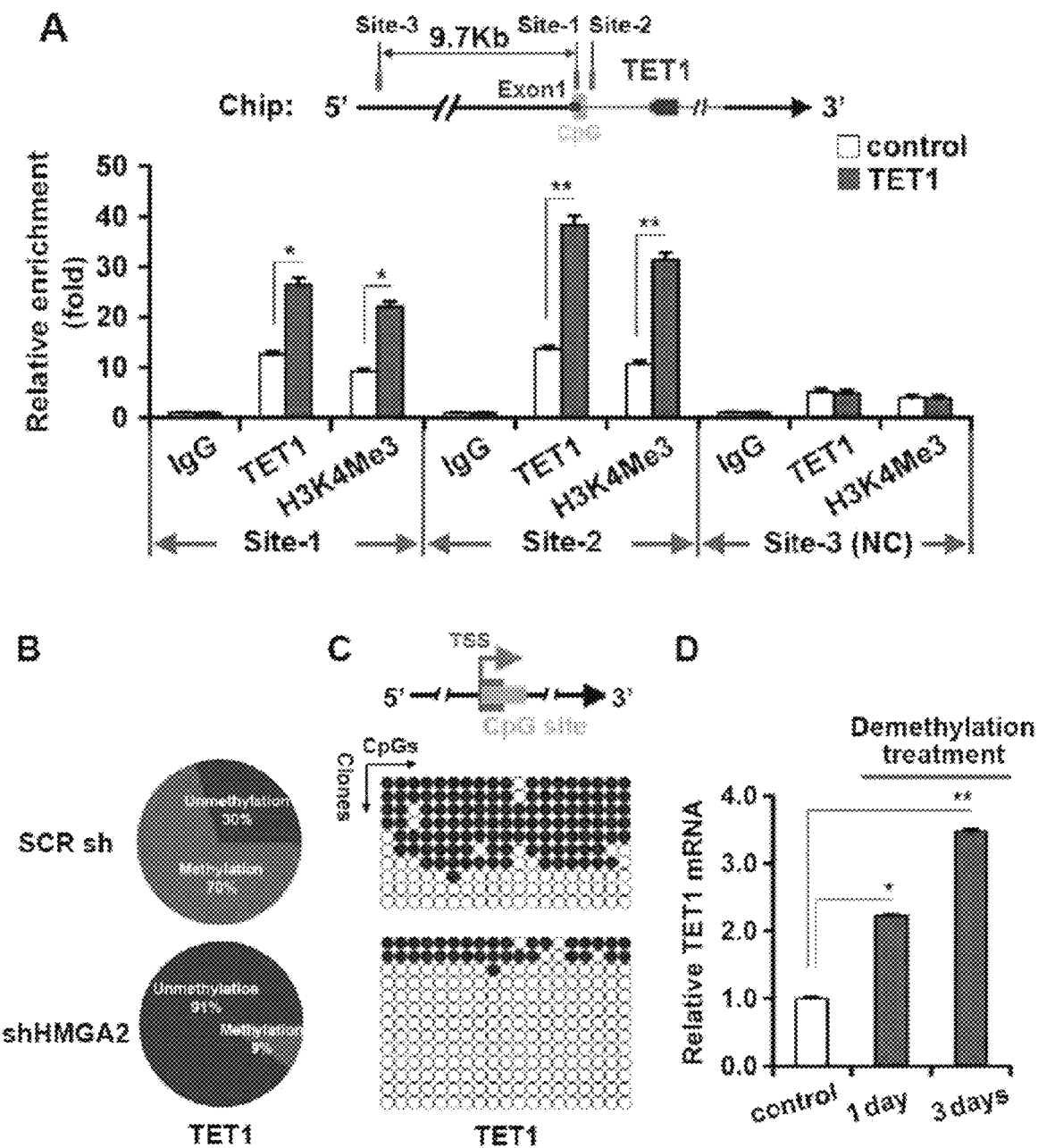
FIG. 18A-D

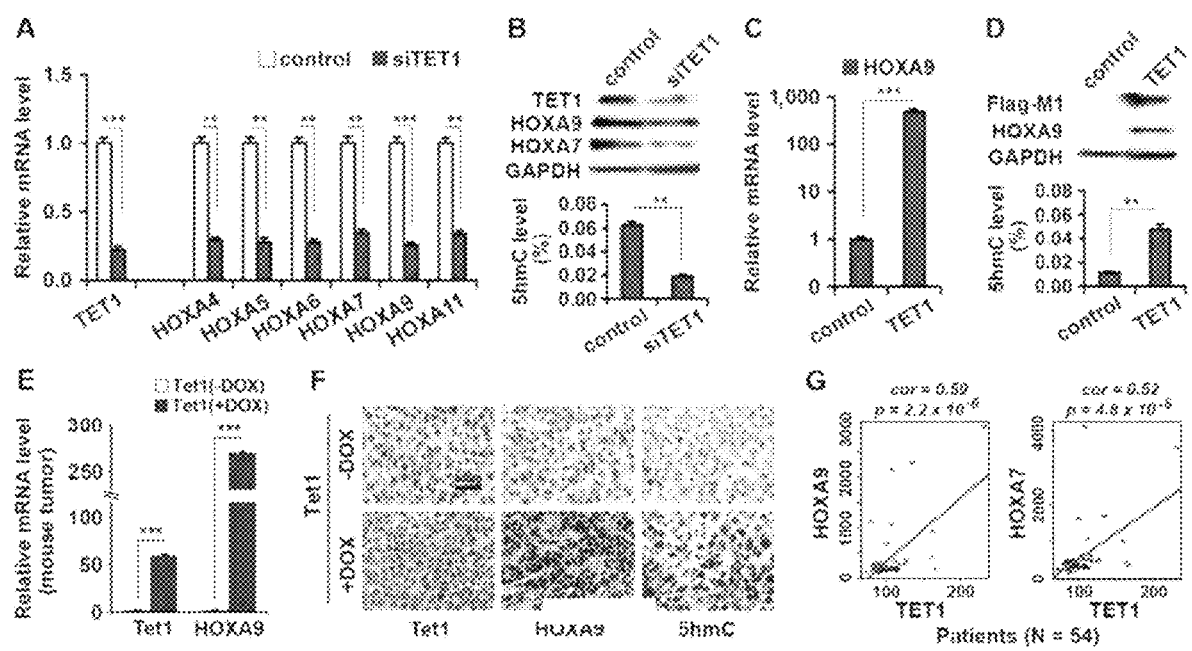
FIG. 19A-G

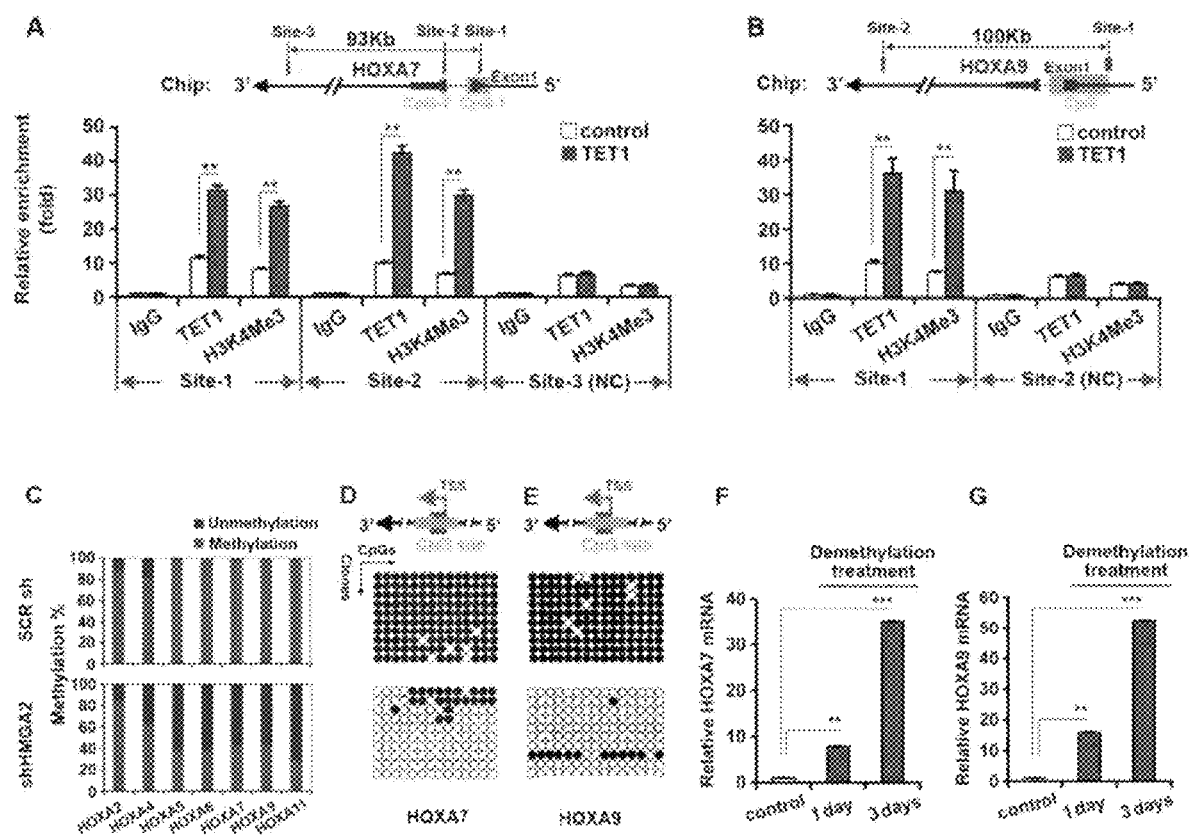
FIG. 20A-G

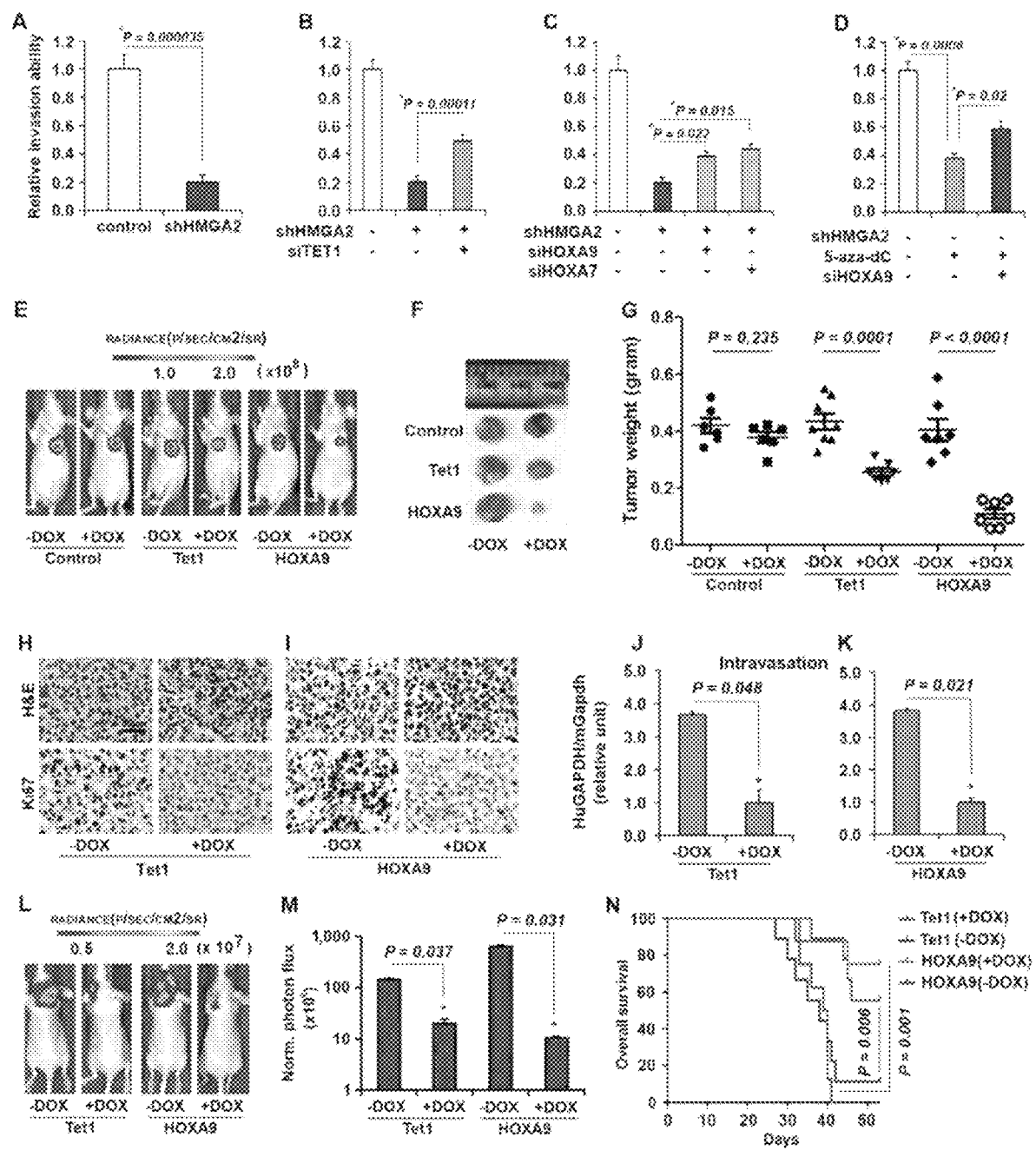
FIG. 21A-N

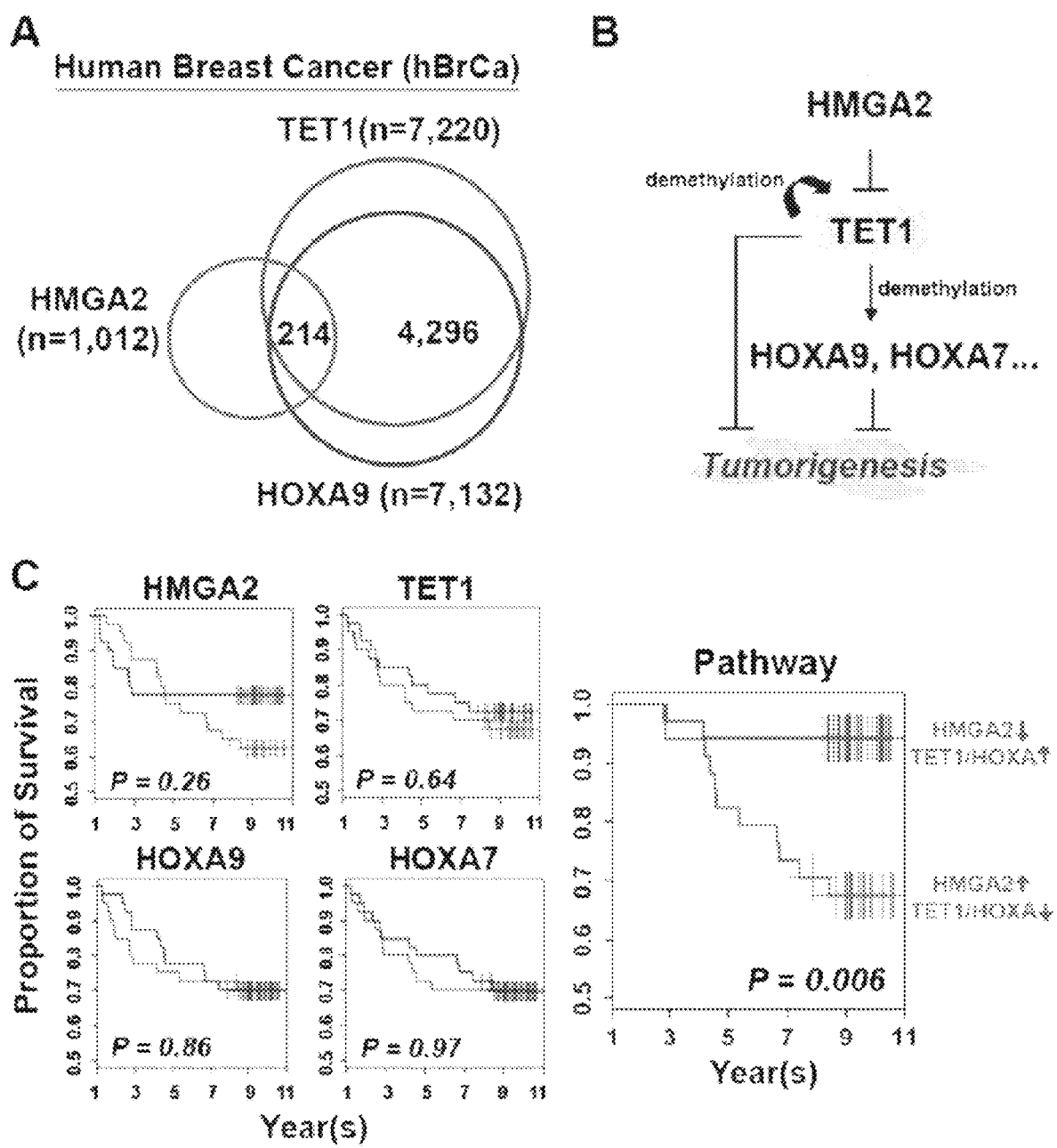
FIG. 22A-C

FIG. 24A-G

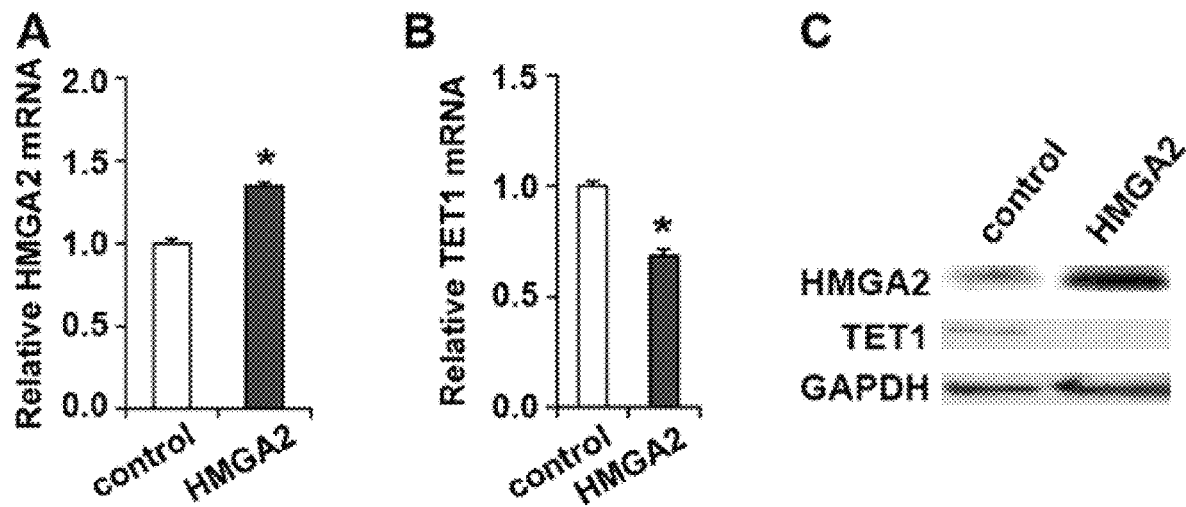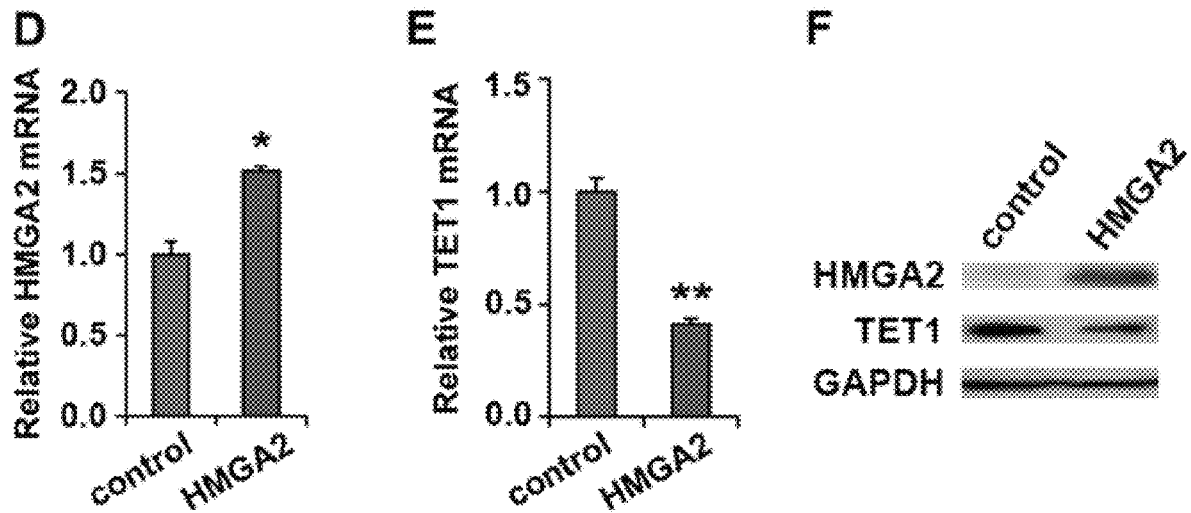
FIG. 26A-F

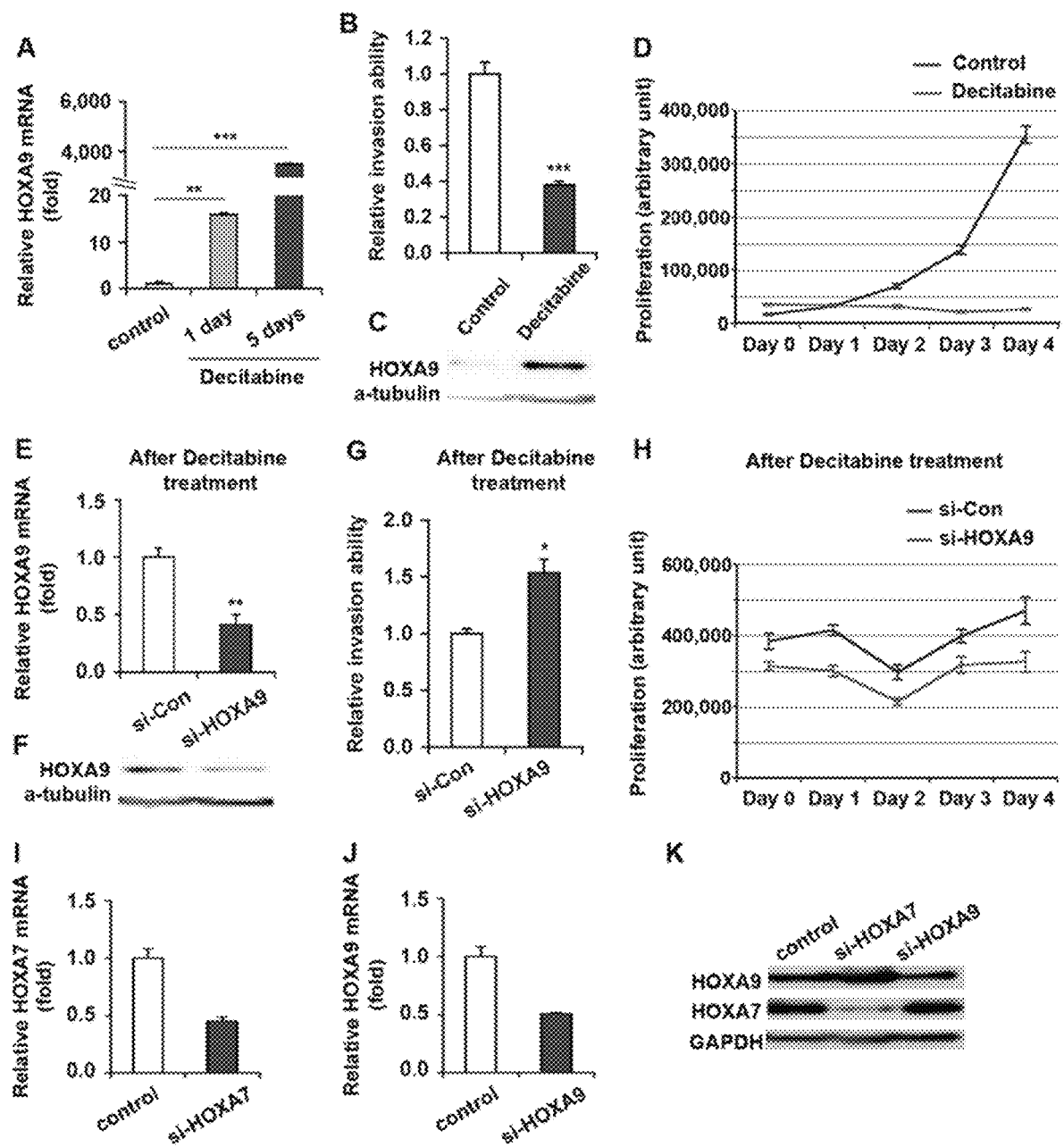
FIG. 27A-K

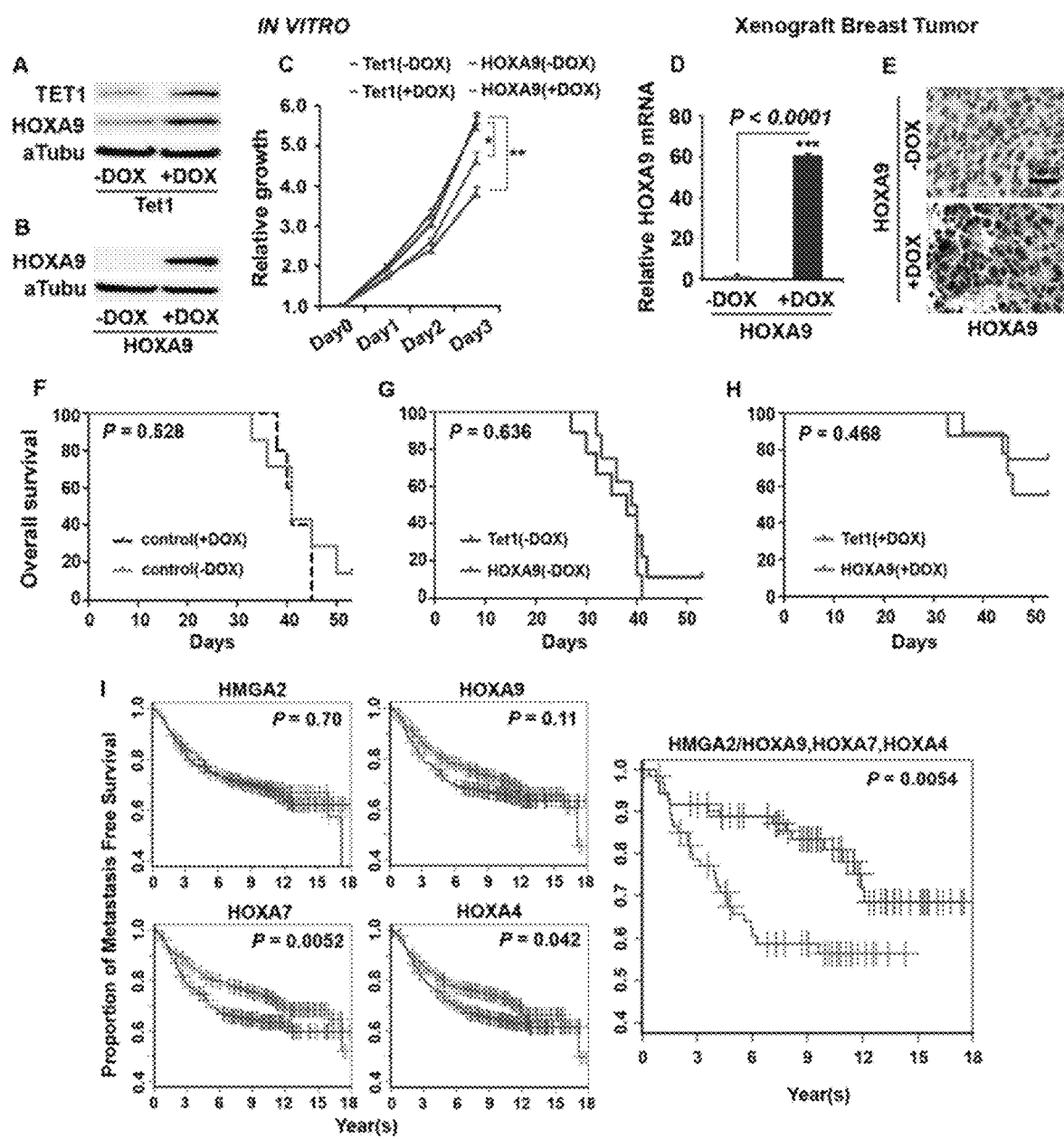
FIG. 28A-I

PROGNOSTIC AND PREDICTIVE BREAST CANCER SIGNATURE

CROSS REFERENCE TO RELATED APPLICATIONS

This application claims priority to U.S. Application Ser. No. 62/090,809, filed Dec. 11, 2014 and is a continuation in part of International Patent Application Serial No. PCT/US2014/039807 filed May 28, 2014, which claims the benefit of U.S. Application Ser. No. 61/828,103 filed May 28, 2013. The entire contents of each of the above-referenced disclosures are specifically incorporated herein by reference without disclaimer.

STATEMENT OF GOVERNMENT SUPPORT

This invention was made with government support under GM 87630, GM 71440, CA127277, NIGMS DP2 OD006481 04 (NIH Director's New Innovator Award Program), NIH SPORE grant P50 CA125183-05 (DRP), and NCI U54 CA112970 08 awarded by the National Institutes of Health and grant number W81XWH-10-1-0396 awarded by the Department of Defense. The government has certain rights in the invention.

BACKGROUND OF THE INVENTION

I. Field of the Invention

Embodiments are directed generally to biology and medicine. In certain aspects methods involve determining the prognosis for a breast cancer patient.

II. Background

There are over 1 million cases of breast cancer per year on a global basis, of which around 0.5 million are in the US, 40,000 are in the UK and nearly 2,000 in Ireland. It is the leading cause of cancer deaths among women (Keen and Davidson, 2003). Although the overall incidence of the disease is increasing within the western world, wider screening and improved treatments have led to a gradual decline in the fatality rate of about 1% per year since 1991. Inheritance of susceptibility genes, such as BRCA1 and BRCA2, account for only 5% of breast cancer cases and the factors responsible for the other 95% remain obscure (Grover and Martin, 2002).

Mere classification of breast cancers into a few subgroups characterized by low to absent gene expression of the estrogen receptor (ER) alone may not reflect the cellular and molecular heterogeneity of breast cancer, and may not allow the design of treatment strategies maximizing patient response. Once a patient is diagnosed with cancer, such as breast or ovarian cancer, or an individual wants predisposition analysis, there is a strong need for methods that allow the physician to predict the expected course of disease, including the likelihood of cancer recurrence, long-term survival of the patient, and the like, and accordingly select an appropriate treatment option that is effective.

SUMMARY OF THE INVENTION

Embodiments concern methods, compositions, tangible, computer-readable medium, and apparatuses related to assessing, prognosing, and/or treating cancer patients, particularly breast cancer patients.

According to a first embodiment, a method of diagnosing a subject is provided, which includes analyzing a biological sample from the subject for expression of HMGA2, TET1, HOXA7, and HOXA9; comparing expression levels of the HMGA2, TET1, HOXA7, and HOXA9 in the biological sample to a respective expression reference level of HMGA2, TET1, HOXA7, and HOXA9 in a control sample; and diagnosing the subject with at least one of a decreased survival rate, a poor prognosis, a faster progression of the cancer, and a higher risk of relapse of the cancer if the expression level of HMGA2 in the biological sample is higher than that of the respective control sample and the expression levels of TET1, HOXA7, and HOXA9 in the biological sample are lower than that of the respective control sample.

In another embodiment, the method further includes administering a therapeutically-effective amount of at least one of a chemotherapeutic agent or a radiotherapeutic agent to the diagnosed subject.

In yet another embodiment, the chemotherapeutic agent is a DNA demethylation agent.

In another embodiment, the DNA demethylation agent is zacitidine or decitabine, or a combination thereof.

In still another embodiment, the subject exhibits at least one of an increased chance of survival, a better prognosis, a slower progression of the disease, and a lower risk of relapse of the cancer as compare to the diagnosis before the administering of the therapeutically-effective amount of at least one of the chemotherapeutic agent or the radiotherapeutic agent to the subject.

In another embodiment, the method further includes diagnosing the subject with at least one of an increase survival rate, a better prognosis, a slower progression of the cancer, and a lower risk of relapse of the cancer if the expression level of HMGA2 in the biological sample is lower than that of the respective control sample and the expression levels of TET1, HOXA7, and HOXA9 in the biological sample are higher than the that of the control sample.

In yet another embodiment, the cancer is breast cancer.

In one embodiment, the expression levels are determined by quantifying at least one of respective expression of a mRNA encoding HMGA2, TET1, HOXA7, or HOXA9; and a respective quantity of a nucleic acid of at least one of HMGA2, TET1, HOXA7, and HOXA9; or a respective functional fragment or variant thereof.

In another embodiment, the expression levels are determined immunochemically and based on an antibody-based detection system.

In yet another embodiment, the antibody binds specifically to a protein of at least one of the HMGA2, TET1, HOXA7, and HOXA9 or a fragment thereof.

In one embodiment, the control sample is obtained from the subject.

In another embodiment, the control sample is obtained from a tissue not diagnosed with cancer.

In yet another embodiment, the HMGA2 expression in the biological sample is greater than about 20% of the expression reference level of HMGA2 in the control sample and the expression levels of TET1, HOXA7, and HOXA9 in the biological sample are about 20% lower than the respective expression of that of the control sample.

In another embodiment, a method of treating cancer (for example, breast cancer) in a subject in need thereof is provided that includes obtaining a biological sample from the subject; measuring expression levels of HMGA2, TET1, HOXA7, and HOXA9 in the biological sample; comparing the expression levels of HMGA2, TET1, HOXA7, and HOXA9 in the biological sample to a respective reference level of HMGA2, TET1, HOXA7, and HOXA9 in a control sample; and administering a therapeutically-effective amount of at least one of a chemotherapeutic agent or a radiotherapeutic agent to the subject when the expression level of HMGA2 in the biological sample is higher than that of the respective control sample and the expression levels of TET1, HOXA7, and HOXA9 in the biological sample are lower than that of the control sample.

In one embodiment, the expression level of HMGA2 in the biological sample is at least 20% higher than that of the respective control sample and the expression levels of TET1, HOXA7, and HOXA9 in the biological sample are at least 20% lower than that of the respective expression of the control sample.

In yet another embodiment, the therapeutically-effective amount of at least one of the chemotherapeutic agent or the radiotherapeutic agent decreases the expression of HMGA2 in the subject.

In yet another embodiment, the therapeutically-effective amount of at least one of the chemotherapeutic agent or the radiotherapeutic agent increases expression of at least one of TET1, HOXA7, and HOXA9 in the subject.

In one embodiment, a method of determining a prognosis for survival of a subject diagnosed with cancer is provided that includes analyzing a biological sample from the subject for expression of HMGA2, TET1, HOXA7, and HOXA9; comparing expression levels of the HMGA2, TET1, HOXA7, and HOXA9 in the biological sample to a respective reference level of HMGA2, TET1, HOXA7, and HOXA9 in a control sample; and diagnosing the subject with a poor prognosis if the expression level of HMGA2 in the biological sample is higher than that of the respective control sample and the expression levels of TET1, HOXA7, and HOXA9 in the biological sample are lower than the respective expression of the control sample; or a better prognosis if the expression level of HMGA2 in the biological sample is lower than that of the respective control sample and the expression levels of TET1, HOXA7, and HOXA9 in the biological sample are higher than the respective expression of the control sample. \

In yet another embodiment, the method further includes administering to the subject diagnosed with the poor prognosis a therapeutically-effective amount of at least one of a chemotherapeutic agent or a radiotherapeutic agent; and/or a kit comprising at least one agent to detect the expression levels of at least one of HMGA2, TET1, HOXA7, and HOXA9 in the biological sample.

In further aspects, methods concern calculating a prognosis score of a patient. In certain aspects, the cancer to be treated, assessed, prognosed, evaluated or diagnosed may be brain, lung, liver, spleen, kidney, lymph node, small intestine, pancreas, blood cells, colon, stomach, breast, endometrium, prostate, testicle, ovary, skin, head and neck, esophagus, bone marrow or blood cancer. Particularly, it may be breast cancer, such as a triple negative breast cancer.

Embodiments include: evaluating a biological sample from a patient; evaluating breast cancer cells from a patient; evaluating a biological sample from a breast cancer patient; assessing a breast cancer patient; testing a breast cancer sample or biopsy; testing a breast tumor; treating a breast cancer patient, particularly a patient with a particular profile related to one or more gene signatures described herein or a calculated prognosis score; determining a treatment for a breast cancer patient; altering a treatment plan for a breast cancer patient; generating an expression profile for a breast cancer patient involving one or more of biomarkers or genes described herein; comparing a patient's expression profile to a standardized profile; and/or, evaluating and/or determining treatment options for a breast cancer patient based on the patient's expression profile of one or more biomarkers or genes, or a prognosis score described herein (alone or in combination with triple-negative status or any gene signature known in the art).

Certain embodiments include methods of measuring the level of expression or activity in the breast cancer sample of at least one, two, three, four, five, six or all of the following seven biomarkers: RKIP, MMP1, OPN, HMGA2, CXCR4, let-7, and BACH1. In some embodiments, the methods may comprise comparing the level of expression or activity of each biomarker measured in any measuring steps to a reference expression level or activity. The methods may further comprise calculating a prognosis score wherein the prognosis score is based on comparisons in any comparison steps. Any of the steps may optionally involve the use of a computer algorithm.

In some embodiments, the method comprises or further comprises measuring the level of expression or activity in the breast cancer sample of TET1 and comparing the level of expression or activity of TET1 to a reference expression level or activity. In some embodiments, a patient's response to DNA methyltransferase (DNMT) inhibitor therapy is predicted based on the compared expression level or activity. In some embodiments, the method includes measuring the activity of TET1. In some embodiments, measuring the activity of TET1 comprises measuring the level of expression of any of TET1 target genes, including, but not limited to, one, two, or more of AKAP12, APOC1, BAI3, BRWD1, CA2, CALCRL, CAMKV, CDC37L1, CNTN1, COX7C, DIXDC1, DLX2, DSC2, DYNC2LI1, EML1, EPHA3, EPHA7, EPHB1, EPM2AIP1, ERC2, FABP6, FLRT3, GFOD2, GPM6B, H3F3A, HEY1, HIST1H2BJ, HMGN3, HNRNPA1, HOXD13, IFT57, IFT81, JHDM1D, KCNJ2, KLHL3, LMBR1L, LOC646934, LPHN2, LPHN3, LRP1B, LZTFL1, MOAP1, NDUFA1, NDUFB4, NEBL, NEK3, NR2F1, NUP62CL, PAK1, PCDH17, PCDH7, PCDH9, PDE5A, PES1, PLTP, PTPRB, RAB40A, RAPGEF4, RARB, RBM3, RNF128, RPL3, RPL35, RPL36A, RPL39, SEPP1, SERPINF1, SLC13A4, SNCA, SPON1, SPPL2B, STK38L, SYT1, TCF4, TGDS, TSC22D3, TSPAN7, UXT, VAV1, WDR48, ZNF74 and ZNF84. In some embodiments, a patient is predicted to respond to DNMT inhibitor therapy when the expression or activity of TET1 is lower than the reference level.

Some embodiments include methods of measuring the activity of let-7. The measurement may comprise comprises measuring the level of expression of any of let-7 target genes, including, but not limited to, one, two or more of ARID3B, CCNJ, GOLT1B, HIC2, IGF2BP3, IL13, MAP4K4, NF2, PAPPA, SLC6A1, TGFBR1, ZC3H3, and BMPER.

Additional embodiments include methods of measuring the activity of BACH1. The measurement may comprise comprises measuring the level of expression of any of BACH1 target genes, including, but not limited to, one, two or more of DYM, FBXO42, FRMPD4, HERC3, HS3ST3B1, IL1RAP, IL7, MAGEC1, MYCT1, PDE1C, PRDM1, and RCAN3.

In further embodiments, methods may include calculating a prognosis score. Any calculating methods may comprise calculating the thresholding/activation function, di(a,b), for each of the seven genes or meta-genes i (=1-7). In further embodiments, a is the expression level of genes or meta-genes measured in a), b is an optimized cutoff value for gene or meta-gene i: for example, b is −0.27 for RKIP, −0.23 for MMP1, 0.19 for OPN, −0.20 HMGA2, −0.19 for CXCR4, −0.020 for meta-LET7 comprising a weighted average of ARID3B, CCNJ, GOLT1B, HIC2, IGF2BP3, IL13, MAP4K4, NF2, PAPPA, SLC6A1, TGFBR1, ZC3H3, and BMPER, and −0.15 for meta-BACH1 comprising a weighted average of DYM, FBXO42, FRMPD4, HERC3, HS3ST3B1, IL1RAP, IL7, MAGEC1, MYCT1, PDE1C, PRDM1, and RCAN3.

In certain embodiments, di(a,b)=1 if a>b, i is not RKIP; di(a,b)=1 if a<b, i is RKIP; and di(a,b)=0 otherwise. Methods may further comprise calculating the prognosis score as a BACH1 pathway metastasis signature (BPMS), wherein BPMS=1 if the sum, from i=1 to i=7, of di(a,b) is equal to 7; and wherein BPMS=0 otherwise.

In some embodiments, methods may comprise determining a prognosis of the breast cancer sample: wherein BPMS=1 indicates a poor prognosis and wherein BPMS=0 indicates a favorable prognosis.

In certain embodiments, methods may further be defined as comprising measuring the level of expression or activity in the breast cancer sample of at least 1, 2, 3, 4, 5, 6, 7, 8, 9, 11, 12, 13, 14, 15, 16, 17, 18, 19, 20, 21, 22, 23, 24, 25, 26, 27, 28, 29, or all of the following 30 genes: RKIP, MMP1, OPN, HMGA2, CXCR4, ARID3B, CCNJ, GOLT1B, HIC2, IGF2BP3, IL13, MAP4K4, NF2, PAPPA, SLC6A1, TGFBR1, ZC3H3, BMPER, DYM, FBXO42, FRMPD4, HERC3, HS3ST3B1, IL1RAP, IL7, MAGEC1, MYCT1, PDE1C, PRDM1, and RCAN3. It is specifically contemplated that one or more of the genes discussed herein or in the incorporated references may be excluded in certain embodiments.

Methods may comprise comparing the level of expression of each gene measured in a) to a reference expression level. Methods may further comprise calculating a prognosis score based on comparisons, with or without the use of a computer algorithm.

In further embodiments, calculating a prognosis score comprises calculating the thresholding/activation function, di(a,b), for each of the 30 genes i (=1-30), where a is the expression level of gene score measured in a), b is an optimized cutoff value for gene i (−0.27 for RKIP, −0.23 for WP 1, 0.19 for OPN, −0.20 HMGA2, −0.19 for CXCR4, −0.020 for ARID3B, CCNJ, GOLT1B, HIC2, IGF2BP3, IL13, MAP4K4, NF2, PAPPA, SLC6A1, TGFBR1, ZC3H3, and BMPER, and −0.15 for DYM, FBXO42, FRMPD4, HERC3, HS3ST3B1, IL1RAP, IL7, MAGEC1, MYCT1, PDE1C, PRDM1, and RCAN3, wherein di(a,b)=1 if a>b, i is not RKIP; and wherein di(a,b)=1 if a<b, i is RKIP; and wherein di(a,b)=0 otherwise.

Methods may further comprise calculating the prognosis score as a BACH1 pathway metastasis signature (BPMS) as the prognosis score: wherein BPMS=1 if the sum, from i=1 to i=30, of di(a,b) is equal to 30; and wherein BPMS=0 otherwise. Additional embodiments may comprise determining the prognosis of the breast cancer sample: wherein BPMS=1 indicates a poor prognosis and wherein BPMS=0 indicates a favorable prognosis.

In some embodiments, the patient is determined to have a triple negative (ER−/PR−/HER2−) breast cancer (TNBC) subtype. The methods may further comprise determining whether the breast cancer sample has a triple negative breast cancer (TNBC) subtype.

In some embodiments, the method comprises or further comprises measuring the level of expression or activity in a breast cancer sample of RKIP. In some embodiments, the level of expression of the RKIP protein is measured. In some embodiments, the method further comprises predicting a patient's response to DNMT inhibitor therapy, wherein the patient is predicted to respond to DNMT therapy when the level of expression or activity of RKIP is lower than a reference expression level or activity or wherein the patient is predicted to not benefit from DNMT therapy when the level of expression or activity of RKIP is higher than a reference expression level or activity. In some embodiments, the method comprises treating the patient with a DNMT inhibitor when the level of expression or activity of RKIP is lower than a reference expression level or activity. DNMT inhibitor therapy includes, for example, azacitidine, decitabine, RG108, thioguanine, zebularine, SGI-1027, lomeguatrib, and procainamide HCl. In some embodiments, the DNMT inhibitor is azacitidine, decitabine, RG108, thioguanine, zebularine, SGI-1027, lomeguatrib, and procainamide HCl. In some embodiments, the DNMT inhibitor is azacitidine or decitabine.

In further embodiments, methods may be further defined as a method of treating the patient. Treatment methods may comprise treating the patient based on the calculated prognosis score. In additional embodiments, treatment methods may further comprise administering any conventional cancer therapy for breast cancers or triple negative breast cancers, such as surgery, radiation, or a conventional chemotherapy such as an anthracyclines, taxanes, beta-blockers, ixabepilone, bevacizumab, eribulin, or platinum-based therapy, to the patient whose calculated prognosis score indicates a favorable prognosis. For example, triple-negative breast cancer may be typically treated with a combination of therapies such as surgery, radiation therapy, and chemotherapy.

The methods may further comprise administering any treatments that are different from a treatment that would be given without the prognosis, such as a RKIP-targeted therapy or a DNMT inhibitor, to the patient whose calculated prognosis score indicates a poor prognosis.

Certain methods may involve the use of a normalized sample or control that is based on one or more breast cancer samples that are not from the patient being tested. Methods may also involve obtaining a biological sample comprising breast cancer cells from the patient or obtaining a breast cancer sample.

Methods may further comprise assaying nucleic acids or testing protein expression in the breast cancer sample. In some embodiments, assaying nucleic acids comprises the use of polymerase chain reaction (PCR), microarray analysis, next generation RNA sequencing, any methods known in the art, or a combination thereof. In further embodiments, testing protein expression comprises ELISA, RIA, FACS, dot blot, Western Blot, immunohistochemistry, antibody-based radioimaging, mass spectroscopy, any methods known in the art, or a combination thereof.

In further embodiments, methods may comprise recording the expression level or the prognosis score in a tangible medium or reporting the expression level or the prognosis score to the patient, a health care payer, a physician, an insurance agent, or an electronic system.

In certain embodiments, the patient is determined to be in a subgroup classified by one or more of the gene signatures selected from the group consisting of Mammaprint®, Oncotype®, GAB2 signaling scaffold, 28-kinase metagene, glucocorticoid receptor, and 76-gene signatures.

The prognosis score may be calculated using weighted coefficients for one or more of the measured expression levels of the genes, particularly for measuring the activity of Let-7 or BACH1.

In certain embodiments, there may be provided a method for evaluating the response of a breast cancer patient to a breast cancer treatment, comprising: a) determining in a breast cancer sample from a patient under or after a breast cancer treatment that the sample has a prognosis score that indicates a poor prognosis. For example, the prognosis score is calculated based on: i) the level of expression or activity of at least four of the following seven biomarkers: RKIP, MMP1, OPN, HMGA2, CXCR4, let-7, and BACH1; or ii) the level of expression of at least four of the following 30 genes in the breast cancer sample: RKIP, MMP1, OPN, HMGA2, CXCR4, ARID3B, CCNJ, GOLT1B, HIC2, IGF2BP3, IL13, MAP4K4, NF2, PAPPA, SLC6A1, TGFBR1, ZC3H3, BMPER, DYM, FBXO42, FRMPD4, HERC3, HS3ST3B1, IL1RAP, IL7, MAGEC1, MYCT1, PDE1C, PRDM1, and RCAN3. Method may further comprise b) identifying the patient as being at high risk of a poor response to the breast cancer treatment.

Methods may further comprise calculating a prognosis score for the patient based on the measured expression levels or activity. For any of the patients evaluated or tested, certain embodiments may further comprise, monitoring the patient for breast cancer recurrence or metastasis, or prescribing another treatment different from the treatment previously administered to the patient prior to the prognosis or would be prescribed without the prognosis.

There may be provided a method of treating a patient determined to have a breast cancer, comprising: a) identifying the patient as having a prognosis score that indicates a poor prognosis, wherein the prognosis score is calculated based on: i) the level of expression or activity of at least four of the following seven biomarkers: RKIP, MMP1, OPN, HMGA2, CXCR4, let-7, and BACH1; or ii) the level of expression of at least four of the following 30 genes in the breast cancer sample: RKIP, MMP1, OPN, HMGA2, CXCR4, ARID3B, CCNJ, GOLT1B, HIC2, IGF2BP3, IL13, MAP4K4, NF2, PAPPA, SLC6A1, TGFBR1, ZC3H3, BMPER, DYM, FBXO42, FRMPD4, HERC3, HS3ST3B1, IL1RAP, IL7, MAGEC1, MYCT1, PDE1C, PRDM1, and RCAN3; and b)

administering a treatment that inhibits or reduces the expression level of the RKIP gene and/or increases or enhances the expression level of one or more of genes: MMP1, OPN, HMGA2, CXCR4, ARID3B, CCNJ, GOLT1B, HIC2, IGF2BP3, IL13, MAP4K4, NF2, PAPPA, SLC6A1, TGFBR1, ZC3H3, BMPER, DYM, FBXO42, FRMPD4, HERC3, HS3ST3B1, IL1RAP, IL7, MAGEC1, MYCT1, PDE1C, PRDM1, and RCAN3.

Additionally methods may be provided for treating a patient determined to have a breast cancer, comprising: a) identifying the patient as having a prognosis score that indicates a favorable prognosis, wherein the prognosis score is calculated based on: i) the level of expression or activity of at least four of the following seven biomarkers: RKIP, MMP1, OPN, HMGA2, CXCR4, let-7, and BACH1; or ii) the level of expression of at least four of the following 30 genes in the breast cancer sample: RKIP, MMP1, OPN, HMGA2, CXCR4, ARID3B, CCNJ, GOLT1B, HIC2, IGF2BP3, IL13, MAP4K4, NF2, PAPPA, SLC6A1, TGFBR1, ZC3H3, BMPER, DYM, FBXO42, FRMPD4, HERC3, HS3ST3B1, IL1RAP, IL7, MAGEC1, MYCT1, PDE1C, PRDM1, and RCAN3; and; and b) administering a treatment comprising an anthracycline, taxane, beta-blocker, ixabepilone, bevacizumab, eribulin, or platinum-based therapy alone or combined with surgery, like before, after, or in conjunction with surgery.

There may be provided a tangible, computer-readable medium comprising computer-readable code that, when executed by a computer, causes the computer to perform operations comprising: a) receiving information corresponding to: i) the level of expression or activity of at least four of the following seven biomarkers: RKIP, MMP1, OPN, HMGA2, CXCR4, let-7, and BACH1; or ii) the level of expression of at least four of the following 30 genes in the breast cancer sample: RKIP, MMP1, OPN, HMGA2, CXCR4, ARID3B, CCNJ, GOLT1B, HIC2, IGF2BP3, IL13, MAP4K4, NF2, PAPPA, SLC6A1, TGFBR1, ZC3H3, BMPER, DYM, FBXO42, FRMPD4, HERC3, HS3ST3B1, IL1RAP, IL7, MAGEC1, MYCT1, PDE1C, PRDM1, and RCAN3 in a breast cancer sample from a patient; and b) calculating a prognosis score, using a computer algorithm, based on the level of expression or activity of each biomarker gene received in a) as compared to a reference expression level or activity.

Use of the one or more compositions may be employed based on methods described herein. Other embodiments are discussed throughout this application. Any embodiment discussed with respect to one aspect of the invention applies to other aspects of the invention as well and vice versa. The embodiments in the Example section are understood to be embodiments o that are applicable to all aspects of the technology described herein.

The term "recurrence" refers to the detection of breast cancer in the form of metastatic spread of tumor cells, local recurrence, contralateral recurrence or recurrence of breast cancer at any site of the body of the patient after breast cancer had been substantially undetectable or responsive to treatments.

The term "metastasis," as used herein, refers to the condition of spread of cancer from the organ of origin to additional distal sites in the patient. The process of tumor metastasis is a multistage event involving local invasion and destruction of intercellular matrix, intravasation into blood vessels, lymphatics or other channels of transport, survival in the circulation, extravasation out of the vessels in the secondary site and growth in the new location (Fidler et al., 1978; Liotta et al., 1988; Nicolson, 1988; and Zetter, 1990). Increased malignant cell motility has been associated with enhanced metastatic potential in animal as well as human tumors (Hosaka et al., 1978 and Haemmerlin et al., 1981).

"Cancer prognosis" generally refers to a forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer. As used herein, "prognostic for cancer" means providing a forecast or prediction of the probable course or outcome of the cancer. In some embodiments, "prognostic for cancer" comprises providing the forecast or prediction of (prognostic for) any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer.

"Subject" or "patient" refers to any single subject for which therapy is desired, including humans, cattle, dogs, guinea pigs, rabbits, chickens, and so on. Also intended to be included as a subject are any subjects involved in clinical research trials not showing any clinical sign of disease, or subjects involved in epidemiological studies, or subjects used as controls. The terms "subject" and "patient" may be used interchangeably.

"Remission" refers to a period during which symptoms of disease are reduced (partial remission) or disappear (complete remission). With regard to cancer, remission means there is no sign of it on scans or medical examination. "Remission" is used instead of cure regarding cancer because it cannot be sure that there are no cancer cells at all in the body. So the cancer could recur in the future, although there is no sign of it at the time. More specifically, "remission" could mean the tumor-free time period, and is dated from the first, not the last, therapy session. Patients with tumors that recur within one month of treatment ending are considered to have had no remission. Disappearance of all disease is complete remission; reduction tumor size by more than 50 percent is considered partial remission.

By "gene" is meant any polynucleotide sequence or portion thereof with a functional role in encoding or transcribing a protein or regulating other gene expression. The gene may consist of all the nucleic acids responsible for encoding a functional protein or only a portion of the nucleic acids responsible for encoding or expressing a protein. The polynucleotide sequence may contain a genetic abnormality within exons, introns, initiation or termination regions, promoter sequences, other regulatory sequences or unique adjacent regions to the gene.

As used herein, "treatment" or "therapy" is an approach for obtaining beneficial or desired clinical results. This includes: reduce the number of cancer cells; reduce the tumor size; inhibit (i.e., slow to some extent and/or stop) cancer cell infiltration into peripheral organs; inhibit (i.e., slow to some extent and/or stop) tumor metastasis; inhibit, to some extent, tumor growth; and/or relieve to some extent one or more of the symptoms associated with the disorder, shrinking the size of the tumor, decreasing symptoms resulting from the disease, increasing the quality of life of those suffering from the disease, decreasing the dose of other medications required to treat the disease, delaying the progression of the disease, and/or prolonging survival of patients.

The term "therapeutically effective amount" refers to an amount of the drug that may reduce the number of cancer cells; reduce the tumor size; inhibit (i.e., slow to some extent and particularly stop) cancer cell infiltration into peripheral organs; inhibit (i.e., slow to some extent and particularly stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The terms "overexpress", "overexpression", "overexpressed", "up-regulate", or "up-regulated" interchangeably refer to a biomarker that is transcribed or translated at a detectably greater level, usually in a cancer cell, in comparison to a non-cancer cell or cancer cell that is not associated with the worst or poorest prognosis. The term includes overexpression due to transcription, post transcriptional processing, translation, post-translational processing, cellular localization, and/or RNA and protein stability, as compared to a non-cancer cell or cancer cell that is not associated with the worst or poorest prognosis. Overexpression can be detected using conventional techniques for detecting mRNA (i.e., RT-PCR, PCR, hybridization) or proteins (i.e., ELISA, immunohistochemical techniques, mass spectroscopy). Overexpression can be 10%, 20%, 30%, 40%, 50%, 60%, 70%, 80%, 90% or more (or any range derivable therein) in comparison to a normal cell or cancer cell that is not associated with the worst or poorest prognosis. In certain instances, overexpression is 1-fold, 2-fold, 3-fold, 4-fold 5, 6, 7, 8, 9, 10, or 15-fold or more higher levels of transcription or translation (or any range derivable therein) in comparison to a non-cancer cell or cancer cell that is not associated with the worst or poorest prognosis. The comparison may be a direct comparison where the expression level of a control is measured at the same time as the test sample or it may be a level of expression that is determined from a previously evaluated sample or an average of levels of expression of previously evaluated sample(s).

"Biological sample" includes sections of tissues such as biopsy and autopsy samples, and frozen sections taken for histologic purposes. Such samples include breast cancer tissues, cultured cells, e.g., primary cultures, explants, and transformed cells. A biological sample is typically obtained from a mammal, such as a primate, e.g., human. The biological sample, in some embodiments, may include metastatic tissue.

A "biopsy" refers to the process of removing a tissue sample for diagnostic or prognostic evaluation, and to the tissue specimen itself. Any biopsy technique known in the art can be applied to the diagnostic and prognostic methods. The biopsy technique applied will depend on the tissue type to be evaluated (e.g., breast), the size and type of the tumor, among other factors. Representative biopsy techniques include, but are not limited to, excisional biopsy, incisional biopsy, needle biopsy, and surgical biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy", or a "fine-needle aspiration biopsy" which generally obtains a suspension of cells from within a target tissue. Biopsy techniques are discussed, for example, in Harrison's Principles of Internal Medicine, 2005. Obtaining a biopsy includes both direct and indirect methods, including obtaining the biopsy from the patient or obtaining the biopsy sample after it is removed from the patient.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-B. The optimized solutions yield larger cohort sizes and better p-values. Distribution density plots for non-optimized (control) and optimized signatures verify that significantly better cohort sizes (A) and p-values (B) were generated using a cost function in conjunction with the Nelder-Mead optimization algorithm.

FIG. 2A-B. Optimization procedure for the BPMS. After separating the overall training set (BrCa871) into a training set and a cross validation set, (A) a series of 24,800 potential solutions are produced by optimizing the inventors cost function using the Nelder-Mead downhill simplex algorithm. These solutions were trained on survival data with no year-specific endpoint defined to maximize signal sensitivity (See FIG. 4). Using these 24,800 potential solutions, (B) significance in both training and cross-validation sets was assessed. To control for over-fitting solutions, 556 solutions yielding significance in both sets were extracted and used to estimate the final BPMS signature.

FIG. 16A-Q BPMS source code. This figure shows computer-program source code that is the property of the assignee. Copies of the source code may be made as part of making facsimile reproductions of this specification, but all other rights in the source code are reserved. Those with skill in the art having the benefit of this disclosure will understand that the appended source code may be modified as necessary for use with operating systems other than the standard, UNIX-based operating system for which it is currently written. For example, the appended source code may be modified for use with any Microsoft Windows operating system.

FIG. 17A-J shows the induction of TET1 and homeobox gene (HOX) gene expression upon depletion of high mobility group AT-hook 2 (HMGA2) in 1833 cells, a bone-tropic derivative of human breast cancer cell line MDA-MB-231, or in MMTV-Wnt1 transgenic mouse breast tumors. (A,B, D-H) 1833 cells were stably transduced with HMGA2 shRNA (shHMGA2) or control scrambled shRNA (SCR sh): (A) Gene expression array analysis showing up-regulation of TET1 and 20 out of 39 HOX genes in HMGA2-depleted cells. The expression levels of HOXA genes are also shown in (B). *, fold change <2; **, fold change >2 based on the signal intensity of gene expression arrays. (C) Genomic transcription units of human HOXA genes on chromosome 7 viewed using the UCSC genome browser (39). HOXA genes are transcribed from right to left with the order: 5'UTR (thin bar), Coding Sequence (thick bar) and 3'UTR (thin bar). Bar length is proportional to length of DNA sequence. (D-H) QRT-PCR and immunoblotting analyses validated induction of TET1 and HOXA gene expression in HMGA2-depleted cells: (D) HMGA2, (E) TET1, or (F) HOXA4/5/6/7/9/11 mRNA analyzed by qRT-PCR (GAPDH as normalization control); (G) HMGA2, TET1 and HOXA9/7 protein analyzed by immunoblotting (GAPDH as control); (H) genome-wide 5-hydroxymethylcytosine (5hmC) levels analyzed by dot blot assay. (I,J) Loss of Hmga2 in MMTV-Wnt1 transgenic mouse breast tumors induced Tet1 and Hoxa9/7 expression. Wnt1 transgenic mice were crossed with Hmga2 specific knockout mice. Mouse primary breast tumors were obtained from Hmga2 wildtype (Hmga2+/+), heterozygous (Hmga2+/−) or null (Hmga2−/−) mice: (I) Murine Hmga2, Tet1 and Hoxa9/7 mRNA analyzed by qRT-PCR (mouse Gapdh as normalization control); (J) Murine TET1 and HOXA9 protein, and 5hmC levels analyzed by immunostaining. (D-F,H,I) Data are mean±s.e., n=3. *, P<0.05; , P<0.01; *, P<0.001;

FIG. 18A-D shows that TET1 involvement in an auto-regulation in human breast cancer cells. (A) TET1 binds to its own promoter. 1833 cells expressing TET1 or vector control were analyzed by ChIP assay with anti-TET1 or anti-H3K4Me3 antibody followed by qPCR analysis: TET1 and H3K4Me3 binding to the CpG island proximal to the transcription start site (TSS) of TET1 (see site-1 and site-2 in Table S5). Site-3 is a negative control. (B,C) HMGA2 depletion causes demethylation of CpG islands at the TET1 promoter region. 1833 cells stably expressing HMGA2 shRNA (shHMGA2) or control scrambled shRNA (SCR sh) were analyzed for CpG island methylation status by multiple approaches: (B) TET1 promoter region was analyzed within ±1 Kb from the TSS. Methylation-specific digestions followed by qPCR distinguished between methylated CpGs versus unmethylated or other modified (e.g. 5hmC) CpGs. The percentage of methylation versus unmethylation (includes unmethylated or other modified C) is indicated; (C) Bisulfite sequencing of specific CpGs (see Table S4 for primers) at the TET1 promoter proximal to the TSS. Results show unmethylated CpGs (open circles) versus methylated or modified CpGs (black circles) in 10 or more independent clones encompassing the region of interest. (D) 1833 cells were subjected to 5-azacytidine treatment followed by qRT-PCR analysis for TET1 mRNA expression (GAPDH as normalization control). (A,B,D) Data are mean s.e., n=3. *, P<0.05; **, P<0.01;

FIG. 19A-G illustrates TET1 inducement of HOXA gene expression. (A,B) Depletion of TET1 by siRNA partially countered induction of HOXA genes. 1833 cells stably expressing HMGA2 shRNA were transfected with control or TET1 siRNA: (A) Analysis of TET1 and HOXA gene mRNA by qRT-PCR; (B) Upper panel: analysis of TET1 and HOXA9/7 protein by immunoblotting; Lower panel: analysis of 5-hydroxymethylcytosine (5hmC) levels by dot blot assay. (C,D) Expression of TET1 dramatically induced HOXA9 expression. 1833 cells expressing constitutive TET1 (Flag-TET1) were analyzed by (C) qRT-PCR for HOXA9 mRNA and by (D) Upper panel: immunoblotting for TET1 (Flag-M1) and HOXA9 protein; Lower panel: dot blot assay for 5hmC levels. (E,F) Induced expression of TET1 in breast xenograft tumors significantly induced HOXA9 expression. 1833 cells stably expressing an inducible TET1 expression vector were orthotopically injected into the second mammary fat pad of nude mice. Tumor tissues were collected and analyzed after 6 weeks with (+DOX) or without (−DOX) addition of Doxycycline in the mouse drinking water: (E) TET1 and HOXA9 mRNA analyzed by qRT-PCR; (F) TET1 and HOXA9 protein and 5hmC levels analyzed by immunostaining. (G) Significant positive correlation between TET1 and HOXA9/7 expression in breast cancer subjects (see Table S3 for patient clinical information). Correlations were determined by Pearson's correlation coefficient. P value is determined by Student's t test. (A-E) GAPDH as normalization control. Data are mean±s.e., n=3. , P<0.01; *, P<0.01;

FIG. 20A-G shows TET1 inducement of HOXA gene expression through binding to the promoter regions of HOXA genes and contributing to local demethylation in human breast cancer cells. (A,B) TET1 binds to the HOXA gene promoters. 1833 cells expressing TET1 or control were analyzed by ChIP assay with anti-TET1 or anti-H3K4Me3 antibody followed by qPCR analysis: TET1 and H3K4Me3 binding to the CpG islands proximal to the transcription start site (TSS) of (A) HOXA7 (see site-1 and site-2 in Table S5). Site-3 is a negative control; or (B) HOXA9 (see site-1 in Table S5). Site-2 is a negative control. (C-E) HMGA2 depletion causes demethylation of CpG islands at HOXA gene promoter regions. 1833 cells stably expressing shHMGA2 or SCR sh were analyzed for CpG island methylation status by multiple approaches (see FIGS. 2B and 2C for the specificity of each method): (C) HOXA promoter regions were analyzed within −5 Kb-+3 Kb from the TSS. The percentage of methylation versus unmethylation is indicated; (D,E) Bisulfite sequencing of specific CpGs (see Table S4 for primers) at (D) HOXA7 and (E) HOXA9 promoters proximal to the TSS. Results show unmethylated CpGs (open circles) versus methylated or modified CpGs (black circles) in 10 independent clones encompassing the region of interest. (F,G) 1833 cells were subjected to 5-azacytidine treatment followed by qRT-PCR analysis for expression of (F) HOXA7 or (G) HOXA9 mRNA (GAPDH as normalization control). (A-C,F,G) Data are mean±s.e., n=3. , P<0.01; *, P<0.001;

FIG. 21A-N shows both TET1 and its target, HOXA9, in suppression of breast tumor growth, invasion and metastasis. (A-D) HMGA2/TET1/HOXA pathway regulates breast cancer cell invasion: (A) Inhibition of cell invasion in 1833 cells with depleted HMGA2 expression; (B) Transfection of TET1 siRNA into HMGA2-depleted 1833 cells increases invasion; (C) Transfection of HOXA7 or HOXA9 siRNA into HMGA2-depleted 1833 cells increases invasion; (D) Decitabine (5-aza-dC) treatment of 1833 cells decreases cell invasion, and transfection of HOXA9 siRNA into treated cells partially reversed cell invasion. (A-D) Data are mean±s.e., n=3. (E-K) 1833 cells stably expressing an inducible control, TET1 or HOXA9 expression vector were orthotopically injected into the mammary fat pad of nude mice. Mice were administered drinking water with (+DOX) or without (−DOX) addition of Doxycycline: (E-G) Both TET1 and HOXA9 suppress xenograft breast tumor growth: (E) Representative bioluminescence images of mice bearing 1833 cells treated as indicated; (F) Photograph of representative xenograft breast tumors of 1833 cells treated as indicated; (G) Xenograft breast tumors of 1833 cells treated as indicated and analyzed for tumor weight. (F,G) Tumors were dissected at 6 weeks after implantation. (H,I) Both TET1 and HOXA9 suppress the proliferation in xenograft breast tumors: immunostaining showing Ki67 positive cells in tumor sample of 1833 cells with induced (+DOX) versus non-induced (−DOX) expression of (H) TET1; or (I) HOXA9. (J,K) Both TET1 and HOXA9 inhibit intravasation of 1833 cells. Cells isolated from the blood after 6 weeks were analyzed for GAPDH/Gapdh transcripts derived from human (tumor) or mouse (control) by qRT-PCR: intravasation of 1833 cells with induced (+DOX) versus non-induced (−DOX) expression of (J) TET1; or (K) HOXA9. Data are mean±s.e., n=8 per group. (L-N) Both TET1 and HOXA9 suppress bone metastasis of 1833 cells. 1833 cells stably expressing an inducible TET1 or HOXA9 expression vector were injected into the left ventricle of mice. Mice were administered drinking water with (+DOX) or without (−DOX) addition of Doxycycline, and imaged for luciferase activity after 3 weeks: (L) Representative bioluminescence images of mice with bone metastasis; (M) Quantification of bone colonization by 1833 cells with induced (+DOX) versus non-induced (−DOX) expression of TET1 or HOXA9. Data are mean±s.e. n=7-9 per group; (N) Kaplan-Meier survival analysis of mice over 8 weeks after injection of the tumor cells;

FIG. 22A-C shows the HMGA2/TET1/HOXA pathway regulates breast cancer tumorigenesis. (A) Comparison of the genes regulated by HMGA2, TET1 or HOXA9 in 1833 cells (human breast cancer cells, hBrCa). (B) Scheme illustrating HMGA2/TET1/HOXA signaling pathway in breast tumorigenesis. (C) Kaplan-Meier analysis of gene expression data from 101 breast tumor subjects (see Table S3 for patient clinical information). Subjects were stratified for survival using HMGA2, TET1, HOXA9, HOXA7 or the complete pathway as indicated. Right panel: Light gray line, high HMGA2 and low TET1/HOXAs (n=34); Dark gray line, low HMGA2 and high TET1/HOXAs (n=35); P, chi-square p value;

FIG. 26A-F show the effect of HMGA2 expression on TET1 in 1833 and MDA-MB-436 cells. (A-C) We analyzed 1833 cells transfected with HMGA2 lacking the let-7 binding region by qRT-PCR for HMGA2 (A) and TET1 (B) mRNA and by immunoblotting for HMGA2 and TET1 protein (C). (D-F) MDA-MB-436 cells transfected with HMGA2 lacking the let-7 binding region were analyzed by qRT-PCR for HMGA2 (D) and TET1 mRNA (E) and by immunoblotting for HMGA2 and TET1 protein (F). GAPDH was the normalization control for mRNA and protein expression. Data are means±SEM; n=3. *P<0.05; **P<0.01;

FIG. 27A-K shows induction of HOXA9 by a demethylation reagent suppresses cell invasion and proliferation. (A-D) We analyzed 1833 cells subjected to mock (Control) or decitabine treatment for HOXA9 mRNA by qRT-PCR (A), cell invasion from 3-d treatment (B), HOXA9 protein from 3-d treatment by immunoblotting (C), or cell proliferation (D). (E-H) Inhibition of HOXA9 expression by HOXA9 siRNA after decitabine treatment. We transiently transfected HOXA9 siRNA into 1833 cells treated with decitabine and analyzed for HOXA9 mRNA by qRT-PCR (E), HOXA9 protein by immunoblotting (F), cell invasion (G), or cell proliferation (H). (I-K) Inhibition of HOXA7 or HOXA9 expression by siRNAs. HMGA2-depleted 1833 cells transfected with siRNA for HOXA7 or HOXA9 were analyzed for HOXA7 (I) or HOXA9 mRNA (J) by qRT-PCR or for HOXA7 and HOXA9 protein by immunoblotting (K). (A, E, I, and J) GAPDH as normalization control. (C, F, and K) a-tubulin or GAPDH as control. (A, B, D, E, and G-J) Data are means±SEM; n=3. *P<0.05; P<0.01; *P<0.001; and FIG. 28A-I shows induced expression of Tet1 or HOXA9 suppresses breast cancer cell growth and enhances survival, and the HMGA2/HOXA pathway stratifies subjects for metastasis-free survival. (A) In vitro analysis of induced TET1 and HOXA9 protein by immunoblotting upon induction of Tet1 expression. (B) In vitro analysis of induced HOXA9 protein by immunoblotting upon induction of HOXA9 expression. (C) Relative growth of cells with induced (+DOX) vs. noninduced (−DOX) Tet1 or HOXA9 expression. Data are means±SEM; n=3. *P<0.05; P<0.01. (D and E) Xenograft breast tumors with (+DOX) or without (−DOX) induction of HOXA9 were analyzed for HOXA9 mRNA by qRT-PCR (D) or HOXA9 protein by immunostaining (E). *P<0.001. (F-H) We injected 1833 cells stably expressing an inducible control, Tet1, or HOXA9 expression vector into the left ventricle of mice. Mice were administered drinking water with (+DOX) or without (−DOX) addition of doxycycline. Kaplan-Meier survival analysis of mice over 8 wk after injection of the tumor cells (n=7-9 per group). (F) Induced (+DOX) vs. noninduced (−DOX) control group. (G) Noninduced Tet1 (−DOX) vs. noninduced HOXA9 (−DOX) group. (H) Induced Tet1 (+DOX) vs. induced HOXA9 (+DOX) group. P values were determined by Student t test. (I) Kaplan-Meier analysis of gene expression data from 735 breast tumor subjects. Subjects were stratified for metastasis-free survival by using HMGA2, HOXA9, HOXA7, HOXA4, or the HMGA2/HOXA pathway as indicated. (Right) Light gray line, high HMGA2 and low HOXAs (n=69); dark gray line, low HMGA2 and high HOXAs (n=72); P, $\chi 2$ P value.

DETAILED DESCRIPTION OF THE INVENTION

Figure 3:
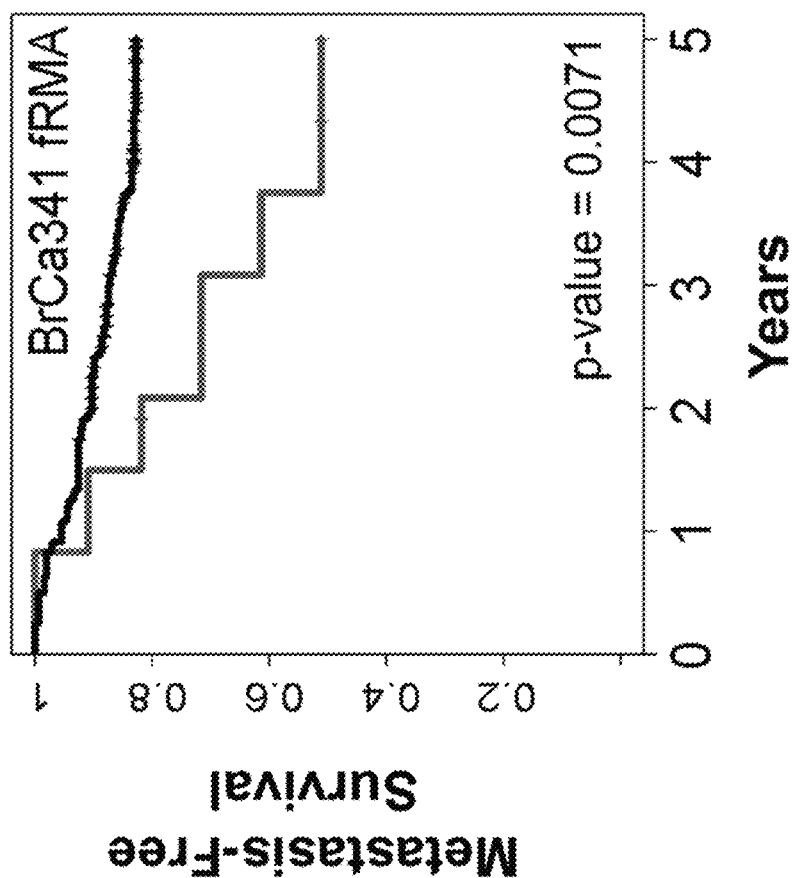
FIG. 3. The BPMS is a single patient predictor. Using frozen RMA pre-processed data, the BPMS was trained to be applied on a patient-to-patient basis. The BrCa871 set was processed using fRMA, divided into the BrCa436-Train and BrCa435-CV sets and 7,500 potential solutions were optimized. Using a cross-validation strategy, a final set of BPMS parameters were trained for fRMA processed data. Shown is the application of these parameters to the fRMA processed BrCa341 data set.

Although triple negative breast cancers (TNBC) are the most aggressive subtype of breast cancer, they currently lack targeted therapies. Because this classification still includes a heterogeneous collection of tumors, new tools to classify TNBCs are urgently required in order to improve the inventors prognostic capability for high risk patients and predict response to therapy. The inventors previously defined a gene expression signature, RKIP Pathway Metastasis Signature (RPMS), based upon a metastasis-suppressive signaling pathway initiated by Raf Kinase Inhibitory Protein (RKIP). The inventors have now generated a new BACH1 Pathway Metastasis gene signature (BPMS) that utilizes targets of the metastasis regulator BACH1. Specifically, the inventors substituted experimentally validated target genes to generate a new BACH1 metagene, developed an approach to optimize patient tumor stratification, and reduced the number of signature genes to 30. The BPMS significantly and selectively stratified metastasis-free survival in basal-like and, in particular, TNBC patients. In addition, the BPMS further stratified patients identified as having a good or poor prognosis by other signatures including the Mammaprint® and Oncotype® clinical tests. The BPMS is thus complementary to existing signatures and is a prognostic tool for high risk ER-HER2− patients. The inventors also demonstrate the potential clinical applicability of the BPMS as a single sample predictor. Together, these results reveal the potential of this pathway-based BPMS gene signature to identify high risk TNBC patients that can respond effectively to targeted therapy, and highlight BPMS genes as novel drug targets for therapeutic development.

The application of gene expression array technology to breast cancer has emphasized the heterogeneity of this disease and also provided new tools to classify breast cancers into subtypes based on gene expression patterns. Ideally each subtype would reflect distinct molecular characteristics corresponding to discrete cancer phenotypes. This information could be used to gain prognostic insight and, eventually, to predict response to therapy. In addition to the traditional clinical parameters (size, grade and node status) and pathological markers (ER, PR and HER2 status), breast cancer can be classified into at least 5 'intrinsic' subtypes (Luminal A, Luminal B, HER2-enriched, Basal-like, Normal-like) that were derived from a hierarchical clustering analysis of expression profiles of human breast tumors. This classification has generated a gene-expression predictor, the PAM50 Classifier, that measures the expression of 50 genes to establish the intrinsic tumor subtypes and has been useful as a prognostic marker but has not yet reached its potential impact on clinical care.

Recently other gene expression signatures have been developed in order to stratify patients by survival and to provide more accurate prognostic tools. Most of these signatures however identify a few groups of patients that are mainly separated based on ER status, HER2 status and proliferation markers and thus partially overlap with the molecular subtyping. Supervised analysis of expression data has also led to clinical assays like the OncotypeDX®, a diagnostic test that analyzes expression of 21 genes and provides a likelihood of recurrence for early stage, estrogen receptor positive (ER+) patients. Similarly, Mammaprint® analyzes the expression of 70 genes, mostly related to proliferation, and can stratify early-stage, node negative patients based on the risk of recurrence. Both these tests have a prognostic significance but their applicability with respect to targeted therapy is primarily limited to a well defined group of patients whose tumors express ER or HER2.

One of the main challenges in the breast cancer field is to gain a better knowledge of the biology of triple negative (ER−/PR−/HER2−) breast cancer (TNBC) in order to develop clinical approaches to this disease. TNBC represents 14 to 20 percent of all breast cancers, has a high incidence in young women, is more frequent in African American women compared to Caucasian, and is often associated with BRCA1 mutations. TNBC represents the most aggressive type of breast cancer and the one with the poorest prognosis. This is due in part to the fact that there is no targeted therapy available and in part because of the high risk of recurrence. Moreover, recurrence occurs generally within a few years and often involves metastasis, especially to the brain and lung. TNBC largely comprises a subset of basal-like breast tumors. Although chemotherapy is often initially beneficial in basal-like tumors, those with residual disease after treatment have a high risk of relapse. Targeted therapy has potential value for treatment; however, it is important to first identify the subpopulations of patients that are most at risk.

A signaling pathway-based gene signature named the RKIP pathway metastasis signature (RPMS) was defined previously, which is predictive for metastasis-free survival in a heterogeneous cohort of breast cancer patients. This signature was based upon statistically determined regulatory relationships that were experimentally validated and then applied using a cut-off based model. These include the metastasis suppressor gene Raf Kinase Inhibitory protein (RKIP), targets of the downstream let-7 microRNA family including the pro-metastatic let-7 targets BACH1 and HMGA2, and finally their downstream targets MMP1, CXCR4 and OPN. It was experimentally demonstrated that the microRNA let-7 suppresses breast cancer metastasis, and BACH1, a leucine zipper transcription factor, promotes breast cancer metastasis. By basing prognostic signatures for TNBC patient survival on signaling pathway information, it is theoretically possible to identify drug targets that will enable effective response of this patient cohort to treatment.

It was contemplated to improve the RPMS to make it more clinically relevant and more targeted to specifically discriminate among subgroups of TNBC patients. New gene expression array data, obtained using a TNBC cell line, to experimentally define the BACH1 target genes were used. With this refined set of genes, an optimization process was applied to gene expression data from human breast tumors to obtain a prognostic signature. Finally, the capability of being a single sample predictor was added.

A novel BACH1 pathway metastasis signature (BPMS) was thus defined and was shown to function as a prognostic indicator of metastasis-free survival in a heterogeneous cohort of patients as well as TNBC patients. In addition, because the BPMS is based on a signaling pathway, it also has the potential for guiding the development of new therapy targeted to genes within this signaling network that promote metastasis in TNBC patients.

I. Analysis of Gene Expression

In certain aspects a meta-analysis of expression or activity can be performed. In statistics, a meta-analysis combines the results of several studies that address a set of related research hypotheses. This is normally done by identification of a common measure of effect size, which is modeled using a form of meta-regression. Generally, three types of models can be distinguished in the literature on meta-analysis: simple regression, fixed effects meta-regression and random effects meta-regression. Resulting overall averages when controlling for study characteristics can be considered meta-effect sizes, which are more powerful estimates of the true effect size than those derived in a single study under a given single set of assumptions and conditions. A meta-gene expression value, in this context, is to be understood as being the median of the normalized expression of a marker gene or activity. Normalization of the expression of a marker gene may be achieved by dividing the expression level of the individual marker gene to be normalized by the respective individual median expression of this marker genes, wherein said median expression may be calculated from multiple measurements of the respective gene in a sufficiently large cohort of test individuals. The test cohort may comprise at least 3, 10, 100, 200, 1000 individuals or more including all values and ranges thereof. Dataset-specific bias can be removed or minimized allowing multiple datasets to be combined for meta-analyses (See Sims et al. BMC Medical Genomics (1:42), 1-14, 2008, which is incorporated herein by reference in its entirety).

The calculation of a meta-gene expression value is performed by: (i) determining the gene expression value of at least two, or more genes (ii) "normalizing" the gene expression value of each individual gene by dividing the expression value with a coefficient which is approximately the median expression value of the respective gene in a representative breast cancer cohort (iii) calculating the median of the group of normalized gene expression values.

A gene shall be understood to be specifically expressed in a certain cell type if the expression level of said gene in said cell type is at least 2-fold, 5-fold, 10-fold, 100-fold, 1000-fold, or 10000-fold higher than in a reference cell type, or in a mixture of reference cell types. Reference cell types include non-cancerous breast tissue cells or a heterogeneous population of breast cancers.

In certain algorithms a suitable threshold level is first determined for a marker gene. The suitable threshold level can be determined from measurements of the marker gene expression in multiple individuals from a test cohort. The median expression of the marker gene in said multiple expression measurements is taken as the suitable threshold value.

Comparison of multiple marker genes with a threshold level can be performed as follows:

1. The individual marker genes are compared to their respective threshold levels.

2. The number of marker genes, the expression level of which is above their respective threshold level, is determined.

3. If a marker genes is expressed above its respective threshold level, then the expression level of the marker gene is taken to be "above the threshold level".

In certain aspects, the determination of expression levels is on a gene chip, such as an Affymetrix™ gene chip.

In another aspect, the determination of expression levels is done by kinetic real time PCR.

In certain aspects, the methods can relate to a system for performing such methods, the system comprising (a) apparatus or device for storing data on the receptors status (ER, AR, or PR, GR) or nodal status of the patient; (b) apparatus or device for determining the expression level of at least one marker gene or activity; (c) apparatus or device for comparing the expression level of the first marker gene or activity with a predetermined first threshold value; (d) apparatus or device for determining the expression level of at least one second, third, fourth, $5^{th}$, $6^{th}$ or more marker gene or activity and for comparing with a corresponding predetermined threshold; and (e) computing apparatus or device programmed to provide a unfavorable or poor prognosis or favorable prognosis based on the comparisons.

The person skilled in the art readily appreciates that an unfavorable or poor prognosis can be given if the expression level of the first marker gene with the predetermined first threshold value indicates a tumor that is likely to recur or not respond well to standard therapies.

The expression patterns can also be compared by using one or more ratios between the expression levels of different breast cancer biomarkers. Other suitable measures or indicators can also be employed for assessing the relationship or difference between different expression patterns.

The expression levels of breast cancer biomarkers can be compared to reference expression levels using various methods. These reference levels can be determined using expression levels of a reference based on all breast cancer patients or all breast cancer patients. Alternatively, it can be based on an internal reference such as a gene that is expressed in all cells. In some embodiments, the reference is a gene expressed in breast cancer cells at a higher level than any biomarker. Any comparison can be performed using the fold change or the absolute difference between the expression levels to be compared. One or more breast cancer biomarkers can be used in the comparison. It is contemplated that 1, 2, 3, 4, 5, 6, 7, 8, and/or 9 biomarkers (or any range derivable therein) may be compared to each other and/or to a reference that is internal or external. A person of ordinary skill in the art would know how to do such comparisons.

Comparisons or results from comparisons may reveal or be expressed as x-fold increase or decrease in expression relative to a standard or relative to another biomarker or relative to the same biomarker but in a different class of prognosis. In some embodiments, patients with a poor prognosis have a relatively high level of expression (overexpression) or relatively low level of expression (underexpression) when compared to patients with a better or favorable prognosis, or vice versa.

Fold increases or decreases may be, be at least, or be at most 1-, 2-, 3-, 4-, 5-, 6-, 7-, 8-, 9-, 10-, 11-, 12-, 13-, 14-, 15-, 16-, 17-, 18-, 19-, 20-, 25-, 30-, 35-, 40-, 45-, 50-, 55-, 60-, 65-, 70-, 75-, 80-, 85-, 90-, 95-, 100- or more, or any range derivable therein. Alternatively, differences in expression may be expressed as a percent decrease or increase, such as at least or at most 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 900, 1000% difference, or any range derivable therein.

Other ways to express relative expression levels are by normalized or relative numbers such as 0.001, 0.002, 0.003, 0.004, 0.005, 0.006, 0.007, 0.008, 0.009, 0.01, 0.02, 0.03. 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, or any range derivable therein.

Algorithms, such as the weighted voting programs, can be used to facilitate the evaluation of biomarker levels. In addition, other clinical evidence can be combined with the biomarker-based test to reduce the risk of false evaluations. Other cytogenetic evaluations may be considered in some embodiments.

Any biological sample from the patient that contains breast cancer cells may be used to evaluate the expression pattern of any biomarker discussed herein. In some embodiments, a biological sample from a breast tumor is used. Evaluation of the sample may involve, though it need not involve, panning (enriching) for cancer cells or isolating the cancer cells.

II. Measurement of Gene Expression Using Nucleic Acids

Testing methods based on differentially expressed gene products are well known in the art. In accordance with one aspect, the differential expression patterns of breast cancer biomarkers can be determined by measuring the levels of RNA transcripts of these genes, or genes whose expression is modulated by the these genes, in the patient's breast cancer cells. Suitable methods for this purpose include, but are not limited to, RT-PCR, Northern Blot, in situ hybridization, Southern Blot, slot-blotting, nuclease protection assay and oligonucleotide arrays.

In certain aspects, RNA isolated from breast cancer cells can be amplified to cDNA or cRNA before detection and/or quantitation. The isolated RNA can be either total RNA or mRNA. The RNA amplification can be specific or non-specific. Suitable amplification methods include, but are not limited to, reverse transcriptase PCR, isothermal amplification, ligase chain reaction, and Qbeta replicase. The amplified nucleic acid products can be detected and/or quantitated through hybridization to labeled probes. In some embodiments, detection may involve fluorescence resonance energy transfer (FRET) or some other kind of quantum dots.

Amplification primers or hybridization probes for a breast cancer biomarker can be prepared from the gene sequence or obtained through commercial sources, such as Affymatrix. In certain embodiments the gene sequence is identical or complementary to at least 8 contiguous nucleotides of the coding sequence.

Sequences suitable for making probes/primers for the detection of their corresponding breast cancer biomarkers include those that are identical or complementary to all or part of genes or SEQ ID NOs described herein. These sequences are all nucleic acid sequences of breast cancer biomarkers.

The use of a probe or primer of between 13 and 100 nucleotides, particularly between 17 and 100 nucleotides in length, or in some aspects up to 1-2 kilobases or more in length, allows the formation of a duplex molecule that is both stable and selective. Molecules having complementary sequences over contiguous stretches greater than 20 bases in length may be used to increase stability and/or selectivity of the hybrid molecules obtained. One may design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

In one embodiment, each probe/primer comprises at least 15 nucleotides. For instance, each probe can comprise at least or at most 20, 25, 50, 75, 100, 125, 150, 175, 200, 225, 250, 275, 300, 325, 350, 400 or more nucleotides (or any range derivable therein). They may have these lengths and have a sequence that is identical or complementary to a gene or SEQ ID NO described herein. Particularly, each probe/primer has relatively high sequence complexity and does not have any ambiguous residue (undetermined "n" residues). The probes/primers can hybridize to the target gene, including its RNA transcripts, under stringent or highly stringent conditions. In some embodiments, because each of the biomarkers has more than one human sequence, it is contemplated that probes and primers may be designed for use with each of these sequences. For example, inosine is a nucleotide frequently used in probes or primers to hybridize to more than one sequence. It is contemplated that probes or primers may have inosine or other design implementations that accommodate recognition of more than one human sequence for a particular biomarker.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

In another embodiment, the probes/primers for a gene are selected from regions which significantly diverge from the sequences of other genes. Such regions can be determined by checking the probe/primer sequences against a human genome sequence database, such as the Entrez database at the NCBI. One algorithm suitable for this purpose is the BLAST algorithm. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence to increase the cumulative alignment score. Cumulative scores are calculated using, for nucleotide sequences, the parameters M (reward score for a pair of matching residues; always >0) and N (penalty score for mismatching residues; always <0). The BLAST algorithm parameters W, T, and X determine the sensitivity and speed of the alignment. These parameters can be adjusted for different purposes, as appreciated by one of ordinary skill in the art.

In one embodiment, quantitative RT-PCR (such as Taq-Man, ABI) is used for detecting and comparing the levels of RNA transcripts in breast cancer samples. Quantitative RT-PCR involves reverse transcription (RT) of RNA to cDNA followed by relative quantitative PCR (RT-PCR). The concentration of the target DNA in the linear portion of the PCR process is proportional to the starting concentration of the target before the PCR was begun. By determining the concentration of the PCR products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived may be determined for the respective tissues or cells. This direct proportionality between the concentration of the PCR products and the relative mRNA abundances is true in the linear range portion of the PCR reaction. The final concentration of the target DNA in the plateau portion of the curve is determined by the availability of reagents in the reaction mix and is independent of the original concentration of target DNA. Therefore, the sampling and quantifying of the amplified PCR products may be carried out when the PCR reactions are in the linear portion of their curves. In addition, relative concentrations of the amplifiable cDNAs may be normalized to some independent standard, which may be based on either internally existing RNA species or externally introduced RNA species. The abundance of a particular mRNA species may also be determined relative to the average abundance of all mRNA species in the sample.

In one embodiment, the PCR amplification utilizes one or more internal PCR standards. The internal standard may be an abundant housekeeping gene in the cell or it can specifically be GAPDH, GUSB and β-2 microglobulin. These standards may be used to normalize expression levels so that the expression levels of different gene products can be compared directly. A person of ordinary skill in the art would know how to use an internal standard to normalize expression levels.

A problem inherent in clinical samples is that they are of variable quantity and/or quality. This problem can be overcome if the RT-PCR is performed as a relative quantitative RT-PCR with an internal standard in which the internal standard is an amplifiable cDNA fragment that is similar or larger than the target cDNA fragment and in which the abundance of the mRNA encoding the internal standard is roughly 5-100 fold higher than the mRNA encoding the target. This assay measures relative abundance, not absolute abundance of the respective mRNA species.

In another embodiment, the relative quantitative RT-PCR uses an external standard protocol. Under this protocol, the PCR products are sampled in the linear portion of their amplification curves. The number of PCR cycles that are optimal for sampling can be empirically determined for each target cDNA fragment. In addition, the reverse transcriptase products of each RNA population isolated from the various samples can be normalized for equal concentrations of amplifiable cDNAs.

Nucleic acid arrays can also be used to detect and compare the differential expression patterns of breast cancer biomarkers in breast cancer cells. The probes suitable for detecting the corresponding breast cancer biomarkers can be stably attached to known discrete regions on a solid substrate. As used herein, a probe is "stably attached" to a discrete region if the probe maintains its position relative to the discrete region during the hybridization and the subsequent washes. Construction of nucleic acid arrays is well known in the art. Suitable substrates for making polynucleotide arrays include, but are not limited to, membranes, films, plastics and quartz wafers.

A nucleic acid array can comprise at least 1, 2, 3, 4, 5, 6, 7, 8, 9, 10, 15, 20, 25, 30, 35, 40, 45, 50, 60, 70, 80, 90, 100, 150, 200, 250 or more different polynucleotide probes, which may hybridize to different and/or the same biomarkers. Multiple probes for the same gene can be used on a single nucleic acid array. Probes for other disease genes can also be included in the nucleic acid array. The probe density on the array can be in any range. In some embodiments, the density may be 50, 100, 200, 300, 400, 500 or more probes/cm$^2$.

Specifically contemplated are chip-based nucleic acid technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al, 1991). It is contemplated that this technology may be used in conjunction with evaluating the expression level of one or more breast cancer biomarkers with respect to diagnostic, prognostic, and treatment methods.

Certain embodiments may involve the use of arrays or data generated from an array. Data may be readily available. Moreover, an array may be prepared in order to generate data that may then be used in correlation studies.

An array generally refers to ordered macroarrays or microarrays of nucleic acid molecules (probes) that are fully or nearly complementary or identical to a plurality of mRNA molecules or cDNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon. Such arrays may vary in a number of different ways, including average probe length, sequence or types of probes, nature of bond between the probe and the array surface, e.g. covalent or non-covalent, and the like. The labeling and screening methods and the arrays are not limited in its utility with respect to any parameter except that the probes detect expression levels; consequently, methods and compositions may be used with a variety of different types of genes.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,525,464; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610; 287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference.

It is contemplated that the arrays can be high density arrays, such that they contain 100 or more different probes. It is contemplated that they may contain 1000, 16,000, 65,000, 250,000 or 1,000,000 or more different probes. The probes can be directed to targets in one or more different organisms. The oligonucleotide probes range from 5 to 50, 5 to 45, 10 to 40, or 15 to 40 nucleotides in length in some embodiments. In certain embodiments, the oligonucleotide probes are 20 to 25 nucleotides in length.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols include information found in WO 9743450; WO 03023058; WO 03022421; WO 03029485; WO 03067217; WO 03066906; WO 03076928; WO 03093810; WO 03100448A1, all of which are specifically incorporated by reference.

In one embodiment, nuclease protection assays are used to quantify RNAs derived from the breast cancer samples. There are many different versions of nuclease protection assays known to those practiced in the art. The common characteristic that these nuclease protection assays have is that they involve hybridization of an antisense nucleic acid with the RNA to be quantified. The resulting hybrid double-stranded molecule is then digested with a nuclease that digests single-stranded nucleic acids more efficiently than double-stranded molecules. The amount of antisense nucleic acid that survives digestion is a measure of the amount of the target RNA species to be quantified. An example of a nuclease protection assay that is commercially available is the RNase protection assay manufactured by Ambion, Inc. (Austin, Tex.).

III. Measurement of Gene Expression Using Proteins and Polypeptides

In other embodiments, the differential expression patterns of breast cancer biomarkers can be determined by measuring the levels of polypeptides encoded by these genes in breast cancer cells. Methods suitable for this purpose include, but are not limited to, immunoassays such as ELISA, RIA, FACS, dot blot, Western Blot, immunohistochemistry, and antibody-based radioimaging. Protocols for carrying out these immunoassays are well known in the art. Other methods such as 2-dimensional SDS-polyacrylamide gel electrophoresis can also be used. These procedures may be used to recognize any of the polypeptides encoded by the breast cancer biomarker genes described herein.

One example of a method suitable for detecting the levels of target proteins in peripheral blood samples is ELISA. In an exemplifying ELISA, antibodies capable of binding to the target proteins encoded by one or more breast cancer biomarker genes are immobilized onto a selected surface exhibiting protein affinity, such as wells in a polystyrene or polyvinylchloride microtiter plate. Then, breast cancer cell samples to be tested are added to the wells. After binding and washing to remove non-specifically bound immunocomplexes, the bound antigen(s) can be detected. Detection can be achieved by the addition of a second antibody which is specific for the target proteins and is linked to a detectable label. Detection may also be achieved by the addition of a second antibody, followed by the addition of a third antibody that has binding affinity for the second antibody, with the third antibody being linked to a detectable label. Before being added to the microtiter plate, cells in the peripheral blood samples can be lysed using various methods known in the art. Proper extraction procedures can be used to separate the target proteins from potentially interfering substances.

In another ELISA embodiment, the breast cancer cell samples containing the target proteins are immobilized onto the well surface and then contacted with the antibodies. After binding and washing to remove non-specifically bound immunocomplexes, the bound antigen is detected. Where the initial antibodies are linked to a detectable label, the immunocomplexes can be detected directly. The immunocomplexes can also be detected using a second antibody that has binding affinity for the first antibody, with the second antibody being linked to a detectable label.

Another typical ELISA involves the use of antibody competition in the detection. In this ELISA, the target proteins are immobilized on the well surface. The labeled antibodies are added to the well, allowed to bind to the target proteins, and detected by means of their labels. The amount of the target proteins in an unknown sample is then determined by mixing the sample with the labeled antibodies before or during incubation with coated wells. The presence of the target proteins in the unknown sample acts to reduce the amount of antibody available for binding to the well and thus reduces the ultimate signal.

Different ELISA formats can have certain features in common, such as coating, incubating or binding, washing to remove non-specifically bound species, and detecting the bound immunocomplexes. For instance, in coating a plate with either antigen or antibody, the wells of the plate can be incubated with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test samples. Examples of these nonspecific proteins include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means can also be used. After binding of a protein or antibody to the well, coating with a non-reactive material to reduce background, and washing to remove unbound material, the immobilizing surface is contacted with the control and/or clinical or biological sample to be tested under conditions effective to allow immunocomplex (antigen/antibody) formation. These conditions may include, for example, diluting the antigens and antibodies with solutions such as BSA, bovine gamma globulin (BGG) and phosphate buffered saline (PBS)/Tween and incubating the antibodies and antigens at room temperature for about 1 to 4 hours or at 49° C. overnight. Detection of the immunocomplex then requires a labeled secondary binding ligand or antibody, or a secondary binding ligand or antibody in conjunction with a labeled tertiary antibody or third binding ligand.

After all of the incubation steps in an ELISA, the contacted surface can be washed so as to remove non-complexed material. For instance, the surface may be washed with a solution such as PBS/Tween, or borate buffer. Following the formation of specific immunocomplexes between the test sample and the originally bound material, and subsequent washing, the occurrence of the amount of immunocomplexes can be determined.

To provide a detecting means, the second or third antibody can have an associated label to allow detection. In one embodiment, the label is an enzyme that generates color development upon incubating with an appropriate chromogenic substrate. Thus, for example, one may contact and incubate the first or second immunocomplex with a urease, glucose oxidase, alkaline phosphatase or hydrogen peroxidase-conjugated antibody for a period of time and under conditions that favor the development of further immunocomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl)-benzhiazoline-6-sulfonic acid (ABTS) and hydrogen peroxide, in the case of peroxidase as the enzyme label. Quantitation can be achieved by measuring the degree of color generation, e.g., using a spectrophotometer.

Another suitable method is RIA (radioimmunoassay). An example of RIA is based on the competition between radiolabeled-polypeptides and unlabeled polypeptides for binding to a limited quantity of antibodies. Suitable radiolabels include, but are not limited to, $I^{125}$. In one embodiment, a fixed concentration of $I^{125}$-labeled polypeptide is incubated with a series of dilution of an antibody specific to the polypeptide. When the unlabeled polypeptide is added to the system, the amount of the I'-polypeptide that binds to the antibody is decreased. A standard curve can therefore be constructed to represent the amount of antibody-bound I'-polypeptide as a function of the concentration of the unlabeled polypeptide. From this standard curve, the concentration of the polypeptide in unknown samples can be determined. Various protocols for conducting RIA to measure the levels of polypeptides in breast cancer cell samples are well known in the art.

Suitable antibodies include, but are not limited to, polyclonal antibodies, monoclonal antibodies, chimeric antibodies, humanized antibodies, single chain antibodies, Fab fragments, and fragments produced by a Fab expression library.

Antibodies can be labeled with one or more detectable moieties to allow for detection of antibody-antigen complexes. The detectable moieties can include compositions detectable by spectroscopic, enzymatic, photochemical, biochemical, bioelectronic, immunochemical, electrical, optical or chemical means. The detectable moieties include, but are not limited to, radioisotopes, chemiluminescent compounds, labeled binding proteins, heavy metal atoms, spectroscopic markers such as fluorescent markers and dyes, magnetic labels, linked enzymes, mass spectrometry tags, spin labels, electron transfer donors and acceptors, and the like.

Protein array technology is discussed in detail in Pandey and Mann (2000) and MacBeath and Schreiber (2000), each of which is herein specifically incorporated by reference. These arrays typically contain thousands of different proteins or antibodies spotted onto glass slides or immobilized in tiny wells and allow one to examine the biochemical activities and binding profiles of a large number of proteins at once. To examine protein interactions with such an array, a labeled protein is incubated with each of the target proteins immobilized on the slide, and then one determines which of the many proteins the labeled molecule binds. In certain embodiments such technology can be used to quantitate a number of proteins in a sample, such as a breast cancer biomarker proteins.

The basic construction of protein chips has some similarities to DNA chips, such as the use of a glass or plastic surface dotted with an array of molecules. These molecules can be DNA or antibodies that are designed to capture proteins. Defined quantities of proteins are immobilized on each spot, while retaining some activity of the protein. With fluorescent markers or other methods of detection revealing the spots that have captured these proteins, protein microarrays are being used as powerful tools in high-throughput proteomics and drug discovery.

The earliest and best-known protein chip is the ProteinChip by Ciphergen Biosystems Inc. (Fremont, Calif.).

The ProteinChip is based on the surface-enhanced laser desorption and ionization (SELDI) process. Known proteins are analyzed using functional assays that are on the chip. For example, chip surfaces can contain enzymes, receptor proteins, or antibodies that enable researchers to conduct protein-protein interaction studies, ligand binding studies, or immunoassays. With state-of-the-art ion optic and laser optic technologies, the ProteinChip system detects proteins ranging from small peptides of less than 1000 Da up to proteins of 300 kDa and calculates the mass based on time-of-flight (TOF).

The ProteinChip biomarker system is the first protein biochip-based system that enables biomarker pattern recognition analysis to be done. This system allows researchers to address important clinical questions by investigating the proteome from a range of crude clinical samples (i.e., laser capture microdissected cells, biopsies, tissue, urine, and serum). The system also utilizes biomarker pattern software that automates pattern recognition-based statistical analysis methods to correlate protein expression patterns from clinical samples with disease phenotypes.

In other aspects, the levels of polypeptides in samples can be determined by detecting the biological activities associated with the polypeptides. If a biological function/activity of a polypeptide is known, suitable in vitro bioassays can be designed to evaluate the biological function/activity, thereby determining the amount of the polypeptide in the sample.

IV. Cancer Therapy

Certain embodiments are directed to methods of treating breast cancer based on the calculated prognosis score of the breast cancer tissue. Any known treatments that are contemplated for treating a triple negative breast cancer can be used (for example, see Andre et al., 2012, which is incorporated herein by reference in its entirety)

In certain aspects, there may be provided methods for treating a subject determined to have cancer and with a predetermined expression profile of one or more biomarkers disclosed herein.

In a further aspect, biomarkers and related systems that can establish a prognosis of cancer patients can be used to identify patients who may get benefit of conventional single or combined modality therapy. In the same way, those patients who do not get much benefit from such conventional single or combined modality therapy can be identified and can be offered alternative treatment(s).

In certain aspects, conventional cancer therapy may be applied to a subject wherein the subject is identified or reported as having a good prognosis based on the assessment of the biomarkers as disclosed. On the other hand, at least an alternative cancer therapy may be prescribed, as used alone or in combination with conventional cancer therapy, if a poor prognosis is determined by the disclosed methods, systems, or kits.

Conventional cancer therapies include one or more selected from the group of chemical or radiation based treatments and surgery. Chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristin, vinblastin and methotrexate, or any analog or derivative variant of the foregoing.

Suitable therapeutic agents include, for example, vinca alkaloids, agents that disrupt microtubule formation (such as colchicines and its derivatives), anti-angiogenic agents, therapeutic antibodies, RKIP pathway targeting agents, tyrosine kinase targeting agent (such as tyrosine kinase inhibitors), serine kinase targeting agents, transitional metal complexes, proteasome inhibitors, antimetabolites (such as nucleoside analogs), alkylating agents, platinum-based agents, anthracycline antibiotics, topoisomerase inhibitors, macrolides, therapeutic antibodies, retinoids (such as all-trans retinoic acids or a derivatives thereof); geldanamycin or a derivative thereof (such as 17-AAG), and other standard chemotherapeutic agents well recognized in the art.

Certain chemotherapeutics are well known for use against breast cancer. These breast cancer chemotherapeutics are capecitabine, carboplatin, cyclophosphamide (Cytoxan), daunorubicin, docetaxel (Taxotere), doxorubicin (Adriamycin), epirubicin (Ellence), fluorouracil (also called 5-fluorouracil or 5-FU), gemcitabine, eribulin, ixabepilone, methotrexate, mitomycin C, mitoxantrone, paclitaxel (Taxol), thiotepa, vincristine, vinorelbine.

In some embodiments, the chemotherapeutic agent is any of (and in some embodiments selected from the group consisting of) adriamycin, colchicine, cyclophosphamide, actinomycin, bleomycin, daunorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof (e.g., paclitaxel and derivatives thereof, taxotere and derivatives thereof, and the like), topetecan, vinblastine, vincristine, tamoxifen, piposulfan, nab-5404, nab-5800, nab-5801, Irinotecan, HKP, Ortataxel, gemcitabine, Herceptin®, vinorelbine, Doxil®, capecitabine, Gleevec®, Alimta®, Avastin®, Velcade®, Tarceva®, Neulasta®, Lapatinib, STI-571, ZD1839, Iressa® (gefitinib), SH268, genistein, CEP2563, SU6668, SU11248, EMD121974, and Sorafenib.

In some embodiments, the chemotherapeutic agent is a composition comprising nanoparticles comprising a thiocolchicine derivative and a carrier protein (such as albumin).

In further embodiments a combination of chemotherapeutic agents is administered to breast cancer cells. The chemotherapeutic agents may be administered serially (within minutes, hours, or days of each other) or in parallel; they also may be administered to the patient in a pre-mixed single composition. Combinations of breast cancer therapeutics include, but are not limited to the following: AT (Adriamycin and Taxotere), AC±T: (Adriamycin and Cytoxan, with or without Taxol or Taxotere), CMF (Cytoxan, methotrexate, and fluorouracil), CEF (Cytoxan, Ellence, and fluorouracil), FAC (fluorouracil, Adriamycin, and Cytoxan), CAF (Cytoxan, Adriamycin, and fluorouracil) (the FAC and CAF regimens use the same medicines but use different doses and frequencies), TAC (Taxotere, Adriamycin, and Cytoxan), and GET (Gemzar, Ellence, and Taxol).

Various combinations of more than an anticancer modality, agent or compound (or a combination of such agents and/or compounds) may be employed, for example, a first anticancer modality, agent or compound is "A" and a second anticancer modality, agent or compound (or a combination of such modalities, agents and/or compounds) given as part of an anticancer therapy regime, is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |

| | | | | | |
|---|---|---|---|---|---|
| A/B/B/A | B/B/A/A | B/A/B/A | B/A/A/B | A/A/A/B | B/A/A/A |
| A/B/A/A | A/A/B/A | | | | |

Administration of the therapeutic compounds or agents to a patient will follow general protocols for the administration of such compounds, taking into account the toxicity, if any, of the therapy. It is expected that the treatment cycles would be repeated as necessary. It also is contemplated that various standard therapies, as well as surgical intervention, may be applied in combination with the described therapy.

The term "a serine/threonine kinase inhibitor", as used herein, relates to a compound which inhibits serine/threonine kinases. An example of a target of a serine/threonine kinase inhibitor includes, but is not limited to, dsRNA-dependent protein kinase (PKR). Examples of indirect targets of a serine/threonine kinase inhibitor include, but are not limited to, MCP-1, NF-kappaB, eIF2alpha, COX2, RANTES, IL8, CYP2A5, IGF-1, CYP2B1, CYP2B2, CYP2H1, ALAS-1, HIF-1, erythropoietin and/or CYP1A1. An example of a serine/theronin kinase inhibitor includes, but is not limited to, Sorafenib and 2-aminopurine, also known as 1H-purin-2-amine (9CI). Sorafenib is marketed as NEXAVAR.

The term "an angiogenesis inhibitor", as used herein, relates to a compound which targets, decreases or inhibits the production of new blood vessels. Targets of an angiogenesis inhibitor include, but are not limited to, methionine aminopeptidase-2 (MetAP-2), macrophage inflammatory protein-1 (MIP-1a), CCL5, TGF-β, lipoxygenase, cyclooxygenase, and topoisomerase. Indirect targets of an angiogenesis inhibitor include, but are not limited to, p21, p53, CDK2 and collagen synthesis. Examples of an angiogenesis inhibitor include, but are not limited to, Fumagillin, which is known as 2,4,6,8-decatetraenedioic acid, mono[3R,4S,5S,6R)-5-methoxy-4-[(2R,3R)-2-methyl-3-(3-methyl-2-butenyl)oxi-ranyl]-1-oxaspiro[2.5]oct-6-yl]ester, (2E,4E,6E,8E)-(9CI); Shikonin, which is also known as 1,4-naphthalenedione, 5,8-dihydroxy-2-[(1R)-1-hydroxy-4-methyl-3-pentenyl]-(9CI); Tranilast, which is also known as benzoic acid, 2-[[3-(3,4-dimethoxyphenyl)-1-oxo-2-propenyl]amino]-(9CI); ursolic acid; suramin; thalidomide and lenalidomide, and marketed as REVLIMID.

Radiation therapy that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Approximately 60% of persons with cancer will undergo surgery of some type, which includes preventative, diagnostic or staging, curative and palliative surgery. Curative surgery is a cancer treatment that may be used in conjunction with other therapies, such as the treatment, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the treatment methods described herein may be used in conjunction with removal of superficial cancers, precancers, or incidental amounts of normal tissue.

Laser therapy is the use of high-intensity light to destroy tumor cells. Laser therapy affects the cells only in the treated area. Laser therapy may be used to destroy cancerous tissue and relieve a blockage in the esophagus when the cancer cannot be removed by surgery. The relief of a blockage can help to reduce symptoms, especially swallowing problems.

Photodynamic therapy (PDT), a type of laser therapy, involves the use of drugs that are absorbed by cancer cells; when exposed to a special light, the drugs become active and destroy the cancer cells. PDT may be used to relieve symptoms of esophageal cancer such as difficulty swallowing.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well. A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg (or any range derivable therein). A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg/kg/day (or any range derivable therein).

Alternative cancer therapy include any cancer therapy other than surgery, chemotherapy and radiation therapy, such as immunotherapy, gene therapy, hormonal therapy or a combination thereof. Subjects identified with poor prognosis using the present methods may not have favorable response to conventional treatment(s) alone and may be prescribed or administered one or more alternative cancer therapy per se or in combination with one or more conventional treatments.

For example, the alternative cancer therapy may be a targeted therapy. The targeted therapy may be a RKIP-targeted treatment. In one embodiment of the method, the RKIP-targeted treatment used is a RKIP protein or expression vector or any agents that inhibits downstream targets (e.g., Let-7 target genes, BACH1, HMGA1, MMP1, CXCR4, OPN) repressed by RKIP activity, such as antibodies that bind to any of these downstream targets. In a further embodiment, the inhibitory antibody is an intact antibody, i.e. a full-length antibody, or a fragment.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Gene therapy is the insertion of polynucleotides, including DNA or RNA, into an individual's cells and tissues to treat a disease. Antisense therapy is also a form of gene therapy. A therapeutic polynucleotide may be administered before, after, or at the same time of a first cancer therapy. Delivery of a vector encoding a variety of proteins is encompassed in certain aspects. For example, cellular expression of the exogenous tumor suppressor oncogenes would exert their function to inhibit excessive cellular proliferation, such as p53, p16 and C-CAM.

Additional agents to be used to improve the therapeutic efficacy of treatment include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with treatment methods described herein to improve the anti-hyperproliferative efficacy of the treatments. Inhibitors of cell adhesion are contemplated to improve the efficacy. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with treatment methods described herein to improve the treatment efficacy.

Hormonal therapy may also be used or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

V. Kits

Certain aspects also encompass kits for performing the diagnostic or therapeutic methods. Such kits can be prepared from readily available materials and reagents. For example, such kits can comprise any one or more of the following materials: enzymes, reaction tubes, buffers, detergent, primers, probes, antibodies. In a particular embodiment, these kits allow a practitioner to obtain samples of neoplastic cells in breast, blood, tears, semen, saliva, urine, tissue, serum, stool, sputum, cerebrospinal fluid and supernatant from cell lysate. In another particular embodiment, these kits include the needed apparatus for performing RNA extraction, RT-PCR, and gel electrophoresis. Instructions for performing the assays can also be included in the kits.

In a particular aspect, these kits may comprise a plurality of agents for assessing the differential expression of a plurality of biomarkers, wherein the kit is housed in a container. The kits may further comprise instructions for using the kit for assessing expression, means for converting the expression data into expression values and/or means for analyzing the expression values to generate prognosis. The agents in the kit for measuring biomarker expression may comprise a plurality of PCR probes and/or primers for qRT-PCR and/or a plurality of antibody or fragments thereof for assessing expression of the biomarkers. In another embodiment, the agents in the kit for measuring biomarker expression may comprise an array of polynucleotides complementary to the mRNAs of the biomarkers. Possible means for converting the expression data into expression values and for analyzing the expression values to generate scores that predict survival or prognosis may be also included.

Kits may comprise a container with a label. Suitable containers include, for example, bottles, vials, and test tubes. The containers may be formed from a variety of materials such as glass or plastic. The container may hold a composition which includes a probe that is useful for prognostic or non-prognostic applications, such as described above. The label on the container may indicate that the composition is used for a specific prognostic or non-prognostic application, and may also indicate directions for either in vivo or in vitro use, such as those described above. The kit may comprise the container described above and one or more other containers comprising materials desirable from a commercial and user standpoint, including buffers, diluents, filters, needles, syringes, and package inserts with instructions for use.

VI. Additional Embodiments

Treatment of a cancer in a subject in need thereof is provided herein, as are compositions, kits, and methods for treating cancer; methods for identifying genes and pathways having a role in the treatment and prognosis of cancer; therapies to treat and identify cancers based on these genes and pathways; and a method for monitoring the effectiveness of a course of treatment for a subject diagnosed cancer. While the present disclosure may be embodied in different forms, several specific embodiments are discussed herein with the understanding that the present disclosure is to be considered only an exemplification and is not intended to limit the invention to the illustrated embodiments.

While not wishing to be bound by theory, we believe we have identified not only an important upstream regulator (HMGA2) of TET1, but also a new downstream regulatory pathway for TET1 involving HOXA genes; we also believe that TET1 and HOXA9 play an important role not only in breast tumor invasion and growth, but also in metastasis via commonly regulated genes. Because HMGA2 is a genomic architectural factor, we also contemplate that HMGA2 might be able to regulate TET1 gene expression by direct binding to the TET1 promoter or alteration of its chromatin structure.

While this work was under completion, it was reported that TET1 inhibits growth and metastasis in prostate and breast cancer (Winter N, Nimzyk R, Bösche C, Meyer A, Bullerdiek J (2011) Chromatin immunoprecipitation to analyze DNA binding sites of HMGA2. PLoS ONE 6(4): e18837). In that report, TET1 was shown to inhibit invasion in culture in part via tissue inhibitors of metalloproteinases (TIMPs). By contrast, we did not observe significant induction of TIMP expression by TET1. Instead, we identified a group of genes commonly altered by HMGA2 depletion or induction of either TET1 or HOXA9, including a subset of induced genes that promote development and a subset of inhibited genes that promote cell proliferation, consistent with a role for TET1/HOXA9 in suppression of breast tumor growth and metastasis.

The TET1/HOXA9 signaling pathway we identify here also highlights the importance of cell context in determining the pathological function of TET1. In contrast to our results for breast cancer, the MLL-TET1 fusion protein and the HOXA9 protein both promote leukemogenesis (See, Hsu C H, et al. (2012) TET1 suppresses cancer invasion by activating the tissue inhibitors of metalloproteinases. Cell Rep 2(3):568-579; Ono R, et al. (2002) LCX, leukemia-associated protein with a CXXC domain, is fused to MLL in acute myeloid leukemia with trilineage dysplasia having t(10;11) (q22;q23). Cancer Res 62(14):4075-4080). Recently, HOX family members were reported to play key roles in regulating tumorigenesis including the epithelial/mesenchymal transition, invasion and apoptosis (Shah N, Sukumar S (2010) The Hox genes and their roles in oncogenesis. Nat Rev Cancer 10(5):361-371). Highly methylated HOXA gene loci have been reported in human breast cancer (Faber J, et al. (2009) HOXA9 is required for survival in human MLL-rearranged acute leukemias. Blood 113(11):2375-2385), although mutations in these genes are not common. Whether these genes function in similar ways or promote different phenotypes is an interesting question that requires further investigation.

Further, in one embodiment, we have identified a gene signature comprising three mechanistically linked genes (HMGA2, TET1, HOXA9) that is prognostic for breast cancer survival and other cancers as well. This signature has the potential to identify subjects harbouring breast or other tumors with suppressed TET1/HOXA9 signaling who might benefit from DNA demethylation agents currently used in the clinic.

Additionally, it is believed that the high mobility group AT-hook 2 (HMGA2), a chromatin-remodeling factor, binds to AT-rich regions in DNA, altering chromatin architecture to either promote or inhibit the action of transcriptional enhancers. HMGA2 is highly expressed in ES cells but is generally low or lacking in normal somatic cells. Interestingly, HMGA2 is highly expressed in most malignant epithelial tumors, including, for example, breast, pancreas, oral squamous cell carcinoma, and non-small-cell lung cancer. HMGA2 overexpression in transgenic mice causes tumor formation, whereas Hmga2-knockout mice have a pygmy phenotype indicative of a growth defect. We have reported that HMGA2 promotes tumor invasion and metastasis in breast cancer in part through regulation of prometastatic genes, including Snail, osteopontin, and CXCR4. To systematically identify critical downstream mediators of HMGA2 that regulate invasion and metastasis, we performed gene expression array analysis by knocking down HMGA2 in breast cancer cells. Here we show that TET1 is an important effecter of HMGA2 in breast cancer. We further show that TET1 regulates homeobox A (HOXA) genes, including HOXA7 and HOXA9. Both TET1 and HOXA9 suppress breast tumor growth and metastasis. Our study reveals a regulatory pathway that stratifies subject survival.

Further, as described more fully herein, we have identified upstream activators and downstream effectors of TET1 in a breast cancer model using human breast cancer cells and a genetically engineered mouse model. We show that depleting the architectural transcription factor HMGA2 induces TET1. TET1 binds and demethylates its own promoter and the promoter of HOXA genes, enhancing its own expression and stimulating expression of HOXA genes including HOXA7 and HOXA9. Both TET1 and HOXA9 suppress breast tumor growth and metastasis in mouse xenografts. The genes comprising the HMGA2-TET1-HOXA9 pathway are believed to be coordinately regulated in breast cancer and together encompass a prognostic signature for subject survival. These results implicate the HMGA2-TET1-HOX signaling pathway in the epigenetic regulation of human breast cancer and highlight the importance of targeting methylation in specific subpopulations as a potential therapeutic strategy.

From our studies, we provide a method for at least one of: determining the progression of a disease and/or a prognosis for survival of a subject diagnosed with cancer; determining the risk of a relapse of cancer in a subject diagnosed with a cancer, and a treatment regimen for cancer in a diagnosed subject. In one embodiment, the method includes: (a) determining the expression levels of at least one of HMGA2, TET1, HOXA7, and HOXA9 in a biological sample obtained from the subject, and (b) comparing the expression levels of HMGA2, TET1, HOXA7, and HOXA9 in the sample to respective reference levels of HMGA2, TET1, HOXA7, and HOXA9 in a control non-disease state sample. When the expression profile in the subject exhibits at least one of: (a) a higher level of HMGA2 expression, (b) a lower level of TET1 expression, (c) a lower level of HOXA7, and (d) a lower level of HOXA9 expression as compare to the respective reference levels, the expression profile correlates with at least one of: (a) decreased survival, (b) poor prognosis, (c) faster progression of the disease, and (d) higher risk of relapse of the cancer in the subject. In one embodiment, the expression profile in the subject has a higher level of HMGA2 expression, a lower level of TET1 expression, a lower level of HOXA7, and a lower level of HOXA9 expression as compared to the reference levels and correlates with a decreased survival rate, a poorer prognosis, a faster progression of the disease, and a higher risk of relapse of the cancer in the subject as compare to a subject exhibiting a different expression profile.

In yet another embodiment, when the expression profile of the subject exhibits at least one of: (a) a lower level of HMGA2 expression, (b) a higher level of TET1 expression, (c) a higher level of HOXA7 expression, and (d) a higher level of HOXA9 expression as compare to the reference levels in a control non-disease state sample, the expression profile correlates with at least one of: (a) increased chance of survival, (b) better prognosis, (c) slower progression of the disease, and (d) lower risk of relapse of the cancer in the subject. In one embodiment, the expression profile in the subject has a lower level of HMGA2 expression, a higher level of TET1 expression, a higher level of HOXA7 expression, and a higher level of HOXA9 expression as compare to the reference levels, the expression profile correlates with an increased chance of survival, a better prognosis, a slower progression of the disease, and a lower risk of relapse of the cancer in the subject. as compare to a subject exhibiting a different expression profile.

In yet another embodiment, a method for stratifying a subject diagnosed with cancer is provided to determine a therapy regimen for the treatment of the cancer. The method comprises: (a) determining the relative and/or absolute expression levels of at least one of HMGA2, TET1, HOXA7, and HOXA9 in a biological sample obtained from the subject; and (b) comparing the levels obtained in step (a) to the relative and/or absolute expression levels of HMGA2, TET1, HOXA7, and/or HOXA9 in a control non-disease state sample.

In one embodiment, the relative and/or absolute expression levels of HMGA2, TET1, HOXA7, and/or HOXA9 in the biological sample obtained from the subject are obtained prior to beginning therapy with the subject or obtained in the early stages of therapy of the subject.

In yet another embodiment, the expression levels of HMGA2, TET1, HOXA7, and/or HOXA9 are determined by quantifying the levels of a functional fragment or variant as is known in the art.

In yet another embodiment, the expression levels of HMGA2, TET1, HOXA7, and/or HOXA9 are determined using primers readily identified by those skilled in the art including, for example, web-based tools such as Primer3 (Untergrasser A, Cutcutache I, Koressaar T, Ye J, Faircloth B C, Remm M, Rozen S G (2012) Primer3—new capabilities and interfaces. Nucleic Acids Research 40(15):e115; Koressaar T, Remm M (2007) Enhancements and modifications of primer design program Primer3Bioinformatics 23(10):1289-91; Source code available on the World Wide Web at sourceforge.net/projects/primer3/). Such primers are also commercially available, including from, for example, Taqman® and Applied Biosystems® from Life Technologies, Inc.

In another embodiment, the expression levels of HMGA2, TET1, HOXA7, and/or HOXA9 are determined immunochemically, for example, using an antibody-based detection system known to those skilled in the art. In one embodiment, the antibody binds specifically to a protein encoded by the respective gene or a fragment thereof.

In still another embodiment, the expression levels of HMGA2, TET1, HOXA7, and/or HOXA9 in the subject are determined by quantifying the respective expression of mRNA encoding HMGA2, TET1, HOXA7, and/or HOXA9 as known in art, or quantifying a nucleic acid comprising a sequence determined by those skilled in the art.

In another embodiment, an increased HMGA2 expression, a lower level of TET1 expression, a lower level of HOXA7, and a lower level of HOXA9 expression in a subject as compared to a control tissue indicates that the subject will likely have decreased survival, poor prognosis, faster progression of the disease, and/or higher risk of relapse, as compared to, for example, a normal non-disease state subject. Such subjects will also benefit from chemotherapy, including a DNA demethylation agent, such as azacitidine or decitabine, or radiotherapy, to treat or alleviate the symptoms and/or severity of the disease. On the other hand, lower level of HMGA2 expression, a higher level of TET1 expression, a higher level of HOXA7 expression, and a higher level of HOXA9 expression in a subject as compared to a control tissue correlates with an increased chance of survival and better prognosis, slower progression of the disease, or lower risk of relapse. In another embodiment, a therapeutic regime to treat a cancer in a subject is determined based on the expression levels of HMGA2, TET1, HOXA7, and/or HOXA9. For example, expression levels are measured before and after a subject is treated with chemotherapy and/or radiotherapy. If a lower level of HMGA2 expression, and a higher level of TET1, HOXA7, and HOXA9 expression are detected in the subject post-treatment, continued dosing of the subject with the chemotherapy or radiotherapy is desirable and/or recommended. If little or no difference in post-therapy expression levels are detected, alternate therapeutic regimes should be utilized until the subject positively responds to treatment indicated by a decreased level of HMGA2 expression and higher levels of TET1, HOXA7, and/or HOXA9 expression. It is contemplated that the expression level profiles required to effectively treat a particular cancer are subject and/or cancer type and/or stage related. In some instances, a complete shut down (0% expression as compared to a control) in expression of HMGA2 may be required to effectuate treatment, while in other instances, the level may be about 5%, 10%, 20%, 30% 40%, 50%, 60% 70%, 80% or 90% of the control and beneficial results of a therapeutic regime may be seen in a subject. In most circumstance, however, it is believed that a reduction of HMGA2 expression of about 20% will result in the desired therapeutic result. Likewise, a small increase in expression of TET1, HOXA7, and/or HOXA9 may have the required therapeutic effect in certain subjects, while in others it may require an increase of about 5%, 10%, 20%, 30% 40%, 50%, 60% 70%, 80%, 90%, 100% or 200% or more in expression levels of one or more of these genes to show the desired therapeutic effect in the subject. As above, in most circumstance, it is believed that an increase in expression of TET1, HOXA7, and/or HOXA9 of about 20%, respectively, will result in the desired therapeutic result. Therapeutic effects and the prognosis, progression and/or regression of the cancer can be determined by those skilled in the art.

Expression levels in a subject can be measured in cells of a biological sample obtained from the subject by methods known to those skilled in the art. For example, a tissue sample can be removed from a subject by conventional biopsy techniques. In another example, a body fluid sample, such as a lymph, blood or serum sample, or an exudate fluid sample such as a cancerous organ exudate (for example, exudate from the breast) may be used as the sample. A blood sample can be removed from the subject and white blood cells can be isolated for DNA extraction by standard techniques. The fluid or tissue sample obtained from the subject can be done prior to the initiation of radiotherapy, chemotherapy or other therapeutic treatment. A corresponding control tissue or blood sample can be obtained from unaffected or non-disease state tissues of the subject, from a normal (non-disease or non-cancerous) subject or population of normal subjects, or from cultured cells corresponding to the majority of cells in the subject's sample. The control tissue or blood sample is then processed along with the sample from the subject, so that the levels of expression in cells from the subject's sample can be compared to the corresponding expression levels from cells of the control sample.

The level of a gene product in a sample can be measured using any technique that is suitable for detecting RNA expression levels in a biological sample. Suitable techniques for determining RNA expression levels in cells from a biological sample are well known to those of skill in the art, including, for example, Northern blot analysis, RT-PCR, in situ hybridization. In one embodiment, the level of gene product is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labelled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

Once the gene expression level of a sample in a subject is measured, the survival, prognosis, progression of the disease, and risk of relapse of the subject can be determined by comparing the gene expression of the sample of the reference control sample (i.e., disease free). As used herein, when the level of expression in the sample is greater than that of the control sample, the expression is termed "up-regulated." When the level of expression in the sample is less than that of the control sample, the expression is termed "down-regulated." In one embodiment, the HMGA2 expression level in the sample is greater than the level of corresponding HMGA2 expression in the control sample, that is, the HMGA2 expression in the sample is "up-regulated." In yet another embodiment, at least one expression level of TET1, HOXA7, and HOXA9 in the sample is less than the level of the corresponding TET1, HOXA7, and HOXA9 expression level in the control sample, that is the expression level of the TET1, HOXA7, and HOXA9 in the sample is "down-regulated." When the HMGA2 expression is up-regulated and the TET1, HOXA7, and/or HOXA9 expression levels are down-regulated in the subject's test sample, the subject will likely experience a decreased survival rate, a poor prognosis, a faster progression of the disease, and/or higher risk of relapse. However, if the HMGA2 expression is down-regulated, and the TET1, HOXA7, and/or HOXA9 expression levels are up-regulated in the subject's test sample, the subject will likely experience an increased chance of survival a better prognosis, a slower progression of the disease, and/or a lower risk of relapse.

In one embodiment, a kit is provided to determine the levels of HMGA2, TET1, HOXA7, and/or HOXA9 expression in the sample of a subject. Such a kit may include a reagent for detecting either the DNA encoding HMGA2, TET1, HOXA7, and/or HOXA9, the mRNA encoding HMGA2, TET1, HOXA7, and/or HOXA9, the HMGA2, TET1, HOXA7, and/or HOXA9 polypeptides, or any combination thereof. The reagent may include one or more molecules capable of specifically binding a nucleic acid sequence (DNA or RNA) encoding HMGA2, TET1, HOXA7, and/or HOXA9, or the HMGA2, TET1, HOXA7, and/or HOXA9 polypeptides.

The kit may include one or more nucleic acid reagents for the detection of either DNA encoding HMGA2, TET1, HOXA7, and/or HOXA9, mRNA encoding HMGA2, TET1, HOXA7, and/or HOXA9, or both. The one or more nucleic acid reagents may be used for hybridization or amplification with the DNA and/or mRNA encoding HMGA2, TET1, HOXA7, and/or HOXA9. The kit may include one or more pairs of primers for amplifying the DNA and/or mRNA encoding HMGA2, TET1, HOXA7, and/or HOXA9. The kit may further include samples of total mRNA derived from tissue of various physiological states, such as normal, and metastatically progressive tumor, for example, to be used as controls. The kit may also include buffers, nucleotide bases, and other compositions to be used in hybridization and/or amplification reactions. Each solution or composition may be contained in a vial or bottle and all vials held in close confinement in a box for commercial sale. Another embodiment of the present invention encompasses a kit for use in detecting the DNA and/or mRNA encoding HMGA2, TET1, HOXA7, and/or HOXA9 in cancer cells in a biological sample that includes oligonucleotide probes effective to bind with high affinity to DNA and/or mRNA encoding HMGA2, TET1, HOXA7, and/or HOXA9 in vitro or in situ and containers for each of these probes.

In a further embodiment, a kit is provided for use in determining the level of HMGA2, TET1, HOXA7, and/or HOXA9 expression in a biological sample that includes one or more agents, such as, for example, one or more antibodies, specific for one or more HMGA2, TET1, HOXA7, and/or HOXA9 polypeptides. In one particular embodiment, the kit will include one or more agents and one or more nucleic acid markers wherein the agents and nucleic acid markers are modified in a fashion appropriate for carrying out immuno-polymerase chain reaction assays.

In another embodiment, a kit is provided for determining a prognosis for survival for a subject with cancer, characterized in that the kit includes compounds capable of detecting the levels of HMGA2, TET1, HOXA7, and/or HOXA9 expression in a biological sample. In a further embodiment, such compounds may be hydrolysis probes targeting any of SEQ ID NO:1-22 for determining HMGA2, TET1, HOXA7, and/or HOXA9 expression. In a further embodiment, the kit may be adapted for RT-PCR and where the kit includes primers amplifying any one or more of SEQ ID NO:1-22. In a further embodiment, such compounds may be one or more antibodies, for example a polyclonal antibody or a monoclonal antibody, wherein the antibody interacts with one of the HMGA2, TET1, HOXA7, or HOXA9 polypeptides. In a further embodiment, a kit is provided for measuring HMGA2, TET1, HOXA7, and/or HOXA9 expression by a DNA, RNA, or protein array.

One embodiment of the invention is directed to a kit for determining the levels of HMGA2, TET1, HOXA7, and/or HOXA9 expression in a mammalian biological sample, there the levels of HMGA2, TET1, HOXA7, and/or HOXA9 expression is an indicator of the prognosis of a cancer, such as breast cancer. The kit includes: a) one or more antibodies that specifically bind to the HMGA2, TET1, HOXA7, or HOXA9 polypeptides or antigen binding fragments thereof, b) a reagent useful for detecting the extent of interaction between the antibody(ies) and HMGA2, TET1, HOXA7, or HOXA9 polypeptides; c) one or more reagents or solutions useful for antigen retrieval; and c) positive and/or negative control samples. The antibody may be directly linked to an indicator reagent, where the indicator reagent may include one or more fluorescent, colorimetric, immunoperoxidase and isotopic reagents. Alternatively, the kit may further include a second indicator antibody linked to an indicator reagent, where the indicator reagent may include one or more fluorescent, calorimetric, immunoperoxidase and isotopic reagents.

In one embodiment, the kit contains at least one primary antibody (e.g., anti-HMGA2, TET1, HOXA7, or HOXA9 monoclonal antibodies), at least one labeled secondary antibody (e.g., anti-human HMGA2, TET1, HOXA7, or HOXA9 polyclonal antibodies labeled with a detection enzyme such as HRP), and at least one substrate (e.g., TMB). Alternatively, the kits can contain radiolabeled secondary antibody in place of the secondary antibody labelled with an enzyme. The kits may also contain disposable supplies for carrying out detection assays (e.g., microtiter plates, pipettes).

A kit is also provided for use in treating a cancer in a subject, and/or determining prognosis or survival, progression of, or stratification of a subject diagnosed with cancer. The kit may include, for example, compounds capable of detecting the levels of expression levels of HMGA2, TET1, HOXA7, and HOXA9 in a biological sample obtained from a subject diagnosed with cancer; supplies to take a sample from a subject; and/or instructions for us.

A kit may also include an agent that induces the expression of at least one of TET1 or HOXA9 in the subject and/or an agent that regulates the HMGA2/TET1/HOXA pathway directed at one or more targets as identified by the present disclosure. It is envisioned that a particular kit may be designed for a particular type of cancer and/or a specific tissue. The kit may further include means for administering the agent to a subject in need thereof. In addition, the kit may also include one or more chemotherapeutic and radiotherapeutic agents directed at the specific type of cancer against which the kit is directed.

Kits may further be a packaged collection of related materials, including, for example, a single and/or a plurality of dosage forms each approximating an therapeutically effective amount of an active ingredient, such as, for example, an expression inhibitor and/or a pharmaceutical compound as described herein that slows, stops, or reverses the growth or proliferation of a tumor or cancer or kills tumor or cancer cells, and/or an additional drug. The included dosage forms may be taken at one time, or at a prescribed interval. Contemplated kits may include any combination of dosage forms.

Conveniently, HMGA2, TET1, HOXA7, and/or HOXA9 expression may be evaluated using a kit including at least one probe suitable for detecting one or more HMGA2, TET1, HOXA7, and/or HOXA9 markers. As used herein, a probe may include any molecule capable of detecting an HMGA2, TET1, HOXA7, and/or HOXA9 marker, including, but not limited to, monoclonal and polyclonal antibodies and oligonucleotides. For example, the kit may include an antibody specific for an epitope of any of the HMGA2, TET1, HOXA7, and/or HOXA9 proteins encoded by any of the HMGA2, TET1, HOXA7, and/or HOXA9 genes, an oligonucleotide probe complementary to at least a portion of any of the HMGA2, TET1, HOXA7, and/or HOXA9 genes or to at least a portion an RNA (e.g., mRNA) encoded by any of the HMGA2, TET1, HOXA7, and/or HOXA9 genes, or primer pairs suitable for evaluating HMGA2, TET1, HOXA7, and/or HOXA9 gene expression by a polymerase chain reaction (PCR)-based method, such as real time PCR or reverse transcription PCR. Other methodologies for measuring expression of an HMGA2, TET1, HOXA7, and/or HOXA9 marker may include ribonuclease protection assay, S1 nuclease assay, and Northern blot analysis. Optionally, the kits may include instructions for detecting HMGA2, TET1, HOXA7, and/or HOXA9 detection or for performing the methods of the invention.

The kit may include a microarray that may be used to determine expression of at least one HMGA2, TET1, HOXA7, and/or HOXA9 marker by a tumor sample and instructions for analyzing the information for use in the methods of the invention. The microarray includes at least one oligonucleotide complementary to a sequence of at least one of SEQ ID NO:1-22. Preferably, the microarray includes a set of oligonucleotides complementary to a set of at least one each of the HMGA2, TET1, HOXA7, and/or HOXA9 sequences selected from SEQ ID NO:1-22. The term "microarray" refers to an ordered arrangement of hybridizable array elements, e.g. oligonucleotide probes, on a substrate, e.g. glass slide or silica. Illustratively, the microarray includes control probes to allow for detection of expression levels that can be used in TSP classifiers to determine HMGA2, TET1, HOXA7, and/or HOXA9 status.

Although not wishing to be bound by theory, it is believed that the agent depletes transcription factor HMGA2 in the subject when provided in an amount that induces TET1 expression. It is further believed that the TET1 binds and demethylates its own promoter and a promoter of HOXA genes. The TET1 expression and/or HOXA9 expression in the subject is therefore enhanced or stimulated. Illustratively, an amount of the agent administered to the subject is in an amount that suppresses cancer tumor growth or metastasis in the subject as determined by those skilled in the art and described herein. It is also contemplated that such agent(s) can be administered as pharmaceutical compositions in therapeutically effective amounts to subject, and if desired and/or beneficial, in combination with one or more other chemotherapeutic and radiotherapeutic agents, or as part of a kit as described herein. It is further contemplated that a method of treating a cancer in a subject can be provided by administering a therapeutically effective amount of an agent that at least one of: (a) induces the expression (up-regulates) of at least one of TET1, HOXA7, and HOXA9 in the subject, or (b) down-regulates HMGA2 expression in the subject. In one embodiment, the agent induces the expression TET1 in the subject. In yet another embodiment, the agent induces the expression of HOXA7 in the subject. In still another embodiment, the agent induces the expression of HOXA9 in the subject. In another embodiment the agent down-regulates HMGA2 expression in the subject. In one embodiment, the subject experiences at least one of an increased chance of survival, a better prognosis, a slower progression of the disease, and/or a lower risk of relapse after the agent that resulted in the desired up-regulation of TET1, HOXA7, and/or HOXA9, and/or the desired down-regulation of HMGA2 is administered to the subject. In one embodiment, the prognosis of the subject is determined about 12, 24, 36, 48, 72, 96, 120, or 144 hours after the agent is initially administered to the subject, or about 1, 2, 3, or 4 weeks after the agent is initially administered to the subject.

Examples of agents useful in the present disclosure that down-regulate HMGA2 include: 1) panobinostat (LBH-589, Novartis, CAS 404950-80-7 (U.S. Pat. No. 7,067,551)), and 2) microRNA let-7. Panobinostat is a pan-deacetylase inhibitor and has recently been described by Di Fazio, et al., Exp Cell Res. 2012 Sep. 10; 318(15):1832-43. doi: 10.1016/j.yexcr.2012.04.018. Epub 2012 Jun. 8. Downregulation of HMGA2 by the pan-deacetylase inhibitor panobinostat is dependent on hsa-let-7b expression in liver cancer cell lines. MicroRNA let-7 and has been described by Liu Qi, et al. (See Liu Qi, et al., Histopathology. 2014 Feb. 26. doi: 10.1111/his.12401. [Epub ahead of print] HMGA2 is down-regulated by microRNA let-7 and associated with epithelial-mesenchymal transition in oesophageal squamous cell carcinomas of Kazakhs.).

It is also believed that HOXA9 expression is regulated by several genes, including UTX (Ubiquitously transcribed tetratricopeptide repeat, X chromosome), WHSC1 (Wolf-Hirschhorn syndrome candidate 1), MLL (Myeloid/lymphoid or mixed-lineage leukemia) and MEN1 (Multiple endocrine neoplasia I). It is contemplated that an agent that regulates one or more of these genes that results in the up-regulation of HOXA9 are also useful in the present disclosure. Similarly, it is believed that one or more genes regulate the expression of TET1 and/or HOXA7 and can also be identified by those skilled in the art. Agents that target such genes that result in upregulation of TET1 and/or HOXA7 are also useful in the present disclosure. Combinations of gene regulatory agents can also be used in the present disclosure.

As used herein, the term "cancer" refers to a class of diseases of mammals characterized by uncontrolled cellular growth. The term "cancer" is used interchangeably with the terms "tumor," "solid tumor," "malignancy," "hyperproliferation" and "neoplasm." Cancer includes all types of hyperproliferative growth, hyperplasic growth, neoplastic growth, cancerous growth or oncogenic processes, metastatic tissues or malignantly transformed cells, tissues, or organs, irrespective of histopathologic type or stage of invasiveness. Illustrative examples include, lung, prostate, head and neck, breast and colorectal cancer, melanomas and gliomas (such as a high grade glioma, including glioblastoma multiforme (GBM), the most common and deadliest of malignant primary brain tumors in adult humans).

As used herein, the phrase "solid tumor" includes, for example, lung cancer, head and neck cancer, brain cancer, oral cancer, colorectal cancer, breast cancer, prostate cancer, pancreatic cancer, and liver cancer. Other types of solid tumors are named for the particular cells that form them, for example, sarcomas formed from connective tissue cells (for example, bone cartilage, fat), carcinomas formed from epithelial tissue cells (for example, breast, colon, pancreas) and lymphomas formed from lymphatic tissue cells (for example, lymph nodes, spleen, thymus). Treatment of all types of solid tumors regardless of naming convention is within the scope of this invention.

As used herein, the phrases "chemotherapeutic agent," "cytotoxic agent," "anticancer agent," "antineoplastic agent" and "antitumor agent" are used interchangeably and refer to an agent that has the effect of inhibiting the growth or proliferation, or inducing the killing, of a tumor or cancer cell. The chemotherapeutic agent may inhibit or reverse the development or progression of a tumor or cancer, such as for example, a solid tumor.

As used herein, the term "chemotherapy" refers to administration of at least one chemotherapeutic agent to a subject having a tumor or cancer.

An illustrative antineoplastic agent or chemotherapeutic agent includes, a DNA demethylation agent, such as, for example, azacitidine (Vidaza®, Celgene Corporation, CAS 310-6702) or decitabine (Dacogen®, Eisai, Inc., CAS 2353-33-5). Another example is a standard taxane. Taxanes are produced by the plants of the genus Taxus and are classified as diterpenes and widely uses as chemotherapy agents including, for example, paclitaxel, (Taxol®, Bristol-Meyers Squibb, CAS 33069-62-4) and docetaxel (Taxotere®, Sanofi-Aventis, CAS 114977-28-5). Other chemotherapeutic agents include semi-synthetic derivatives of a natural taxoid such as cabazitaxel (Jevtana®, Sanofi-Aventis, CAS 183133-96-2). Other chemotherapeutic agents also include an androgen receptor inhibitor or mediator. Illustrative androgen receptor inhibitors include, a steroidal antiandrogen (for example, cypterterone, CAS 2098-66-0); a non-steroidal antiandrogen (for example, flutamide, Eulexin®, Schering-Plough, CAS 13311-84-7); nilutamide (Nilandron®, CAS 63612-50-0); enzalutamide (Xtandi®, Medivation®, CAS 915087-33-1); bicalutamide (Casodex, AstraZeneca, CAS 903 57-06-5); a peptide antiandrogen; a small molecule antiandrogen (for example, RU58642 (Roussel-Uclaf SA, CAS 143782-63-2); LG120907 and LG105 (Ligand Pharmaceuticals); RD162 (Medivation, CAS 915087-27-3); BMS-641988 (Bristol-Meyers Squibb, CAS 573738-99-5); and CH5137291(Chugai Pharmaceutical Co. Ltd., CAS 104344603904)); a natural antiandrogen (for example, ataric acid (CAS 4707-47-5) and N-butylbensensulfonamide (CAS 3622-84-2); a selective androgen receptor modulator (for example, enobosarm (Ostarine®, Merck & Company, CAS 841205-47-8); BMS-564,929 (Bristol-Meyer Squibb, CAS 627530-84-1); LGD-4033 (CAS 115910-22-4); AC-262,356 (Acadia Pharmaceuticals); LGD-3303 (Ganolix Lifescience Co., Ltd., 9-chloro-2-ethyl-1-methyl-3-(2,2,2-trifluoroethyl)-3H-pyrrolo[3,2-f]quinolin-7(6H)-one; S-40503, Kaken Pharmaceuticals, 2-[4-(dimethylamino)-6-nitro-1,2,3,4-tetrahydroquinolin-2-yl]-2-methylpropan-1-ol); andarine (GTx-007, S-4, GTX, Inc., CAS 401900-40-1); and S-23 (GTX, Inc., (2S)—N-(4-cyano-3-trifluoromethyl-phenyl)-3-(3-fluoro-4-chlorophenoxy)-2-hydroxy-2-methyl-propanamide)); or those described in U.S. Patent Appln. No. 2009/0304663. Other neoplastic agents or chemotherapeutic agents that may be used include, for example: alkylating agents such as nitrogen mustards such as mechlorethamine (HN2), cyclophosphamide, ifosfamide, melphalan (L-sarcolysin) and chlorambucil; ethylenimines and methylmelamines such as hexamethylmelamine, thiotepa; alkyl sulphonates such as busulfan; nitrosoureas such as carmustine (BCNU), lomustine (CCNU), semustine (methyl-CCNU) and streptozocin (streptozotocin); and triazenes such as decarbazine (DTIC; dimethyltriazenoimidazole-carboxamide); antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside; and purine analogues and related inhibitors such as mercaptopurine (6-mercaptopurine; 6-MP), thioguanine (6-thioguanine; TG) and pentostatin (2'-deoxycoformycin); natural products including vinca alkaloids such as vinblastine (VLB) and vincristine; epipodophyllotoxins such as etoposide and teniposide; antibiotics such as dactinomycin (actinomycin D), daunorubicin (daunomycin; rubidomycin), doxorubicin, bleomycin, plicamycin (mithramycin) and mitomycin (mitomycin C); enzymes such as L-asparaginase; biological response modifiers such as interferon alphenomes; other agents such as platinum coordination complexes such as cisplatin (cis-DDP) and carboplatin; anthracenedione such as mitoxantrone and anthracycline; substituted urea such as hydroxyurea; methyl hydrazine derivative such as procarbazine (N-methylhydrazine, MTH); adrenocortical suppressant such as mitotane (o,p'-DDD) and aminoglutethimide; taxol analogues/derivatives; hormone agonists/antagonists such as flutamide and tamoxifen; and GnRH and analogues thereof. Examples of other chemotherapeutic can be found in Cancer Principles and Practice of Oncology by V. T. Devita and S. Hellman (editors), 6.sup.th edition (Feb. 15, 2001), Lippincott Williams & Wilkins Publishers.

As used herein, the term "radiotherapy" refers to administration of at least one "radiotherapeutic agent" to a subject having a tumor or cancer and refers to any manner of treatment of a tumor or cancer with a radiotherapeutic agent. A radiotherapeutic agent includes, for example, ionizing radiation including, for example, external beam radiotherapy, stereotatic radiotherapy, virtual simulation, 3-dimensional conformal radiotherapy, intensity-modulated radiotherapy, ionizing particle therapy and radioisotope therapy.

Radiotherapy is based on ionizing radiation delivered to a target area that results in death of reproductive tumor cells. Some examples of radiotherapy include the radiation of cesium, palladium, iridium, iodine, or cobalt and is usually delivered as ionizing radiation delivered from a linear accelerator or an isotopic source such as a cobalt source. Also variations on linear accelerators are Cyberkine and Tomotherapy. Particle radiotherapy from cyclotrons such as Protons or Carbon nuclei may be employed. Also radioisotopes delivered systemically such as p32 or radium 223 may be used. The external radiotherapy may be systemic radiation in the form of sterotacktic radiotherapy total nodal radiotherapy or whole body radiotherapy but is more likely focused to a particular site, such as the location of the tumor or the solid cancer tissues (for example, abdomen, lung, liver, lymph nodes, head, etc.). The radiation dosage regimen is generally defined in terms of Gray or Sieverts time and fractionation, and must be carefully defined by the radiation oncologist. The amount of radiation a subject receives will depend on various consideration but the two important considerations are the location of the tumor in relation to other critical structures or organs of the body, and the extent to which the tumor has spread. One illustrative course of treatment for a subject undergoing radiation therapy is a treatment schedule over a 5 to 8 week period, with a total dose of 50 to 80 Gray (Gy) administered to the subject in a single daily fraction of 1.8 to 2.0 Gy, 5 days a week. A Gy is an abbreviation for Gray and refers to 100 rad of dose.

Radiotherapy can also include implanting radioactive seeds inside or next to an site designated for radiotherapy and is termed brachytherapy (or internal radiotherapy, endo-curietherapy or sealed source therapy). For prostate cancer, there are currently two types of brachytherapy: permanent and temporary. In permanent brachytherapy, radioactive (iodine-125 or palladium-103) seeds are implanted into the prostate gland using an ultrasound for guidance. Illustratively, about 40 to 100 seeds are implanted and the number and placement are generally determined by a computer-generated treatment plan known in the art specific for each subject. Temporary brachytherapy uses a hollow source placed into the prostate gland that is filled with radioactive material (iridium-192) for about 5 to about 15 minutes, for example. Following treatment, the needle and radioactive material are removed. This procedure is repeated two to three times over a course of several days.

Radiotherapy can also include radiation delivered by external beam radiation therapy (EBRT), including, for example, a linear accelerator (a type of high-powered X-ray machine that produces very powerful photons that penetrate deep into the body); proton beam therapy where photons are derived from a radioactive source such as iridium-192, caesium-137, radium-226 (no longer used clinically), or colbalt-60; Hadron therapy; multi-leaf collimator (MLC); and intensity modulated radiation therapy (IMRT). During this type of therapy, a brief exposure to the radiation is given for a duration of several minutes, and treatment is typically given once per day, 5 days per week, for about 5 to 8 weeks. No radiation remains in the subject after treatment. There are several ways to deliver EBRT, including, for example, three-dimensional conformal radiation therapy where the beam intensity of each beam is determined by the shape of the tumor. Illustrative dosages used for photon based radiation is measured in Gy, and in an otherwise healthy subject (that is, little or no other disease states present such as high blood pressure, infection, diabetes, etc.) for a solid epithelial tumor ranges from about 60 to about 80 Gy, and for a lymphoma ranges from about 20 to about 40 Gy. Illustrative preventative (adjuvant) doses are typically given at about 45 to about 60 Gy in about 1.8 to about 2 Gy fractions for breast, head, and neck cancers.

When radiation therapy is a local modality, radiation therapy as a single line of therapy is unlikely to provide a cure for those tumors that have metastasized distantly outside the zone of treatment. Thus, the use of radiation therapy with other modality regimens, including chemotherapy, have important beneficial effects for the treatment of metastasized cancers.

Radiation therapy has also been combined temporally with chemotherapy to improve the outcome of treatment. There are various terms to describe the temporal relationship of administering radiation therapy and chemotherapy, and the following examples are illustrative treatment regimens and are generally known by those skilled in the art and are provided for illustration only and are not intended to limit the use of other combinations. "Sequential" radiation therapy and chemotherapy refers to the administration of chemotherapy and radiation therapy separately in time in order to allow the separate administration of either chemotherapy or radiation therapy. "Concomitant" radiation therapy and chemotherapy refers to the administration of chemotherapy and radiation therapy on the same day. Finally, "alternating" radiation therapy and chemotherapy refers to the administration of radiation therapy on the days in which chemotherapy would not have been administered if it were given alone.

It should be noted that other therapeutically effective doses of radiotherapy can be determined by a radiation oncologist skilled in the art and can be based on, for example, whether the subject is receiving chemotherapy, if the radiation is given before or after surgery, the type and/or stage of cancer, the location of the tumor, and the age, weight and general health of the subject.

Compositions herein may be formulated for oral, rectal, nasal, topical (including buccal and sublingual), transdermal, vaginal, injection/injectable, and/or parental (including subcutaneous, intramuscular, intravenous, and intradermal) administration. Other suitable administration routes are incorporated herein. The compositions may be presented conveniently in unit dosage forms and may be prepared by any methods known in the pharmaceutical arts. Examples of suitable drug formulations and/or forms are discussed in, for example, Hoover, John E. Remington's Pharmaceutical Sciences, Mack Publishing Co., Eston, Pa.; 18.sup.th edition (1995); and Liberman, H. A. and Lachman, L. Eds., Pharmaceutical Dosage Forms, Marcel Decker, New York, N.Y., 1980. Illustrative methods include the step of bringing one or more active ingredients into association with a carrier that constitutes one or more accessory ingredients. In general, the compositions may be prepared by bringing into association uniformly and intimately one or more active ingredients with liquid carriers or finely divided solid carriers or both, and then, if necessary, shaping the product.

Pharmaceutical formulations may include those suitable for oral, intramuscular, rectal, nasal, topical (including buccal and sub-lingual), vaginal or parenteral (including intramuscular, subcutaneous and intravenous) administration or in a form suitable for administration by inhalation or insufflation. One or more of the compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

A salt may be a pharmaceutically suitable (i.e., pharmaceutically acceptable) salt including, but not limited to, acid addition salts formed by mixing a solution of the instant compound with a solution of a pharmaceutically acceptable acid. A pharmaceutically acceptable acid may be, for example, hydrochloric acid, methanesulphonic acid, fumaric acid, maleic acid, succinic acid, acetic acid, benzoic acid, oxalic acid, citric acid, tartaric acid, carbonic acid or phosphoric acid.

Suitable pharmaceutically-acceptable salts may further include, but are not limited to salts of pharmaceutically-acceptable inorganic acids, including, for example, sulfuric, phosphoric, nitric, carbonic, boric, sulfamic, and hydrobromic acids, or salts of pharmaceutically-acceptable organic acids such propionic, butyric, maleic, hydroxymaleic, lactic, mucic, gluconic, benzoic, succinic, phenylacetic, toluenesulfonic, benzenesulfonic, salicyclic sulfanilic, aspartic, glutamic, edetic, stearic, palmitic, oleic, lauric, pantothenic, tannic, ascorbic, and valeric acids.

Various pharmaceutically acceptable salts include, for example, the list of FDA-approved commercially marketed salts including acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, mitrate, pamoate, pantothenate, phosphate, diphosphate, polygalacturonate, salicylate, stearate, subacetate, succinate, sulfate, tannate, tartrate, teoclate, and triethiodide.

A hydrate may be a pharmaceutically suitable (i.e., pharmaceutically acceptable) hydrate that is a compound formed by the addition of water or its elements to a host molecule (for example, the free form version of the compound) including, but not limited to, monohydrates, dihydrates, etc. A solvate may be a pharmaceutically suitable (i.e., pharmaceutically acceptable) solvate, whereby solvation is an interaction of a solute with a solvent that leads to stabilization of the solute species in a solution, and whereby the solvated state is an ion in a solution complexed by solvent molecules. Solvates and hydrates may also be referred to as "analogues."

A prodrug may be a compound that is pharmacologically inert but is converted by enzyme or chemical action to an active form of the drug (i.e., an active pharmaceutical ingredient) at or near the predetermined target site. In other words, prodrugs are inactive compounds or partially active compounds that yield an active compound upon metabolism in the body, which may or may not be enzymatically controlled. Prodrugs may also be broadly classified into two groups: bioprecursor and carrier prodrugs. Prodrugs may also be subclassified according to the nature of their action. Bioprecursor prodrugs are compounds that already contain the embryo of the active species within their structure, whereby the active species are produced upon metabolism.

Carrier prodrugs are formed by combining the active drug (e.g., active ingredient) with a carrier species forming a compound having desirable chemical and biological characteristics, whereby the link is an ester or amide so that the carrier prodrug is easily metabolized upon absorption or delivery to the target site. For example, lipophilic moieties may be incorporated to improve transport through membranes. Carrier prodrugs linked by a functional group to carrier are referred to as bipartite prodrugs. Prodrugs where the carrier is linked to the drug by a separate structure are referred to as tripartite prodrugs, whereby the carrier is removed by an enzyme-controlled metabolic process, and whereby the linking structure is removed by an enzyme system or by a chemical reaction. A hydroxy-protecting group includes, for example, a tert-butyloxy-carbonyl (t-BOC) and t-butyl-dimethyl-silyl (TBS). Other hydroxy protecting groups contemplated are known in the art.

In another embodiment, a dosage form and/or composition may include one or more active metabolites of the active ingredients in place of or in addition to the active ingredients disclosed herein.

Dosage form compositions containing the active ingredients may also contain one or more inactive pharmaceutical ingredients such as diluents, solubilizers, alcohols, binders, controlled release polymers, enteric polymers, disintegrants, excipients, colorants, flavorants, sweeteners, antioxidants, preservatives, pigments, additives, fillers, suspension agents, surfactants (for example, anionic, cationic, amphoteric and nonionic), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b) (7). Alcohol is a good example of an ingredient that may be considered either active or inactive depending on the product formulation.

As used herein, an oral dosage form may include capsules (a solid oral dosage form consisting of a shell and a filling, whereby the shell is composed of a single sealed enclosure, or two halves that fit together and which are sometimes sealed with a band and whereby capsule shells may be made from gelatin, starch, or cellulose, or other suitable materials, may be soft or hard, and are filled with solid or liquid ingredients that can be poured or squeezed), capsule or coated pellets (solid dosage form in which the drug is enclosed within either a hard or soft soluble container or "shell" made from a suitable form of gelatin; the drug itself is in the form of granules to which varying amounts of coating have been applied), capsule coated extended release (a solid dosage form in which the drug is enclosed within either a hard or soft soluble container or "shell" made from a suitable form of gelatin; additionally, the capsule is covered in a designated coating, and which releases a drug or drugs in such a manner to allow at least a reduction in dosing frequency as compared to that drug or drugs presented as a conventional dosage form), capsule delayed release (a solid dosage form in which the drug is enclosed within either a hard or soft soluble container made from a suitable form of gelatin, and which releases a drug (or drugs) at a time other than promptly after administration, whereby enteric-coated articles are delayed release dosage forms), capsule delayed release pellets (solid dosage form in which the drug is enclosed within either a hard or soft soluble container or "shell" made from a suitable form of gelatin); the drug itself is in the form of granules to which enteric coating has been applied, thus delaying release of the drug until its passage into the intestines), capsule extended release (a solid dosage form in which the drug is enclosed within either a hard or soft soluble container made from a suitable form of gelatin, and which releases a drug or drugs in such a manner to allow a reduction in dosing frequency as compared to that drug or drugs presented as a conventional dosage form), capsule film-coated extended release (a solid dosage form in which the drug is enclosed within either a hard or soft soluble container or "shell" made from a suitable form of gelatin; additionally, the capsule is covered in a designated film coating, and which releases a drug or drugs in such a manner to allow at least a reduction in dosing frequency as compared to that drug or drugs presented as a conventional dosage form), capsule gelatin coated (a solid dosage form in which the drug is enclosed within either a hard or soft soluble container made from a suitable form of gelatin; through a banding process, the capsule is coated with additional layers of gelatin so as to form a complete seal), and capsule liquid filled (a solid dosage form in which the drug is enclosed within a soluble, gelatin shell which is plasticized by the addition of a polyol, such as sorbitol or glycerin, and is therefore of a somewhat thicker consistency than that of a hard shell capsule; typically, the active ingredients are dissolved or suspended in a liquid vehicle).

Oral dosage forms contemplated herein also include granules (a small particle or grain), pellet (a small sterile solid mass consisting of a highly purified drug, with or without excipients, made by the formation of granules, or by compression and molding), pellets coated extended release (a solid dosage form in which the drug itself is in the form of granules to which varying amounts of coating have been applied, and which releases a drug or drugs in such a manner to allow a reduction in dosing frequency as compared to that drug or drugs presented as a conventional dosage form), pill (a small, round solid dosage form containing a medicinal agent intended for oral administration), powder (an intimate mixture of dry, finely divided drugs and/or chemicals that may be intended for internal or external use), elixir (a clear, pleasantly flavored, sweetened hydroalcoholic liquid containing dissolved medicinal agents; it is intended for oral use), chewing gum (a sweetened and flavored insoluble plastic material of various shapes which when chewed, releases a drug substance into the oral cavity), or syrup (an oral solution containing high concentrations of sucrose or other sugars; the term has also been used to include any other liquid dosage form prepared in a sweet and viscid vehicle, including oral suspensions).

Oral dosage forms contemplated herein may further include a tablet (a solid dosage form containing medicinal substances with or without suitable diluents), tablet chewable (a solid dosage form containing medicinal substances with or without suitable diluents that is intended to be chewed, producing a pleasant tasting residue in the oral cavity that is easily swallowed and does not leave a bitter or unpleasant after-taste), tablet coated (a solid dosage form that contains medicinal substances with or without suitable diluents and is covered with a designated coating), tablet coated particles (a solid dosage form containing a conglomerate of medicinal particles that have each been covered with a coating), tablet delayed release (a solid dosage form which releases a drug or drugs at a time other than promptly after administration, whereby enteric-coated articles are delayed release dosage forms), tablet delayed release particles (a solid dosage form containing a conglomerate of medicinal particles that have been covered with a coating which releases a drug or drugs at a time other than promptly after administration, whereby enteric-coated articles are delayed release dosage forms), tablet dispersible (a tablet that, prior to administration, is intended to be placed in liquid, where its contents will be distributed evenly throughout that liquid, whereby term 'tablet, dispersible' is no longer used for approved drug products, and it has been replaced by the term 'tablet, for suspension'), tablet effervescent (a solid dosage form containing mixtures of acids, for example, citric acid, tartaric acid, and sodium bicarbonate, which release carbon dioxide when dissolved in water, whereby it is intended to be dissolved or dispersed in water before administration), tablet extended release (a solid dosage form containing a drug which allows at least a reduction in dosing frequency as compared to that drug presented in conventional dosage form), tablet film coated (a solid dosage form that contains medicinal substances with or without suitable diluents and is coated with a thin layer of a water-insoluble or water-soluble polymer), tablet film coated extended release (a solid dosage form that contains medicinal substances with or without suitable diluents and is coated with a thin layer of a water-insoluble or water-soluble polymer; the tablet is formulated in such manner as to make the contained medicament available over an extended period of time following ingestion), tablet for solution (a tablet that forms a solution when placed in a liquid), tablet for suspension (a tablet that forms a suspension when placed in a liquid, which is formerly referred to as a 'dispersible tablet'), tablet multilayer (a solid dosage form containing medicinal substances that have been compressed to form a multiple-layered tablet or a tablet-within-a-tablet, the inner tablet being the core and the outer portion being the shell), tablet multilayer extended release (a solid dosage form containing medicinal substances that have been compressed to form a multiple-layered tablet or a tablet-within-a-tablet, the inner tablet being the core and the outer portion being the shell, which, additionally, is covered in a designated coating; the tablet is formulated in such manner as to allow at least a reduction in dosing frequency as compared to that drug presented as a conventional dosage form), tablet orally disintegrating (a solid dosage form containing medicinal substances which disintegrates rapidly, usually within a matter of seconds, when placed upon the tongue), tablet orally disintegrating delayed release (a solid dosage form containing medicinal substances which disintegrates rapidly, usually within a matter of seconds, when placed upon the tongue, but which releases a drug or drugs at a time other than promptly after administration), tablet soluble (a solid dosage form that contains medicinal substances with or without suitable diluents and possesses the ability to dissolve in fluids), tablet sugar coated (a solid dosage form that contains medicinal substances with or without suitable diluents and is coated with a colored or an uncolored water-soluble sugar), and the like.

Injection and infusion dosage forms (i.e., parenteral dosage forms) include, but are not limited to, the following. Liposomal injection includes or forms liposomes or a lipid bilayer vesicle having phospholipids that encapsulate an active drug substance. Injection includes a sterile preparation intended for parenteral use. Five distinct classes of injections exist as defined by the USP. Emulsion injection includes an emulsion comprising a sterile, pyrogen-free preparation intended to be administered parenterally. Lipid complex and powder for solution injection are sterile preparations intended for reconstitution to form a solution for parenteral use.

Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization.

Solution injection involves a liquid preparation containing one or more drug substances dissolved in a suitable solvent or mixture of mutually miscible solvents that is suitable for injection. Solution concentrate injection involves a sterile preparation for parenteral use that, upon addition of suitable solvents, yields a solution suitable for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

A parenteral carrier system may include one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

Inhalation dosage forms include, but are not limited to, aerosol being a product that is packaged under pressure and contains therapeutically active ingredients that are released upon activation of an appropriate valve system intended for topical application to the skin as well as local application into the nose (nasal aerosols), mouth (lingual and sublingual aerosols), or lungs (inhalation aerosols). Inhalation dosage forms further include foam aerosol being a dosage form containing one or more active ingredients, surfactants, aqueous or nonaqueous liquids, and the propellants, whereby if the propellant is in the internal (discontinuous) phase (i.e., of the oil-in-water type), a stable foam is discharged, and if the propellant is in the external (continuous) phase (i.e., of the water-in-oil type), a spray or a quick-breaking foam is discharged. Inhalation dosage forms also include metered aerosol being a pressurized dosage form consisting of metered dose valves which allow for the delivery of a uniform quantity of spray upon each activation; powder aerosol being a product that is packaged under pressure and contains therapeutically active ingredients, in the form of a powder, that are released upon activation of an appropriate valve system; and aerosol spray being an aerosol product which utilizes a compressed gas as the propellant to provide the force necessary to expel the product as a wet spray and being applicable to solutions of medicinal agents in aqueous solvents.

Pharmaceutically suitable inhalation carrier systems may include pharmaceutically suitable inactive ingredients known in the art for use in various inhalation dosage forms, such as (but not limited to) aerosol propellants (for example, hydrofluoroalkane propellants), surfactants, additives, suspension agents, solvents, stabilizers and the like.

A transdermal dosage form may include, but is not limited to, a patch being a drug delivery system that often contains an adhesive backing that is usually applied to an external site on the body, whereby the ingredients either passively diffuse from, or are actively transported from some portion of the patch, and whereby depending upon the patch, the ingredients are either delivered to the outer surface of the body or into the body; and other various types of transdermal patches such as matrix, reservoir and others known in the art. The "pharmaceutically suitable transdermal carrier system" includes pharmaceutically suitable inactive ingredients known in the art for use in various transdermal dosage forms, such as (but not limited to) solvents, adhesives, diluents, additives, permeation enhancing agents, surfactants, emulsifiers, liposomes, and the like.

Suitable dosage amounts and dosing regimens may be selected in accordance with a variety of factors, including one or more particular conditions being treated, the severity of the one or more conditions, the genetic profile, age, health, sex, diet, and weight of the subject, the route of administration alone or in combination with pharmacological considerations including the activity, efficacy, bioavailability, pharmacokinetic, and toxicological profiles of the particular compound employed, whether a drug delivery system is utilized and whether the drug is administered as part of a drug combination. Therefore, the dosage regimen to be employed may vary widely and may necessarily deviate from the dosage regimens set forth herein.

Contemplated dosage forms may include an amount of one or more expression inhibitors (or inhibitors of expression) ranging from about 1 to about 1200 mg, or about 5 to about 100 mg, or about 25 to about 800 mg, or about 100 to about 500 mg, or 0.1 to 50 milligrams (±10%), or 10 to 100 milligrams (±10%), or 5 to 500 milligrams (±10%), or 0.1 to 200 milligrams (±10%), or 1 to 100 milligrams (±10%), or 5 to 50 milligrams (±10%), or 30 milligrams (±10%), or 20 milligrams (±10%), or 10 milligrams (±10%), or 5 milligrams (±10%), per dosage form, such as, for example, a tablet, a pill, a bolus, and the like.

In another embodiment, a dosage form may be administered to a subject in need thereof once per day, or twice per day, or once every 6 hours, or once every 4 hours, or once every 2 hours, or hourly, or twice an hour, or twice a day, or twice a week, or monthly.

The phrase "therapeutically effective" is intended to qualify the amount that will achieve the goal of improvement in disease severity and/or the frequency of incidence over non-treatment, while limiting, reducing, or avoiding adverse side effects typically associated with disease therapies. A "therapeutic effect" relieves to some extent one or more of the symptoms of a cancer disease or disorder. In reference to the treatment of a cancer, a therapeutic effect refers to one or more of the following: 1) reduction in the number of cancer cells by, for example, killing the cancer cells; 2) reduction in tumor size; 3) inhibition (i.e., slowing to some extent, preferably stopping) of cancer cell infiltration into peripheral organs; 4) inhibition (i.e., slowing to some extent, preferably stopping) of tumor metastasis; 5) inhibition, to some extent, of tumor growth; 6) relieving or reducing to some extent one or more of the symptoms associated with the disorder; and/or 7) relieving or reducing the side effects associated with the administration of anti-cancer agents. "Therapeutic effective amount" is intended to qualify the amount required to achieve a therapeutic effect.

A therapeutically effective amount of an expression inhibitor (or inhibitors of expression) may be any amount that begins to improve cancer treatment in a subject. In one embodiment, an effective amount of an expression inhibitor used in the therapeutic regime described herein may be, for example, about 1 mg, or about 5 mg, or about 10 mg, or about 25 mg, or about 50 mg, or about 100 mg, or about 200 mg, or about 400 mg, or about 500 mg, or about 600 mg, or about 1000 mg, or about 1200 mg, or about 1400 mg, or from about 10 to about 60 mg, or about 50 mg to about 200 mg, or about 150 mg to about 600 mg per day. Further, another effective amount of an expression inhibitor used herein may be that which results in a detectable blood level of above about 1 ng/dL, 5, ng/dL, 10 ng/dL, 20 ng/dL, 35 ng/dL, or about 70 ng/dL, or about 140 ng/dL, or about 280 ng/dL, or about 350 ng/dL, or lower or higher.

The term "pharmaceutically acceptable" is used herein to mean that the modified noun is appropriate for use in a pharmaceutical product. Pharmaceutically acceptable cations include metallic ions and organic ions. Other metallic ions include, but are not limited to appropriate alkali metal salts, alkaline earth metal salts and other physiological acceptable metal ions. Exemplary ions include aluminium, calcium, lithium, magnesium, potassium, sodium and zinc in their usual valences. Organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid oxalacetic acid, fumaric acid, propionic acid, aspartic acid, glutamic acid, benzoic acid, and the like.

It is further contemplated that one active ingredient may be in an extended release form, while an optional second, third, or fourth other active ingredient, for example, may or may not be, so the recipient experiences, for example, a spike in the second, third, or fourth active ingredient that dissipates rapidly, while the first active ingredient is maintained in a higher concentration in the blood stream over a longer period of time. Similarly, one of the active ingredients may be an active metabolite, while another may be in an unmetabolized state, such that the active metabolite has an immediate effect upon administration to a subject whereas the unmetabolized active ingredient administered in a single dosage form may need to be metabolized before taking effect in the subject.

Also contemplated are solid form preparations that include at least one active ingredient which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like. Solutions or suspensions may be applied topically and/or directly to the nasal cavity, respiratory tract, eye, or ear by conventional means, for example with a dropper, pipette or spray.

Alternatively, one or more of the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier may form a gel in the nasal cavity. The powder composition may be presented in unit dose form, for example, in capsules or cartridges of, for example, gelatin, or blister packs from which the powder may be administered by means of an inhaler.

The pharmaceutical preparations may be in unit dosage forms. In such form, the preparation may be subdivided into unit doses containing appropriate quantities of the active component. The unit dosage form can be a packaged preparation, such as a kit or other form, the package containing discrete quantities of preparation, such as packeted tablets, capsules, liquids or powders in vials or ampoules. Also, the unit dosage form can be a capsule, tablet, cachet, or lozenge, or it can be the appropriate number of any of these in packaged form.

EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Materials and Methods

Breast Cancer Patient Tumor Datasets:

Three datasets on the Affymetrix hg-u133a platform were assembled and utilized: BrCa871 (n=871) and BrCa443 (n=443), and BrCa341 (n=341). The training set BrCa871, consisting of 871 patients, contains five cohorts identified by their GEO accession numbers: GSE1456, GSE2990, GSE3494, GSE7390, and GSE11121. The first testing data set BrCa443 (443 patients) is composed of three cohorts: GSE5327, GSE2034, and GSE2603 and the second testing set BrCa341 (341 patients) is also composed of three cohorts: GSE6532, GSE12093, GSE31519. These datasets were RMA pre-processed, median centered by sample, and z-score transformed. One further dataset, METABRIC, was also utilized for validation. For details on dataset composition as well as preprocessing methodology, see below. The BrCa871 set was split into two sets for training purposes: BrCa436-Train for training and BrCa435-CV for cross-validation. BrCa341 and BrCa443 were not utilized in the training process and used only for validation. A further dataset consisting of genes regulated by shBACH1 depletion in breast tumor cells was generated to identify potential genes of interest but was not used for training purposes. All data was analyzed using R.

Generation of stable cell lines, RNA isolation and microarray analysis:

Stable depletion of BACH1 in MDA-MB-231-derived 1833 (also termed BM1) human metastatic breast cancer cells was achieved using shRNA lentiviral vectors as described previously [Dangi-Garimella (2009)]. RNA was isolated from cells using RNeasy Mini Kit according to manufacturer's instruction (Qiagen) and reverse transcription was performed. Affymetrix GeneChip Human Gene 1.0 ST arrays were used for expression analysis of RNA samples, in triplicate, from 1833 cells expressing shBACH1 or a scrambled control RNA (3× scrambled RNA control and 3× shBACH1 accessible as GSE50226). All microarray data (including both cell line and patient tumor gene expression data) were preprocessed using the Robust Multi-array Average (RMA) framework (R Bioconductor libraries 'oligo' and 'pd.hugene.1.0.st.v1'); samples were then median-centered by subtracting the median expression value from each sample.

Generation of let-7-TG and BACH1 Meta-Genes:

A high-confidence set of let-7 target genes was previously generated using target prediction programs [Yun (2011)]. A list of BACH1 target genes was generated by analyzing differences in expression levels between control and shBACH1 1833 cells using the Significance Analysis in Microarrays package (R library 'samr') with a high stringency cutoff (median FDR=0.125; p<0.001) [Tusher (2001)]. The lists of both significantly up-regulated and down-regulated genes were imported into DAVID for annotation of global function-related themes [Efron (2007)].

Meta-genes were constructed as previously described [Yun (2011), Efron (2007)] (see below for detailed description). Briefly, downstream targets of let-7 and BACH1 were combined into weighted averages to serve as an estimate of regulation by both the microRNA (let-7) and the transcription factor (BACH1). As let-7 suppresses its downstream targets, an increase in let-7 should cause a decrease in the overall let-7 target gene meta-gene (meta-let-7-TG). Conversely, as BACH1 activates its downstream targets, an increase in BACH1 should cause a net increase in the BACH1 target gene meta-gene (meta-BACH1). The meta-genes serve to define activity of these regulators in individual patients relative to RKIP expression.

Threshold Selection and Cost Function Optimization Overview:

In order to find a set of cutoff values for the genes in the signature that was significant and also remained prognostic across multiple datasets, the problem was treated as an inversion and optimization problem. A cost function was formulated to reflect significance using the logrank test p-value and well as cohort size. All p-values are logrank p-values unless otherwise noted. Furthermore, all survival data was right-censored at 5 years with the exception of the training sets. Cutoff values were adjusted to minimize the cost function using a non-linear optimizer. In this case, the inventors utilized the Nelder-Mead algorithm natively in R (R function 'optim') to find local minima of the cost function.

The inventors utilized the BrCa871 dataset as the overall training set and the BrCa443 and BrCa341 datasets as the testing sets. An additional dataset, the METABRIC, was also used as a validation set [Curtins (2012)]. It is important to note that the BrCa443 and BrCa341 datasets are independent datasets and were never utilized in the entire training process. Furthermore, the cell line data was not utilized for training or validation but only for gene selection. The BrCa871 dataset was separated into two smaller sets of approximately the same size: a training set including 436 patients (BrCa436-Train) and a cross-validation set of 435 patients (BrCa435-CV). A series of 24,800 potential combinations of cutoffs was first generated in the BrCa436-Train set by minimizing the cost function. Of these, 556 combinations produced a significant P-value in both BrCa436-Train and BrCa435-CV and for each gene the mean was calculated from these 556 significant cutoffs, yielding the final set of cutoff values.

Signaling System Model:

In the system, the primary concern was with the consequences of RKIP suppression. Using relationships between genes previously demonstrated [Bertucci (2012)], it was contemplated that RKIP suppression should reduce expression of let-7. Since let-7 inhibits BACH1 and HMGA2, suppression of let-7 should activate both BACH1 and HMGA2. Similarly, activation of both BACH1 and HMGA2 should induce activation of MMP1, CXCR4, and OPN. Summation over the d function (equation 2) returns values between 0 and 7. Values less than 7 represent incomplete pathway activation, while values exactly equal to 7 indicate that the entire BPMS pathway is activated. Given information on either complete or incomplete activation, the inventors classifier function (equation 1) returns a value of either 0 or 1. If the sample's gene expression values are consistent with complete RKIP pathway activation, the function's output is 1. Otherwise, if at least one gene in the RKIP pathway does not properly reflect complete activation, the function's output is 0.

The BACH1 Pathway Metastasis Signature functions as a classifier between high risk and low risk of future metastasis when applied to a 2-dimensional data matrix X of gene expression values with elements $X_{i,j}$ representing the $i^{th}$ gene of the $j^{th}$ sample. The inventors classifier function, designed to reflect pathway activation in downstream targets of RKIP and BACH1, is written $$F_{BPMS}(X_{,j}, c) = \begin{cases} 1 & \text{if } \sum_{i=1}^{7} d_i(X_{i,j}, c_i) = 7 \\ 0 & \text{otherwise} \end{cases} \quad (1)$$

$$d_i(a, b) = \begin{cases} 1 & \text{if } a > b, i \neq RKIP \\ 1 & \text{if } a < b, i = RKIP \\ 0 & \text{otherwise} \end{cases} \quad (2)$$

Here, $d_i(a, b)$ is the thresholding/activation function for gene, and $c_i$ is the inventors corresponding threshold. These thresholds were trained on gene expression values running from i=1 through 7, representing RKIP, meta-let-7-TG, meta-BACH1, HMGA2, MMP1, CXCR4, and OPN respectively. With the exception of meta-let-7-TG, if a given gene's expression levels are greater than its threshold, that gene is said to be activated; similarly, if the same gene's expression levels are less than its threshold, it is said to be repressed. Since the meta-let-7-TG is an aggregation of various downstream targets of let-7, suppression of let-7 should cause an overall increase in meta-let-7-TG. Therefore, if meta-let-7-TG is greater than its threshold, let-7-TG is said to be activated. Inherent to this methodology is an inverse relationship between the number of gene-parameters and the predicted size of cohorts identified.

Cost Function:

The aim of the classifier function is to demonstrate within a specified subpopulation of breast cancer patients a correlation between the mRNA expression values of the inventors given set of BPMS genes and the phenotype of decreased likelihood of metastasis-free survival. Therefore, a relationship between the relative expression levels of the inventors 7 BPMS genes and certain statistical properties of the BPMS subpopulation was studied. In order to increase the predictability and effectiveness of the classifier function, the inventors searched for a set of thresholds that simultaneously maximizes the size of the potential BPMS subpopulation, and minimizes the metastasis-free survival stratification of that subpopulation. To that end, the inventors defined a cost function whose parameters are the expression levels of the 7 genes and whose values are a linear sum of functions $\alpha$ and $\beta$. $\alpha$ (equation 4) is a discretization of the raw log-rank p-value of the potential BPMS cohort reflecting the significance of the potential solution; $\beta$ (equation 5) is a linear transformation of the relative proportion of BPMS patients, reflecting the effect size (patient population size) of the solution. By optimizing $\alpha$, the inventors select for solutions that maximize the significance of the signature. However, to avoid over-fitting for significance, optimizing the $\beta$ function selects for solutions that maximize the effect size of the signature.

An alternative statistical parameter to the log-rank p-value that can be directly interrogated by the function $\alpha$ is the hazard ratio. However, the hazard ratio can be shown to be simply a linear transformation of raw log-rank values. Raw log-rank values go to a chi-squared distribution, and the inventors are using the p-values on the extreme end of the chi-squared distribution. Therefore, the hazard ratio (to a high approximation) can be explained linearly as a function of the log-rank p-value.

The inventors minimized the cost function using a numerical optimizer. The inventors now describe these steps in detail. The cost function's first component $\alpha$ was discretized to match the discrete nature of the second component $\beta$. Similarly, the range of $\beta$ for typical parameter values was roughly scaled to match the range of $\alpha$. The net effect of this discretization and scaling is the creation of a very frugal cost function that rejects small changes that merely add a patient or two and instead rewards larger jumps that drastically change the raw log-rank p-value of potential BPMS thresholds.

The inventors cost function $f(X,c)$ is written as, $$f(X, c) = \alpha(X, c) + \beta(X, c) \quad (3)$$

where $$\alpha(X, c) = \quad (4)$$

$$\begin{cases} 2 \times Pr[Q(X, c) > q] & Pr[Q(X, c) > q] > 0.05 \\ 0.05 & 0.05 \geq Pr[Q(X, c) > q] > 0.03 \\ 0.03 & 0.03 \geq Pr[Q(X, c) > q] > 0.01 \\ 0.01 & 0.01 \geq Pr[Q(X, c) > q] > 0.005 \\ 0.005 & \text{otherwise} \end{cases}$$

and $$\beta(X, c) = \frac{1}{2} \times \left(0.1 - \frac{N_{BPMS}}{N_{ALL}}\right) \quad (5)$$

$Pr[Q(X,c)>q]$ is the log-rank p-value of the inventors potential BPMS cohort, $N_{BPMS}$ is the number of potential BPMS patients, and $N_{ALL}$ is the total number of patients in X Optimizer:

The optimizer used to produce solutions was the default R implementation (R function optim) of the downhill simplex algorithm [Nelder (1965)]. Random solutions drawn from a normal distribution with mean zero and variance one were selected as starting points.

Survival Analysis:

To determine the significance of differential survival between BPMS and non-BPMS patients, the logrank test was performed on annotated metastasis-free survival (MFS) data paired to each sample. Kaplan-Meier plots were also generated for each dataset to provide a visualization of survival stratification. Comparisons of five year survival were determined using right-censoring of survival data in all validation sets.

When assessing the overall significance of the BPMS compared to other prognostic signatures, an analysis of variance (ANOVA) test was performed. To compare two models in an ANOVA, a hypothesis test called the likelihood ratio test can be performed. The likelihood ratio test compares the ratio of likelihoods for a given multivariate Cox model (e.g. published prognostic signatures) relative to a second model (e.g., the published prognostic signatures plus the BPMS) and determines whether or not a particular regressor (e.g. BPMS) imparts significant information to the first model. The ANOVA utilizes repeated application of the likelihood ratio test from a null model to a full model by successively adding single prognostic signatures. Thus, using multivariate Cox proportional hazards models, the inventors calculated the significance of the BPMS when compared to all other prognostic signatures examined. For more information on the multivariate ANOVA test, see below.

BPMS on Alternate Array Platforms:

To test the BPMS for cross platform compatibility, the inventors utilized the METABRIC expression array dataset of 2000 breast tumors performed on the Illumina BeadArrays [Curtins (2012)]. To compare survival the inventors applied the BPMS as above in these datasets and compared metastasis-free survival using the logrank test on Kaplan-Meier survival curves.

Signature Comparisons:

Implementation of intrinsic subtype, proliferation, triple-negative, Mammaprint®, Oncotype®, GAB2 signaling scaffold, 28-kinase metagene, glucocorticoid receptor, and 76-gene signatures were performed as previously described [Sorlie (2001), Perou (2000), Wirapati (2008), Pan (2011), Lehmann (2011), McCall (2010)]. Comparisons to intrinsic subtyping, proliferation, GAB2 signaling scaffold, 28-kinase metagene, glucocorticoid receptor and triple-negative signatures were used to demonstrate the significance of the BPMS within basal breast cancer populations. Further comparisons to the 76-gene signature were used to predict overall survival, and Mammaprint and Oncotype signatures were included to establish the complementarity of the BPMS signature to these clinically-relevant signatures. Patient subgroup survival was compared in a pairwise manner using the logrank test (R library 'survival') and across the combination of all signatures using the multivariate likelihood ratio/ANOVA test.

Software Code: Attached as Appendix 1.

Data set pre-processing.

Three data sets were assembled from 11 cohorts retrieved from the Gene Expression Omnibus (GEO) based on previously published studies. All gene expression arrays were conducted on the Affymetrix Human Genome u133a platform, with the exception of the METABRIC data set, which was performed on Illumina Bead Arrays. The transcripts were isolated from breast cancer tumors that were annotated with clinical follow up including metastasis-free survival data. The training set BrCa871, consisting of 871 patients, contains five cohorts identified by their GEO accession numbers: GSE1456, GSE2990, GSE3494, GSE7390, and GSE11121. The first testing data set BrCa443 (443 patients) is composed of three cohorts: GSE5327, GSE2034, and GSE2603 and the second testing set BrCa341 (341 patients) is also composed of three cohorts: GSE6532, GSE12093, GSE31519.

Cohorts were extracted as compressed raw CEL files into a single directory for each BrCa871, BrCa443, and BrCa341 data set. The CEL files were then converted into Biobase (R library 'Biobase', v 2.16.0) ExpressionSet objects in R (versions 2.13.0 through 2.15.0) using the default R Affymetrix package (R library 'affy' 0, v 1.34). Data sets were then RMA preprocessed (R library 'affy'). If multiple probes mapped to a single gene in the HG-u133a package (R library 'hgu133a.db'), the probe with the highest overall variance was selected. Each array was subsequently normalized ~N(0,1) by sample in BrCa871, BrCa443, and BrCa341 and by gene in the METABRIC data set. Each sample was also median-centered.

By definition, batch effects are data trends that correspond to non-biological effects. One method that has been used to account for data-processing batch effects is data normalization. However, as all of the inventors cohorts have biological differences, trends apparent in the publicly available data relating to data source cannot be assumed to be non-biological [Leek (2010)].

Meta-Gene Construction

In order to define a measure of let-7 and BACH1 activity, their corresponding meta-genes, metaLET7 and metaBACH1 respectively, were generated, each defined as a weighted average of the transcriptional levels of their downstream targets. The relative weights were individual gene scores calculated in the Gene Set Analysis package (R library 'GSA'), and served as an estimate of regulatory strength of the given regulator (let-7 or BACH1) to its target genes.

In preprocessing, where multiple probes can map to single genes, those probes were selected with highest overall variance to represent expression. It was sought to minimize the number of genes by selecting a smaller target set for both metaLET7 and metaBACH1 in a fashion that would maximize consistency across data sets. An initial list of targets was constructed for the metaLET7 target gene group using the TRANSFAC database while a similar list was constructed by applying 'samr' to shBACH1 1833 cells. Beginning with these initial genes, the inventors selected for gene targets with lowest overall variance in the BrCa871 data set. For the let-7 target gene set, the 12 targets with lowest variance were selected, excluding BACH1 and HMGA2 as they are represented separately in the signature. Similarly, the 13 targets of BACH1 with lowest variance was chosen to represent the BACH1 target gene set.

Multivariate Survival Analysis

All survival analysis was performed using the R library 'survival'. As the BPMS is a binary classifier (patients are either BPMS-positive or BPMS-negative), the log-rank test of significance was used (implementation as R commands 'survdiff' or 'coxph', library 'survival'). Comparison between existing prognostic signatures was performed using linear Cox proportional hazards models. Further comparison against prognostic signatures was performed by applying the log-rank test for the BPMS within individual cohorts of those signatures.

Linear Cox proportional hazards models for metastasis-free survival were fit against a large range of prognostic breast cancer signatures (R function 'coxph', library 'survival'). Two sets of gene signatures were employed: a primary set and a secondary set. Full Cox models were fit using the entirety of the primary set as well as a set consisting of both the primary and secondary sets. For each of these two models, additional models were fit including the BPMS. In total, there are four models: A) Surv(MFS, met)~primary set, B) Surv(MFS, met)~primary set+BPMS, C) Surv(MFS, met) primary set+secondary set, D) Surv (MFS, met)~primary set+secondary set+BPMS. Using the likelihood of each of these models, the hypothesis that the model with the BPMS is more likely to explain the data than the model not including the BPMS can be tested. This is called the likelihood-ratio test. To be specific, models B and A were compared, as were models D and C. This results of the analysis are reported in the main text. A summary of this test as well as hazard ratios with 95% confidence intervals for these fits can be found in Table 6.

While the likelihood-ratio test can evaluate whether the addition of BPMS against an aggregation of other gene signatures is significant, examining the stratifications of the BPMS within individual subgroups determined by other prognostic signatures (such as the BPMS within the Basal cohort of the PAM50) allows for an more specific analysis of the intersection of these signatures.

Generation of the BPMS

In the provided R code, the function 'genBPMSSig' can be used to generate estimates for the thresholds in the BPMS signature. The 'genBPMSSig' function generates a distribution of thresholds that will produce significance in a training set and a validation set—therefore the quality of the estimate depends on the size of the distribution. As such, 'genBPMSSig' takes as parameters a data set for training, a data set for cross-validation, the set of BPMS genes, and n number of potential solutions that the function will generate to create the final estimates.

A number of solutions (n) is generated within the 'genBPMSSig' function through a call to the function 'analysisPipelineRPMS.v2'. This pipeline function optimizes for each n solutions a cost function as described in the main text. This cost function is the function 'ensembleCostFcn.v2' and can be found in the provided R code. Optimizations were performed using the downhill simplex algorithm as implemented in the R function 'optim' and described in the main text.

Figure 13:
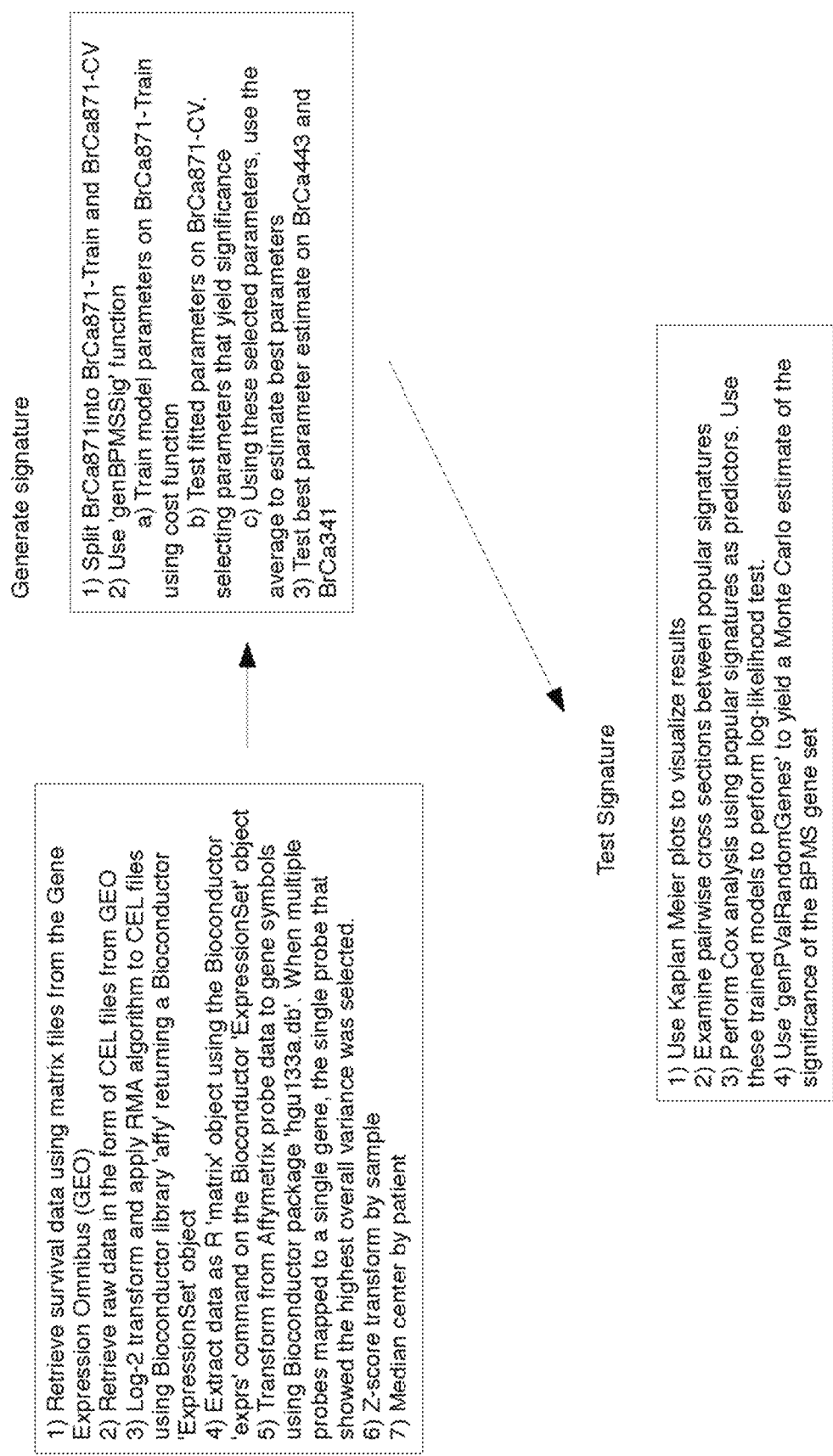
FIG. 13 Summary flow chart
Figure 14:
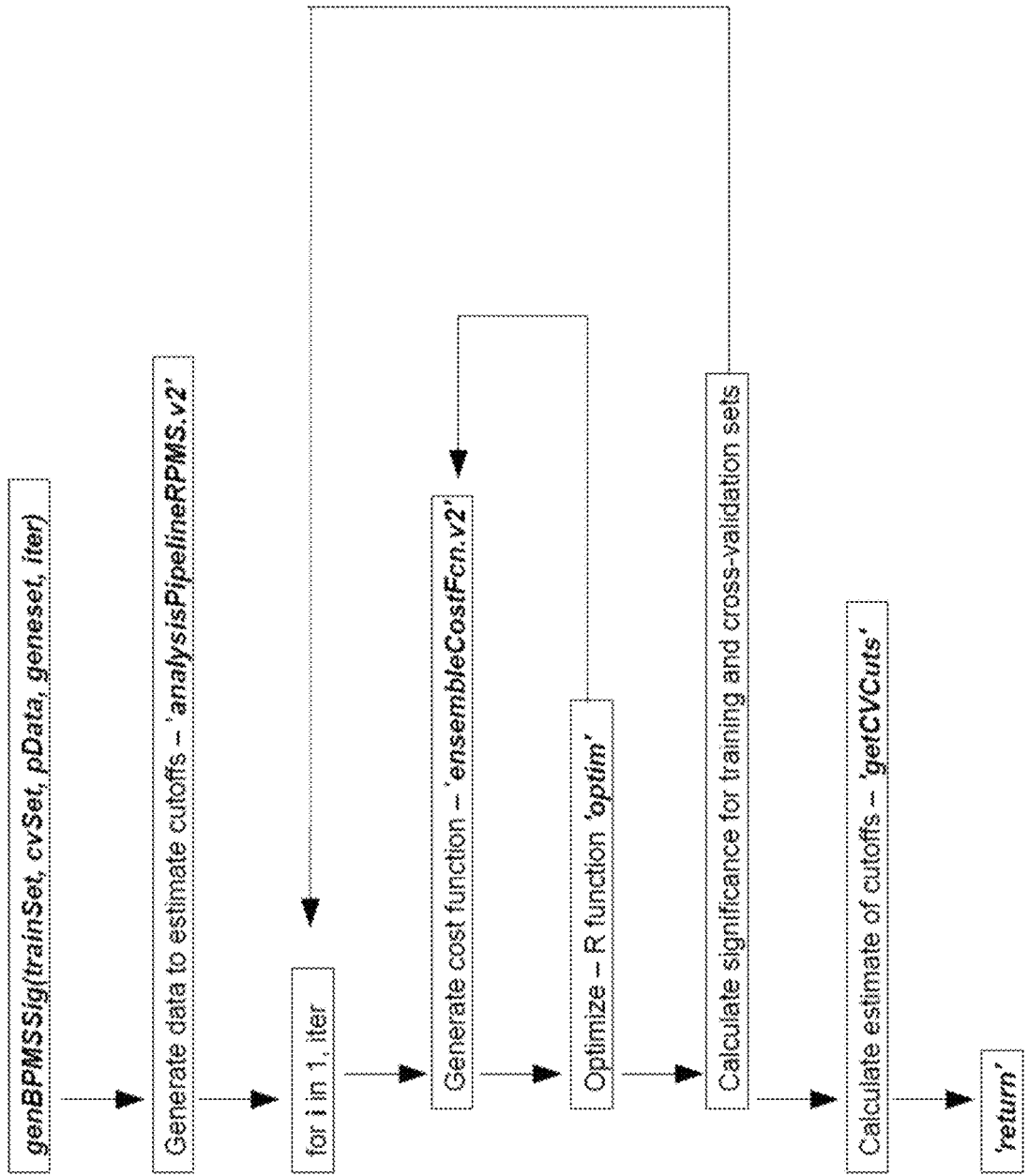
FIG. 14 Flow chart showing the process of calculating the optimal cutoff values.
Figure 15:
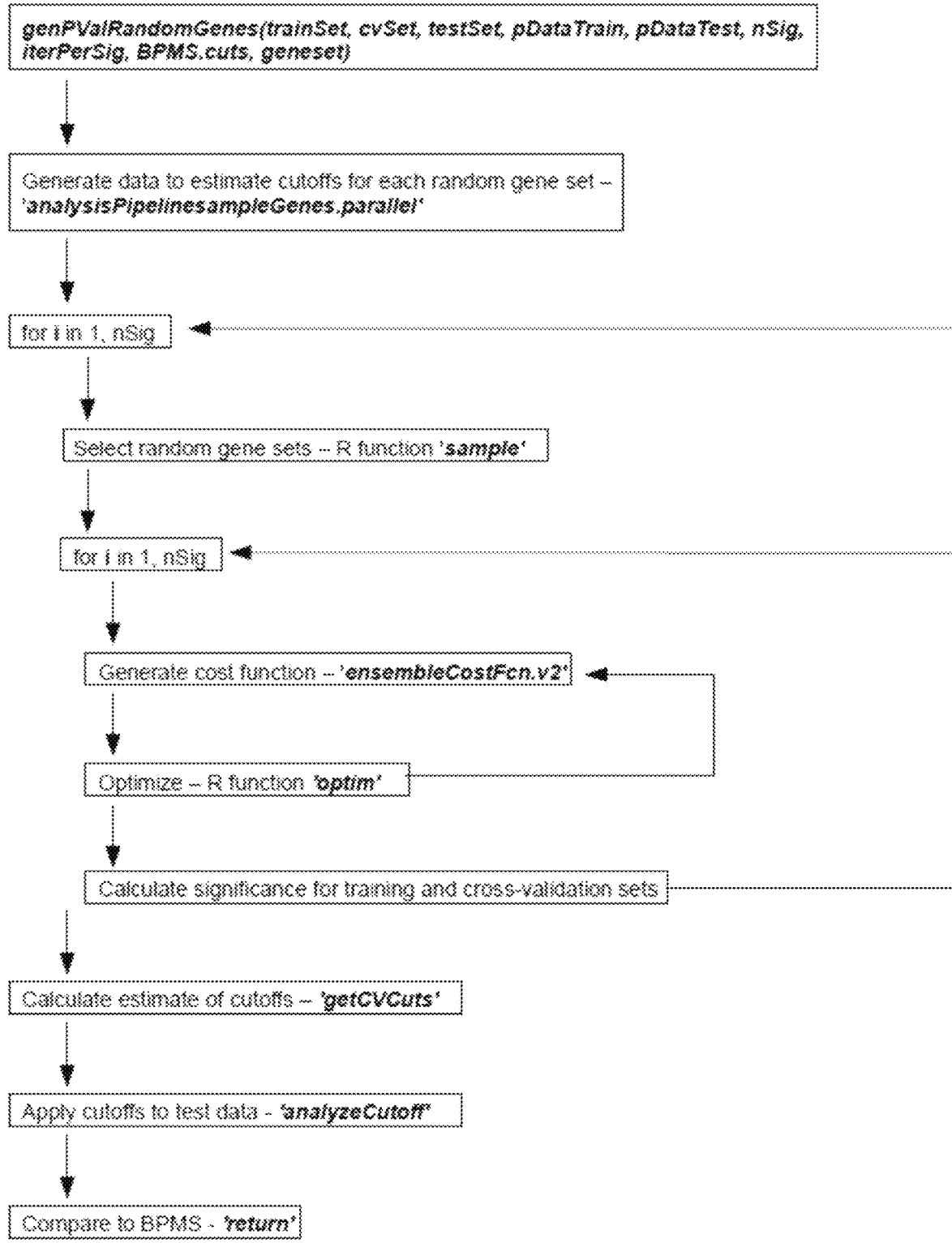
FIG. 15 Flow chart showing the process by which alternative gene signatures were tested and compared with the BPMS.

Given these n potential solutions, the significance of these solutions is calculated in both the training and cross-validation sets. Those solutions producing significance in both sets were then averaged to form a final set of BPMS thresholds. A summary of this process is provided in FIGS. 13-15, as flow charts.

Comparison Against Random Signatures

Following the pipeline described in the previous section, the function 'genPValueRandomGenes' applies the same optimization and estimation process to m number of random 7-gene signatures using an identical model and cost function. This process produces a distribution of p-values for random 7-gene signatures. Statistically, this distribution of p-values should follow a uniform distribution. Using this distribution of p-values, the probability of producing the BPMS signature as a random effect is less than 5%, as described in the manuscript.

Example 2

Analysis of Gene Expression Changes in a BACH1-Depleted TNBC Cell Line and Generation of Meta-Genes:

To build a BACH1 pathway metastasis signature (BPMS), it was determined whether the use of experimentally derived BACH1 targets to build the BACH1-metagene could reduce the number of genes included in the signature and improve the ability of the inventors signature to predict patient outcome. Meta-genes combine the individual expression of a group of genes into a single value. For the RPMS signature [Minn (2012)], the inventors used meta-genes as surrogates for let-7 and BACH1 since expression of their target genes could reflect their activity better than their expression level alone. Moreover, the meta-gene was necessary for estimating the level of let-7 expression, as its expression level was not measured directly on the Affymetrix hgu133a platform. The BACH1 meta-gene was built in order to estimate the level of transcriptionally active BACH1 as its activity is regulated at multiple levels including cofactor association and cytoplasmic sequestration [Yamasaki (2005), Ishikawa (2005)]. The original BACH1 meta-gene in the RPMS was based on predicted targets for BACH1 obtained from the TRANSAFAC database [Yun (2011)].

To build a new BACH1 meta-gene, BACH1 was stably depleted via shRNA transfection of 1833 cells, a bone tropic derivative of MDA-MD-231 TNBC cells [Kang (2003)]. Microarray analysis was performed on these cells and a group of genes that had significant (p<0.001) differential expression following BACH1 depletion was identified. Specifically, 80 genes were increased and 88 genes were decreased (Table 4). Using the functional annotation software tool DAVID, the inventors determined that BACH1 expression correlated positively with genes in categories related to the cytoskeleton and extracellular matrix including actin-binding to Wiskott-Aldrich homology 2 (WH2), extracellular/secreted and EGF-like. BACH1 expression correlated negatively with genes in categories related to phospholipid metabolism including calcium binding, sterile alpha motif, inositol phosphate metabolism, plasma membrane and phospholipase activity. These results are consistent with previous findings demonstrating that BACH1 promotes breast cancer metastasis [Yun (2011), Liang (2012)].

The experimentally-derived BACH1 target genes were utilized to minimize the number of components required to generate meta-genes in order to facilitate clinical application of the new BACH1-based signature. The RPMS signature was comprised of approximately 100 genes of which most were contained in the BACH1 TG meta-gene. To reduce the number of genes that act as surrogates of BACH1, the variance of each gene across 871 gene expression arrays conducted on resected breast cancer tumors (termed the BrCa871 training dataset) was determined, and the BACH1 targets were filtered by selecting genes with the lowest variance. A similar analysis was conducted for let-7 TG. This procedure yielded a list of 12 genes for the let-7 TG meta-gene and 13 genes for the BACH1 meta-gene (Table 1). The new let-7 meta-gene is a subgroup of the one previously used [Yum (2011)]. By contrast, the new BACH1 meta-gene has no genes in common with those in the RPMS and thus had to be further tested to assess how well it represents BACH1 as a component of the RKIP signaling pathway.

Let-7-TG and BACH1 Meta-Genes Correlate to Other Components of the RKIP Signaling Pathway and to Previous Meta-Genes:

In order to test if the new let-7-TG and BACH1 meta-genes behave as elements of the RKIP signaling cascade and maintain the expected correlation to other components of the pathway in patient datasets, gene set analysis was performed [Minn (2012)]. As observed previously, expression of the genes that were selected as let-7 targets (meta-let-7-TG) correlated inversely to RKIP expression when tested as a set (p<0.001, FDR<0.001, score=−0.46). Similarly, expression of the BACH1 target set (metaBACH1) correlated positively to the let-7-TG meta-gene, to BACH1 expression and to the BMS gene set when tested using the BrCa871 dataset (scores=1.06, 0.93, and 1.60, respectively; p<0.001, FDR<0.001 for all). To determine whether these newly defined meta-genes for let-7 TG and BACH1 are representative of the let-7-TG and BACH1 meta-genes used for the RPMS, the distributions of these two sets of meta-genes across the BrCa871 dataset were correlated. Analysis yielded a Pearson correlation of 0.71 for the let-7-TG meta-genes and 0.69 for BACH1 meta-genes. These results showed a high degree of correlation between the respective meta-genes suggesting that the newly created meta-genes are a good representation of the old one when interrogated using breast cancer patient gene expression data.

It was then determined whether these new meta-genes follow a normal distribution.

Figure 9:
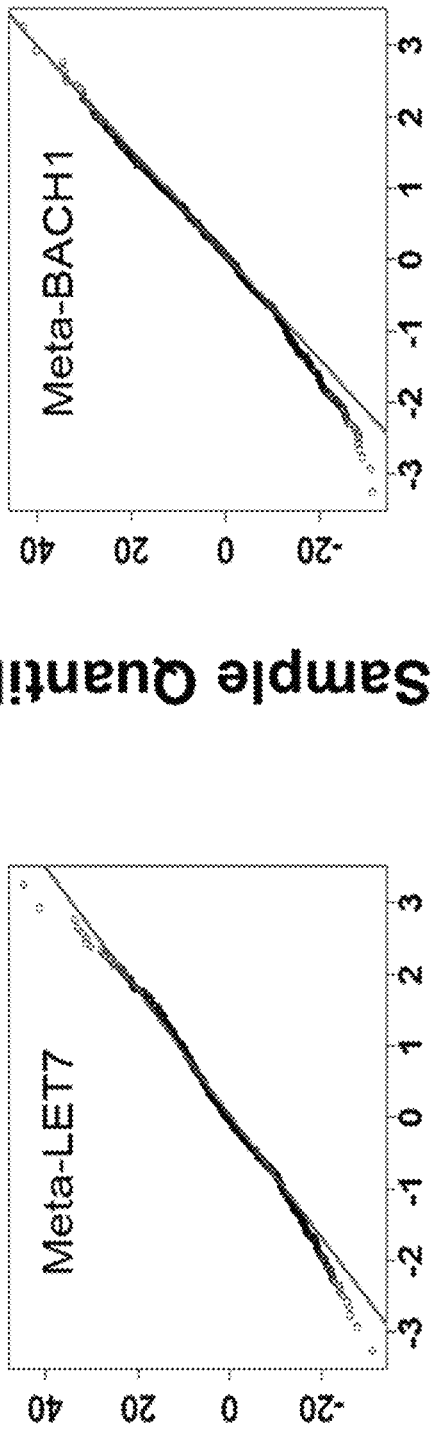
FIG. 9A-B. The Let-7-TG and BACH1 meta-genes exhibit a normal distribution of expression in breast tumors. Q-Q plots were used to verify the normal distribution of (A) Let-7-TG and (B) BACH1 meta-genes. Meta-gene values were analyzed using the BrCa871 dataset. The gray line refers to an idealized normal distribution of gene expression.
Figure 10:
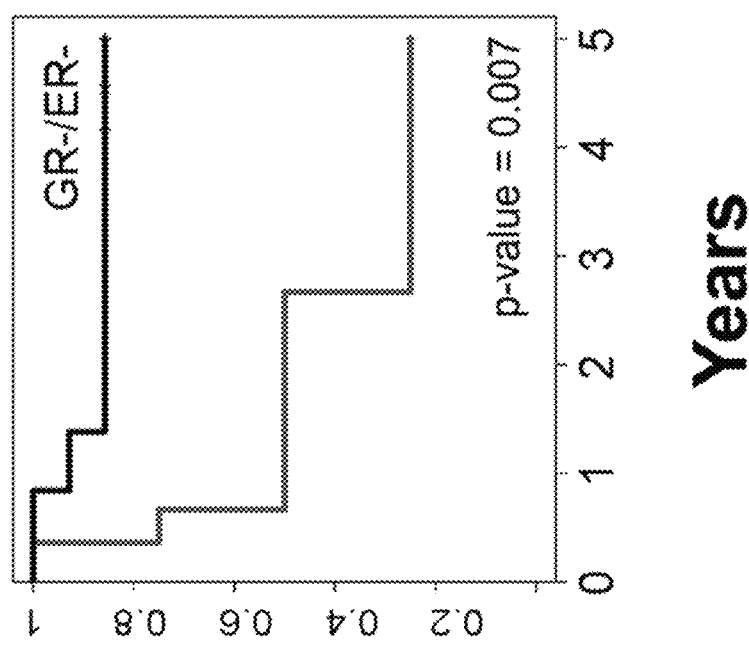
FIG. 10. The BPMS in GR−/ER−. BPMS within the cohort of patients classified as GR−/ER−. GR− patients were classified using GR probe expression below the 25th quartile. Similarly, ER− patients were classified using ESR1 probe expression below −3.416

Initially, the preprocessing approach and the Central Limit Theorem ensured that all genes in all datasets that were used in this study were distributed normally. However, it is possible that the inventors processing method for creating meta-genes engendered major bias. To test this possibility, Q-Q plots were generated for the let-7-TG and BACH1 meta-genes. The results indicate that each meta-gene is extremely linear in this representation and thus is normally distributed (FIG. 9).

Setting Signature Cutoffs Using Cost Function Optimization and Cross Validation:

Although the inventors previous RPMS gene signature used a median cutoff for individual genes to stratify patients, the median cutoff is an arbitrary value and may not be the most appropriate way to establish gene activity. The median cutoff assumes that the threshold for activation is the same for all genes and corresponds to the median value. To improve threshold selection beyond the median cutoff, the inventors developed a novel methodology involving cost function optimization.

Specifically, a mathematical approach that optimized the cost function was utilized to define the most effective gene cutoffs for stratifying patients while maximizing the patient group size. To accomplish this, the R implementation of Nelder-Mead optimization (R function 'optim') was used, setting the cutoffs of the genes and meta-genes in the signature (5 genes and 2 meta-genes) as the values to be optimized. Using a subset of the BrCa871 dataset (BrCa436-Train), the inventors optimized the inventors cost function by adjusting the cutoffs, thereby maximizing power and specificity. Instead of using the median value as a cutoff for all genes, the inventors chose a value for each gene that was able to maximize significant differences in metastasis-free survival.

As a control to determine whether the optimizer will yield better solutions than non-optimized solutions, the cost function was optimized 1444 times using the BrCa871 dataset. The inventors compared these optimized results to a set of 1056 randomly generated solutions that were not optimized. The inventors then analyzed the p-values (statistical significance) and cohort size (number of patients expressing the 7 gene signature) of these solutions. The optimized solutions yielded an average p-value of 0.0868 with a variance of 0.0041 while also yielding an average cohort size of 14.43 with a variance of 0.15. The random solutions yielded a mean p-value of 0.223 with a variance of 0.008 as well as an average cohort size of 10.82 with a variance of 0.16. Using a t-test to compare the two, the inventors found that the optimized solutions give significantly better p-values ($p<0.0001$), as well as a significantly larger cohort size ($p<0.0001$) (FIG. 1A, B). These results indicate that optimization over the cost function produces significantly better thresholds for gene expression than random methods.

To build a predictive model, results were obtained from 24800 optimizations in BrCa436-Train and cross-validated using the remainder of the data (BrCa435-CV) as a control for over-fitting. Specifically all 24800 potential solutions were applied to the BrCa435-CV dataset. Solutions that did not produce significance in both the training as well as cross-validation sets were discarded, leaving a remaining 556 potential solutions. Using this underlying distribution of significant solutions ($p<0.05$), an estimate of the final set of the cutoffs was generated (FIG. 2). The final cutoff values were set by averaging the results within each gene (or meta-gene) using normalized (0, 1) data that was median-centered by patient. This analysis generated 7 cutoff values: −0.27 for RKIP, −0.23 for MMP1, 0.19 for OPN, −0.20 HMGA2, −0.19 for CXCR4, −0.020 for meta-let7-TG, and −0.15 for meta-BACH1. These results identified a new metastasis gene signature with a greatly reduced number of genes. The inventors term this new signature the BACH1 pathway metastasis signature or BPMS.

BPMS as a Single Sample Predictor:

Ideally, for clinical purposes, a prognostic signature would enable one to predict survival for a single sample independent of the context of a larger patient population. Since the previous RPMS gene signature used a median cutoff for individual genes that cannot be defined outside of a statistical distribution, the RPMS cannot be applied on a patient-to-patient basis. Individual patients may be added to already existing distributions of gene expression values, but the addition of each patient would, in fact, change the median threshold for each gene. Similarly, using RMA preprocessing as above prevents us from generating a single sample predictor (SSP) from the BPMS. An alternative approach is to use the frozen RMA (fRMA) package (Bioconductor package 'fRMA') to perform quantile normalization and pre-processing of all samples. Unlike RMA, which calculates normalization parameters using a given dataset, fRMA utilizes a "frozen" set of parameters that are independent of other samples within a dataset.

To determine whether the BPMS can function as a single sample predictor (SSP), the BrCa871 and BrCa341 datasets were processed using fRMA. After splitting BrCa871 into both BrCa436-Train and BrCa435-CV, 7500 solutions were trained on BrCa436-Train. These 7500 solutions were then cross-validated using BrCa435-CV, and solutions that did not produce significance within both BrCa436-Train and BrCa435-CV were discarded. All remaining solutions were averaged to yield a single sample predictor. This SSP version of the BPMS was then validated using fRMA-processed BrCa341 data (FIG. 3). The results indicate that the BPMS, when used as a SSP, has the potential to significantly predict patient survival.

Signature Hypothesis Testing:

To address concerns that random gene signatures of a similar size are equally effective or even more significant at stratifying patient data than the inventors experimentally derived BPMS, the inventors used a Monte Carlo method to sample 1,520 sets of 7 random genes [Venet (2011)]. Optimizations were run over the inventors 1,520 gene sets using identical methodology to that used for analysis of the BPMS target genes. To be specific, the inventors optimized each gene set using the cutoff model on the BrCa436-Train data, selected solutions that produced significance in the BrCa435-CV data, and estimated the most effective cutoff values of the gene set. The inventors then applied the resulting signature for each random gene set to the BrCa443 data, yielding a log-rank p-value for each gene set. The inventors used these 1,520 gene sets to provide an estimate of the proportion of 7-gene permutations that the inventors BPMS gene set outperformed. The BPMS out-performed a significant portion of the randomly produced signatures, yielding a p-value of 0.0389. These results indicate that the group of genes the inventors chose for the signature is significantly different from a random group.

BPMS is Prognostic for Metastasis-Free Survival:

To determine whether the BPMS is associated with metastatic risk, logrank tests were performed on different breast cancer patient datasets, applying the cutoffs generated previously. When applied to the entire BrCa871 set that was used for training, the analysis yielded a p-value of less than $4.0\times10'$. Similarly, analysis of two other datasets, BrCa443 and BrCa341, yielded p-values of $6.3\times10^{-3}$, and $<2.0\times10^{-5}$ for 5 year survival, respectively (FIG. 4A-C). While a relatively low number of BPMS patients in the BrCa341 set may suggest an instability in the signature, a chi-squared test demonstrates that there is no significant deviation from the expected number of patients when compared to the BrCa871 dataset ($\chi2=3.1657$, dof=1, p=0.0752). These analyses indicate that the BPMS signature is significant and has prognostic value, effectively stratifying patients for risk of metastasis.

BPMS Stratifies Patients Identified by Other Signatures:

Previous signatures have been used to classify breast cancer patient tumors into molecularly defined groups based on gene expression levels. In addition, these gene signatures have been applied as clinical tests for patient prognosis. Based on these criteria, the inventors defined two categories of signatures, molecular and clinical, and then tested the prognostic value of BPMS patients using the BrCa443 dataset with these two types of signatures. Within the molecular classifiers, the PAM50 signature identifies five subgroups: Luminal A, Luminal B, Normal, Her2+ and Basal. The BPMS patients overlap primarily with basal patients. However, the BPMS significantly enhances patient stratification for MFS (p-value<$2\times10^{-4}$; FIG. 5A-E) Specifically, the BPMS can significantly differentiate between higher and lower risk patients within the highly aggressive basal subtype.

Figure 6:
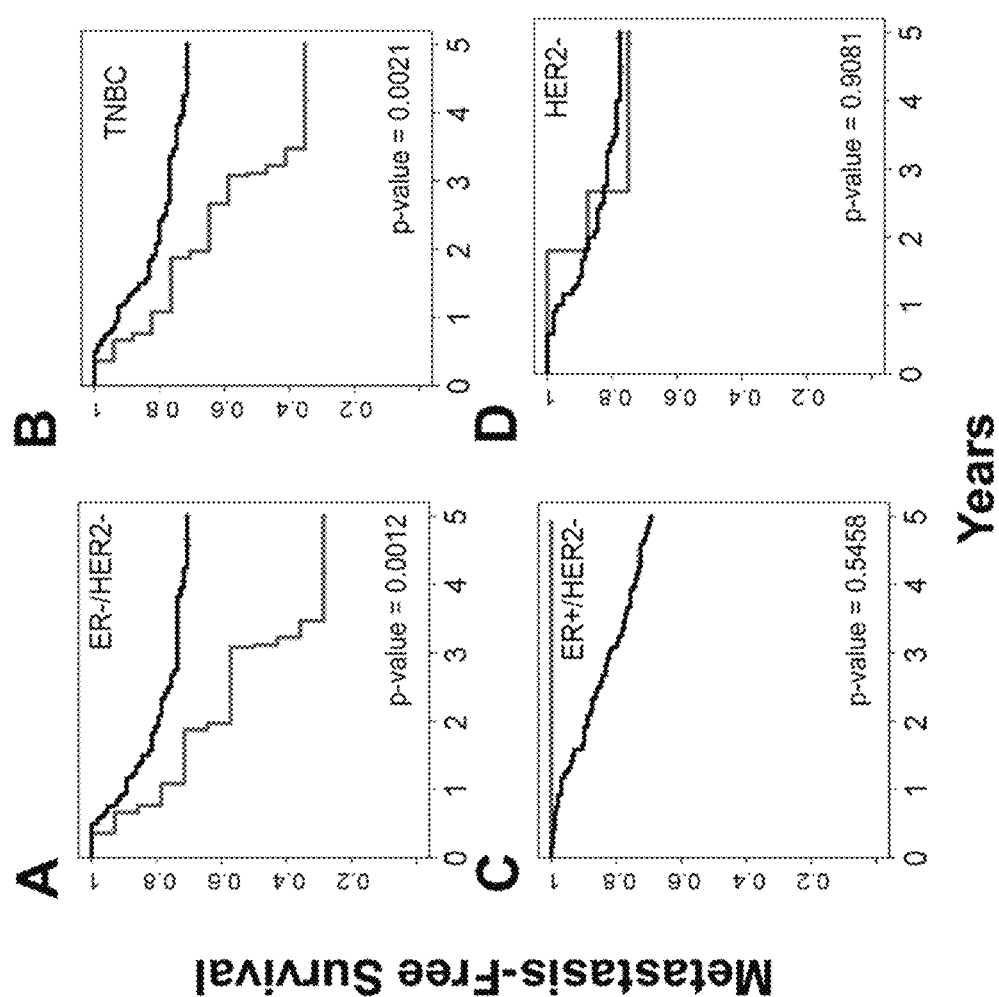
FIG. 6A-D. The BPMS is prognostic for metastasis-free survival of TNBC patients. The proliferation signature was used to categorize breast tumors into (A) ER-HER2− (15 BPMS+ patients out of 121 ER-HER− patients, $\chi^2=10.5$), (B) TNBC (18 BPMS+ patients out of 118 TNBC patients, $\chi^2=9.4$), (C) ER+HER2− (n=1), and (D) HER2+(8 BPMS+ patients out of 117 HER2 patients, $\chi^2=0$). BrCa443 patients were stratified for MFS using the BPMS. Gray indicates patient tumors that express the BPMS signature while black indicates patient tumors that do not. Survival curves were generated by Kaplan-Meier analysis, and the indicated P-values were calculated by the log-rank test.
Figure 7:
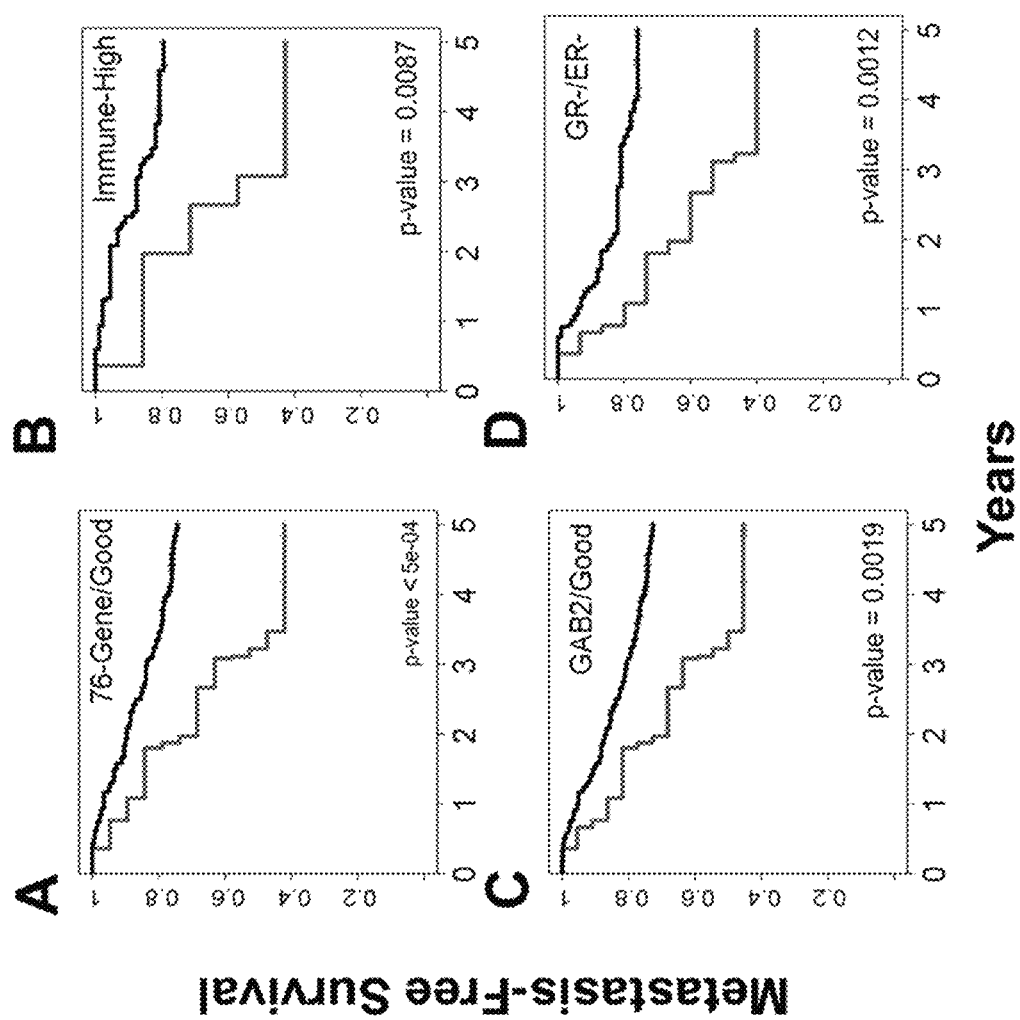
FIG. 7A-D. The BPMS is prognostic for high risk patients among good prognosis patients. Good prognosis categories examined were: (A) the 76-gene (20 BPMS+ patients out of 290 good-prognosis patients, $\chi^2=12.2$), (B) 28-kinase meta-gene (8 BPMS+ patients out of 104 high immune response patients, $\chi^2=6.9$), (C) GAB2 Scaffolding (23 BPMS+ patients out of 429 good prognosis patients, $\chi^2=9.7$), and (D) glucocorticoid receptor signature (16 BPMS+ patients out of 121 GR−/ER− patients as defined by 50% cutoff, $\chi^2=10.5$). Patients were stratified for MFS using the BPMS. Gray indicates patient tumors that express the BPMS signature while black indicates patient tumors that do not. Survival curves were generated by Kaplan-Meier analysis, and the indicated P-values were calculated by the log-rank test.

Within the molecular phenotypes, the inventors first looked at the proliferation signature, a classification that builds meta-genes to predict whether patients are ER positive or negative as well as Her2 positive or negative. The inventors analysis indicated that the BPMS patients overlap the ER−/Her2− group, and the BPMS again significantly stratifies them further for MFS (p-value=0.0012; FIG. 6A-C). In addition, TNBC patients, although typically defined through histological assays, were recently categorized by a gene expression signature [Efron (2007)]. TNBC patients identified by this signature significantly overlapped with the BPMS patients; however, as above, the BPMS signature further stratified these patients for MFS (p-value=0.00214; FIG. 6D). Using the entire BrCa443 dataset, the inventors also applied the BPMS to four other molecular signatures: 1) a 76-gene signature predictive of distant metastasis-free survival [Wang (2005)]; 2) a 28-kinase metagene signature related to immune response of cytotoxic T-cells [Sabatier (2011)]; 3) a 205 gene transcriptional GAB2 scaffold signature related to proliferation and cell adhesion/migration/invasion [Mira (2009)]; and 4) a glucocorticoid receptor signature whose stratification is dependent on ER status [Pan (2011)]. In the latter case, the inventors also analyzed only the top and bottom 25% of the patients as in the original report [Pan (2011)] (Figure. 26). Interestingly, in all four cases, the BPMS identified poor prognosis patients within the good prognosis cohort (FIG. 7). These results suggest that the BPMS can be used in conjunction with other molecular signatures to identify patients that might otherwise be considered low risk.

Figure 8:
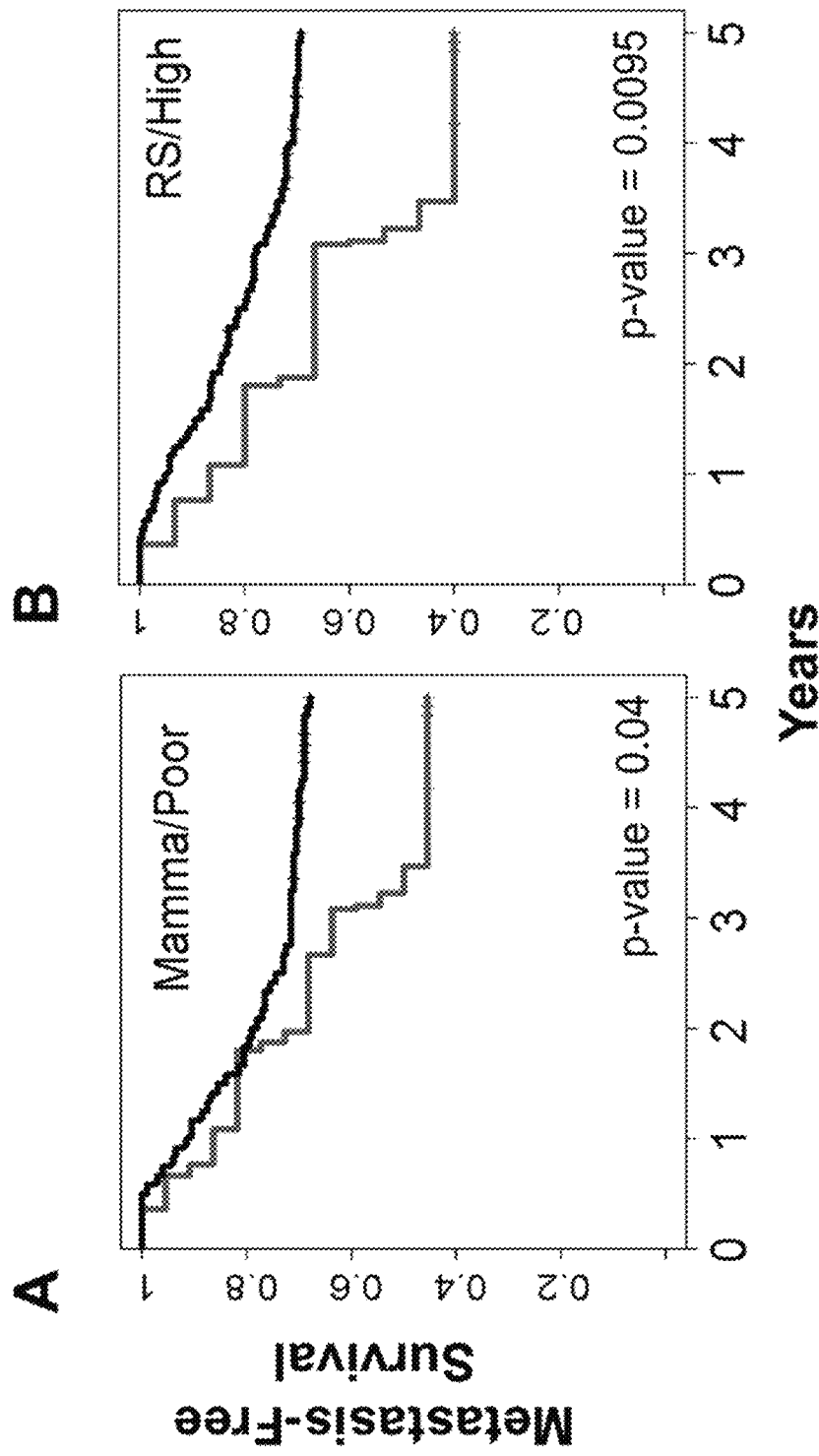
FIG. 8A-B. The BPMS is prognostic for high risk patients among the clinically predicted poor outcome and high recurrence patients. Clinically relevant gene signatures (A) Mammaprint® Poor (23 BPMS+ patients out of 226 Mammaprint Poor patients, $\chi^2=4.3$) and (B) OncotypeDX® Recurrence High (16 BPMS+ patients out of 257 RS High patients, $\chi^2=6.7$) were stratified for MFS using the BPMS. Gray indicates patient tumors that express the BPMS signature while black indicates patient tumors that do not. Survival curves were generated by Kaplan-Meier analysis, and the indicated P-values were calculated by the log-rank test.
Figure 11:
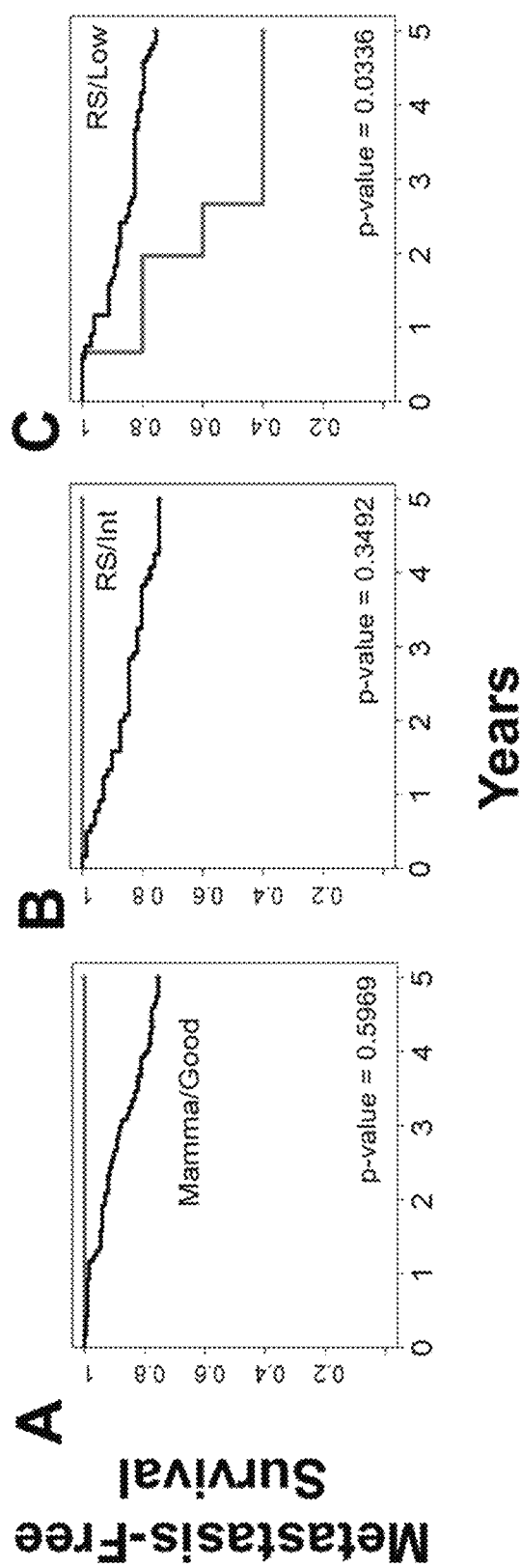
FIG. 11A-C. The BPMS is not prognostic for low risk patients among the clinically predicted poor outcome and high recurrence patients. Clinically relevant gene signatures (A) Mammaprint® Good, (B) OncotypeDX® Recurrence Low, or (C) OncotypeDX® Recurrence Intermediate were stratified for MFS using the BPMS. Gray indicates patient tumors that express the BPMS signature while black indicates patient tumors that do not. Survival curves were generated by Kaplan-Meier analysis, and the indicated P-values were calculated by the log-rank test.

Finally, the inventors applied the BPMS to gene signatures that are currently used in the clinic (OncotypeDX® and MammaPrint®). The BPMS was able to further stratify patients in the poor prognosis subgroup of patients analyzed by Mammaprint® and the high recurrence subgroup of patients analyzed by OncotypeDX® (p-value=0.04 and 0.01 respectively; FIG. 8A,B; FIG. 11). Thus, the BPMS gene signature is significantly different than these other signatures and adds information when combined pairwise.

A multivariate analysis of common clinical factors consisting of nodal status, grade, size, ER status, and age was also performed. As clinical data was sparsely available, a combined set of BrCa443 and BrCa341 was used for this analysis. Using the methodology of Sabatier, et. al. [Sabatier (2011)], the inventors first fit univariate Cox models to each clinical factor individually. Of those factors, only nodal status and size were significant predictors on their own. The inventors then fit a multivariate Cox model to nodal status, size, and the BPMS (Table 2). Analysis of variance using a likelihood ratio test with competitive linear Cox models shows that the BPMS significantly adds value independent of clinical factors (p=0.0073, Survival~clinical factors vs Survival~clinical factors+BPMS) (Table 2). Additionally, a similar comparison of all the molecular and prognostic signatures mentioned above indicates that the BPMS signature significantly adds prognostic value to the combined signatures (p=0.028; Survival~combined signatures vs. Survival~combined signatures+BPMS) (Table 3). Together, these analyses show that the BPMS is a significant predictive variable even after adjustment for all available clinical and prognostic factors.

Figure 12:
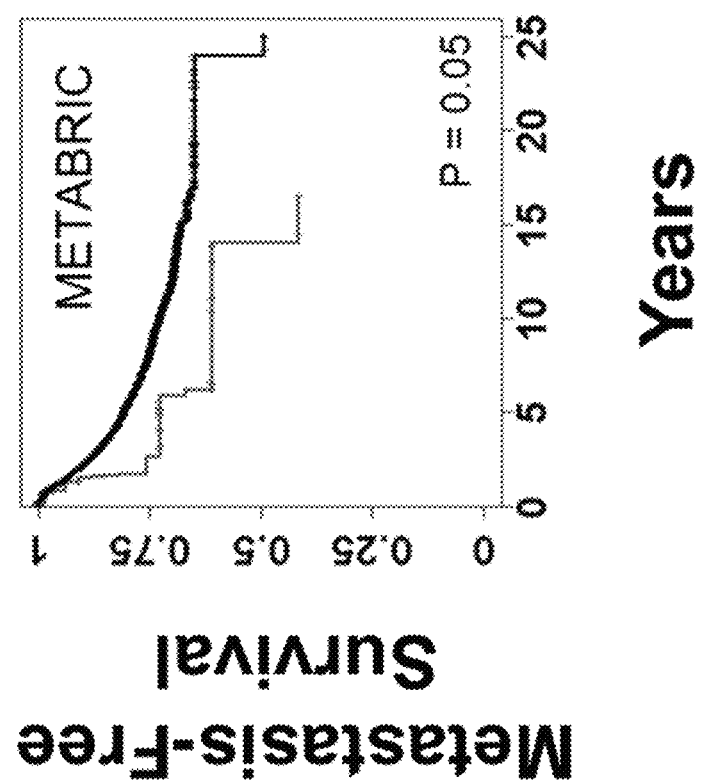
FIG. 12. The BPMS is prognostic for metastasis-free survival (MFS) of patients in the METABRIC cohort. The METABRIC expression data set was generated from 2000 heterogeneous breast cancer tumors using Illlumina BeadArrays. Gray indicates patient tumors that express the BPMS signature while black indicates patient tumors that do not. Survival curves were generated by Kaplan-Meier analysis, and the indicated P-values were calculated by the log-rank test.

BPMS Signature is Effective in Other Array Platforms:

To test for the potential of cross platform use, the inventors applied the BPMS to the recently-derived METABRIC expression dataset generated from 2000 heterogeneous breast cancer tumors using Illlumina BeadArrays. Using the BPMS, the inventors observed a more modest but significant stratification of high risk METABRIC patients (p-value=0.0481; FIG. 12). Thus, the BPMS has utility even when applied to different platforms.

Table 1. Gene targets comprising the let-7 meta-gene (left) and BACH1 meta-gene (right).

Table 2. The BPMS is a significant predictor of metastasis-free survival (MFS) after adjustment for clinical variables. All available clinical data in a combined BrCa443/BrCa341 dataset was fit individually to Cox proportional hazards models. A) Clinical factors that were significant univariate predictors of MFS were placed into a full model along with the BPMS. B) An analysis of the variance (likelihood ratio test) comparing the multivariate model with and without the BPMS (L0 and L1 respectively) demonstrates the prognostic ability of the BPMS (p=0.0073, $\chi2='7.2$, df=1).

Table 3. The BPMS is a significant predictor of metastasis-free survival (MFS) after adjustment for 7 other prognostic gene signatures. A) Multivariate cox models for prognostic signatures. Survival data was fit in the BrCa443 validation setagainst the 7 combined signatures in a multivariate Cox proportional hazards model. Similarly, the same data was fit in the BrCa443 set against the 7 combined signatures including the BPMS. B) Likelihood ratio test for competitive models. Using the likelihood of the multivariate models, an analysis of variance (likelihood ratio test) demonstrates that the BPMS selects a cohort of patients independent of all other gene signatures (p=0.028, $\chi2=4.8$, df=1).

Table 4. All genes differentially expressed (p<0.001) from BACH1 depletion in a TNBC cell line. Gene up-regulated (left three columns) and down-regulated (right three columns) through stable expression of shBACH1 when compared to vector control in MDA-MB-231 derived 1833 cells.

Table 5. List of the 30 genes in the BPMS (I=1-30), the gene name, and the value of the optimized cut-off value for gene i, determined based on the Affymetrix GeneChip Human Gene 1.0 ST array data. Multiple genes with the same cut-off value comprise the meta-genes.

Table 6. Multivariate analysis results.

Example 3

Materials and Methods
Affymetrix Gene Arrays.

A total of 24 samples including 3 biological replicates of each [1833 cells expressing control scrambled shRNA (SCR sh) or high mobility group AT-hook 2 (HMGA2) shRNA (shHMGA2), MDA-MB-436 cells expressing SCR sh or shHMGA2, xenograft 1833 tumor cells expressing inducible ten-eleven translocation 1 (Tet1) or homeobox A9 (HOXA9) with or without induction of Tet1 or HOXA9] were analyzed by using Affymetrix GeneChip Human Gene 1.0 ST Array. The RNA quality control, cRNA amplification, hybridization, and image scan were conducted in the Functional Genomics Facility at the University of Chicago. The quantified signals were normalized by using Robust Multiarray Average (RMA) (1). R (Version 2.11) (2) and related packages from Bioconductor (Version 2.4) (3) were used for the analysis of the normalized data. Differential expression was defined as fold≥1.25, P<0.05, and false discovery rate (FDR) <0.05. We also performed median-centering gene across all arrays for heatmap illustration. The microarray data have been deposited in the Gene Expression Ominibus repository (accession no. GSE43741).

Cell Culture and Generation of Cell Lines.

Cell lines (1833, MDAMB-231, and MDA-MB-436) were cultured in a complete medium consisting of DMEM supplemented with 10% (vol/vol) FBS, 50 U/mL penicillin, and 50 µg/mL streptomycin. For inducible cell lines, Tet System Approved FBS was used instead. HMGA2 depletion and control were achieved by transducing the cells with HMGA2 shRNA or scrambled control in a pLKO.1 lentiviral vector (Open Biosystems). After transduction, cells were selected and maintained in 0.5 µg/mL puromycin. The HMGA2 expressing cell line was generated by transfection with pH3HX-HMGA2 plasmid using Attractene transfection reagent (Qiagen). Cells were selected in 500 µg/mL geneticin (G418). The TET1 expressing cell line was generated by transfection with pMSCV-Flag-TET1-puro plasmid using Attractene (Qiagen). Cells were selected in 0.5 µg/mL puromycin. The inducible Tet1- or HOXA9-expressing cell line was generated by cotransducing the cells with pLVX-TRE3G-Flag-Tet1 (expressing inducible Tet1) or pLVX-TRE3G-HOXA9 (expressing inducible HOXA9) and pCMV-Tet3G (expressing Tet-On 3G element) in lentiviral vectors (Clontech). Cells were selected and maintained in 0.5 µg/mL puromycin and 500 µg/mL G418.

Transient Transfection with siRNA.

Cell lines were transiently transfected by using HiPerFect transfection reagent (Qiagen) following the manufacturer's protocols. TET1, HOXA7, or HOXA9 siRNA On-TARGET plus SMARTpool and the relevant control were from Dharmacon RNAi Technologies.

RNA Isolation and Quantitative RT-PCR Analysis.

Total RNA was isolated from cells by using miRNeasy Mini Kit (Qiagen) following the manufacturer's instructions. Quantitative RT-PCR (qRT-PCR) was performed as described (4). The qPCR primers for human or murine HMGA2, TET1, HOXA genes and GAPDH were Taqman and were purchased from Applied Biosystems.

Immunoblotting.

Cells were lysed in complete lysis buffer (pH 7.5) by using Nuclear Extract Kit (Active Motif) following the manufacturer's protocols. Proteins were measured, separated, and probed as described (4). Antibodies specific for each protein were HMGA2 (61042; Active Motif), TET1 (sc-163446; Santa Cruz Biotechnologies), HOXA7 (09-086; Millipore), HOXA9 (09-178; Millipore), GAPDH (ab9484; Abcam), and Flag-M1 (F3040; Sigma).

Genomic DNA Isolation and Analysis of DNA Methylation by Methylation-Specific Digestion Combined with qPCR or by Bisulfite Modification Sequencing. Genomic DNA was isolated from cells with the DNeasy Blood and Tissue Kit (Qiagen) following the manufacturer's instructions. For detection of TET1 and HOX gene promoter CpG island methylation, genomic DNA was subjected to four digestions (mock, methylation-sensitive, methylationdependent, or both) by using the EpiTect Methyl DNA Restriction Kit (SABiosciences) following the manufacturer's instructions. Products from the digestion were quantified for levels of methylation by qPCR using either the Human HOX Genes DNA Methylation PCR Array or the EpiTect Methyl qPCR Primer Assay for TET1 (SABiosciences). Results were analyzed by software from SABiosciences (see, for example the world wide web at sabiosciences.com/dna_methylation_data_analysis.php). For bisulfite sequencing assay, genomic DNA was subjected to sodium bisulfite treatment by using the EpiTect Bisulfite Kits (Qiagen). Products from the treatment were amplified by PCR using specific primers designed with MethPrimer software (5):

```
TET1 Forward (5'-3'):
                                       SEQ ID NO: 23
TTATGTAGTTTTATTTGTTTTTTATTGTG TET1 Reverse (5'-3'):
                                       SEQ ID NO: 24
CAACTCCAAACCTACACCAAC HOXA7 Forward (5'-3'):
                                       SEQ ID NO: 25
TATAATTTTGATTTGTGATTTGTTGTT HOXA7 Reverse (5'-3'):
                                       SEQ ID NO: 26
AAACCTCTTACCCTTCCATTCTAAA HOXA9 Forward (5'-3'):
                                       SEQ ID NO: 27
TTGGGAATTTTGATTGTTAGTTGA HOXA9 Reverse (5'-3'):
                                       SEQ ID NO: 28
TACCAAAACACTCCAAACAAAAAC
```

PCR products were purified by using a PCR purification kit (Qiagen). Purified products were subcloned by using a TA Cloning Kit (Invitrogen), and individual inserts from 10 or more randomly selected clones were sequenced.

5-Hydroxymethylcytosine Labeling Reaction and Dot-Blot Assay.

The 5-hydroxymethylcytosine (5-hmC) labeling reactions and dot-blot assays were performed as described (6). Briefly, 600 ng of genomic DNA samples were spotted and measured for levels of 5-hmC. Quantification was calculated by using a working curve generated by 1-8 ng of 32-bp synthetic biotin-5-N3-gmC-containing DNA.

ChIP Assay.

The ChIP assay was performed with the Champion-ChIP One-Day Kit (SABiosciences) following the manufacturer's instructions. Briefly, cells were fixed and cross-linked with 1% formaldehyde. Cross-linked chromatin was sheared by using a sonicator. Antibody used for immunoprecipitation was anti-Tet1 (Santa Cruz Biotechnologies), anti-H3K4Me3, or anti-IgG (Abcam). Precipitated DNA was purified and then analyzed by qPCR with primers specific for the TET1, HOXA7, or HOXA9 region:

```
TET1 Site-1 Forward (5'-3'):
                                       SEQ ID NO: 29
TTTGGGAACCGACTCCTCACCT TET1 Site-1 Reverse (5'-3'):
                                       SEQ ID NO: 30
TCGGGCAAACTTTCCAACTCGC TET1 Site-2 Forward (5'-3'):
                                       SEQ ID NO: 31
ACGCTGGGCATTTCTGATCCACTA TET1 Site-2 Reverse (5'-3'):
                                       SEQ ID NO: 32
TATTGTGCAGCTCGTTTAGTGCCC TET1 Site-3 Forward (5'-3'):
```

-continued

ACTTTGACCTCCCAAAGTGCTGGA
SEQ ID NO: 33

TET1 Site-3 Reverse (5'-3'):
ACCTGAGTGATGCTGAGACTTCCT
SEQ ID NO: 34

HOXA7 Site-1 Forward (5'-3'):
AAAGCGCGTTCACATAATAC
SEQ ID NO: 35

HOXA7 Site-1 Reverse (5'-3'):
GTTATCATATATCACTCTACCTCGT
SEQ ID NO: 36

HOXA7 Site-2 Forward (5'-3'):
CATTCCTGCTCCGGTTT
SEQ ID NO: 37

HOXA7 Site-2 Reverse (5'-3'):
GGTCCATAAAGGCCGAAG
SEQ ID NO: 38

HOXA7 Site-3 Forward (5'-3'):
CCACCCTGCCTTGTTTCAACATCA
SEQ ID NO: 39

HOXA7 Site-3 Reverse (5'-3'):
ACCAAGTTGTCAGTGAGCCTTCCA
SEQ ID NO: 40

HOXA9 Site-1 Forward (5'-3'):
TTCATCCTCACCAGCAGTTCCAGT
SEQ ID NO: 41

HOXA9 Site-1 Reverse (5'-3'):
GGGCCATTTCGGAGTTCATTGTGT
SEQ ID NO: 42

HOXA9 Site-2 Forward (5'-3'):
CCACCCTGCCTTGTTTCAACATCA
SEQ ID NO: 43

HOXA9 Site-2 Reverse (5'-3'):
ACCAAGTTGTCAGTGAGCCTTCCA
SEQ ID NO: 44

For the input control, 1% of sonicated DNA was directly purified and analyzed by qPCR with the same primers.

Demethylation Treatment.

Cells were subjected to 5-azacytidine (1 or 3.6 µM), decitabine (5-aza-dC; 220 or 440 nM), or mock treatment by addition into cell culture at indicated concentration. Cells were treated daily. RNA and protein were isolated respectively.

Cloning of pMSCV-Flag-TET1-Puro, Inducible Tet1, or Inducible HOXA9 Plasmid.

The DNA sequence containing a Flag sequence encoding DYKDDDDK SEQ ID NO:45 and the mouse Tet1 gene C-terminal 673 amino acids including the catalytic domain (GU079948) was synthesized by GenScript, and then was inserted into a MSCVpuro plasmid at XhoI/EcoRI sites. For cloning of inducible Tet1, the Tet1 sequence fragment was fused into the pLVX-TRE3G, a Tet-On 3G inducible lentiviral vector (Clontech) at BamHI/EcoRI sites. A similar strategy was applied for cloning of inducible HOXA9 plasmid. The DNA sequence for HOXA9 coding sequence was obtained from the pMSCVPIG-HOXA9 plasmid, a gift from Jianjun Chen (The University of Chicago, Chicago). All constructs were confirmed by sequencing.

Cell Proliferation and In Vitro Cell Invasion Assays.

Cell proliferation assays were performed by using the CellTiter-Blues assay (Promega) as described (4). Invasion assays were performed as described (4) with modifications. Briefly, the inserts were coated with Matrigel basement membrane matrix (BD Biosciences). To assess the cell invasion ability, 105 cells were seeded on top of the polymerized Matrigel in serum-free medium, and complete medium (10% FBS) was placed in the lower compartment. After 24 h, cells on the lower part of the insert were stained with BD Calcein AM Fluorescent Dye. The inserts with the invaded cells were incubated in dissociation buffer (Travigen) with gentle shaking. Fluorescence measurements were used to record data with 485 nm for excitation and 530 nm for emission.

Animal Studies.

Treatment of mice was done in accordance with a protocol approved by the Institutional Animal Care and Use Committee of The University of Chicago. Xenograft breast tumor growth and bone metastasis assay have been described (4). For the induction of Tet1 or HOXA9, 1833 Tet1 or HOXA9 inducible cells were plated in the presence of 1 µg/mL doxycycline. Twenty-four hours later, 106 cells were orthotopically injected into the second mammary fat pad of mice for tumor growth assay, or 105 cells were injected into the left ventricle of mice for bone metastasis assay. Mice were administered drinking water containing 4% sucrose only or 2 mg/mL doxycycline and 4% sucrose. Mice were imaged for luciferase activity after 3 wk. After 6 wk, tumor tissues were dissected, fixed, and embedded. For intravasation assays, the mouse blood was taken from heart and lysed by the addition of red blood cell lysis buffer (pH 7.2) (STEMCELL). Cells were collected by centrifugation, and total RNA isolated from cells was analyzed for human (tumor) and mouse (control) GAPDH transcripts by qRT-PCR.

MMTV-Wnt1 Hmga2 Knockout Mice.

Wnt1 transgenic mice in the Hmga2 wild-type (Hmga2+/+), heterozygous (Hmga2+/−), or null (Hmga2−/−) genetic backgrounds have been described (7). Briefly, C57BL/6J-Hmga2+/− female mice were mated with C57BL/6J-Wnt1 male mice (Jackson Laboratory). F1 Wnt1 transgenic Hmga2+/− male mice were then mated with F1 Wnt1 transgenic Hmga2+/− female littermates to obtain the F2 transgenic mice in the Hmga2+/+, Hmga2+/−, and Hmga2−/− genetic backgrounds. Wnt and Hmga2 loci have been confirmed by PCRbased genotyping.

Immunostaining.

Immunostaining for paraffin-embedded tumor samples was performed by the Human Tissue Resource Centre Core Facility at the University of Chicago. Section of the samples was stained with hematoxylin and eosin (H&E), anti-Tet1 (Abcam), anti-Hoxa9 (Abcam), anti-5-hydroxy-methylcytosine (Active Motif), or anti-Ki67 (Thermo Scientific) antibody.

Statistical Analysis of Experimental Results.

Samples were analyzed by using the two-sample Student t test assuming equal variances (two-tailed). P values were calculated for samples from three independent experiments unless otherwise indicated. Gene annotation enrichment analysis was performed by using Database for Annotation, Visualization and Integrated Discovery software (8). Gene set enrichment analysis was performed by using GSEA software (9).

Subject Data and Kaplan-Meier Analysis.

Gene expression array data (10-13) and relevant clinical information for >800 breast cancer subject samples were downloaded either from the relative publication Web sites or from the World Wide Web at ncbi.nlm.nih.gov/geo repository. The data were organized into two sets based on the platform on which the arrays were performed. Set one includes 101 microarrays for the breast cancer subject samples; set two includes 735 microarrays. Kaplan-Meier analysis was performed by using survival package in R (2).

References for this Section

1. Irizarry R A, et al. (2003) Summaries of Affymetrix GeneChip probe level data. Nucleic Acids Res 31(4):e15.
2. R Development Core Team (2009) R: A language and environment for statistical computing (R Foundation for Statistical Computing, Vienna).
3. Gentleman R C, et al. (2004) Bioconductor: Open software development for computational biology and bioinformatics. Genome Biol 5(10):R80.
4. Dangi-Garimella S, et al. (2009) Raf kinase inhibitory protein suppresses a metastasis signalling cascade involving LIN28 and let-7. EMBO J 28(4):347-358.
5. Li L C, Dahiya R (2002) MethPrimer: Designing primers for methylation PCRs. Bioinformatics 18(11):1427-1431.
6. Song C X, et al. (2011) Selective chemical labeling reveals the genome-wide distribution of 5-hydroxymethylcytosine. Nat Biotechnol 29(1):68-72.
7. Morishita A, et al. (2013) HMGA2 is an in vivo driver of tumor metastasis. Cancer Res, in press.
8. Huang W, Sherman B T, Lempicki R A (2009) Systematic and integrative analysis of large gene lists using DAVID bioinformatics resources. Nat Protoc 4(1):44-57.
9. Subramanian A, et al. (2005) Gene set enrichment analysis: A knowledge-based approach for interpreting genome-wide expression profiles. Proc Natl Acad Sci USA 102(43):15545-15550.
10. Enerly E, et al. (2011) miRNA-mRNA integrated analysis reveals roles for miRNAs in primary breast tumors. PLoS ONE 6(2):e16915.
11. Miller L D, et al. (2005) An expression signature for p53 status in human breast cancer predicts mutation status, transcriptional effects, and patient survival. Proc Natl Acad Sci USA 102(38):13550-13555.
12. Desmedt C, et al.; TRANSBIG Consortium (2007) Strong time dependence of the 76-gene prognostic signature for node-negative breast cancer patients in the TRANSBIG multicenter independent validation series. Clin Cancer Res 13(11): 3207-3214.
13. Wang Y, et al. (2005) Gene-expression profiles to predict distant metastasis of lymphnode-negative primary breast cancer. Lancet 365(9460):671-679.

HMGA2 depleted cell lines were generated by lentiviral transduction with HMGA2 shRNA; TET1 and HOXA gene knock-down were generated by transfection with relative siRNA; TET and HOXA9 inducible expression cells were generated by lentiviral transduction with relative inducible expression vector.

Example 4: TET1 and HOX Gene Expression are Dramatically Induced Upon Depletion of HMGA2 in Both Invasive Human Breast Cancer Cells and MMTV-Wnt1 Mouse Breast Tumors Gene expression arrays were conducted using two invasive human breast cancer cell lines expressing either HMGA2 shRNA or control scrambled shRNA: 1833, a bone-tropic derivative of the human breast cancer cell line MDA-MB-231 (23), and MDA-MB-436. We found a dramatic induction of Homeobox (HOX) genes particularly at the HOXA loci in the more invasive 1833 cells (FIGS. 17A-C and S23). The HOX genes are comprised of four clusters (A, B, C, and D) located on different human chromosomes. This transcriptional factor family with 39 members controls posterior-anterior patterning during embryogenesis and the development of specific organs (reviewed in Ref. (24)). We validated the induction of HOXA gene expression including HOXA4, HOXA5, HOXA6, HOXA7, HOXA9 and HOXA11 in HMGA2-depleted 1833 cells at both mRNA (FIGS. 17D and F) and protein (FIG. 17G) levels.

Figure 23:
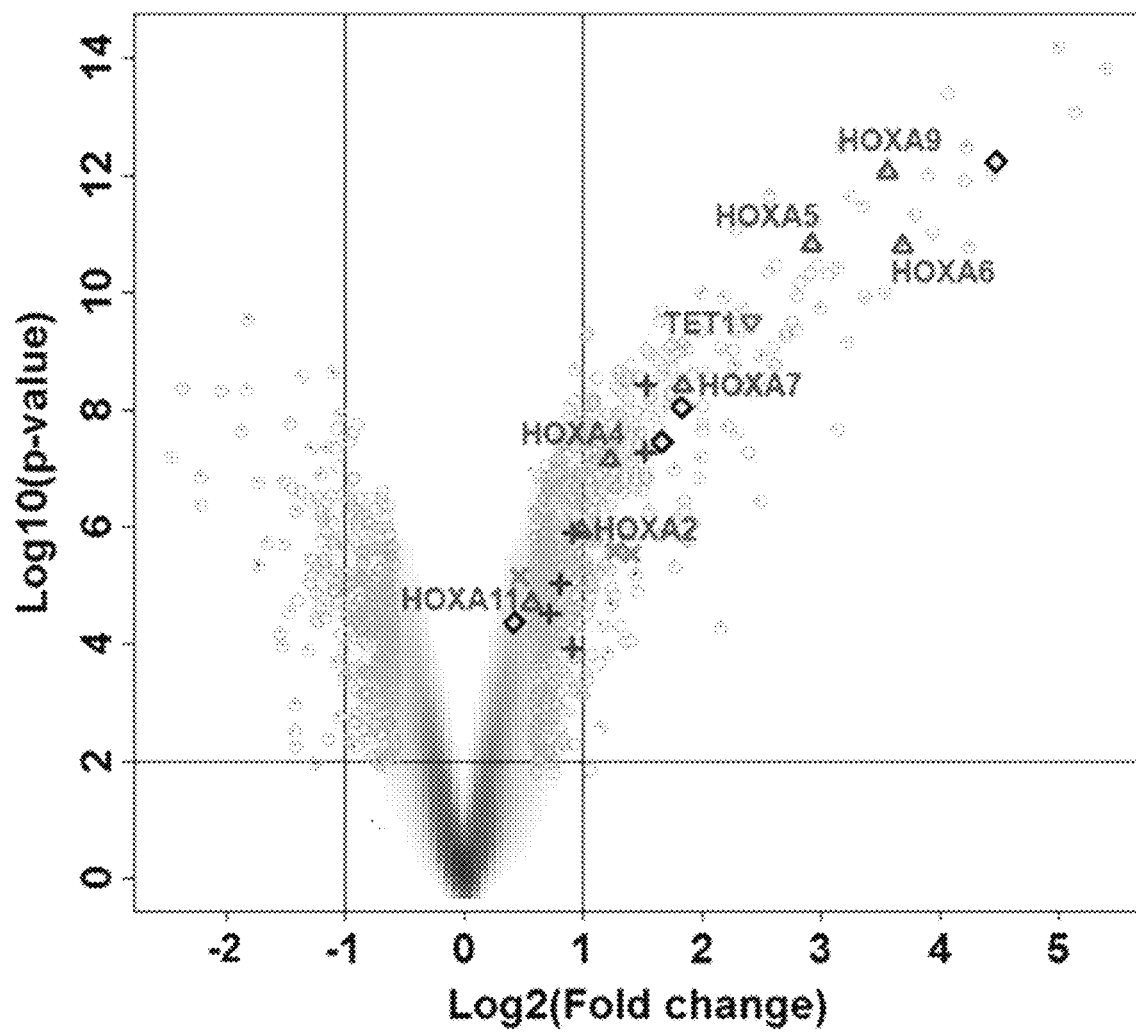
FIG. 23 shows a volcano plot for gene expression in 1833 cells stably transduced with either shHMGA2 or control SCR sh. TET1 and HOX gene expression (particularly HOXA4-A9) was significantly increased in HMGA2-depleted 1833 cells. Yellow circles represent 1,012 differentially expressed genes (fold change >1.5, P<0.05, and FDR<0.01). Differentially up-regulated HOXA genes are labeled in triangle symbols; differentially up-regulated HOXB genes are labeled in plus symbols; differentially up-regulated HOXC genes are labeled in "x" symbols; differentially up-regulated HOXD genes are labeled in diamond symbols; and TET1 is labeled with an inverted triangle.
Figure 24:
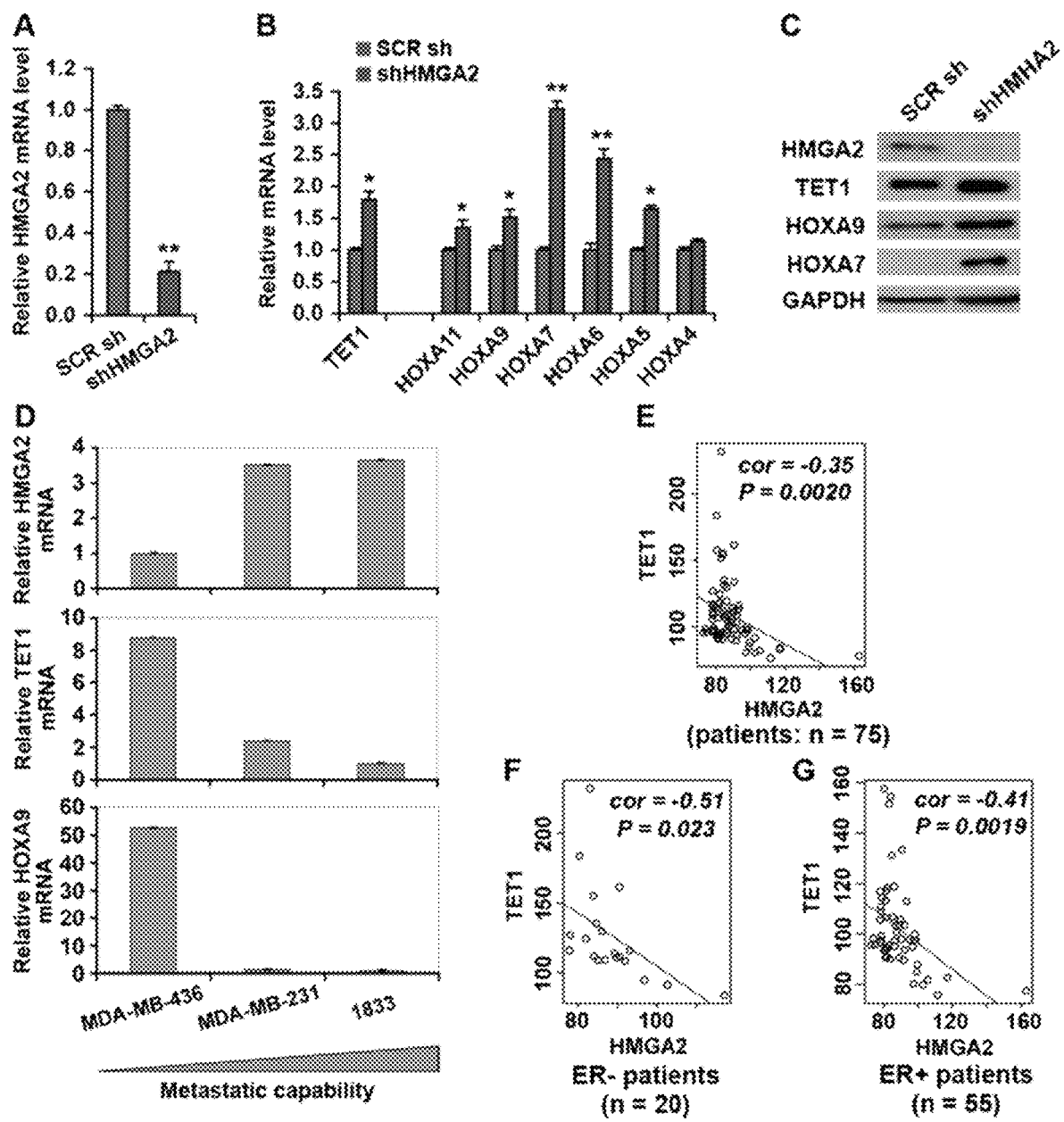
FIG. 24A-G qRT-PCR and immunoblotting analyses showing induction of TET1 and HOXA gene expression and clinical relevance. MDA-MB-436 cells were stably transduced with HMGA2 shRNA (shHMGA2) or control SCR sh. (A and B) HMGA2 (A) and TET1 and HOXA4/5/6/7/9/11 (B) mRNA analyzed by qRT-PCR (GAPDH as normalization control). (C) HMGA2, TET1, and HOXA9/7 protein analyzed by immunoblotting (GAPDH as control). (D) HMGA2, TET1, and HOXA9 mRNA in MDA-MB-436, MDA-MB-231, or 1833 cells analyzed by qRT-PCR (GAPDH as normalization control). (E-G) Significant negative correlation between HMGA2 and TET1 expression in breast cancer subjects (E; n=75) including estrogen receptor (ER)-negative (F; n=20) and ER-positive (G; n=55) subsets. Correlations were determined by Pearson's correlation coefficient. P value was determined by Student t test. (A-D) Data are means±SEM; n=3. *P<0.05; **P<0.01.

Among the other genes induced by HMGA2 depletion was TET1 (FIGS. 17A and 23). We confirmed that HMGA2 is a negative regulator of TET1 in 1833 cells by qRT-PCR and immunoblotting (FIGS. 17E and G). Consistent with increased TET1 expression, we observed elevated 5hmC levels in HMGA2-depleted 1833 cells (FIG. 17H). We also observed similar induction of TET1 and HOXA gene expression following HMGA2 depletion by shRNA in MDA-MB-436 cells, although the effects were not as robust, consistent with their relatively higher basal levels of TET1 and HOXA protein and the less invasive phenotype of these cells (FIGS. 24A-D). Consistent with these observations, analysis of gene expression in a cohort of 75 human breast tumors (25) showed a significantly negative correlation between HMGA2 and TET1 gene expression (FIG. 24E), and this relationship existed in both ER-negative (FIG. 24F) and ER-positive (FIG. 24G) subject subpopulations.

Figure 25:
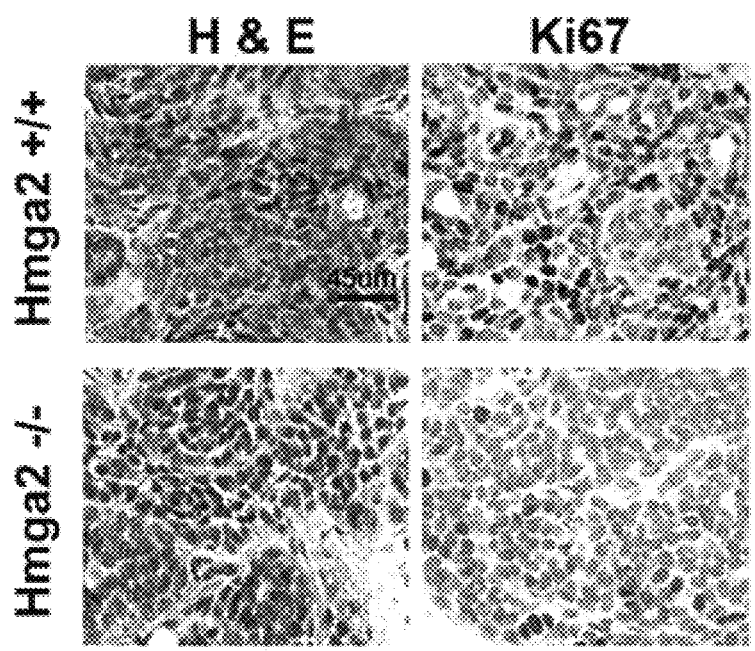
FIG. 25 shows loss of Hmga2 in MMTV-Wnt1 transgenic mice suppresses primary breast tumor growth. Wnt1 transgenic mice were crossed with Hmga2-specific knockout mice (SI Materials and Methods). Mouse primary breast tumors were obtained from Hmga2 wild-type (Hmga2+/+) or null (Hmga2−/−) mice. Immunostaining for H&E (Left) and anti-Ki67 (Right) was conducted on those tumor samples.

To validate the regulation of TET1 and HOXA genes by HMGA2 in vivo, we used an WTV-Wnt1 transgenic mouse model for breast cancer. Deletion of Hmga2 by crossing MMTV-Wnt1 mice with Hmga2-specific knock-out mice reduced tumor incidence (26) and decreased tumor cell proliferation as assessed by immunostaining of Ki67 (FIG. 25). Analysis by qRT-PCR or immunohistochemistry showed a strong induction of Tet1, 5hmC and Hoxa gene expression including Hoxa9 and Hoxa7 in tumors from the WTV-Wnt1/Hmga2$^{-/-}$ mice (FIGS. 17I and J). Moreover, expression of HMGA2 in both 1833 and MDA-MB-436 cells inhibited TET1 expression (FIG. 26). These results indicate that induction of TET1 by depletion of HMGA2 is not an off-target effect, and raise the possibility that loss of HMGA2 suppresses breast tumor growth by inducing TET1 and HOXA genes.

Example 5: TET1 is Involved in an Auto-Regulation in Human Breast Cancer Cells

Since the TET1 protein may bind directly to its own promoter region as suggested by the ChIP-seq data for Tet1 in mouse ES cells (9, 10, 27, 28), we investigated whether TET1 was also involved in regulating its own expression in human breast cancer cells. Conventional ChIP assays using 1833 cells expressing TET1' or vector control showed that TET1 bound to its own promoter region (FIG. 18A). Consistent with increased expression of TET1, ChIP assays also showed that 1833 cells expressing TET1 exhibited increased binding of H3K4Me3, a histone marker for transcriptional activation, to the TET1 promoter region (FIG. 18A). Furthermore, because TET proteins are typically involved in DNA demethylation pathways (2-5, 29, 30), we analyzed the effect of TET1 on the methylation status of its own promoter regions. Our DNA methylation-specific digestion combined with qPCR showed that about 70% of the TET1' promoter region within ±1 kilobase from the transcription start site (TSS) in the parent 1833 cells contained methylated CpG islands, whereas the fraction decreased to 9% following HMGA2 depletion (FIG. 18B). Similarly, bisulfite sequencing within the same region of the TET1 promoter showed an increase in demethylated CpGs from 38% in 1833 cells to 86% in HMGA2-depleted cells (FIG. 18C). 1833 cells treated with 5-azacytidine, a demethylation reagent that inhibits DNMTs, also showed an increase in TET1 expression (FIG. 18D). Together, our results suggest that HMGA2 depletion in 1833 cells causes extensive demethylation of the TET1 promoter, and therefore results in a robust induction of TET1 expression.

Example 6. TET1 Directly Induces HOXA Gene Expression in Breast Cancer Cells Through Binding to the Promoter Regions of HOXA Genes and Contributing to Local Demethylation Previous ChIP-seq analyses of TET1 in mouse ES cells also implied that Hoxa genes might be downstream targets of TET1 as their promoter regions are enriched with TET1 protein binding (9, 10, 27, 28). To investigate whether TET1 is an upstream regulator of the HOXA cluster in human breast cancer cells, we transfected HMGA2-depleted 1833 cells with TET1 siRNA and observed a significant decrease in HOXA gene expression and 5hmC levels along with decreased TET1 expression (FIGS. 19A and B). Conversely, ectopic expression of TET1 in the parent 1833 cells dramatically increased HOXA9 expression and 5hmC levels (FIGS. 19C and D).

To test whether TET1 can regulate HOXA gene expression in vivo, we stably transduced 1833 cells with an inducible TET1 expression vector. Cells were orthotopically injected into the mammary fat pad of mice. QRT-PCR and immunohistochemistry analysis of the mouse xenografts after six weeks of treatment with doxycycline showed a dramatic induction of TET1 and HOXA9 expression (FIGS. 19E and F) as well as increased 5hmC levels (FIG. 19F). Gene expression analysis in a cohort of 54 human breast tumors (25) also showed a strong positive correlation between TET1 and HOXA gene expression (FIG. 19G).

We next investigated whether the induction of HOXA gene expression can also be attributed to direct binding of TET1 and subsequent demethylation of the HOXA promoter regions. Our ChIP-qPCR assays confirmed that TET1 and H3K4Me3 also bound to the HOXA gene promoter regions (FIGS. 20A and B). Our DNA methylation-specific digestion combined with qPCR assay showed that, in the parent 1833 cells, only a small fraction of the promoter region of the HOXA4-A11 genes lacked methylation (FIG. 20C), accounting for the low expression of HOXA transcripts; by contrast, HMGA2 depletion caused dramatic loss of methylation at the HOXA gene loci (FIG. 20C). Bisulfite sequencing of the 14 CpGs near the HOXA7 transcription start site showed only 4% were unmethylated, whereas HMGA2 depletion caused over 80% demethylation (FIG. 20D). Similarly, bisulfite sequencing of the 15 CpGs in the upstream 1 kb locus of the HOXA9 promoter showed that only 5% of the CpG sites were unmethylated, while unmethylated CpGs increased to 91% upon loss of HMGA2 in 1833 cells (FIG. 20E). 1833 cells treated with 5-azacytidine to demethylate DNA also showed a dramatic increase in HOXA7 and HOXA9 expression (FIGS. 20F and G). These results suggest that TET1 binds directly to the HOXA promoter regions and contributes to local demethylation, inducing activating histone binding and gene transcription in breast cancer cells.

Example 7. HMGA2/TET1/HOXA Pathway Regulates Breast Cancer Cell Invasion

To assess the pathological significance of this HMGA2/TET1/HOXA signaling cascade, we determined the effect of manipulating these genes on cell invasion. HMGA2 depletion in 1833 cells decreased cell invasion (FIG. 21A); this effect was reversed in part by siRNA depletion of TET1, HOXA9 or HOXA7 (FIGS. 21B, 21C and 27I-K). 1833 cells treated by demethylation reagent 5-azacytidine or decitabine showed a similar decreased cell invasion and a partial rescue in invasion followed by siRNA depletion of HOXA9 (FIGS. 21D, 27A-C and 27E-G). These data are consistent with a previous study showing that HOXA9 is a breast cancer inhibitor (31). Taken together, our results reveal a signaling cascade whereby HMGA2 promotes breast cancer cell invasion in part through inhibition of TET1-mediated demethylation and HOXA gene expression.

Example 8. Both TET1 and its Downstream Target, HOXA9, Suppress Breast Tumor Growth, Intravasation and Metastasis To determine whether TET1 or HOXA9 can reverse the tumorigenic phenotype in breast cancer cells transformed by HMGA2, we injected 1833 cells expressing inducible TET1 or HOXA9 into the mammary fat pad of mice followed by doxycycline treatment and tested their effect on xenograft tumor growth. Consistent with our in vitro observation (FIGS. 27D, 28A-C), induced expression of TET1 (FIGS. 19E and F) or HOXA9 (FIGS. 28D and E) significantly suppressed xenograft tumor growth (FIGS. 21E-G) and tumor cell proliferation (FIGS. 21H and I).

To test TET1 or HOXA9 regulation of invasion in vivo, we determined their effect on tumor cell intravasation from a primary site in a murine orthotopic model. The 1833 cells expressing inducible TET1 or HOXA9 were injected into the mammary fat pad of mice. After 6 weeks of treatment with doxycycline, cells isolated from the blood were lysed and analyzed for human (tumor) or mouse (control) GAPDH transcripts. QRT-PCR analysis showed that both TET1 and HOXA9 significantly inhibited tumor cell intravasation (FIGS. 21J and K).

Since HMGA2 depletion suppresses breast tumor cell invasion and bone metastasis (21, 22), we determined whether its downstream effects TET1 and HOXA9 similarly inhibit tumor metastasis. Luciferase-labeled 1833 cells expressing inducible TET1 or HOXA9 were injected into the left ventricle of mice that were subsequently treated with doxycycline. After 3 weeks, mice were imaged for luciferase activity. TET1 or HOXA9 expression caused a dramatic decrease in bone metastasis (FIGS. 21L and M), and a significant increase in overall survival rate (FIGS. 21N and 28F-H).

Example 9. HMGA2/TET1/HOXA9 Regulate a Common Set of Important Genes and Encompass a Prognostic Signature for Subject Survival To identify and compare target genes of HMGA2, TET1 and HOXA9, we performed additional microarray assays for cells expressing induced TET1 and HOXA9. Compared to the parental 1833 cells, there were 1012, 7220 and 7132 genes differentially expressed (p<0.05, FDR<0.05, and fold change >1.25) upon HMGA2 depletion, TET1 induction or HOXA9 induction, respectively (FIG. 22A). Interestingly, over 60% of the genes differentially regulated by TET1 or HOXA9 were the same (4510 genes, FIG. 22A), indicating that HOXA9 is a major downstream effecter of TET1. There were 214 genes that overlapped among all three sets including 144 up-regulated and 70 down-regulated genes (FIG. 22A; Table 51). Gene annotation enrichment analysis (DA- VID) (32) indicated that the 144 up-regulated set was enriched in genes that have functions such as binding, catalytic activity, transcription regulator activity, and developmental processes, whereas the 70 down-regulated set was enriched in genes related to epithelial cell proliferation (p=0.041), and the extracellular matrix (p=0.0077) (Table S2). Gene set enrichment analysis (GSEA) (33) indicated that the down-regulated set was also enriched in genes that promote tumor growth and comprise metastasis signatures, such as CCL2, EFEMP1, IL7R, PPAP2B and STX3 (34). This pattern of gene regulation is consistent with a role for TET1 through its effecter HOXA9 in the suppression of breast tumor growth and metastasis.

These data illustrate a novel signaling cascade in human breast cancer progression, by which expression of the oncogene HMGA2 leads to TET1 suppression. Since TET1 binds and demethylates itself as well as HOXA genes including HOXA7 and HOXA9, decreased TET1 causes further inhibition of TET1 as well as loss of HOXA gene expression. Suppression of TET1 and HOXA9 then enables expression of genes that promote breast tumor growth and metastasis (FIG. 22B). When considered individually, neither gene expression of HMGA2, TET HOXA7 nor HOXA9 significantly predicts survival in a heterogeneous group of breast cancer subjects (FIG. 22C, left panel). By contrast, Kaplan-Meier analysis using the complete HMGA2-TET1-HOXA pathway (HMGA2 high, and TET1 low, HOXA9/7 low versus HMGA2 low, and TET1 high, HOXA9/7 high) or a combination of HMGA2 and HOXA genes was able to stratify subjects and predict survival (FIG. 22C, right panel). There are no significant differences in the composition of cancer subtypes between the two stratified groups of subjects (Table S3), suggesting that this regulatory mechanism exists in a variety of breast cancer subtypes. These results indicate that the individual genes are not predictive alone but together define a relevant signaling environment that can be used to identify subjects for targeted DNA methylation-based therapy.

References for this Section

1. Hansen K D, et al. (2011) Increased methylation variation in epigenetic domains across cancer types. Nat Genet 43(8):768-775.
2. Guo J U, Su Y, Zhong C, Ming G L, Song H (2011) Hydroxylation of 5-methylcytosine by TET1 promotes active DNA demethylation in the adult brain. Cell 145(3):423-434.
3. Ito S, et al. (2011) Tet proteins can convert 5-methylcytosine to 5-formylcytosine and 5-carboxylcytosine. Science 333(6047):1300-1303.
4. He Y F, et al. (2011) Tet-Mediated Formation of 5-Carboxylcytosine and Its Excision by TDG in Mammalian DNA. Science 333:1303-1307.
5. Tahiliani M, et al. (2009) Conversion of 5-methylcytosine to 5-hydroxymethylcytosine in mammalian DNA by MLL partner TET1. Science 324(5929):930-935.
6. Inoue A, Zhang Y (2011) Replication-dependent loss of 5-hydroxymethylcytosine in mouse preimplantation embryos. Science 334(6053):194.
7. Ito S, et al. (2010) Role of Tet proteins in 5mC to 5hmC conversion, ES-cell self-renewal and inner cell mass specification. Nature 466(7310):1129-1133.
8. Koh K P, et al. (2011) Tet1 and Tet2 regulate 5-hydroxymethylcytosine production and cell lineage specification in mouse embryonic stem cells. Cell Stem Cell 8(2):200-213.
9. Xu Y, et al. (2011) Genome-wide regulation of 5hmC, 5mC, and gene expression by Tet1 hydroxylase in mouse embryonic stem cells. Mol Cell 42(4):451-464.
10. Williams K, et al. (2011) TET1 and hydroxymethylcytosine in transcription and DNA methylation fidelity. Nature 473(7347):343-348.
11. Haffner M C, et al. (2011) Global 5-hydroxymethylcytosine content is significantly reduced in tissue stem/progenitor cell compartments and in human cancers. Oncotarget 2(8):627-637.
12. Kudo Y, et al. (2012) Loss of 5-hydroxymethylcytosine is accompanied with malignant cellular transformation. Cancer Sci 103(4):670-676.
13. Yang H, et al. (2013) Tumor development is associated with decrease of TET gene expression and 5-methylcytosine hydroxylation. Oncogene 32(5):663-669.
14. Lian C G, et al. (2012) Loss of 5-hydroxymethylcytosine is an epigenetic hallmark of melanoma. Cell 150(6):1135-1146.
15. Fusco A, Fedele M (2007) Roles of HMGA proteins in cancer. Nature reviews. Cancer 7(12):899-910.
16. Rogalla P, et al. (1997) Expression of HMGI-C, a member of the high mobility group protein family, in a subset of breast cancers: relationship to histologic grade. Mol Carcinog 19(3): 153-156.
17. Abe N, et al. (2003) An increased high-mobility group A2 expression level is associated with malignant phenotype in pancreatic exocrine tissue. Br J Cancer 89(11): 2104-2109.
18. Miyazawa J, Mitoro A, Kawashiri S, Chada K K, Imai K (2004) Expression of mesenchyme-specific gene HMGA2 in squamous cell carcinomas of the oral cavity. Cancer Res 64(6):2024-2029.
19. Meyer B, et al. (2007) HMGA2 overexpression in non-small cell lung cancer. Mol Carcinog 46(7):503-511.
20. Benson K F, Chada K (1994) Mini-mouse: phenotypic characterization of a transgenic insertional mutant allelic to pygmy. Genet Res 64(1):27-33.
21. Yun J, et al. (2011) Signalling pathway for RKIP and Let-7 regulates and predicts metastatic breast cancer. EMBO J 30(21):4500-4514.
22. Dangi-Garimella S, et al. (2009) Raf kinase inhibitory protein suppresses a metastasis signalling cascade involving LIN28 and let-7. EMBO J 28(4):347-358.
23. Kang Y, et al. (2003) A multigenic program mediating breast cancer metastasis to bone. Cancer Cell 3(6):537-549.
24. Shah N, Sukumar S (2010) The Hox genes and their roles in oncogenesis. Nat Rev Cancer 10(5):361-371.
25. Enerly E, et al. (2011) miRNA-mRNA integrated analysis reveals roles for miRNAs in primary breast tumors. PLoS One 6(2):e16915.
26. Morishita A, et al. (2013) HMGA2 is an in vivo driver of tumor metastasis. Cancer Res In press.
27. Wu H, et al. (2011) Dual functions of Tet1 in transcriptional regulation in mouse embryonic stem cells. Nature 473(7347):389-393.
28. Wu H, Zhang Y (2011) Tet1 and 5-hydroxymethylation: A genome-wide view in mouse embryonic stem cells. Cell Cycle 10(15):2428-2436.
29. Bhutani N, Burns D M, Blau H M (2011) DNA demethylation dynamics. Cell 146(6):866-872.
30. Cortellino S, et al. (2011) Thymine DNA glycosylase is essential for active DNA demethylation by linked deamination-base excision repair. Cell 146(1):67-79.

31. Gilbert P M, et al. (2010) HOXA9 regulates BRCA1 expression to modulate human breast tumor phenotype. The Journal of clinical investigation 120(5):1535-1550.
32. Huang da W, Sherman B T, Lempicki R A (2009) Systematic and integrative analysis of large gene lists using DAVID bioinformatics resources. Nat Protoc 4(1):44-57.
33. Subramanian A, et al. (2005) Gene set enrichment analysis: a knowledge-based approach for interpreting genome-wide expression profiles. Proc Natl Acad Sci USA 102(43): 15545-15550.
34. Han H J, Russo J, Kohwi Y, Kohwi-Shigematsu T (2008) SATB1 reprogrammes gene expression to promote breast tumour growth and metastasis. Nature 452(7184):187-193.
35. Hsu C H, et al. (2012) TET1 suppresses cancer invasion by activating the tissue inhibitors of metalloproteinases. Cell reports 2(3):568-579.
36. Ono R, et al. (2002) LCX, leukemia-associated protein with a CXXC domain, is fused to MLL in acute myeloid leukemia with trilineage dysplasia having t(10;11)(q22;q23). Cancer research 62(14):4075-4080.
37. Faber J, et al. (2009) HOXA9 is required for survival in human MLL-rearranged acute leukemias. Blood 113(11):2375-2385.
38. Novak P, et al. (2006) Epigenetic inactivation of the HOXA gene cluster in breast cancer. Cancer Res 66(22):10664-10670.
39. Dreszer T R, et al. (2012) The UCSC Genome Browser database: extensions and updates 2011. Nucleic Acids Res 40(Database issue):D918-923.

Tables

TABLE S1

List of the 214 genes commonly regulated by HMGA2, TET1 and HOXA9 in 1833 cells.

| SYMBOL | Depleted HMGA2 vs. control | Induced TET1 vs. control | Induced HOXA9 vs. control | Tet1 target in mES |
|---|---|---|---|---|
| ABCG2 | down | down | down | no |
| ACVR1C | up | up | up | yes |
| ADAMTS12 | down | down | down | no |
| AK5 | down | down | down | yes |
| AKAP12 | up | up | up | yes |
| APOC1 | up | up | up | no |
| ARL6 | up | up | up | no |
| ASAM | down | down | down | no |
| BAI3 | up | up | up | yes |
| BCL6B | up | up | up | yes |
| BMP4 | down | down | down | no |
| BRWD1 | up | up | up | yes |
| C15orf51 | up | up | up | no |
| C1orf91 | up | up | up | no |
| C3orf28 | up | up | up | no |
| C6orf211 | up | up | up | no |
| C9orf86 | up | up | up | no |
| CA2 | up | up | up | no |
| CALCRL | up | up | up | no |
| CAMKV | up | up | up | yes |
| CASKIN1 | up | up | up | yes |
| CCDC120 | up | up | up | no |
| CCL2 | down | down | down | no |
| CDA | down | down | down | yes |
| CDC37L1 | up | up | up | yes |
| CENTA2 | up | up | up | no |
| CLCN4 | down | down | down | no |
| CMBL | down | down | down | no |
| CNTN1 | up | up | up | no |
| COX7C | up | up | up | no |
| CREB3L2 | down | down | down | yes |
| CSRP1 | down | down | down | yes |
| CYP4V2 | down | down | down | no |
| DDAH1 | down | down | down | yes |
| DEPDC2 | up | up | up | no |
| DIXDC1 | up | up | up | yes |
| DKFZp434H1419 | down | down | down | no |
| DLX2 | up | up | up | yes |
| DNAJC6 | down | down | down | yes |
| DSC2 | up | up | up | no |
| DTX3L | down | down | down | yes |
| DUSP10 | down | down | down | yes |
| DYNC2LI1 | up | up | up | yes |
| DYSF | down | down | down | yes |
| EFEMP1 | down | down | down | yes |
| EIF5A2 | down | down | down | yes |
| EML1 | up | up | up | yes |
| EPHA3 | up | up | up | yes |
| EPHA7 | up | up | up | no |
| EPHB1 | up | up | up | yes |
| EPM2AIP1 | up | up | up | yes |
| ERC2 | up | up | up | yes |
| ETV5 | down | down | down | yes |
| EVI2A | down | down | down | no |
| FABP6 | up | up | up | no |
| FAM130A2 | up | up | up | no |
| FAM83B | up | up | up | no |
| FBXO27 | down | down | down | yes |
| FKBP10 | up | up | up | yes |
| FLJ32810 | down | down | down | no |
| FLJ37396 | up | up | up | no |
| FLJ37453 | up | up | up | no |
| FLJ43315 | up | up | up | no |
| FLJ44253 | up | up | up | no |
| FLRT3 | up | up | up | no |
| FUZ | up | up | up | no |
| GALNT3 | down | down | down | yes |
| GALNTL1 | up | up | up | yes |
| GFOD2 | up | up | up | yes |
| GFPT1 | down | down | down | yes |
| GJC1 | up | up | up | yes |
| GPM6B | up | up | up | no |
| GPRIN3 | up | up | up | yes |
| GSTM4 | down | down | down | yes |
| GSTO2 | up | up | up | no |
| GULP1 | down | down | down | yes |
| H3F3A | up | up | up | yes |
| HEY1 | up | up | up | yes |
| HIST1H2BJ | up | up | up | yes |
| HMGN3 | up | up | up | yes |
| HNRNPA1 | up | up | up | no |
| HOXD13 | up | up | up | yes |
| HSPC105 | down | down | down | no |
| IFFO | up | up | up | no |
| IFT57 | up | up | up | yes |
| IFT81 | up | up | up | yes |
| IL7R | down | down | down | no |
| INADL | up | up | up | yes |
| JARID1A | up | up | up | no |
| JHDM1D | up | up | up | yes |
| JMJD1A | up | up | up | no |
| JUB | down | down | down | yes |
| KAL1 | down | down | down | no |
| KCNJ2 | up | up | up | no |
| KCNQ3 | down | down | down | yes |
| KIAA1199 | down | down | down | no |
| KLHDC8B | up | up | up | yes |
| KLHL3 | up | up | up | no |
| LGR4 | down | down | down | no |
| LIPH | down | down | down | yes |
| LMBR1L | up | up | up | yes |
| LOC286297 | up | up | up | no |
| LOC389833 | up | up | up | no |
| LOC440737 | up | up | up | no |
| LOC646934 | up | up | up | no |

TABLE S1-continued

List of the 214 genes commonly regulated by HMGA2, TET1 and HOXA9 in 1833 cells.

| SYMBOL | Depleted HMGA2 vs. control | Induced TET1 vs. control | Induced HOXA9 vs. control | Tet1 target in mES |
|---|---|---|---|---|
| LOC728220 | up | up | up | no |
| LOC728914 | up | up | up | no |
| LOC729530 | up | up | up | no |
| LPHN2 | up | up | up | no |
| LPHN3 | up | up | up | yes |
| LRP1B | up | up | up | no |
| LZTFL1 | up | up | up | yes |
| MAMLD1 | down | down | down | no |
| MARCH3 | down | down | down | no |
| MFGE8 | down | down | down | yes |
| MID1 | down | down | down | no |
| MOAP1 | up | up | up | yes |
| MPND | up | up | up | yes |
| MTIF3 | up | up | up | yes |
| NCOA5 | down | down | down | no |
| NDUFA1 | up | up | up | yes |
| NDUFB4 | up | up | up | no |
| NEBL | up | up | up | yes |
| NEK3 | up | up | up | yes |
| NEXN | down | down | down | yes |
| NPHP3 | up | up | up | yes |
| NR2F1 | up | up | up | yes |
| NR3C2 | down | down | down | yes |
| NRK | down | down | down | no |
| NSF | down | down | down | no |
| NUP62CL | up | up | up | yes |
| OAF | down | down | down | yes |
| OAS3 | down | down | down | no |
| PAR1 | up | up | up | no |
| PAXIP1 | down | down | down | yes |
| PCDH17 | up | up | up | no |
| PCDH18 | up | up | up | yes |
| PCDH19 | up | up | up | yes |
| PCDH7 | up | up | up | yes |
| PCDH9 | up | up | up | yes |
| PDE5A | up | up | up | yes |
| PDE7B | down | down | down | no |
| PES1 | up | up | up | no |
| PHACTR1 | down | down | down | yes |
| PLK2 | down | down | down | yes |
| PLTP | up | up | up | yes |
| PPAP2B | down | down | down | yes |
| PPARA | down | down | down | yes |
| PTPRB | up | up | up | yes |
| RAB40A | up | up | up | no |
| RANBP9 | down | down | down | yes |
| RAPGEF4 | up | up | up | no |
| RARB | up | up | up | no |
| RASGEF1B | up | up | up | yes |
| RBM3 | up | up | up | no |
| RBM34 | up | up | up | yes |
| RNF128 | up | up | up | yes |
| RNU2 | up | up | up | no |
| RNU2B | up | up | up | no |
| ROR1 | down | down | down | yes |
| RPL3 | up | up | up | no |
| RPL35 | up | up | up | no |
| RPL36A | up | up | up | no |
| RPL39 | up | up | up | no |
| SCARNA8 | up | up | up | no |
| SCARNA9 | up | up | up | no |
| SECTM1 | down | down | down | no |
| SEPP1 | up | up | up | no |
| SERINC2 | down | down | down | yes |
| SERPINF1 | up | up | up | no |
| SERTAD4 | down | down | down | yes |
| SESN3 | up | up | up | yes |
| SLAMF7 | down | down | down | no |
| SLC13A4 | up | up | up | no |
| SLC16A2 | down | down | down | no |
| SLC22A3 | down | down | down | yes |
| SLC29A4 | up | up | up | yes |
| SLC44A5 | up | up | up | yes |
| SNCA | up | up | up | yes |
| SNORA14B | up | up | up | no |
| SNORA50 | up | up | up | no |
| SNORD15A | up | up | up | no |
| SNORD15B | up | up | up | no |
| SNTB1 | down | down | down | yes |
| SP140 | down | down | down | no |
| SPON1 | up | up | up | yes |
| SPPL2B | up | up | up | no |
| SPRED2 | down | down | down | yes |
| SPRY2 | down | down | down | yes |
| ST3GAL6 | down | down | down | yes |
| STK38L | up | up | up | yes |
| STX3 | down | down | down | no |
| SYT1 | up | up | up | yes |
| TCF4 | up | up | up | yes |
| TGDS | up | up | up | no |
| THOC3 | up | up | up | yes |
| TIMP3 | down | down | down | no |
| TMEM67 | up | up | up | yes |
| TNFRSF21 | down | down | down | yes |
| TSC22D3 | up | up | up | no |
| TSPAN7 | up | up | up | no |
| UXT | up | up | up | no |
| VAV1 | up | up | up | yes |
| VKORC1 | up | up | up | yes |
| WDR48 | up | up | up | yes |
| WDR63 | up | up | up | no |
| WNT3 | down | down | down | yes |
| YPEL2 | up | up | up | yes |
| ZBTB26 | up | up | up | yes |
| ZNF484 | up | up | up | no |
| ZNF74 | up | up | up | no |
| ZNF773 | up | up | up | no |
| ZNF84 | up | up | up | no |
| ZSCAN23 | up | up | up | no |

TABLE S2

The list of gene categories in which the 214 genes commonly regulated by HMGA2, TET1 and HOXA9 in 1833 cells were enriched (P Value is hypergeometric probability).

| Term | Count | Fold Enrichment | P Value | Genes | Regulation |
|---|---|---|---|---|---|
| Homophilic cell adhesion | 6 | 6.8 | 0.002 | PCDH9, DSC2, PCDH7, PCDH17, PCDH19, PCDH18 | up |
| Cell adhesion | 9 | 3.4 | 0.005 | FLRT3, CNTN1, PCDH9, DSC2, PCDH7, PCDH17, PCDH19, PCDH18, SPON1 | up |

TABLE S2-continued

The list of gene categories in which the 214 genes commonly regulated by HMGA2, TET1 and HOXA9 in 1833 cells were enriched (P Value is hypergeometric probability).

| Term | Count | Fold Enrichment | P Value | Genes | Regulation |
|---|---|---|---|---|---|
| Plasma membrane | 35 | 1.4 | 0.011 | SYT1, SNCA, AKAP12, TSPAN7, KCNJ2, EPHB1, ACVR1C, GJC1, RAB40A, CAMKV, LPHN2, LPHN3, SLC29A4, BAI3B, CALCRL, PAK1, FLRT3, PTPRB, DIXDC1, INADL, PCDH9, PCDH7, PCDH17, VAV1, PCDH19, PCDH18, EPHA3, TMEM67, LMBR1L, EPHA7, CNTN1, DSC2, CA2, SLC13A4, ERC2 | up |
| Cell junction | 7 | 2.8 | 0.038 | SYT1, DIXDC1, INADL, DSC2, ERC2, PAK1, GJC1 | up |
| Methylation | 6 | 4.0 | 0.017 | RPL36A, LOC728914, RBM3, HIST1H2BJ, H3F3A, HNRNPA1, RAB40A | up |
| Phosphorylation | 11 | 2.0 | 0.039 | CAMKV, NDUFB4, EPHA7, NEK3, SNCA, PAK1, NDUFA1, STK38L, EPHB1, ACVR1C, EPHA3 | up |
| Translational elongation | 4 | 5.9 | 0.030 | RPL36A, RPL35, RPL3, RPL39 | up |
| Negative regulation of transcription from RNA polymerase II promoter | 6 | 3.4 | 0.032 | DLX2, HEY1, BCL6B, RARB, TCF4, NR2F1 | up |
| Branching morphogenesis of a nerve | 2 | 99.1 | 0.020 | DLX2, EPHA7 | up |
| Proteinaceous extracellular matrix | 6 | 5.1 | 0.006 | BMP4, WNT3, KAL1, EFEMP1, ADAMTS12, TIMP3 | down |
| Extracellular matrix | 6 | 4.7 | 0.008 | BMP4, WNT3, KAL1, EFEMP1, ADAMTS12, TIMP3 | down |
| Response to extracellular stimulus | 5 | 5.4 | 0.013 | BMP4, PPARA, CCL2, SLC22A3, TIMP3 | down |
| Plasma membrane part | 15 | 1.9 | 0.020 | PHACTR1, JUB, STX3, ASAM, MFGE8, NEXN, IL7R, SLC16A2, DYSF, KCNQ3, SNTB1, SPRED2, ROR1, SLC22A3, EIF5A2 | down |
| Extracellular region part | 9 | 2.5 | 0.020 | BMP4, SECTM1, WNT3, CCL2, KAL1, EFEMP1, MFGE8, ADAMTS12, TIMP3 | down |
| Membrane organization | 6 | 3.7 | 0.020 | STX3, DYSF, GULP1, DNAJC6, MFGE8, MARCH3 | down |
| Membrane | 31 | 1.4 | 0.024 | GALNT3, JUB, TNFRSF21, ASAM, NR3C2, IL7R, LGR4, SERINC2, SPRY2, DYSF, KCNQ3, EVI2A, ST3GAL6, SNTB1, SPRED2, CREB3L2, SLC22A3, PPAP2B, SECTM1, STX3, MFGE8, SLAMF7, CYP4V2, ABCG2, MARCH3, SLC16A2, PAXIP1, ROR1, LIPH, EIF5A2, CLCN4 | down |
| Signal | 19 | 1.7 | 0.027 | BMP4, SECTM1, TNFRSF21, CCL2, ASAM, EFEMP1, MFGE8, SLAMF7, OAF, | down |

TABLE S2-continued

The list of gene categories in which the 214 genes commonly regulated by HMGA2, TET1 and HOXA9 in 1833 cells were enriched (P Value is hypergeometric probability).

| Term | Count | Fold Enrichment | P Value | Genes | Regulation |
|---|---|---|---|---|---|
| Epithelial cell proliferation | 2 | 47.5 | 0.041 | IL7R, TIMP3, LGR4, WNT3, KIAA1199, EVI2A, KAL1, ROR1, LIPH, ADAMTS12 BMP4, LGR4 | down |

TABLE S3

The composition of breast cancer subtypes for two groups of subjects stratified by the complete HMGA2/TET1/HOXA pathway in FIG. 6C.

| PATHWAY | | High HMGA2 and Low TET1/HOXA9 (N = 34) | Low HMGA2 and High TET1/HOXA9 (N = 35) |
|---|---|---|---|
| ER negative | | 10 | 11 |
| HER2 negative | | 26 | 27 |
| Tumor subtype | Basal | 2 | 7 |
| | ERBB2+ | 3 | 6 |
| | Lum A | 17 | 13 |
| | Lum B | 5 | 3 |
| | Normal-like | 2 | 3 |
| | Others | 5 | 3 |

The invention has been described in an illustrative manner and it is to be understood the terminology used is intended to be in the nature of description rather than of limitation. All patents and other references cited herein are incorporated herein by reference in their entirety. It is also understood that many modifications, equivalents, and variations of the present disclosure are possible in light of the above teachings. Therefore, it is to be understood that within the scope of the appended claims, the invention may be practiced other than as specifically described.

Additional References

Andre & Zielinski, Optimal strategies for the treatment of metastatic triple-negative breast cancer with currently approved agents. Annals of Oncology. 23 (Suppl 6):vi46-vi51, 2012.

Bertucci F, Finetti P, Birnbaum D (2012) Basal breast cancer: a complex and deadly molecular subtype. Curr Mol Med 12: 96-110.

Curtis C, Shah S P, Chin S F, Turashvili G, Rueda O M, et al. (2012) The genomic and transcriptomic architecture of 2,000 breast tumours reveals novel subgroups. Nature 486: 346-352.

Dangi-Garimella S, Yun J, Eves E M, Newman M, Erkeland S J, et al. (2009) Raf kinase inhibitory protein suppresses a metastasis signalling cascade involving LIN28 and let-7. EMBO J 28: 347-358.

Efron B, Tibshirani R (2007) On testing the significance of sets of genes. Ann Appl Stat 1: 107-129.

Huo D, Ikpatt F, Khramtsov A, Dangou J M, Nanda R, et al. (2009) Population differences in breast cancer: survey in indigenous African women reveals over-representation of triple-negative breast cancer. J Clin Oncol 27: 4515-4521.

Ishikawa M, Numazawa S, Yoshida T (2005) Redox regulation of the transcriptional repressor Bach1. Free Radic Biol Med 38: 1344-1352.

Kang Y, Siegel P M, Shu W, Drobnjak M, Kakonen S M, et al. (2003) A multigenic program mediating breast cancer metastasis to bone. Cancer Cell 3: 537-549.

Ladas E J, Jacobson J S, Kennedy D D, Teel K, Fleischauer A, et al. (2004) Antioxidants and cancer therapy: a systematic review. J Clin Oncol 22: 517-528.

Leek J T, Scharpf R B, Bravo H C, Simcha D, Langmead B, et al. (2010) Tackling the widespread and critical impact of batch effects in high-throughput data. Nat Rev Genet 11: 733-739.

Lehmann B D, Bauer J A, Chen X, Sanders M E, Chakravarthy A B, et al. (2011) Identification of human triple-negative breast cancer subtypes and preclinical models for selection of targeted therapies. J Clin Invest 121: 2750-2767.

Liang Y, Wu H, Lei R, Chong R A, Wei Y, et al. (2012) Transcriptional network analysis identifies BACH1 as a master regulator of breast cancer bone metastasis. J Biol Chem 287: 33533-33544.

McCall M N, Bolstad B M, Irizarry R A (2010) Frozen robust multiarray analysis (fRMA). Biostatistics 11: 242-253.

Melhem-Bertrandt A, Chavez-Macgregor M, Lei X, Brown E N, Lee R T, et al. (2011) Beta-blocker use is associated with improved relapse-free survival in patients with triple-negative breast cancer. J Clin Oncol 29: 2645-2652.

Minn A J, Bevilacqua E, Yun J, Rosner M R (2012) Identification of novel metastasis suppressor signaling pathways for breast cancer. Cell Cycle 11: 2452-2457.

Mira A, Isella C, Renzulli T, Cantarella D, Martelli M L, et al. (2009) The GAB2 signaling scaffold promotes anchorage independence and drives a transcriptional response associated with metastatic progression of breast cancer. Oncogene 28: 4444-4455.

Nelder J A M R (1965) A Simplex Method for Function Minimization. The Computer Journal 7: 308-313.

Paik S, Shak S, Tang G, Kim C, Baker J, et al. (2004) A multigene assay to predict recurrence of tamoxifen-treated, node-negative breast cancer. N Engl J Med 351: 2817-2826.

Pan D, Kocherginsky M, Conzen S D (2011) Activation of the glucocorticoid receptor is associated with poor prognosis in estrogen receptor-negative breast cancer. Cancer Res 71: 6360-6370.

Parker J S, Mullins M, Cheang M C, Leung S, Voduc D, et al. (2009) Supervised risk predictor of breast cancer based on intrinsic subtypes. J Clin Oncol 27: 1160-1167.

Perou C M, Sorlie T, Eisen M B, van de Rijn M, Jeffrey S S, et al. (2000) Molecular portraits of human breast tumours. Nature 406: 747-752.

Sabatier R, Finetti P, Mamessier E, Raynaud S, Cervera N, et al. (2011) Kinome expression profiling and prognosis of basal breast cancers. Mol Cancer 10: 86.

Sorlie T, Perou C M, Tibshirani R, Aas T, Geisler S, et al. (2001) Gene expression patterns of breast carcinomas distinguish tumor subclasses with clinical implications. Proc Natl Acad Sci USA 98: 10869-10874.

Tusher V G, Tibshirani R, Chu G (2001) Significance analysis of microarrays applied to the ionizing radiation response. Proc Natl Acad Sci USA 98: 5116-5121.

van't Veer L J, Dai H, van de Vijver M J, He Y D, Hart A A, et al. (2002) Gene expression profiling predicts clinical outcome of breast cancer. Nature 415: 530-536.

Venet D, Dumont J E, Detours V (2011) Most random gene expression signatures are significantly associated with breast cancer outcome. PLoS Comput Biol 7: e1002240.

Vera-Ramirez L, Sanchez-Rovira P, Ramirez-Tortosa M C, Ramirez-Tortosa C L, Granados-Principal S, et al. (2011) Free radicals in breast carcinogenesis, breast cancer progression and cancer stem cells. Biological bases to develop oxidative-based therapies. Crit Rev Oncol Hematol 80: 347-368.

Wang Y, Klijn J G, Zhang Y, Sieuwerts A M, Look M P, et al. (2005) Gene-expression profiles to predict distant metastasis of lymph-node-negative primary breast cancer. Lancet 365: 671-679.

Warnatz H J, Schmidt D, Manke T, Piccini I, Sultan M, et al. (2011) The BTB and CNC homology 1 (BACH1) target genes are involved in the oxidative stress response and in control of the cell cycle. J Biol Chem 286: 23521-23532.

Wirapati P, Sotiriou C, Kunkel S, Farmer P, Pradervand S, et al. (2008) Meta-analysis of gene expression profiles in breast cancer: toward a unified understanding of breast cancer subtyping and prognosis signatures. Breast Cancer Res 10: R65.

Yamasaki C, Tashiro S, Nishito Y, Sueda T, Igarashi K (2005) Dynamic cytoplasmic anchoring of the transcription factor Bach1 by intracellular hyaluronic acid binding protein IHABP. J Biochem 137: 287-296.

Yun J, Frankenberger C A, Kuo W L, Boelens M C, Eves E M, et al. (2011) Signalling pathway for RKIP and Let-7 regulates and predicts metastatic breast cancer. EMBO J 30: 4500-4514.

Zenke-Kawasaki Y, Dohi Y, Katoh Y, Ikura T, Ikura M, et al. (2007) Heme induces ubiquitination and degradation of the transcription factor Bach1. Mol Cell Biol 27: 6962-6971.

TABLE 1

| Let-7 Targets | | BACH1 Targets | |
|---|---|---|---|
| ARID3B | AT rich interactive domain 3B (BRIGHT-like) | BMPER | BMP binding endothelial regulator |
| CCNJ | cyclin J | DYM | dymeclin |
| GOLT1B | golgi transport 1B | FBXO42 | F-box protein 42 |
| HIC2 | hypermethylated in cancer 2 | FRMPD4 | FERM and PDZ domain containing 4 |
| IGF2BP3 | insulin-like growth factor 2 mRNA binding protein 3 | HERC3 | HECT and RLD domain containing E3 ubiquitin protein ligase 3 |
| IL13 | interleukin 13 | HS3ST3B1 | heparan sulfate (glucosamine) 3-O-sulfotransferase 3B1 |
| MAP4K4 | mitogen-activated protein kinase kinase kinase kinase 4 | IL1RAP | interleukin 1 receptor accessory protein |
| NF2 | neurofibromin 2 (merlin) | IL7 | interleukin 7 |
| PAPPA | pregnancy-associated plasma protein A, pappalysin 1 | MAGEC1 | melanoma antigen family C, 1 |
| SLC6A1 | solute carrier family 6 (neurotransmitter transporter, GABA), member 1 | MYCT1 | myc target 1 |
| TGFBR1 | transforming growth factor, beta receptor 1 | PDE1C | phosphodiesterase 1C, calmodulin-dependent 70 kDa |
| ZC3H3 | zinc finger CCCH-type containing 3 | PRDM1 | PR domain containing 1, with ZNF domain |
| | | RCAN3 | RCAN family member 3 |

TABLE 2A

| | Univariate Analysis | | Multivariate Analysis | |
|---|---|---|---|---|
| Risk Factor | HR (95% CI) | p-value | HR (95% CI) | p-value |
| Nodal Status | 1.47 (1.104-1.971) | 0.0086 | 1.450 (1.0828-1.9425) | 0.013 |
| Grade (1, 2 vs 3) | 0.872 (0.965-1.029) | 0.36 | | |
| Size (> vs ≤ 20 mm) | 0.982 (0.9832-0.9915) | 0.00017 | 0.982 (0.9726-0.9907) | 0.000083 |
| ER status | 1.03 (0.7757-1.358) | 0.86 | | |
| Age | 1 (0.9925-1.015) | 0.54 | | |
| BPMS | 2.3 (1.406-3.762) | 0.0009 | 2.183 (1.3057-3.6495) | 0.0029 |

TABLE 2B

| Model | Log-likelihood |
|---|---|
| S ~ node + size | −1472.7 |
| S ~ node + size + BPMS | −1469.1 |
| −2*(L0 − L1) | 7.2 |
| | p-value = 0.0073 |

TABLE 3A

| Gene Signatures | Hazard Ratio (95% CI) | p-value | Hazard Ratio (95% CI) | p-value |
|---|---|---|---|---|
| Proliferation Meta-gene: ER+/HER2− vs ER−/HER2− | 0.65055 (0.1894-2.2341) | 0.4946 | 0.62060 (0.17661-2.1808) | 0.4569 |
| Proliferation Meta-gene: HER2+ vs ER−/HER2− | 0.30734 (0.1024-0.9226) | 0.0354 | 0.28245 (0.09221-0.8652) | 0.0269 |
| Intrinsic Subtyping HER2+ vs Basal | 2.50472 (0.7916-7.9253) | 0.1182 | 2.76312 (0.85292-8.9515) | 0.0901 |
| Intrinsic Subtyping Luminal-A vs Basal | 0.94615 (0.2521-3.5514) | 0.9346 | 1.05112 (0.27204-4.0614) | 0.9424 |
| Intrinsic Subtyping Luminal-B vs Basal | 1.98719 (0.5674-6.9599) | 0.2829 | 2.19388 (0.60928-7.8997) | 0.2294 |
| Intrinsic Subtyping Normal vs Basal | 1.29351 (0.4278-3.9114) | 0.6485 | 1.38074 (0.44619-4.2727) | 0.5756 |
| Recurrence Score: Intermediate vs High | 0.74021 (0.4402-1.2447) | 0.2566 | 0.75085 (0.44564-1.2651) | 0.2817 |
| Recurrence Score: Low vs High | 0.69454 (0.4449-1.0842) | 0.1087 | 0.73289 (0.46809-1.1475) | 0.1743 |
| Mammaprint: Poor vs Good | 1.48393 (0.9134-2.4109) | 0.1109 | 1.39329 (0.85261-2.2769) | 0.1856 |
| 76-Gene Signature: Poor vs Good | 1.31577 (0.8733-1.9825) | 0.1895 | 0.77205 (0.52729-1.1304) | 0.1925 |
| Sotiriou: Luminal-like vs Basal-like | 0.80253 (0.5487-1.1737) | 0.2567 | 0.53301 (0.23901-1.1886) | 0.1836 |
| Mira: Poor vs Good | 0.53318 (0.2391-1.189) | 0.1243 | 0.46635 (0.24924-0.8726) | 0.1241 |
| BPMS: BPMS− vs BPMS+ | | | 0.4878 (0.261-0.912) | 0.017 |

TABLE 3B

| Model | Log-likelihood |
|---|---|
| S ~ prolif + pam50 + RS + mamma + 76gene + sot + mira | −713.11 |
| S ~ prolif + pam50 + RS + mamma + 76gene + sot + mira + BPMS | −710.71 |
| −2*(L0 − L1) | 4.8 |
| | p-value = 0.028 |

TABLE 4

| Symbols | p-values | Fold Change |
|---|---|---|
| PLCB4 | 3.36E−05 | 1.60 |
| CDH18 | 3.84E−05 | 1.42 |
| TULP3 | 3.60E−05 | 1.38 |
| TMPRSS15 | 1.26E−04 | 1.36 |
| NUP210 | 5.29E−05 | 1.33 |
| BST2 | 1.06E−03 | 1.31 |
| GABBR2 | 2.42E−04 | 1.30 |
| SLC1A3 | 1.47E−04 | 1.29 |
| LTV1 | 4.56E−05 | 1.28 |
| WNT7B | 3.12E−05 | 1.28 |
| KCNAB2 | 2.44E−04 | 1.28 |
| PEX3 | 7.30E−05 | 1.24 |
| GFPT2 | 1.87E−04 | 1.24 |
| F13A1 | 1.30E−04 | 1.22 |
| PIK3CG | 6.46E−04 | 1.22 |
| FBXO30 | 5.05E−05 | 1.21 |
| KIAA1467 | 1.02E−04 | 1.21 |
| ADD2 | 4.19E−04 | 1.21 |
| AIG1 | 8.38E−05 | 1.21 |
| FUCA2 | 2.84E−04 | 1.20 |
| SF3B5 | 3.59E−04 | 1.20 |
| RAB15 | 1.92E−04 | 1.20 |
| PHACTR2 | 1.77E−04 | 1.20 |
| RAP1GAP2 | 1.35E−03 | 1.19 |
| EYA4 | 8.14E−05 | 1.19 |
| SCARA3 | 1.95E−04 | 1.19 |
| C3 | 1.10E−04 | 1.19 |
| PLD5 | 6.96E−04 | 1.18 |
| C6orf192 | 3.19E−04 | 1.18 |
| ADAT2 | 1.22E−03 | 1.18 |
| EEF1A2 | 5.71E−04 | 1.17 |
| AHI1 | 1.20E−04 | 1.17 |
| GPR17 | 1.46E−03 | 1.17 |
| NPEPPS | 4.47E−04 | 1.16 |
| PLXNA1 | 9.14E−05 | 1.16 |
| MYBL2 | 3.64E−04 | 1.16 |
| TBPL1 | 2.19E−04 | 1.15 |
| HBS1L | 4.99E−04 | 1.15 |
| INHBB | 1.69E−04 | 1.15 |
| COX7C | 3.30E−04 | 1.15 |
| PCSK6 | 3.51E−04 | 1.14 |
| ATXN7L3B | 1.50E−04 | 1.14 |
| AGAP2 | 4.69E−04 | 1.14 |
| GCLM | 1.38E−03 | 1.14 |

TABLE 4-continued

| Symbols | p-values | Fold Change |
|---|---|---|
| STX11 | 2.52E−04 | 1.14 |
| CCDC28A | 8.69E−04 | 1.14 |
| SHANK1 | 4.30E−04 | 1.13 |
| DMD | 1.28E−04 | 1.13 |
| C9orf86 | 3.54E−04 | 1.12 |
| SFXN2 | 8.02E−04 | 1.12 |
| GPR126 | 8.22E−04 | 1.12 |
| CMTM3 | 1.23E−03 | 1.12 |
| ZAK | 7.28E−04 | 1.12 |
| SCARB1 | 1.02E−03 | 1.12 |
| KLF11 | 1.03E−03 | 1.12 |
| HMOX1 | 9.10E−04 | 1.12 |
| VTA1 | 8.15E−04 | 1.11 |
| LSP1 | 1.04E−03 | 1.11 |
| DMKN | 1.46E−03 | 1.11 |
| PERP | 5.80E−04 | 1.11 |
| AVPI1 | 1.48E−03 | 1.11 |
| CYB5A | 8.13E−04 | 1.10 |
| AK4 | 8.39E−04 | 1.10 |
| MED23 | 1.42E−03 | 1.10 |
| GLB1L2 | 5.52E−04 | 1.10 |
| REPS1 | 3.14E−04 | 1.10 |
| EIF4E2 | 1.10E−03 | 1.10 |
| PLCD3 | 2.17E−04 | 1.09 |
| ZMAT4 | 9.41E−04 | 1.09 |
| PCDHB3 | 8.25E−04 | 1.09 |
| MTHFSD | 5.69E−04 | 1.08 |
| DKFZp686O24166 | 7.40E−04 | 1.08 |
| RHOB | 1.40E−03 | 1.08 |
| HS6ST1 | 1.31E−03 | 1.08 |
| MRPL39 | 1.37E−03 | 1.08 |
| EPHB4 | 3.97E−04 | 1.07 |
| C3orf23 | 1.22E−03 | 1.06 |
| LOC729444 | 6.15E−04 | 1.06 |
| CTDP1 | 1.32E−03 | 1.06 |
| MAML2 | 1.10E−03 | 0.93 |
| NARS | 1.28E−03 | 0.93 |
| TTC30B | 1.40E−03 | 0.93 |
| IFI27 | 1.52E−04 | 0.92 |
| AMPH | 4.27E−04 | 0.92 |
| CD177 | 1.37E−03 | 0.92 |
| ALG10B | 7.37E−04 | 0.92 |
| RNF19B | 1.02E−03 | 0.92 |
| NIPAL3 | 7.48E−04 | 0.91 |
| FHOD3 | 8.17E−04 | 0.91 |
| HS3ST3B1 | 1.30E−03 | 0.91 |
| PTGR1 | 1.44E−03 | 0.91 |
| FAM160B1 | 1.41E−03 | 0.91 |
| RIOK3 | 8.53E−04 | 0.91 |
| DDX60L | 7.22E−04 | 0.91 |
| HERC3 | 1.26E−03 | 0.91 |
| MEX3C | 1.38E−03 | 0.90 |
| C5orf30 | 8.76E−04 | 0.90 |
| RCAN3 | 3.99E−04 | 0.90 |
| EMB | 1.99E−04 | 0.90 |
| GSPT2 | 2.50E−04 | 0.90 |
| ADAMTS1 | 1.47E−03 | 0.90 |

TABLE 4-continued

Figure 4:
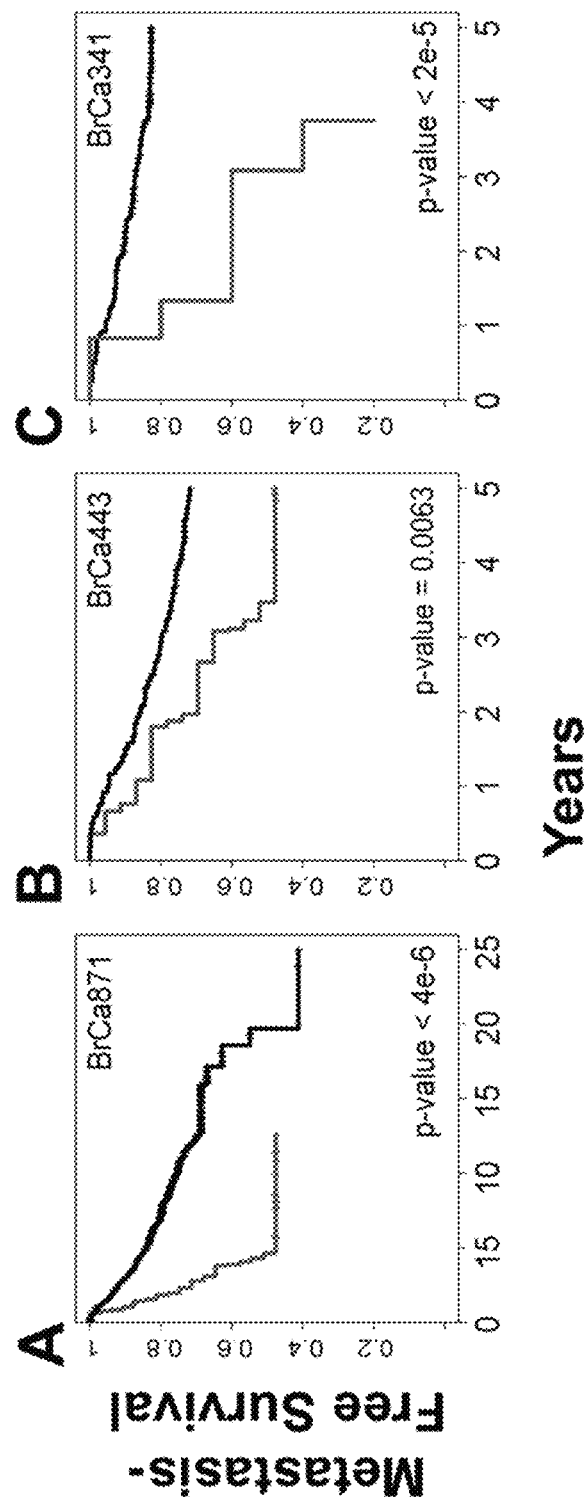
FIG. 4A-C. The BPMS is prognostic for metastasis-free survival (MFS). Patients from three breast cancer datasets, (A) BrCa871 (35 BPMS+ out of 871 patients), (B) BrCa443 (24 BPMS+ out of 443 patients) and (C) BrCa341 (6 BPMS+ out of 341 patients), were stratified for MFS using the BPMS. BrCa871 is shown with no year-specific clinical endpoint to reflect the training data. Gray indicates patient tumors that express the BPMS signature while black indicates patient tumors that do not. Survival curves were generated by Kaplan-Meier analysis, and the indicated P-values were calculated by the log-rank test.
Figure 5:
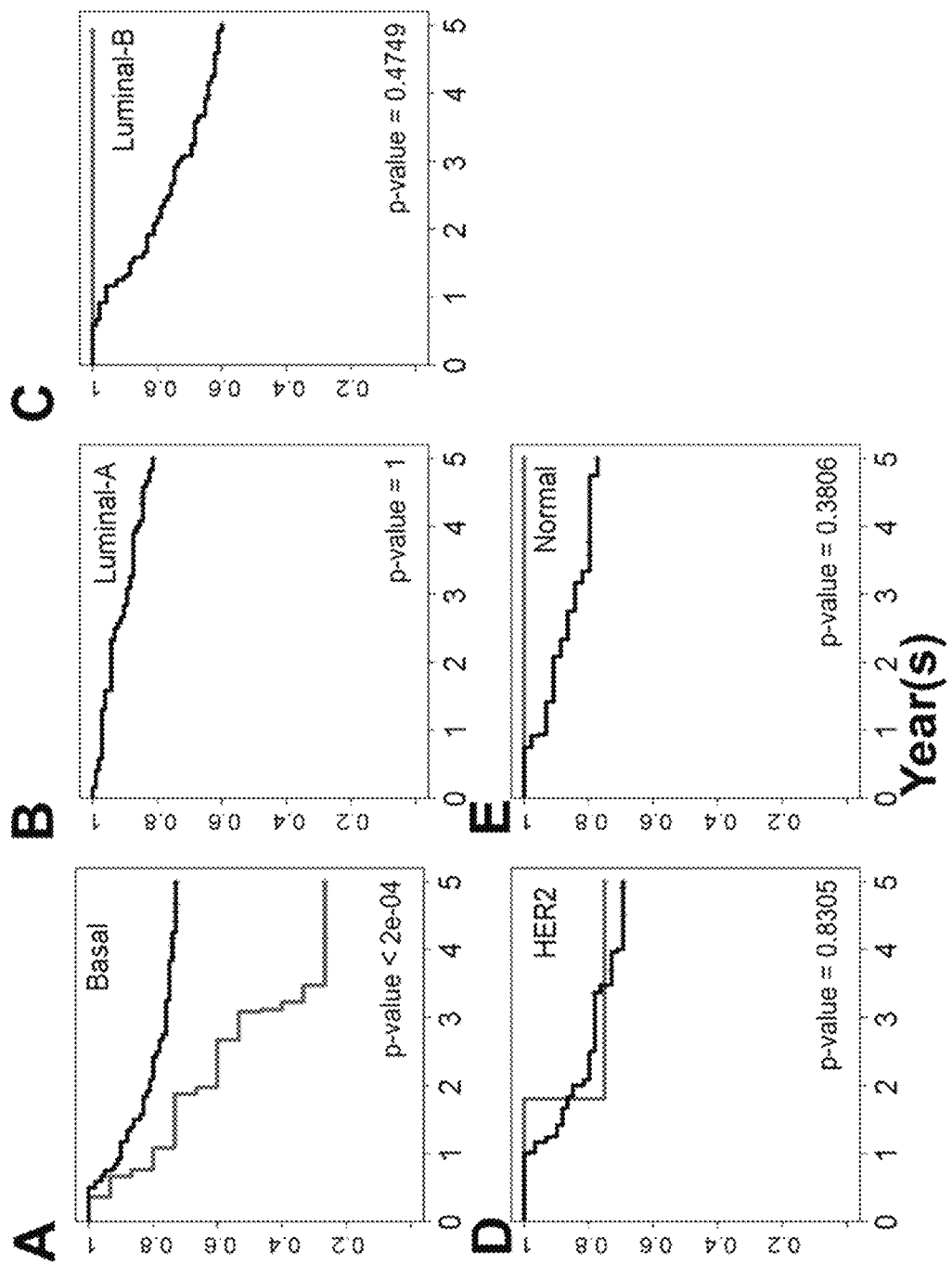
FIG. 5A-E. The BPMS is prognostic for metastasis-free survival of breast cancer patients with tumors of the basal subtype. PAM50 was used to categorize breast tumors into (A) Basal (16 BPMS+ patients out of 120 Basal patients, $\chi^2=13.7$), (B) luminal A (0 BPMS+ patients out of 110 luminal A patients), (C) luminal B (1 BPMS+ patient out of 97 luminal B patients, $\chi^2=0.5$), (D) HER2 (4 BPMS+ patients out of 67 HER2 patients, $\chi^2=0$) and (E) normal (3 BPMS+ patients out of 48 Normal patients, $\chi^2=0.8$) subtypes as indicated. BrCa443 patients were stratified for MFS using the BPMS. Gray indicates patient tumors that express the BPMS signature while black indicates patient tumors that do not. Survival curves were generated by Kaplan-Meier analysis, and the indicated P-values were calculated by the log-rank test.

| Symbols | p-values | Fold Change |
|---|---|---|
| FNDC3A | 1.17E-03 | 0.90 |
| ZSCAN30 | 3.89E-04 | 0.90 |
| C18orf54 | 4.58E-04 | 0.90 |
| IL7 | 1.64E-04 | 0.90 |
| KIAA0495 | 5.25E-04 | 0.90 |
| SGMS1 | 6.48E-04 | 0.89 |
| RAD50 | 1.14E-03 | 0.89 |
| PIAS2 | 8.07E-04 | 0.89 |
| OSBPL6 | 6.82E-04 | 0.89 |
| LRRN1 | 6.79E-04 | 0.89 |
| ARPP19 | 4.41E-04 | 0.89 |
| TBXAS1 | 3.81E-04 | 0.88 |
| SMAD4 | 2.36E-04 | 0.88 |
| KAL1 | 1.43E-03 | 0.88 |
| MAPK13 | 9.75E-04 | 0.88 |
| STXBP2 | 3.61E-04 | 0.88 |
| TNFRSF11B | 1.36E-04 | 0.88 |
| COBLL1 | 1.24E-03 | 0.88 |
| PLAT | 4.80E-04 | 0.88 |
| NA | 4.67E-04 | 0.87 |
| TLR4 | 3.49E-04 | 0.87 |
| EFEMP1 | 6.29E-05 | 0.87 |
| ATP8B1 | 5.82E-04 | 0.87 |
| WASF3 | 9.02E-04 | 0.87 |
| C16orf62 | 2.93E-04 | 0.87 |
| TGFBI | 6.62E-04 | 0.87 |
| DYM | 1.15E-04 | 0.87 |
| LRP1 | 6.50E-04 | 0.87 |
| AKD1 | 7.06E-05 | 0.87 |
| LACE1 | 9.69E-05 | 0.86 |
| BMPER | 1.40E-03 | 0.86 |
| SKIL | 3.86E-04 | 0.86 |
| PELI1 | 1.47E-03 | 0.86 |
| RFPL4A | 1.33E-03 | 0.86 |
| GALNT14 | 7.69E-04 | 0.86 |
| RASGRP3 | 1.11E-03 | 0.86 |
| MGAT4A | 8.30E-04 | 0.85 |
| CCDC80 | 1.34E-03 | 0.85 |
| SELENBP1 | 1.13E-04 | 0.85 |
| PRDM1 | 2.22E-04 | 0.85 |
| GPR116 | 2.67E-04 | 0.84 |
| EPB41L4A | 1.18E-03 | 0.84 |
| MAGEC1 | 6.17E-04 | 0.84 |
| PRR16 | 5.57E-04 | 0.84 |
| TIE1 | 1.97E-04 | 0.83 |
| ANO5 | 8.05E-04 | 0.82 |
| CYP24A1 | 8.72E-04 | 0.82 |
| FAM83A | 5.77E-05 | 0.81 |
| CHRM3 | 1.19E-03 | 0.81 |
| LOX | 2.79E-04 | 0.80 |
| 1-Mar | 4.08E-04 | 0.80 |
| FIG4 | 3.02E-04 | 0.80 |
| ENTPD3 | 1.18E-04 | 0.78 |
| SAMD12 | 6.53E-05 | 0.78 |
| FRMPD4 | 4.81E-05 | 0.77 |
| PDE1C | 8.62E-05 | 0.77 |
| TMEM45B | 7.54E-05 | 0.72 |
| PLEKHA7 | 6.26E-04 | 0.72 |
| SPOCK1 | 4.08E-05 | 0.72 |
| NAP1L3 | 1.38E-04 | 0.70 |
| EHF | 6.29E-04 | 0.69 |
| MYCT1 | 4.32E-05 | 0.69 |
| TSPYL5 | 7.63E-04 | 0.68 |
| HIST1H2BA | 1.79E-04 | 0.54 |
| UCA1 | 5.53E-05 | 0.50 |

TABLE 5

| i | gene | b |
|---|---|---|
| 1 | RKIP | −0.27 |
| 2 | MMP1 | −0.23 |
| 3 | OPN | 0.19 |
| 4 | HMGA2 | −0.20 |
| 5 | CXCR4 | −0.19 |
| 6 | ARID3B | −0.02 |
| 7 | CCNJ | −0.02 |
| 8 | GOLT1B | −0.02 |
| 9 | HIC2 | −0.02 |
| 10 | IGF2BP3 | −0.02 |
| 11 | IL13 | −0.02 |
| 12 | MAP4K4 | −0.02 |
| 13 | NF2 | −0.02 |
| 14 | PAPPA | −0.02 |
| 15 | SLC6A1 | −0.02 |
| 16 | TGFBR1 | −0.02 |
| 17 | ZC3H3 | −0.02 |
| 18 | BMPER | −0.15 |
| 19 | DYM | −0.15 |
| 20 | FBXO42 | −0.15 |
| 21 | FRMPD4 | −0.15 |
| 22 | HERC3 | −0.15 |
| 23 | HS3ST3B1 | −0.15 |
| 24 | IL1RAP | −0.15 |
| 25 | IL7 | −0.15 |
| 26 | MAGEC1 | −0.15 |
| 27 | MYCT1 | −0.15 |
| 28 | PDE1C | −0.15 |
| 29 | PRDM1 | −0.15 |
| 30 | RCAN3 | −0.15 |

TABLE 6A

| | Multivariate Analysis Hazard Ratio | Lower 0.95 | Upper 0.95 | p-value |
|---|---|---|---|---|
| Proliferation Meta-gene: ER+/HER2− vs ER−/HER2− | 0.8451 | 0.2592 | 2.755 | 0.7801 |
| Proliferation Meta-gene: HER2+ vs ER−/HER2− | 0.3842 | 0.1324 | 1.115 | 0.0784 |
| Intrinsic Subtyping: HER2+ vs Basal | 2.1945 | 0.7053 | 6.828 | 0.1747 |
| Intrinsic Subtyping: Luminal-A vs Basal | 0.7856 | 0.2134 | 2.892 | 0.7166 |
| Intrinsic Subtyping: Luminal-B vs Basal | 1.7327 | 0.5047 | 5.948 | 0.3824 |
| Intrinsic Subtyping: Normal vs Basal | 1.1487 | 0.3874 | 3.407 | 0.8026 |
| Recurrence Score: Intermediate vs High | 0.7827 | 0.4676 | 1.31 | 0.3512 |
| Recurrence Score: Low vs High | 0.7072 | 0.4555 | 1.098 | 0.1228 |
| Mammaprint: Poor vs Good | 1.5513 | 0.9739 | 2.471 | 0.0645 |
| BPMS: BPMS− vs BPMS+ | | | | |

TABLE 6B

|  | Multivariate Analysis Hazard Ratio | Lower 0.95 | Upper 0.95 | p-value |
|---|---|---|---|---|
| Proliferation Meta-gene: ER+/HER2− vs ER−/HER2− | 0.8257 | 0.2474 | 2.756 | 0.7555 |
| Proliferation Meta-gene: HER2+ vs ER−/HER2− | 0.3591 | 0.1212 | 1.064 | 0.0646 |
| Intrinsic Subtyping: HER2+ vs Basal | 2.3994 | 0.754 | 7.635 | 0.1384 |
| Intrinsic Subtyping: Luminal-A vs Basal | 0.8599 | 0.2268 | 3.26 | 0.8243 |
| Intrinsic Subtyping: Luminal-B vs Basal | 1.8899 | 0.5346 | 6.681 | 0.3232 |
| Intrinsic Subtyping: Normal vs Basal | 1.2103 | 0.3996 | 3.665 | 0.7357 |
| Recurrence Score: Intermediate vs High | 0.7955 | 0.475 | 1.332 | 0.3847 |
| Recurrence Score: Low vs High | 0.74 | 0.4756 | 1.151 | 0.1819 |
| Mammaprint: Poor vs Good | 1.4771 | 0.9235 | 2.363 | 0.1036 |
| BPMS: BPMS− vs BPMS+ | 0.4878 | 0.261 | 0.912 | 0.0245 |

15

TABLE 6C

|  | Multivariate Analysis Hazard Ratio | Lower 0.95 | Upper 0.95 | p-value |
|---|---|---|---|---|
| Proliferation Meta-gene: ER+/HER2− vs ER−/HER2− | 0.65055 | 0.1894 | 2.2341 | 0.4946 |
| Proliferation Meta-gene: HER2+ vs ER−/HER2− | 0.30734 | 0.1024 | 0.9226 | 0.0354 |
| Intrinsic Subtyping: HER2+ vs Basal | 2.50472 | 0.7916 | 7.9253 | 0.1182 |
| Intrinsic Subtyping: Luminal-A vs Basal | 0.94615 | 0.2521 | 3.5514 | 0.9346 |
| Intrinsic Subtyping: Luminal-B vs Basal | 1.98719 | 0.5674 | 6.9599 | 0.2829 |
| Intrinsic Subtyping: Normal vs Basal | 1.29351 | 0.4278 | 3.9114 | 0.6485 |
| Recurrence Score: Intermediate vs High | 0.74021 | 0.4402 | 1.2447 | 0.2566 |
| Recurrence Score: Low vs High | 0.69454 | 0.4449 | 1.0842 | 0.1087 |
| Mammaprint: Poor vs Good | 1.48393 | 0.9134 | 2.4109 | 0.1109 |
| 76-Gene Signature: Poor vs Good | 1.31577 | 0.8733 | 1.9825 | 0.1895 |
| Sotiriou: Luminal-like vs Basal-like | 0.80253 | 0.5487 | 1.1737 | 0.2567 |
| Mira: Poor vs Good | 0.53318 | 0.2391 | 1.189 | 0.1243 |
| BPMS: BPMS− vs BPMS+ |  |  |  |  |

TABLE 6D

|  | Multivariate Analysis Hazard Ratio | Lower 0.95 | Upper 0.95 | p-value |
|---|---|---|---|---|
| Proliferation Meta-gene: ER+/HER2− vs ER−/HER2− | 0.6206 | 0.17661 | 2.1808 | 0.4569 |
| Proliferation Meta-gene: HER2+ vs ER−/HER2− | 0.28245 | 0.09221 | 0.8652 | 0.0269 |
| Intrinsic Subtyping: HER2+ vs Basal | 2.76312 | 0.85292 | 8.9515 | 0.0901 |
| Intrinsic Subtyping: Luminal-A vs Basal | 1.05112 | 0.27204 | 4.0614 | 0.9424 |
| Intrinsic Subtyping: Luminal-B vs Basal | 2.19388 | 0.60928 | 7.8997 | 0.2294 |
| Intrinsic Subtyping: Normal vs Basal | 1.38074 | 0.44619 | 4.2727 | 0.5756 |
| Recurrence Score: Intermediate vs High | 0.75085 | 0.44564 | 1.2651 | 0.2817 |
| Recurrence Score: Low vs High | 0.73289 | 0.46809 | 1.1475 | 0.1743 |
| Mammaprint: Poor vs Good | 1.39329 | 0.85261 | 2.2769 | 0.1856 |
| 76-Gene Signature: Poor vs Good | 1.31399 | 0.8714 | 1.9814 | 0.1925 |
| Sotiriou: Luminal-like vs Basal-like | 0.77205 | 0.52729 | 1.1304 | 0.1836 |
| Mira: Poor vs Good | 0.53301 | 0.23901 | 1.1886 | 0.1241 |
| BPMS: BPMS− vs BPMS+ | 0.46635 | 0.24924 | 0.8726 | 0.017 |

What is claimed is:

1. A method of treating a patient determined to have a breast cancer, comprising administering a treatment comprising anthracyclines, taxanes, beta-blockers, ixabepilone, bevacizumab, eribulin, or platinum-based therapy alone or combined with surgery to a patient identified as being at a low risk for metastasis by identifying a breast cancer sample from the patient as having, relative to a control or reference sample, decreased expression or activity of at least four biomarkers of the following seven biomarkers: RKIP, MMP1, OPN, HMGA2, CXCR4, let-7, and BACH1, wherein the at least four biomarkers comprise BACH1, and wherein identifying the breast cancer sample as having decreased expression or activity of BACH1 comprises identifying the breast cancer sample as having decreased expression of PRDM1.

2. The method of claim 1, wherein the platinum-based therapy is administered to the patient.

3. The method of claim 1, wherein the breast cancer is a basal-like breast cancer or triple negative breast cancer.

4. The method of claim 1, wherein the control or reference sample is a breast cancer sample from a patient identified as being at a high risk for metastasis.

5. The method of claim 1, wherein the at least four biomarkers comprise RKIP, MMP1, OPN, HMGA2, CXCR4, and BACH1.

6. The method of claim 1, wherein identifying the breast cancer sample as having decreased expression or activity of BACH1 further comprises identifying the breast cancer sample as having decreased expression of at least two of BMPER, DYM, FBXO42, FRMPD4, HERC3, HS3ST3B1, IL1RAP, IL7, MAGEC1, MYCT1, PDE1C, and RCAN3.

7. The method of claim 1, wherein identifying the breast cancer sample as having decreased expression or activity of BACH1 comprises identifying the breast cancer sample as having decreased expression of BMPER, DYM, FBXO42, FRMPD4, HERC3, HS3ST3B1, IL1RAP, IL7, MAGEC1, MYCT1, PDE1C, PRDM1, and RCAN3.

8. The method of claim 1, wherein the at least four biomarkers comprise RKIP, MMP1, OPN, HMGA2, CXCR4, let-7, and BACH1.

9. The method of claim 1, wherein the at least four biomarkers further comprise let-7, and wherein identifying the breast cancer sample as having decreased expression or activity of let-7 comprises identifying the breast cancer sample as having increased expression of at least two of ARID3B, CCNJ, GOLT1B, HIC2, IGF2BP3, IL13, MAP4K4, NF2, PAPPA, SLC6A1, TGFBR1, and ZC3H3.

10. The method of claim 1, wherein the at least four biomarkers further comprise let-7, and wherein identifying the breast cancer sample as having decreased expression or activity of let-7 comprises identifying the breast cancer sample as having increased expression of ARID3B, CCNJ, GOLT1B, HIC2, IGF2BP3, IL13, MAP4K4, NF2, PAPPA, SLC6A1, TGFBR1, and ZC3H3.

11. The method of claim 1, wherein the at least four biomarkers further comprise let-7, and wherein:
  (a) identifying the breast cancer sample as having decreased expression or activity of BACH1 further comprises identifying the breast cancer sample as having decreased expression of RKIP, MMP1, OPN, HMGA2, CXCR4, BMPER, DYM, FBXO42, FRMPD4, HERC3, HS3ST3B1, IL1RAP, IL7, MAGEC1, MYCT1, PDE1C, and RCAN3; and
  (b) identifying the breast cancer sample as having decreased expression or activity of let-7 comprises identifying the breast cancer sample as having increased expression of ARID3B, CCNJ, GOLT1B, HIC2, IGF2BP3, IL13, MAP4K4, NF2, PAPPA, SLC6A1, TGFBR1, and ZC3H3.

* * * * *

UNITED STATES PATENT AND TRADEMARK OFFICE
CERTIFICATE OF CORRECTION

PATENT NO. : 10,679,730 B2
APPLICATION NO. : 14/952265
DATED : June 9, 2020
INVENTOR(S) : Marsha Rosner et al.

It is certified that error appears in the above-identified patent and that said Letters Patent is hereby corrected as shown below:

In the Specification

In Column 1, at Line 18, the paragraph should read as follows:
-- This invention was made with government support under grant numbers GM087630, GM071440, CA125183, and CA127277 awarded by the National Institutes of Health, and grant number W81XWH-10-1-0396 awarded by the Department of Defense. The government has certain rights in the invention. --

Signed and Sealed this
Sixteenth Day of August, 2022

Katherine Kelly Vidal
*Director of the United States Patent and Trademark Office*

SEQUENCE LISTING

<160> NUMBER OF SEQ ID NOS: 45

<210> SEQ ID NO 1
<211> LENGTH: 30
<212> TYPE: DNA
<213> ORGANISM: Artificial Sequence
<220> FEATURE:
<223> OTHER INFORMATION: TET1 Forward Primer

<400> SEQUENCE: 1

```
ttatgtagtt ttatttgttt ttttattgtg                                    30

<210> SEQ ID NO 2
<211> LENGTH: 21
<212> TYPE: DNA
<213> ORGANISM: Artificial Sequence
<220> FEATURE:
<223> OTHER INFORMATION: TET1 Reverse Primer

<400> SEQUENCE: 2
caactccaaa cctacaccaa c                                             21

<210> SEQ ID NO 3
<211> LENGTH: 27
<212> TYPE: DNA
<213> ORGANISM: Artificial Sequence
<220> FEATURE:
<223> OTHER INFORMATION: HOXA7 Forward Primer

<400> SEQUENCE: 3
tataattttg atttgtgatt tgttgtt                                       27

<210> SEQ ID NO 4
<211> LENGTH: 25
<212> TYPE: DNA
<213> ORGANISM: Artificial Sequence
<220> FEATURE:
<223> OTHER INFORMATION: HOXA7 Reverse Primer

<400> SEQUENCE: 4
aaacctctta cccttccatt ctaaa                                         25

<210> SEQ ID NO 5
<211> LENGTH: 24
<212> TYPE: DNA
<213> ORGANISM: Artificial Sequence
<220> FEATURE:
<223> OTHER INFORMATION: HOXA9 Forward Primer

<400> SEQUENCE: 5
ttgggaattt tgattgttag ttga                                          24

<210> SEQ ID NO 6
<211> LENGTH: 24
<212> TYPE: DNA
<213> ORGANISM: Artificial Sequence
<220> FEATURE:
<223> OTHER INFORMATION: HOXA9 Reverse Primer

<400> SEQUENCE: 6
taccaaaaca ctccaaacaa aaac                                          24

<210> SEQ ID NO 7
<211> LENGTH: 22
<212> TYPE: DNA
<213> ORGANISM: Artificial Sequence
<220> FEATURE:
<223> OTHER INFORMATION: TET1 Site-1 Forward Primer

<400> SEQUENCE: 7
tttgggaacc gactcctcac ct                                            22

<210> SEQ ID NO 8
<211> LENGTH: 22
<212> TYPE: DNA
```

```
<213> ORGANISM: Artificial Sequence
<220> FEATURE:
<223> OTHER INFORMATION: TET1 Site-1 Reverse Primer

<400> SEQUENCE: 8
tcgggcaaac tttccaactc gc                                         22

<210> SEQ ID NO 9
<211> LENGTH: 24
<212> TYPE: DNA
<213> ORGANISM: Artificial Sequence
<220> FEATURE:
<223> OTHER INFORMATION: TET1 Site-2 Forward Primer

<400> SEQUENCE: 9
acgctgggca tttctgatcc acta                                       24

<210> SEQ ID NO 10
<211> LENGTH: 24
<212> TYPE: DNA
<213> ORGANISM: Artificial Sequence
<220> FEATURE:
<223> OTHER INFORMATION: TET1 Site-2 Reverse Primer

<400> SEQUENCE: 10
tattgtgcag ctcgtttagt gccc                                       24

<210> SEQ ID NO 11
<211> LENGTH: 24
<212> TYPE: DNA
<213> ORGANISM: Artificial Sequence
<220> FEATURE:
<223> OTHER INFORMATION: TET1 Site-3 Forward Primer

<400> SEQUENCE: 11
actttgacct cccaaagtgc tgga                                       24

<210> SEQ ID NO 12
<211> LENGTH: 24
<212> TYPE: DNA
<213> ORGANISM: Artificial Sequence
<220> FEATURE:
<223> OTHER INFORMATION: TET1 Site-3 Reverse Primer

<400> SEQUENCE: 12
acctgagtga tgctgagact tcct                                       24

<210> SEQ ID NO 13
<211> LENGTH: 20
<212> TYPE: DNA
<213> ORGANISM: Artificial Sequence
<220> FEATURE:
<223> OTHER INFORMATION: HOXA7 Site-1 Forward Primer

<400> SEQUENCE: 13
aaagcgcgtt cacataatac                                            20

<210> SEQ ID NO 14
<211> LENGTH: 25
<212> TYPE: DNA
<213> ORGANISM: Artificial Sequence
<220> FEATURE:
<223> OTHER INFORMATION: HOXA7 Site-1 Reverse Primer

<400> SEQUENCE: 14
gttatcatat atcactctac ctcgt                                      25
```

```
<210> SEQ ID NO 15
<211> LENGTH: 17
<212> TYPE: DNA
<213> ORGANISM: Artificial Sequence
<220> FEATURE:
<223> OTHER INFORMATION: HOXA7 Site-2 Forward Primer

<400> SEQUENCE: 15
cattcctgct ccggttt                                              17

<210> SEQ ID NO 16
<211> LENGTH: 18
<212> TYPE: DNA
<213> ORGANISM: Artificial Sequence
<220> FEATURE:
<223> OTHER INFORMATION: HOXA7 Site-2 Reverse Primer

<400> SEQUENCE: 16
ggtccataaa ggccgaag                                             18

<210> SEQ ID NO 17
<211> LENGTH: 24
<212> TYPE: DNA
<213> ORGANISM: Artificial Sequence
<220> FEATURE:
<223> OTHER INFORMATION: HOXA7 Site-3 Forward Primer

<400> SEQUENCE: 17
ccaccctgcc ttgtttcaac atca                                      24

<210> SEQ ID NO 18
<211> LENGTH: 24
<212> TYPE: DNA
<213> ORGANISM: Artificial Sequence
<220> FEATURE:
<223> OTHER INFORMATION: HOXA7 Site-3 Reverse Primer

<400> SEQUENCE: 18
accaagttgt cagtgagcct tcca                                      24

<210> SEQ ID NO 19
<211> LENGTH: 24
<212> TYPE: DNA
<213> ORGANISM: Artificial Sequence
<220> FEATURE:
<223> OTHER INFORMATION: HOXA9 Site-1 Forward Primer

<400> SEQUENCE: 19
ttcatcctca ccagcagttc cagt                                      24

<210> SEQ ID NO 20
<211> LENGTH: 24
<212> TYPE: DNA
<213> ORGANISM: Artificial Sequence
<220> FEATURE:
<223> OTHER INFORMATION: HOXA9 Site-1 Reverse Primer

<400> SEQUENCE: 20
gggccatttc ggagttcatt gtgt                                      24

<210> SEQ ID NO 21
<211> LENGTH: 24
<212> TYPE: DNA
<213> ORGANISM: Artificial Sequence
<220> FEATURE:
```

<223> OTHER INFORMATION: HOXA9 Site-2 Forward Primer

<400> SEQUENCE: 21
ccaccctgcc ttgtttcaac atca                                    24

<210> SEQ ID NO 22
<211> LENGTH: 24
<212> TYPE: DNA
<213> ORGANISM: Artificial Sequence
<220> FEATURE:
<223> OTHER INFORMATION: HOXA9 Site-2 Reverse Primer

<400> SEQUENCE: 22
accaagttgt cagtgagcct tcca                                    24

<210> SEQ ID NO 23
<211> LENGTH: 30
<212> TYPE: DNA
<213> ORGANISM: Artificial Sequence
<220> FEATURE:
<223> OTHER INFORMATION: TET1 Forward Primer

<400> SEQUENCE: 23
ttatgtagtt ttatttgttt ttttattgtg                              30

<210> SEQ ID NO 24
<211> LENGTH: 21
<212> TYPE: DNA
<213> ORGANISM: Artificial Sequence
<220> FEATURE:
<223> OTHER INFORMATION: TET1 Reverse Primer

<400> SEQUENCE: 24
caactccaaa cctacaccaa c                                       21

<210> SEQ ID NO 25
<211> LENGTH: 27
<212> TYPE: DNA
<213> ORGANISM: Artificial Sequence
<220> FEATURE:
<223> OTHER INFORMATION: HOXA7 Forward Primer

<400> SEQUENCE: 25
tataattttg atttgtgatt tgttgtt                                 27

<210> SEQ ID NO 26
<211> LENGTH: 25
<212> TYPE: DNA
<213> ORGANISM: Artificial Sequence
<220> FEATURE:
<223> OTHER INFORMATION: HOXA7 Reverse Primer

<400> SEQUENCE: 26
aaacctctta cccttccatt ctaaa                                   25

<210> SEQ ID NO 27
<211> LENGTH: 24
<212> TYPE: DNA
<213> ORGANISM: Artificial Sequence
<220> FEATURE:
<223> OTHER INFORMATION: HOXA9 Forward Primer

<400> SEQUENCE: 27
ttgggaattt tgattgttag ttga                                    24

```
<210> SEQ ID NO 28
<211> LENGTH: 24
<212> TYPE: DNA
<213> ORGANISM: Artificial Sequence
<220> FEATURE:
<223> OTHER INFORMATION: HOXA9 Reverse Primer

<400> SEQUENCE: 28
taccaaaaca ctccaaacaa aaac                                              24

<210> SEQ ID NO 29
<211> LENGTH: 22
<212> TYPE: DNA
<213> ORGANISM: Artificial Sequence
<220> FEATURE:
<223> OTHER INFORMATION: TET1 Site-1 Forward Primer

<400> SEQUENCE: 29
tttgggaacc gactcctcac ct                                                22

<210> SEQ ID NO 30
<211> LENGTH: 22
<212> TYPE: DNA
<213> ORGANISM: Artificial Sequence
<220> FEATURE:
<223> OTHER INFORMATION: TET1 Site-1 Reverse Primer

<400> SEQUENCE: 30
tcgggcaaac tttccaactc gc                                                22

<210> SEQ ID NO 31
<211> LENGTH: 24
<212> TYPE: DNA
<213> ORGANISM: Artificial Sequence
<220> FEATURE:
<223> OTHER INFORMATION: TET1 Site-2 Forward Primer

<400> SEQUENCE: 31
acgctgggca tttctgatcc acta                                              24

<210> SEQ ID NO 32
<211> LENGTH: 24
<212> TYPE: DNA
<213> ORGANISM: Artificial Sequence
<220> FEATURE:
<223> OTHER INFORMATION: TET1 Site-2 Reverse Primer

<400> SEQUENCE: 32
tattgtgcag ctcgtttagt gccc                                              24

<210> SEQ ID NO 33
<211> LENGTH: 24
<212> TYPE: DNA
<213> ORGANISM: Artificial Sequence
<220> FEATURE:
<223> OTHER INFORMATION: TET1 Site-3 Forward Primer

<400> SEQUENCE: 33
actttgacct cccaaagtgc tgga                                              24

<210> SEQ ID NO 34
<211> LENGTH: 24
<212> TYPE: DNA
<213> ORGANISM: Artificial Sequence
<220> FEATURE:
<223> OTHER INFORMATION: TET1 Site-3 Reverse Primer
```

<400> SEQUENCE: 34
acctgagtga tgctgagact tcct                                  24

<210> SEQ ID NO 35
<211> LENGTH: 20
<212> TYPE: DNA
<213> ORGANISM: Artificial Sequence
<220> FEATURE:
<223> OTHER INFORMATION: HOXA7 Site-1 Forward Primer

<400> SEQUENCE: 35
aaagcgcgtt cacataatac                                       20

<210> SEQ ID NO 36
<211> LENGTH: 25
<212> TYPE: DNA
<213> ORGANISM: Artificial Sequence
<220> FEATURE:
<223> OTHER INFORMATION: HOXA7 Site-1 Reverse Primer

<400> SEQUENCE: 36
gttatcatat atcactctac ctcgt                                 25

<210> SEQ ID NO 37
<211> LENGTH: 17
<212> TYPE: DNA
<213> ORGANISM: Artificial Sequence
<220> FEATURE:
<223> OTHER INFORMATION: HOXA7 Site-2 Forward Primer

<400> SEQUENCE: 37
cattcctgct ccggttt                                          17

<210> SEQ ID NO 38
<211> LENGTH: 18
<212> TYPE: DNA
<213> ORGANISM: Artificial Sequence
<220> FEATURE:
<223> OTHER INFORMATION: HOXA7 Site-2 Reverse Primer

<400> SEQUENCE: 38
ggtccataaa ggccgaag                                         18

<210> SEQ ID NO 39
<211> LENGTH: 24
<212> TYPE: DNA
<213> ORGANISM: Artificial Sequence
<220> FEATURE:
<223> OTHER INFORMATION: HOXA7 Site-3 Forward Primer

<400> SEQUENCE: 39
ccaccctgcc ttgtttcaac atca                                  24

<210> SEQ ID NO 40
<211> LENGTH: 24
<212> TYPE: DNA
<213> ORGANISM: Artificial Sequence
<220> FEATURE:
<223> OTHER INFORMATION: HOXA7 Site-3 Reverse Primer

<400> SEQUENCE: 40
accaagttgt cagtgagcct tcca                                  24

<210> SEQ ID NO 41
<211> LENGTH: 24

```
<212> TYPE: DNA
<213> ORGANISM: Artificial Sequence
<220> FEATURE:
<223> OTHER INFORMATION: HOXA9 Site-1 Forward Primer

<400> SEQUENCE: 41
ttcatcctca ccagcagttc cagt                                              24

<210> SEQ ID NO 42
<211> LENGTH: 24
<212> TYPE: DNA
<213> ORGANISM: Artificial Sequence
<220> FEATURE:
<223> OTHER INFORMATION: HOXA9 Site-1 Reverse Primer

<400> SEQUENCE: 42
gggccatttc ggagttcatt gtgt                                              24

<210> SEQ ID NO 43
<211> LENGTH: 24
<212> TYPE: DNA
<213> ORGANISM: Artificial Sequence
<220> FEATURE:
<223> OTHER INFORMATION: HOXA9 Site-3 Forward Primer

<400> SEQUENCE: 43
ccaccctgcc ttgtttcaac atca                                              24

<210> SEQ ID NO 44
<211> LENGTH: 24
<212> TYPE: DNA
<213> ORGANISM: Artificial Sequence
<220> FEATURE:
<223> OTHER INFORMATION: HOXA9 Site-3 Reverse Primer

<400> SEQUENCE: 44
accaagttgt cagtgagcct tcca                                              24

<210> SEQ ID NO 45
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 45

Asp Tyr Lys Asp Asp Asp Asp Lys
1               5
```